US009696307B2

(12) United States Patent
Gorelik et al.

(10) Patent No.: US 9,696,307 B2
(45) Date of Patent: Jul. 4, 2017

(54) METHODS FOR THE DETECTION OF JC POLYOMA VIRUS

(71) Applicant: Biogen Idec MA Inc., Cambridge, MA (US)

(72) Inventors: Leonid Gorelik, Quincy, MA (US); Alexey Lugovskoy, Woburn, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

(21) Appl. No.: 14/603,002

(22) Filed: Jan. 22, 2015

(65) Prior Publication Data

US 2015/0219651 A1    Aug. 6, 2015

Related U.S. Application Data

(63) Continuation of application No. 13/147,484, filed as application No. PCT/US2010/000342 on Feb. 5, 2010, now abandoned.

(60) Provisional application No. 61/150,310, filed on Feb. 5, 2009.

(51) Int. Cl.
*G01N 33/569* (2006.01)
*C07K 16/08* (2006.01)
*G01N 33/53* (2006.01)

(52) U.S. Cl.
CPC ..... *G01N 33/56983* (2013.01); *C07K 16/081* (2013.01); *C07K 2317/33* (2013.01); *G01N 2333/025* (2013.01); *G01N 2469/20* (2013.01); *G01N 2800/28* (2013.01); *G01N 2800/50* (2013.01); *G01N 2800/52* (2013.01)

(58) Field of Classification Search
CPC . A61K 48/00; Y10S 977/927; Y10S 424/816; Y10S 977/915; C12N 2710/22034; C12N 2710/24121; C12N 2740/16122; C07K 14/005; C12Q 1/708; G01N 2469/20; G01N 33/56983
See application file for complete search history.

(56) References Cited

U.S. PATENT DOCUMENTS

| 6,238,859 | B1 | 5/2001 | Lüke et al. |
| 2004/0259767 | A1 | 12/2004 | Nagashima et al. |
| 2007/0026503 | A1 | 2/2007 | Lacey |
| 2008/0131028 | A1 | 6/2008 | Pillman et al. |
| 2008/0131928 | A1 | 6/2008 | Handa et al. |
| 2011/0118340 | A1 | 5/2011 | Manoharan et al. |
| 2012/0258443 | A1 | 10/2012 | Gorelik et al. |
| 2013/0101985 | A9 | 4/2013 | Gorelik et al. |
| 2014/0255915 | A1 | 9/2014 | Ray |

FOREIGN PATENT DOCUMENTS

| CN | 101351559 A | 1/2009 |
| EP | 1270586 A2 | 1/2003 |
| JP | 2007-020565 | 2/2007 |
| JP | 2008-249433 | 10/2008 |
| WO | WO 97/27316 A1 | 7/1997 |
| WO | WO 2008/077511 A1 | 7/2008 |
| WO | WO 2014/120862 A1 | 8/2014 |

OTHER PUBLICATIONS

Pagani et al. Journal of NeuroVirology, 2003, vol. 9, pp. 559-566.*
Ryschkewitsch et al. Journal of Virological Methods, 2004, vol. 121, pp. 217-221.*
Weber et al. Journal of NeuroVirology, 2001, vol. 7, pp. 311-317.*
Chang et al. Journal of Vriological Methods, 1996, vol. 59, pp. 177-187.*
Polyclonal vs Monoclonal Antibodies in Pacific Immunology, published 2016, pp. 1-2.*
Antiserum Definintion by The Free Dinctionary in 2016 Pacific Immunology, pp. 1-5.*
Abbas et al. Cellular and Molecular immunology, Fourth Eidition, 2000, p. 57.*
Epitope in Encyclopaedia Britannica , 2014, p. 1.*
Aalberse et al., IgG4 breaking the rules. Immunology. Jan. 2002;105(1):9-19.
Aebersold et al., Mass spectrometry-based proteomics. Nature. Mar. 13, 2003;422(6928):198-207.
Agostini et al., Complete genome of a JC virus genotype type 6 from the brain of an African American with progressive multifocal leukoencephalopathy. J Hum Virol. May-Jun. 1998;1(4):267-72.
Agostini et al., Genotypes of JC virus in East, Central and Southwest Europe. J Gen Virol. May 2001;82(Pt 5):1221-1331.
Agostini et al., JC virus (JCV) genotypes in brain tissue from patients with progressive multifocal leukoencephalopathy (PML) and in urine from controls without PML: increased frequency of JCV type 2 in PML. J Infect Dis. Jul. 1997;176(1):1-8.
Allen et al., Endothelial expression of VCAM-1 in experimental crescentic nephritis and effect of antibodies to very late antigen-4 or VCAM-1 on glomerular injury. J Immunol. May 1, 1999;162(9):5519-27.
Ault et al., Two major types of JC virus defined in progressive multifocal leukoencephalopathy brain by early and late coding region DNA sequences. J Gen Virol. Oct. 1992;73 ( Pt 10):2669-78.
Bauer et al., Discrimination between sialic acid-containing receptors and pseudoreceptors regulates polyomavirus spread in the mouse. J Virol. Jul. 1999;73(7):5826-32. Erratum in: J Virol Jun. 2000;74(12):5746. Liu, WR [added].

(Continued)

*Primary Examiner* — Bao Li
(74) *Attorney, Agent, or Firm* — Wolf, Greenfield & Sacks, P.C.

(57) ABSTRACT

Methods and compositions for determining whether a subject is at risk for PML, including subjects being treated with immunosuppressants, by determining whether the subject harbors a JCV variant with reduced binding for sialic acid relative to a normal JCV, are presented. Furthermore, combinations of JCV-VP1 sequence variations that are associated with PML and that can be used as a basis of an assay for identifying subjects susceptible to PML, subjects with PML (e.g., early stage PML), or subjects at risk of developing PML in response to an immunosuppressive treatment are provided.

15 Claims, 29 Drawing Sheets

(56) References Cited

OTHER PUBLICATIONS

Bauer et al., Genetic and structural analysis of a virulence determinant in polyomavirus VP1. J Virol. Dec. 1995;69(12):7925-31.

Berger et al., Progressive multifocal leukoencephalopathy: the evolution of a disease once considered rare. J Neurovirol. Mar. 1995;1(1):5-18.

Bossolasco et al., Prognostic significance of JC virus DNA levels in cerebrospinal fluid of patients with HIV-associated progressive multifocal leukoencephalopathy. Clin Infect Dis. Mar. 1, 2005;40(5):738-44. Epub Feb. 1, 2005.

Chandrasekaran et al., Glycan topology determines human adaptation of avian H5N1 virus hemagglutinin. Nat Biotechnol. Jan. 2008;26(1):107-13. Epub Jan. 6, 2008.

Chang et al., Production of the antigen and the antibody of the JC virus major capsid protein VP1. J Virol Methods. May 1996;59(1-2):177-87.

Chapagain et al., Comparison of real-time PCR and hemagglutination assay for quantitation of human polyomavirus JC. Virol J. Jan. 9, 2006;3:3.

Cinque et al., JC Virus VP1 from cerebrospinal fluid and plasma of patients with progressive multifocal leukoencephalopathy carry specific mutations of aminoacid residues involved in sialic acid binding. 16$^{th}$ Conference on Retroviruses and Opportunistic Infections. Feb. 8-11, 2009. Montreal, Canada. Session 86 Poster Abstracts, HCV and OIs in NeuroAIDS. Abstract # 468b. 1 page.

Cubitt et al., Predicted amino acid sequences for 100 JCV strains. J Neurovirol. Aug. 2001;7(4):339-44.

Du Pasquier et al., Low frequency of cytotoxic T lymphocytes against the novel HLA-A*0201-restricted JC virus epitope VP1(p36) in patients with proven or possible progressive multifocal leukoencephalopathy. J Virol. Nov. 2003;77(22):11918-26.

Dubensky et al., Polyomavirus replication in mice: influences of VP1 type and route of inoculation. J Virol. Jan. 1991;65(1):342-9.

Dundas et al., Comparison of automated nucleic acid extraction methods with manual extraction. J Mol Diagn. Jul. 2008;10(4):311-6. doi: 10.2353/jmoldx.2008.070149. Epub Jun. 13, 2008.

Eash et al., Differential distribution of the JC virus receptor-type sialic acid in normal human tissues. Am J Pathol. Feb. 2004;164(2):419-28.

Farina et al., Treatment with glatiramer acetate induces specific IgG4 antibodies in multiple sclerosis patients. J Neuroimmunol. Feb. 2002;123(1-2):188-92.

Ferenczy et al., Molecular biology, epidemiology, and pathogenesis of progressive multifocal leukoencephalopathy, the JC virus-induced demyelinating disease of the human brain. Clin Microbiol Rev. Jul. 2012;25(3):471-506. doi: 10.1128/CMR.05031-11.

Freund et al., A single-amino-acid substitution in polyomavirus VP1 correlates with plaque size and hemagglutination behavior. J Virol. Jan. 1991;65(1):350-5.

García-Suárez et al., Changes in the natural history of progressive multifocal leukoencephalopathy in HIV-negative lymphoproliferative disorders: impact of novel therapies. Am J Hematol. Dec. 2005;80(4):271-81.

Gee et al., Modeling a sialic acid binding pocket in the external loops of JC virus VP1. J Biol Chem. Nov. 19, 2004;279(47):49172-6. Epub Sep. 3, 2004.

GenBank Submission JF426109.1. JC polyomavirus isolate JCV268RRC-47 control region, partial sequence. Aug. 4, 2011. Retrieved from the Internet on Jun. 14, 2014.

GenBank Submission JX273163.1. JC polyomavirus strain JAL, complete genome. Sep. 17, 2012. Retrieved from the Internet on Jun. 14, 2014.

GenBank Submission PLYJCSS. JC polyomavirus gene for T antigen, partial cds and regulatory region, isolate: SS/c1131. Dec. 18, 2007. Retrieved from the Internet on Jun. 14, 2014.

Genbank Submission; NCBI, Accession No. AAQ88264; Mengistu et al., Oct. 4, 2004. 1 page.

Genbank Submission; NCBI, Accession No. ABH10590; Koralnik et al.; Aug. 14, 2006. 1 page.

Genbank Submission; NCBI, Accession No. ABP33189; Rafique et al.; Apr. 17, 2007. 1 page.

Genbank Submission; NCBI, Accession No. BAA22741; Kitamura et al.; Nov. 9, 2007. 1 page.

Glass et al., Improved detection of JC virus in AIDS patients with progressive multifocal leukoencephalopathy by T-antigen specific fluorescence resonance energy transfer hybridization probe real-time PCR: evidence of diverse JC virus genotypes associated with progressive multifocal leukoencephalopathy in Southern Africa. J Med Virol. Nov. 2009;81(11):1929-37. doi: 10.1002/jmv.21618.

Goldmann et al., Molecular cloning and expression of major structural protein VP1 of the human polyomavirus JC virus: formation of virus-like particles useful for immunological and therapeutic studies. J Virol. May 1999;73(5):4465-9.

Gorelik et al., Progressive multifocal leukoencephalopathy (PML) development is associated with mutations in JC virus capsid protein VP1 that change its receptor specificity. J Infect Dis. Jul. 1, 2011;204(1):103-14.

Iida et al., Origin of JC polyomavirus variants associated with progressive multifocal leukoencephalopathy. Proc Natl Acad Sci U S A. Jun. 1, 1993;90(11):5062-5.

Ikegaya et al., Detection of identical JC virus DNA sequences in both human kidneys. Arch Virol. Jun. 2004;149(6):1215-20. Epub Feb. 12, 2004.

Ikegaya et al., Trial for the geographical identification using JC viral genotyping in Japan. Forensic Sci Int. Jan. 28, 2004;139(2-3):169-72.

Invitrogen. PureLink Viral RNA/DNA Kits. Version C. Nov. 29, 2006. Retrieved from the Internet on Oct. 2, 2012 at http://tools.lifetechnologies.com/content/sfs/manuals/purelink_viral_rna_dna_man pdf. 35 pages.

Jobes et al., Phylogenetic analysis of 22 complete genomes of the human polyomavirus JC virus. J Gen Virol. Oct. 1998;79 (Pt 10):2491-8.

Johnson et al., Polyomavirus JC in the context of immunosuppression: a series of adaptive, DNA replication-driven recombination events in the development of progressive multifocal leukoencephalopathy. Clin Dev Immunol. 2013;2013:197807. doi: 10.1155/2013/197807. Epub Apr. 15, 2013.

Kato et al., Detection of the archetypal regulatory region of JC virus from the tonsil tissue of patients with tonsillitis and tonsilar hypertrophy. J Neurovirol. Aug. 2004;10(4):244-9.

Kato et al., Lack of disease-specific amino acid changes in the viral proteins of JC virus isolates from the brain with progressive multifocal leukoencephalopathy. Arch Virol. 2000;145(10):2173-82.

Kato et al., Phylogenetic comparison between archetypal and disease-associated JC virus isolates in Japan. Jpn J Med Sci Biol. Jun. 1994;47(3):167-78.

Knowles et al., Discovery and epidemiology of the human polyomaviruses BK virus (BKV) and JC virus (JCV). Adv Exp Med Biol. 2006;577:19-45.

Krasner, Biogen Idec turns to expert for Tysabri help. The Boston Globe. Boston.com. Mar. 2, 2005. Last accessed at http://www.boston.com/business/globe/articles/2005/03/02/biogen_idec_turns_to_expert_f . . . on Feb. 15, 2007. 2 pages.

Liddington et al., Structure of simian virus 40 at 3.8-A resolution. Nature. Nov. 28, 1991;354(6351):278-84.

Liu et al., Infection of glial cells by the human polyomavirus JC is mediated by an N-linked glycoprotein containing terminal alpha(2-6)-linked sialic acids. J Virol. Jun. 1998;72(6):4643-9.

Loeber et al., DNA rearrangements in organ-specific variants of polyomavirus JC strain GS. J Virol. May 1988;62(5):1730-5.

Lundstig et al., Chapter 7: Serological diagnosis of human polyomavirus infection. Polyomaviruses and Human Diseases. Springer Science+Business Media. Landes Bioscience / Eurekah.com. 2006;96-101.

Major et al., Pathogenesis and molecular biology of progressive multifocal leukoencephalopathy, the JC virus-induced demyelinating disease of the human brain. Clin Microbiol Rev. Jan. 1992;5(1):49-73.

Martin et al., Differences in regulatory sequences of naturally occurring JC virus variants. J Virol. Jan. 1985;53(1):306-11.

(56) References Cited

OTHER PUBLICATIONS

Miyamura et al., Genomic structure of human polyoma virus JC: nucleotide sequence of the region containing replication origin and small-T-antigen gene. J Virol. Jan. 1983;45(1):73-9.

Monaco et al., Detection of JC virus DNA in human tonsil tissue: evidence for site of initial viral infection. J Virol. Dec. 1998;72(12):9918-23.

Nagashima et al., Progressive multifocal leukoencephalopathy. Neuropathology and virus isolation. Acta Pathol Jpn. Nov. 1981;31(6):953-61.

Nam et al., Identification of the sialic acid structures recognized by minute virus of mice and the role of binding affinity in virulence adaptation. J Biol Chem. Sep. 1, 2006;281(35):25670-7. Epub Jul. 5, 2006.

Notredame et al., T-Coffee: A novel method for fast and accurate multiple sequence alignment. J Mol Biol. Sep. 8, 2000;302(1):205-17.

Padgett et al., Cultivation of papova-like virus from human brain with progressive multifocal leucoencephalopathy. Lancet. Jun. 19, 1971;1(7712):1257-60.

Padgett et al., Prevalence of antibodies in human sera against JC virus, an isolate from a case of progressive multifocal leukoencephalopathy. J Infect Dis. Apr. 1973;127(4):467-70.

Pfister et al., JC virus regulatory region tandem repeats in plasma and central nervous system isolates correlate with poor clinical outcome in patients with progressive multifocal leukoencephalopathy. J Virol. Jun. 2001;75(12):5672-6.

QIAamp, DNA Mini and Blood Mini Handbook. Apr. 2010. Retrieved from the Internet Mar. 22, 2014.

Reid et al., Sequencing and analysis of JC virus DNA from natalizumab-treated PML patients. J Infect Dis. Jul. 15, 2011;204(2):237-44.

Ryschkewitsch et al., Comparison of PCR-southern hybridization and quantitative real-time PCR for the detection of JC and BK viral nucleotide sequences in urine and cerebrospinal fluid. J Virol Methods. Nov. 2004;121(2):217-21.

Safak et al., Human polyomavirus JC virus and its associated disorders. J Neurovirol. 2003;9 Suppl 1:3-9.

Sala et al., Progressive multifocal leukoencephalopathy in human immunodeficiency virus type 1-infected patients: absence of correlation between JC virus neurovirulence and polymorphisms in the transcriptional control region and the major capsid protein loci. J Gen Virol. Apr. 2001;82(Pt 4):899-907.

Schuurman et al., Normal human immunoglobulin G4 is bispecific: it has two different antigen-combining sites. Immunology. Aug. 1999;97(4):693-8.

Schuurman et al., The inter-heavy chain disulfide bonds of IgG4 are in equilibrium with intra-chain disulfide bonds. Mol Immunol. Jan. 2001;38(1):1-8.

Suers et al., QIAamp MinElute virus kit effectively extracts viral nucleic acids from cerebrospinal fluids and nasopharyngeal swabs. J Clin Virol. Feb. 2006;35(2):141-6. Epub Jul. 21, 2005.

Srinivasan et al., Quantitative biochemical rationale for differences in transmissibility of 1918 pandemic influenza A viruses. Proc Natl Acad Sci U S A. Feb. 26, 2008;105(8):2800-5. Epub Feb. 19, 2008.

Stehle et al., High-resolution structure of a polyomavirus VP1-oligosaccharide complex: implications for assembly and receptor binding. EMBO J. Aug. 15, 1997;16(16):5139-48.

Stoner et al., Capsid protein VP1 deletions in JC virus from two AIDS patients with progressive multifocal leukoencephalopathy. J Neurovirol. Jun. 1995;1(2):189-94.

Sunyaev et al., Adaptive mutations in the JC virus protein capsid are associated with progressive multifocal leukoencephalopathy (PML). PLoS Genet. Feb. 2009;5(2):e1000368. Epub Feb. 6, 2009.

Venter et al., Phylogenetic evidence of widespread distribution of genotype 3 JC virus in Africa and identification of a type 7 isolate in an African AIDS patient. J Gen Virol. Aug. 2004;85(Pt 8):2215-9.

Wang et al., Research progress on correlation between monkey polyomavirus, human polyomavirus, JC virus and human brain tumors. J Practical Diagnosis Therapy. Jul. 10, 2004;18(4):303-6.

Yogo et al., JC virus regulatory region rearrangements in the brain of a long surviving patient with progressive multifocal leukoencephalopathy. J Neurol Neurosurg Psychiatry. Sep. 2001;71(3):397-400.

Zheng et al., Characterization of the VP1 loop mutations widespread among JC polyomavirus isolates associated with progressive multifocal leukoencephalopathy. Biochem Biophys Res Commun. Aug. 5, 2005;333(3):996-1002.

Zheng et al., New sequence polymorphisms in the outer loops of the JC polyomavirus major capsid protein (VP1) possibly associated with progressive multifocal leukoencephalopathy. J Gen Virol. Jul. 2005;86(Pt 7):2035-45.

* cited by examiner

```
              10         20         30         40         50         60         70         80
         ....|....|  ....|....|  ....|....|  ....|....|  ....|....|  ....|....|  ....|....|  ....|....|
JCV  VP1 MAPTKRKGER  KDPVQVPKLL  IRGGVEVLEV  KTGVDSITEV  ECFLTPEMGD  PDEHLRGFSK  SISISDTFES  DSPNKDMLPC
SV40 COA1 --PKKPK---  -EPVQVPKLV  IKGGIEVLGV  KTGVDSFTEV  ECFLNPQMGN  PDEHQKGLSK  SLAAEKQFTD  DSPDKEQLPC 90        100        110        120        130        140        150        160
         ....|....|  ....|....|  ....|....|  ....|....|  ....|....|  ....|....|  ....|....|  ....|....|
JCV  VP1 YSVARIPLPN  LNEDLTCGNI  LMWEAVTLKT  EVIGVTTLMN  VHSNGQATHD  NGAAKPVQGT  SFHFFSVGGE  ALELQGVVFN
SV40 COA1 YSVARIPLPN  INEDLTCGNI  LMWEAVTVKT  EVIGVTAMLN  LHSGTQKTHE  NGAGKPIQGS  NFHFFAVGGE  PLELQGVLAN 170        180        190        200        210        220        230        240
         ....|....|  ....|....|  ....|....|  ....|....|  ....|....|  ....|....|  ....|....|  ....|....|
JCV  VP1 YRTTYPDGTI  FPKNATVQSQ  VMNTEHKAYL  DKNKAYPVEC  WVPDPTRNEN  TRYFGTLTGG  ENVPPVLHIT  NTATTVLLDE
SV40 COA1 YRTKYPAQTV  TPKNATVDSQ  QMNTDHKAVL  DKDNAYPVEC  WVPDPSKNEN  TRYFGTYTGG  ENVPPVLHIT  NTATTVLLDE 250        260        270        280        290        300        310        320
         ....|....|  ....|....|  ....|....|  ....|....|  ....|....|  ....|....|  ....|....|  ....|....|
JCV  VP1 FGVGPLCKGD  NLYLSAVDVC  GMFTNRSGSQ  QWRGLSRYFK  VQLRKRRVKN  PYPISFLLTD  LINRRTPRVD  GQPMYGMDAQ
SV40 COA1 QGVGPLCKAD  SLYVSAVDIC  GLFTNTSGTQ  QWKGLPRYFK  ITLRKRSVKN  PYPISFLLSD  LINRRTQRVD  GQPMIGMSSQ 330        340        350
         ....|....|  ....|....|  ....|....|  ....
JCV  VP1 IEEVRVFEGT  EQLPGDPDMM  RYVDRYGQLQ  TKML
SV40 COA1 VEEVRVYEDT  EELPGDPDMI  RYIDEFGQTT  TRMQ
```

Fig. 1

VP1 from Brain Samples of PML subjects:

\>AAB60584   gi|1161319|gb|AAB60584.1|   VP1
NVPPVLHITNTATTVLLDEFGVGPLCKGDNLYLSAVDVCGMFTNRSGSQQWRGLSRYFKVQLRKRRVKN
PYPISFLLTDLINRRTPRVDGQPMYGMDAQVEEVRVFEGTEELPGDPDMMRYVDRYGQLQTKML
(SEQ ID NO: 3)

\>AAB60586   gi|1161322|gb|AAB60586.1|   VP1
NVPPVLHITNTATTVLLDEFGVGPLCKGDNLYLSAVDVCGMFTNRSGSQQWRGLSRYFKVQLRKRRVKN
PYPISFLLTDLINRRTPRVDGQPMYGMDAQVEEVRVFEGTEELPGDPDMMRYVDRYGQLQTKML
(SEQ ID NO: 4)

\>AAB62687   gi|2246615|gb|AAB62687.1|   VP1 [JC virus]
MAPTKRKGERKDPVQVPKLLIRGGVEVLEVKTGVDSITEVECFLTPEMGDPDEHFRGFSKSISISDTFE
SDSPNKDMLPCYSVARIPLPNLNEDLTCGNILMWEAVTLKTEVIGVTTLMNVHSNGQAAHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGSQQWRGLS
RYFKVQLRKRRVKNPYPISFLLTDLINRRTPRVDGQPMYGMDAQVEEVRVFEGTEELPGDPDMMRYVDR
YGQLQTKML
(SEQ ID NO: 5)

\>AAB94036   gi|2735983|gb|AAB94036.1|   VP1 [JC virus]
MAPTKRKGERKDPVQVPKLLIRGGVEVLEVKTGVDSITEVECFLTPEMGDPDEHFRGFSKSISISDTFE
SDSPNKDMLPCYSVARIPLPNLNEDLTCGNILMWEAVTLKTEVIGVTTLMNVHSNGQATHDNGAGKPVQ
GTSFHFFSVGGEALELQGVVFNYRTTYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGSQQWRGLS
RYFKVQLRKRRVKNPYPISFLLTDLINRRTPRVDGQPMYGMDAQVEEVRVFEGTEELPGDPDMMRYVDR
YGQLQTKML
(SEQ ID NO: 6)

\>BAA01965   gi|425206|dbj|BAA01965.1|   VP1 [JC polyomavirus]
MAPTKRKGERKDPVQVPKLLIRGGVEVLEVKTGVDSITEVECFLTPEMGDPDEHLRGFSKSISISDTFE
SDSPNKDMLPCYSVARIPLPNLNEDLTCGNILMWEAVTLKTEVIGVTTLMNVHSNGQAAHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGFQQWRGLS
RYFKVQLRKRRVKNPYPISFLLTDLINRRTPRVDGQPMYGMDAQVEEVRVFEGTEELPGDPDMMRYVDR
YGQLQTKML
(SEQ ID NO: 7)

\>BAA01966   gi|425207|dbj|BAA01966.1|   VP1 [JC polyomavirus]
MAPTKRKGERKDPVQVPKLLIRGGVEVLEVKTGVDSITEVECFLTPEMGDPDEHLRGFSKSISISHTFE
SDSPNRDMLPCYSVARIPLPNLNEDLTCGNILMWEAVTLKTEVIGVTSLMNVHSNGQATHDNGAGKPVQ
GTSFHFFSVGGEALELQGVLFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGSQQWRGLS
RYFKVQLRKRRVKNPYPISFLLTDLINRRTPRVDGQPMYGMDAQVEEVRVFEGTEELPGDPDMMRYVDK
YGQLQTKML
(SEQ ID NO: 8)

\>BAA01967   gi|425208|dbj|BAA01967.1|   VP1 [JC polyomavirus]
MAPTKRKGERKDPVQVPKLLIRGGVEVLEVKTGVDSITEVECFLTPEMGDPDEHLRGFSKSISISDTFE
SDSPNKDMLPCYSVARIPLPNLNEDLTCGNILMWEAVTLKTEVIGVTSLMNVHSNGQATHDNGAGKPVQ
GTSFHFFSVGGEALELQGVLFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRLGSQQWRGLS
RYFKVQLRKRRVKNPYPISFLLTDLINRRTPRVDGQPMYGMDAQVEEVRVFEGTEELPGDPDMMRYVDK
YGQLQTKML
(SEQ ID NO: 9)

Fig. 3-1

>BAA01968 gi|425209|dbj|BAA01968.1| VP1 [JC polyomavirus]
MAPTKRKGERKDPVQVPKLLIRGGVEVLEVKTGVDSITEVECFLTPEMGDPDEHLRGFSKSISISDTFE
SDSPSKDMLPCYSVARIPLPNLNEDLTCGNILMWEAVTLKTEVIGVTSLMNVHSNGQAAHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGSQQWRGLS
RYFKVQLRKRRVKNPYPISFLLTDLINRRTPRVDGQPMYGMDAQVEEVRVFEGTEELPGDPDMMRYVDK
YGQLQTKML
(SEQ ID NO: 10)

>BAA01969 gi|425210|dbj|BAA01969.1| VP1 [JC polyomavirus]
MAPTKRKGERKDPVQVPKLLIRGGVEVLEVKTGVDSITEVECFLTPEMGDPDEHLRGFSKSISISDTFE
SDSPNKDMLPCYSVARIPLPNLNEDLTCGNILMWEAVTLKTEVLGVTTLMNVHSNGQATHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGFQQWRGLS
RYFKVQLRKRRVKNPYPISFLLTDLINRRTPRVDGQPMYGMDAQVEEVRVFEGTEELPGDPDMMRYVDR
YGQLQTKML
(SEQ ID NO: 11)

>BAA01970 gi|425211|dbj|BAA01970.1| VP1 [JC polyomavirus]
MAPTKRKGERKDPVQVPKLLIRGGVEVLEVKTGVDSITEVECFLTPEMGDPDEHLRGFSKSISISDTFE
SDSPNKDMLPCYSVARIPLPNLNEDLTCGNILMWEAVTLKTEVLGVTTLMNVHSNGQATHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGSQQWRGLS
RYFKVQLRKRRVKNPYPISFLLTDLINRRTPRVDGQPMYGMDAQVEEVRVFEGTEELPGDPDMMRYVDR
YGQLQTKML
(SEQ ID NO: 12)

>BAA05636 gi|538231|dbj|BAA05636.1| VP1 (capsid protein) [JC polyomavirus]
MAPTKRKGERKDPVQVPKLLIRGGVEVLEVKTGVDSITEVECFLTPEMGDPDEHLRGFSKSISISDTFE
SDSPNKDMLPCYSVARIPLPNLNEDLTCGNILMWEAVTLKTEVLGVTTLMNVHSNGQATHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGSQQWRGLS
RYFKVQLRKRRVKNPYPISFLLTDLINRRTPRVDGQPMYGMDAQVEEVRVFEGTEELPGDPDMMRYVDR
YGQLQTKML
(SEQ ID NO: 13)

>BAA05637 gi|538234|dbj|BAA05637.1| VP1 (capsid protein) [JC polyomavirus]
MAPTKRKGERKDPVQVPKLLIRGGVEVLEVKTGVDSITEVECFLTPEMGDPDEHLRGFSKSISISDTFE
SDSPNKDMLPCYSVARIPLPNLNEDLTCGNILMWEAVTLKTEVLGVTTLMNVHSNGQATHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGFQQWRGLS
RYFKVQLRKRRVKNPYPISFLLTDLINRRTPRVDGQPMYGMDAQVEEVRVFEGTEELPGDPDMMRYVDR
YGQLQTKML
(SEQ ID NO: 14)

>BAA05638 gi|538238|dbj|BAA05638.1| VP1 (capsid protein) [JC polyomavirus]
MAPTKRKGERKDPVQVPKLLIRGGVEVLEVKTGVDSITEVECFLTPEMGDPDEHLRGFSKSISISDTFE
SDSPNKDMLPCYSVARIPLPNLNEDLTCGNILMWEAVTLKTEVIGVTTLMNVHSNGQATHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGYQQWRGLS
RYFKVQLRKRRVKNPYPISFLLTDLINRRTPRVDGQPMYGMDAQVEEVRVFEGTEELPGDPDMMRYVDR
YGQLQTKML
(SEQ ID NO: 15)

Fig. 3-2

>BAB11728 gi|9796436|dbj|BAB11728.1| VP1 capsid protein [JC polyomavirus]
MAPTKRKGERKDPVQVPKLLIRGGVEVLEVKTGVDSITEVECFLTPEMGDPDEHLRGFSKSISISDTFE
SDSPNKDMLPCYSVARIPLPNLNEDLTCGNILMWEAVTLKTEVLGVTTLMNVHSNGQATHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGFQQWRGLS
RYFKVQLRKRRVKNPYPISFLLTDLINRRTPRVDGQPMYGMDAQVEEVRVFEGTEELPGDPDMMRYVDR
YGQLQTKML
(SEQ ID NO: 16)

>BAB11734 gi|9796443|dbj|BAB11734.1| VP1 capsid protein [JC polyomavirus]
MAPTKRKGERKDPVQVPKLLIRGGVEVLEVKTGVDSITEVECFLTPEMGDPDEHLRGFSKSISISDTFE
SDSPNKDMLPCYSVARIPLPNLNEDLTCGNILMWEAVTLKTEVIGVTTLMNVHSNGQATHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGYQQWRGLS
RYFKVQLRKRRVKNPYPISFLLTDLINRRTPRVDGQPMYGMDAQVEEVRVFEGTEELPGDPDMMRYVDR
YGQLQTKML
(SEQ ID NO: 17)

>BAE00111 gi|67968154|dbj|BAE00111.1| VP1 [JC polyomavirus]
MAPTKRKGERKDPVQVPKLLIRGGVEVLEVKTGVDSITEVECFLTPEMGDPDEHLRGFSKSISISDTFE
SDSPSKDMLPCYSVARIPLPNLNEDLTCGNILMWEAVTLKTEVIGVTSLMNVHSNGQAAHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGSQQWRGLS
RYFKVQLRKRRVKNPYPISFLLTDLINRRTPRVDGQPMYGMDAQVEEVRVFEGTEELPGDPDMMRYVDK
YGQLQTKML
(SEQ ID NO: 18)

>BAE00117 gi|67968161|dbj|BAE00117.1| VP1 [JC polyomavirus]
MAPTKRKGERKDPVQVPKLLIRGGVEVLEVKTGVDSITEVECFLTPEMGDPDEHLRGFSKSISISDTFE
SDSPSKDMLPCYSVARIPLPNLNEDLTCGNILMWEAVTLKTEVIGVTSLMNVHSNGQAAHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGFQQWRGLS
RYFKVQLRKRRVKNPYPISFLLTDLINRRTPRVDGQPMYGMDAQVEEVRVFEGTEELPGDPDMMRYVDK
YGQLQTKML
(SEQ ID NO: 19)

>BAE00123 gi|67968168|dbj|BAE00123.1| VP1 [JC polyomavirus]
MAPTKRKGERKDPVQVPKLLIRGGVEVLEVKTGVDSITEVECFLTPEMGDPDEHLRGFSKSISISDTFE
SDSPSKDMLPCYSVARIPLPNLNEDLTCGNILMWEAVTLKTEVIGVTSLMNVHSNGQAAHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGFQQWRGLS
RYFKVQLRKRRVKNPYPISFLLTDLINRRTPRVDGQPMYGMDAQVEEVRVFEGTEELPGDPDMMRYVDK
YGQLQTKML
(SEQ ID NO: 20)

>BAE00127 gi|67968173|dbj|BAE00127.1| VP2 [JC polyomavirus]
MGAALALLGDLVATVSEAAAATGFSVAEIAAGEAAATIEVEIASLATVEGITSTSEAIAAIGLTPETYA
VITGAPGAVAGFAALVQTVTGGSAIAQLGYRFFADWDHKVSTVGLFQQPAMALQLFNPEDYYDILFPGV
NAFVNNIHYLDPRHWGPSLFSTISQAFWNLVRDDLPSLTSQEIQRRTQKLFVESLARFLEETTWAIVNS
PVNLYNYISDYYSRLSPVRPSMVRQVAQREGTYISFGHSYTQSIDDADSIQEVTQRLDLKTPNVQSGEF
IEKSIAPGGANQRSAPQWMLPLLLGLYGTVTPALEAYEDGPNKKKRRKEGPRASSKTSYKRRSRSSRS
(SEQ ID NO: 21)

Fig. 3-3

>BAE00129 gi|67968175|dbj|BAE00129.1| VP1 [JC polyomavirus]
MAPTKRKGERKDPVQVPKLLIRGGVEVLEVKTGVDSITEVECFLTPEMGDPDEHLRGFSKSISISDTFE
SDSPNKDMLPCYSVARIPLPNLEDLTCGNILMWEAVTLKTEVIGVTTLMNVHSNGQATHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGSQQWRGLS
RYFKVQLRKRRVKNPYPISFLLTDLINRRTPRVDGQPMYGMDAQVEEVRVFEGTEELPGDPDMMRYVDR
YGQLQTKML
(SEQ ID NO: 22)

>BAE00135 gi|67968182|dbj|BAE00135.1| VP1 [JC polyomavirus]
MAPTKRKGERKDPVQVPKLLIRGGVEVLEVKTGVDSITEVECFLTPEMGDPDEHLRGFSKLISISDTFE
SDSPNKDMLPCYSVARIPLPNLEDLTCGNILMWEAVTLKTEVIGVTTLMNVHSNGQATHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGSQQWRGLS
RYFKVQLRKRRVKNPYPISFLLTDLINRRTPRVDGQPMYGMDAQVEEVRVFEGTEELPGDPDMMRYVDR
YGQLQTKML
(SEQ ID NO: 23)

>BAE00141 gi|67968189|dbj|BAE00141.1| VP1 [JC polyomavirus]
MAPTKRKGERKDPVQVPKLLIRGGVEVLEVKTGVDSITEVECFLTPEMGDPDEHLRGFSKSISISDTFE
SDSPNKDMLPCYSVARIPLPNLEDLTCGNILMWEAVTLKTEVIGVTTLMNVHSNGQATHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGSQQWRGLS
RYFKVQLRKRRVKNPYPISFLLTDLINRRTPRVDGQPMYGMDAQVEEVRVFEGTEELPGDPDMMRYVDR
YGQLQTKML
(SEQ ID NO: 24)

>BAE00147 gi|67968204|dbj|BAE00147.1| VP1 [JC polyomavirus]
MAPTKRKGERKDPVQVPKLLIRGGVEVLEVKTGVDSITEVECFLTPEMGDPDEHLRGFSKSISISDTFE
SDSPNKDMLPCYSVARIPLPNLEDLTCGNILMWEAVTLKTEVLGVTTLMNVHSNGQATHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGSQQWRGLS
RYFKVQLRKRRVKNPYPISFLLTDLINRRTPRVDGQPMYGMDAQVEEVRVFEGTEELPGDPDMMRYVDR
YGQLQTKML
(SEQ ID NO: 25)

>BAE00153 gi|67968211|dbj|BAE00153.1| VP1 [JC polyomavirus]
MAPTKRKGERKDPVQVPKLLIRGGVEVLEVKTGVDSITEVECFLTPEMGDPDEHLRGFSKSISISDTFE
SDSPNKDMLPCYSVARIPLPNLEDLTCGNILMWEAVTLKTEVLGVTTLMNVHSNGQATHDNGAGKPVQ
GTSFHFFSVGGEALELQGVVFNYRTKYPDGTIFPKNATVQSQVMNTEHKAYPVECWVPDPTR
NENTRYFGTLTGGENVPPVLHITNTATTVLLDEFGVGPLCKGDNLYLSAVDVCGMFTNRSGYQQWRGLS
RYFKVQLRKRRVKNPYPISFLLTDLINRRTPRVDGQPMYGMDAQVEEVRVFEGTEELPGDPDMMRYVDR
YGQLQTKML
(SEQ ID NO: 26)

>BAE00159 gi|67968218|dbj|BAE00159.1| VP1 [JC polyomavirus]
MAPTKRKGERKDPVQVPKLLIRGGVEVLEVKTGVDSITEVECFLTPEMGDPDEHLRGFSMSISISDTFE
SDSPNKDMLPCYSVARIPLPNLEDLTCGNILMWEAVTLKTEVLGVTTLMNVHSNGQATHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGSQQWRGLS
RYFKVQLRKRRVKNPYPISFLLTDLINRRTPRVDGQPMYGMDAQVEEVRVFEGTEELPGDPDMMRYVDR
YGQLQTKML
(SEQ ID NO: 27)

Fig. 3-4

>BAE00165  gi|67968225|dbj|BAE00165.1|  VP1 [JC polyomavirus]
MAPTKRKGERKDPVQVPKLLIRGGVEVLEVKTGVDSITEVECFLTPEMGDPDEHLRGFSKSISISDTFE
SDSPNKDMLPCYSVARIPLPNLNEDLTCGNILMWEAVTLKTEVLGVTTLMNVHCNGQATHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGSQQWRGLS
RYFKVQLRKRRVKNPYPISFLLTDLINRRTPRVDGQPMYGMDAQVEEVRVFEGTEELPGDPDMMRYVDR
YGQLQTKML
(SEQ ID NO: 28)

>BAE00171  gi|67968232|dbj|BAE00171.1|  VP1 [JC polyomavirus]
MAPTKRKGERKDPVQVPKLLIRGGVEVLEVKTGVDSITEVECFLTPEMGDPDEHLRGFSKSISISDTFE
SDSPNKDMLPCYSVARIPLPNLNEDLTCGNILMWEAVTLKTEVLGVTTLMNVHCNGQATHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGSQQWRGLS
RYFKVQLRKRRVKNPYPISFLLTDLINRRTPRVDGQPMYGMDAQVEEVRVFEGTEELPGDPDMMRYVDR
YGQLQTKML
(SEQ ID NO: 29)

>BAE02837  gi|68445619|dbj|BAE02837.1|  VP1 protein [JC polyomavirus]
FLTPEMGDPDEHLRGFSKSISISDTFESDSPNKDMLPCYSVARIPLPNLNEDLTCGNILMWEAVTLKTE
VIGVTTLMNVHSNGQATHDNGAGKPVQGTSFHFFSVGGEALELQGVVFNYRTKYPDGTIFPKNATVQSQ
VMNTEHKAYLDKNKAYPVECWVPDPTRNENTRYFGTLTGGENVPPVLHITNTATTVLLDEFGVGPLCKG
DNLYLSAVDVCGMFTNRSGSQQWRGLSRYFKVQLRKRR
(SEQ ID NO: 30)

>BAE02838  gi|68445621|dbj|BAE02838.1|  VP1 protein [JC polyomavirus]
FLTPEMGDPDEHLRGFSKSISISHTFESDSPNKDMLPCYSVARIPLPNLNEDLTCGNILMWEAVTLKTE
VIGVTTLMNVHSNGQATHDNGAGKPVQGTSFHFFSVGGEALELQGVVFNYRTKYPDGTIFPKNATVQSQ
VMNTEHKAYLDKNKAYPVECWVPDPTRNENTRYFGTLTGGENVPPVLHITNTATTVLLDEFGVGPLCKG
DNLYLSAVDVCGMFTNRSGSQQWRGLSRYFKVQLRKRR
(SEQ ID NO: 31)

>BAE02839  gi|68445623|dbj|BAE02839.1|  VP1 protein [JC polyomavirus]
FLTPEMGDPDEHLRGFSKSISISNTFESDSPNKDMLPCYSVARIPLPNLNEDLTCGNILMWEAVTLKTE
VIGVTTLMNVHSNGQATHDNGAGKPVQGTSFHFFSVGGEALELQGVVFNYRTKYPDGTIFPKNATVQSQ
VMNTEHKAYLDKNKAYPVECWVPDPTRNENTRYFGTLTGGENVPPVLHITNTATTVLLDEFGVGPLCKG
DNLYLSAVDVCGMFTNRSGSQQWRGLSRYFKVQLRKRR
(SEQ ID NO: 32)

>BAE02840  gi|68445625|dbj|BAE02840.1|  VP1 protein [JC polyomavirus]
FLTPEMGDPDEHLRGFSESISISHTFESDSPNKDMLPCYSVARIPLPNLNEDLTCGNILMWEAVTLKTE
VIGVTTLMNVHSNGQATHDNGAGKPVQGTSFHFFSVGGEALELQGVVFNYRTKYPDGTIFPKNATVQSQ
VMNTEHKAYLDKNKAYPVECWVPDPTRNENTRYFGTLTGGENVPPVLHITNTATTVLLDEFGVGPLCKG
DNLYLSAVDVCGMFTNRSGSQQWRGLSRYFKVQLRKRR
(SEQ ID NO: 33)

>BAE02841  gi|68445627|dbj|BAE02841.1|  VP1 protein [JC polyomavirus]
FLTPEMGDPDEHLRGFSKSISISDTFESDSPNKDMLPCYSVARIPLPNLNEDLTCGNILMWEAVTLKTE
VLGVTTLMNVHSNGQATHDNGAGKPVQGTSFHFFSVGGEALELQGVVFNYRTKYPDGTIFPKNATVQSQ
VMNTEHKAYLDKNKAYPVECWVPDPTRNENTRYFGTLTGGENVPPVLHITNTATTVLLDEFGVGPLCKG
DNLYLSAVDVCGMFTNRFGSQQWRGLSRYFKVQLRKRR
(SEQ ID NO: 34)

Fig. 3-5

>BAE02842  gi|68445629|dbj|BAE02842.1|  VP1 protein [JC polyomavirus]
FLTPEMGDPDEHLRGFSMSISISDTFESDSPNKDMLPCYSVARIPLPNLNEDLTCGNILMWEAVTLKTE
VIGVTTLMNVHSNGQATHDNGAGKPVQGTSFHFFSVGGEALELQGVVFNYRTKYPDGTIFPKNATVQSQ
VMNTEHKAYLDKNKAYPVECWVPDPTRNENTRYFGTLTGGENVPPVLHITNTATTVLLDEFGVGPLCKG
DNLYLSAVDVCGMFTNRSGSQHWRGLSRYFKVQLRKRR
(SEQ ID NO: 35)

>BAE02843  gi|68445631|dbj|BAE02843.1|  VP1 protein [JC polyomavirus]
FLTPEMGDPDEHLRGFSKSISISHTFESDSPNKDMLPCYSVARIPLPNLNEDLTCGNILMWEAVTLKTE
VIGVTTLMNVHSNGQATHDNGAGKPVQGTSFHFFSVGGEALELQGVVFNYRTKYPDGTIFPKNATVQSQ
VMNTEHKAYLDKNKAYPVECWVPDPTRNENTRYFGTLTGGENVPPVLHITNTATTVLLDEFGVGPLCKG
DNLYLSAVDVCGMFTNRSGSQQWRGLSRYFKVQLRKRR
(SEQ ID NO: 36)

>BAE02844  gi|68445633|dbj|BAE02844.1|  VP1 protein [JC polyomavirus]
FLTPEMGDPDEHLRGFSKSISISDTFESDSPNKDMLPCYSVARIPLPNLNEDLTCGNILMWEAVTLKTE
VLGVTTLMNVHSNGQATHDNGAGKPVQGTSFHFFSVGGEALELQGVVFNYRTKYPDGTIFPKNATVQSQ
VMNTEHKAYLDKNKAYPVECWVPDPTRNENTRYFGTLTGGENVPPVLHITNTATTVLLDEFGVGPLCKG
DNLYLSAVDVCGMFTNRSGFQQWRGLSRYFKVQLRKRR
(SEQ ID NO: 37)

>BAE02845  gi|68445635|dbj|BAE02845.1|  VP1 protein [JC polyomavirus]
FLTPEMGDPDEHLRGFSKSISISDTFESDSPNKDMLPCYSVARIPLPNLNEDLTCGNILMWEAVTLKTE
VLGVTTLMNVHSNGQATHDNGAGKPVQGTSFHFFSVGGEALELQGVVFNYRTKYPDGTIFPKNATVQSQ
VMNTEHKAYLDKNKAYPVECWVPDPTRNENTRYFGTLTGGENVPPVLHITNTATTVLLDEFGVGPLCKG
DNLYLSAVDVCGMFTNRFGSQQWRGLSRYFKVQLRKRR
(SEQ ID NO: 38)

>BAE02846  gi|68445637|dbj|BAE02846.1|  VP1 protein [JC polyomavirus]
FLTPEMGDPDEHLRGFSKSISISDTFESDSPNKDMLPCYSVARIPLPNLNEDLTCGNILMWEAVTLKTE
VIGVTTLMNVHSNGQATHDNGAGKPVQGTSFHFFSVGGEALELQGVVFNYRTKYPDGTIFPKNATVQSQ
VMNTEHKAYLDKNKAYPVECWVPDPTRNENTRYFGTLTGGENAPPVLHITNTATTVLLDEFGVGPLCKG
DNLYLSAVDVCGMFTNRSGSQQWRGLSRYFKVQLRKRR
(SEQ ID NO: 39)

>BAE02847  gi|68445639|dbj|BAE02847.1|  VP1 protein [JC polyomavirus]
FLTPEMGDPDEHLRGFSKSISISDTFDSDSPNKDMLPCYSVARIPLPNLNEDLTCGNILMWEAVTLKTE
VIGVTTLMNVHSNGQATHDNGAGKPVQGTSFHFFSVGGEALELQGVVFNYRTKYPDGTIFPKNATVQSQ
VMNTEHKAYLDKNKAYPVECWVPDPTRNENTRYFGTLTGGENVPPVLHITNTATTVLLDEFGVGPLCKG
DNLYLSAVDVCGMFTNRSGFQQWRGLSRYFKVQLRKRR
(SEQ ID NO: 40)

VP1 from Non-brain Samples of PML subjects:
>AAB62680  gi|2246607|gb|AAB62680.1|  VP1 [JC virus]
MAPTKRKGERKDPVQVPKLLIRGGVEVLEVKTGVDSITEVECFLTPEMGDPDEHLRGFSKSISISDTFE
SDSPNKDMLPCYSVARIPLPNLNEDLTCGNILMWEAVTLKTEVIGVTTLMNVHSNGQAAHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGSQQWRGLS
RYFKVQLRKRRVKNPYPISFLLTDLINRRTPRVDGQPMYGMDAQVEEVRVFEGTEELPGDPDMMRYVDR
YGQLQTKML
(SEQ ID NO: 41)

Fig. 3-6

>AAT09819 gi|47078338|gb|AAT09819.1| VP1 [JC virus]
MAPTKRKGERKDPVQVPKLLIRGGVEVLEVKTGVDSITEVECFLTPEMGDPDEHLRGFSKSISISDTFE
SDSPNKDMLPCYSVARIPLPNLNEDLTCGNILMWEAVTLKTEVLGVTTLMNVHSNGQATHDNGAGKPVQ
GTSFHFFSVGGEALELQGVVFNYRTKYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTTRSGSQQWRGLS
RYFKVQLRKRRVKNPYPISFLLTDLINRRTPRVDGQPMYGMDAQIEEVRVFEGTEELPGDPDMMRYVDR
YGQLQTKML
(SEQ ID NO: 42)

>AAT09825 gi|47078345|gb|AAT09825.1| VP1 [JC virus]
MAPTKRKGERKDPVQVPKLLIRGGVEVLEVKTGVDSITEVECFLTPEMGDPDEHLRGFSKSISISDTFE
SDSPNKDMLPCYSVARIPLPNLNEDLTCGNILMWEAVTLKTEVIGVTTLMNVHSNGQATHDNGAAKPVQ
GTSFHFFSVGGEALELQGVVFNYRTTYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRFGSQQWRGLS
RYFKVQLRKRRVKNPYPISFLLTDLINRRTPRVDGQPMYGMDAQIEEVRVFEGTEQLPGDPDMMRYVDR
YGQLQTKML
(SEQ ID NO: 43)

>AAT09831 gi|47078352|gb|AAT09831.1| VP1 [JC virus]
MAPTKRKGERKDPVQVPKLLIRGGVEVLEVKTGVDSITEVECFLTPEMGDPDEHFRGFSKSISISDTFE
SDSPNKDMLPCYSVARIPLPNLNEDLTCGNILMWEAVTLKTEVIGVTTLMNVHSNGQATHDNGAAKPVQ
GTSFHFFSVGGEALELQGVVFNYRTTYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGSQQWRGLS
RYFKVQLRKRRVKNPYPISFLLTDLINRRTPRVDGQPMYGMDAQIEEVRVFEGTEQLPGDPDMMRYVDR
YGQLQTKML
(SEQ ID NO: 44)

>AAT09837 gi|47078359|gb|AAT09837.1| VP1 [JC virus]
MAPTKRKGERKDPVQVPKLLIRGGVEVLEVKTGVDSITEVECFLTPEMGDPDEHLRGFSNSISISDTFE
SDSPNKDMLPCYSVARIPLPNLNEDLTCGNILMWEAVTLKTEVIGVTTLMNVHSNGQATHDNGAAKPVQ
GTSFHFFSVGGEALELQGVVFNYRTTYPDGTIFPKNATVQSQVMNTEHKAYLDKNKAYPVECWVPDPTR
NENTRYFGTLTGGENVPPVLHITNTATTVLLDEFGVGPLCKGDNLYLSAVDVCGMFTNRSGSQQWRGLS
RYFKVQLRKRRVKNPYPISFLLTDLINRRTPRVDGQPMYGMDAQIEEVRVFEGTEQLPGDPDMMRYVDR
YGQLQTKML
(SEQ ID NO: 45)

>BAE02848 gi|68445641|dbj|BAE02848.1| VP1 protein [JC polyomavirus]
FLTPEMGDPDEHLRGFSKSISISDTFESDSPNKDMLPCYSVARIPLPNLNEDLTCGNILMWEAVTLKTE
VLGVTTLMNVHSNGQATHDNGAGKPVQGTSFHFFSVGGEALELQGVVFNYRTKYPDGTIFPKNATVQSQ
VMNTEHKAYLDKNKAYPVECWVPDPTRNENTRYFGTLTGGENVPPVLHITNTATTVLLDEFGVGPLCKG
DNLYLSAVDVCGMFTDRSGSQQWRGLSRYFKVQLRKRR
(SEQ ID NO: 46)

>BAE02849 gi|68445643|dbj|BAE02849.1| VP1 protein [JC polyomavirus]
FLTPEMGDPDEHFRGFSKSISISDTFESDSPNKDMLPCYSVARIPLPNLNEDLTCGNILMWEAVTLKTE
VIGVTTLMNVHSNGQATHDNGAGKPVQGTSFHFFSVGGEALELQGVVFNYRTKYPDGTIFPKNATVQSQ
VMNTEHKAYLDKNKAYPVECWVPDPTRNENTRYFGTLTGGENVPPVLHITNTATTVLLDEFGVGPLCKG
DNLYLSAVDVCGMFTNRSGSQQWRGLSRYFKVQLRKRR
(SEQ ID NO: 47)

Fig. 3-7

>BAE02850 gi|68445645|dbj|BAE02850.1| VP1 protein [JC polyomavirus]
FLTPEMGDPDEHLRGFSKSISISDTFESDSPNKDMLPCYSVARIPLPNLNEDLTCGNILMWEAVTLKTE
VLGVTTLMNVHSNGQATHDNGAGKPVQGTSFHFFSVGGEALELQGVVFNYRTKYPDGTIFPKNATVQSQ
VMNTEHKAYLDKNKAYPVECWVPDPTRNENTRYFGTLTGGENVPPVLHITNTATTVLLDEFGVGPLCKG
DNLYLSAVDVCGMFTDRSGSQQWRGLSRYFKVQLRKRR
(SEQ ID NO: 48)

>BAE02851 gi|68445647|dbj|BAE02851.1| VP1 protein [JC polyomavirus]
FLTPEMGDPDEHLRGFSKSISISDTFESDSPNKDMLPCYSVARIPLPNLNEDLTCGNILMWEAVTLKTE
VLGVTTLMNVHCNGQATHDNGAGKPVQGTSFHFFSVGGEALELQGVVFNYRTKYPDGTIFPKNATVQSQ
VMNTEHKAYLDKNKAYPVECWVPDPTRNENTRYFGTLTGGENVPPVLHITNTATTVLLDEFGVGPLCKG
DNLYLSAVDVCGMFTNRSGSQQWRGLSRYFKVQLRKRR
(SEQ ID NO: 49)

>BAE02852 gi|68445649|dbj|BAE02852.1| VP1 protein [JC polyomavirus]
FLTPEMGDPDEHLRGFSKSISISDTFESDSPNKDMLPCYSVARIPLPNLNEDLTCGNILMWEAVTLKTE
VIGVTTLMNVHSNGQATHDNGAGKPVQGTSFHFFSVGGEALELQGVVFNYRTKYPDGTIFPKNATVQSQ
VMNTEHKAYLDKNKAYPVECWVPDPTRNENTRYFGTLTGGENVPPVLHITNTATTVLLDEFGVGPLCKG
DNLYLSAVDVCGMFTNRSGFQQWRGLSRYFKVQLRKRR
(SEQ ID NO: 50)

>BAE02853 gi|68445651|dbj|BAE02853.1| VP1 protein [JC polyomavirus]
FLTPEMGDPDEHLRGFSKSISISDTFESDSPNKDMLPCYSVARIPLPNLNEDLTCGNILMWEAVTLKTE
VLGVTTLMNVHCNGQATHDNGAGKPVQGTSFHFFSVGGEALELQGVVFNYRTKYPDGTIFPKNATVQSQ
VMNTEHKAYLDKNKAYPVECWVPDPTRNENTRYFGTLTGGENVPPVLHITNTATTVLLDEFGVGPLCKG
DNLYLSAVDVCGMFTNRSGSQQWRGLSRYFKVQLRKRR
(SEQ ID NO: 51)

>BAE02854 gi|68445653|dbj|BAE02854.1| VP1 protein [JC polyomavirus]
FLTPEMGDPDEHFRGFSKSISISDTFESDSPNKDMLPCYSVARIPLPNLNEDLTCGNILMWEAVTLKTE
VIGVTTLMNVHSNGQATHDNGAGKPVQGTSFHFFSVGGEALELQGVVFNYRTKYPDGTIFPKNATVQSQ
VMNTEHKAYLDKNKAYPVECWVPDPTRNENTRYFGTLTGGENVPPVLHITNTATTVLLDEFGVGPLCKG
DNLYLSAVDVCGMFTNRSGSQQWRGLSRYFKVQLRKRR
(SEQ ID NO: 52)

>BAE02855 gi|68445655|dbj|BAE02855.1| VP1 protein [JC polyomavirus]
FLTPEMGDPDEHLRGFSKSISISDTFESDSPNKDMLPCYSVARIPLPNLNEDLTCGNILMWEAVTLKTE
VIGVTTLMNVHSNGQATHDNGAGKPVQGTSFHFFSVGGEALELQGVVFNYRTKYPDGTIFPKNATVQSQ
VMNTEHKAYLDKNKAYPVECWVPDPTRNENTRYFGTLTGGENVPPVLHITNTATTVLLDEFGVGPLCKG
DNLYLSAVDVCGMFTNRSGSQQWRGLSRYFKVQLRKRR
(SEQ ID NO: 53)

>BAE02856 gi|68445657|dbj|BAE02856.1| VP1 protein [JC polyomavirus]
FLTPEMGDPDEHLRGFSKSISISDTFESDSPNKDMLPCYSVARIPLPNLNEDLTCGNILMWEAVTLKTE
VIGVTTLMNVHSNGQATHDNGAGKPVQGTSFHFFSVGGEALELQGVVFNYRTKYPDGTIFPKNATVQSQ
VMNTEHKAYLDKNKAYPVECWVPDPTRNENTRYFGTLTGGENVPPVLHITNTATTVLLDEFGVGPLCKG
DNLYLSAVDVCGMFTDRSGSQQWRGLSRYFKVQLRKRR
(SEQ ID NO: 54)

SEQUENCE LISTING

```
<160> NUMBER OF SEQ ID NOS: 62

<210> SEQ ID NO 1
<211> LENGTH: 354
<212> TYPE: PRT
<213> ORGANISM: JC virus

<400> SEQUENCE: 1

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Thr
        115                 120                 125

His Asp Asn Gly Ala Ala Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Thr Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190
```

```
Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
                260                 265                 270

Arg Gly Leu Ser Arg Tyr Phe Lys Val Gln Leu Arg Lys Arg Arg Val
            275                 280                 285

Lys Asn Pro Tyr Pro Ile Ser Phe Leu Leu Thr Asp Leu Ile Asn Arg
        290                 295                 300

Arg Thr Pro Arg Val Asp Gly Gln Pro Met Tyr Gly Met Asp Ala Gln
305                 310                 315                 320

Ile Glu Glu Val Arg Val Phe Glu Gly Thr Glu Gln Leu Pro Gly Asp
                325                 330                 335

Pro Asp Met Met Arg Tyr Val Asp Arg Tyr Gly Gln Leu Gln Thr Lys
            340                 345                 350

Met Leu

<210> SEQ ID NO 2
<211> LENGTH: 349
<212> TYPE: PRT
<213> ORGANISM: Simian Virus 40

<400> SEQUENCE: 2

Pro Lys Lys Pro Lys Glu Pro Val Gln Val Pro Lys Leu Val Ile Lys
1               5                   10                  15

Gly Gly Ile Glu Val Leu Gly Val Lys Thr Gly Val Asp Ser Phe Thr
            20                  25                  30

Glu Val Glu Cys Phe Leu Asn Pro Gln Met Gly Asn Pro Asp Glu His
        35                  40                  45

Gln Lys Gly Leu Ser Lys Ser Leu Ala Ala Glu Lys Gln Phe Thr Asp
    50                  55                  60

Asp Ser Pro Asp Lys Glu Gln Leu Pro Cys Tyr Ser Val Ala Arg Ile
65                  70                  75                  80

Pro Leu Pro Asn Ile Asn Glu Asp Leu Thr Cys Gly Asn Ile Leu Met
                85                  90                  95

Trp Glu Ala Val Thr Val Lys Thr Glu Val Ile Gly Val Thr Ala Met
            100                 105                 110

Leu Asn Leu His Ser Gly Thr Gln Lys Thr His Glu Asn Gly Ala Gly
        115                 120                 125

Lys Pro Ile Gln Gly Ser Asn Phe His Phe Phe Ala Val Gly Gly Glu
    130                 135                 140

Pro Leu Glu Leu Gln Gly Val Leu Ala Asn Tyr Arg Thr Lys Tyr Pro
145                 150                 155                 160

Ala Gln Thr Val Thr Pro Lys Asn Ala Thr Val Asp Ser Gln Gln Met
                165                 170                 175

Asn Thr Asp His Lys Ala Val Leu Asp Lys Asp Asn Ala Tyr Pro Val
            180                 185                 190

Glu Cys Trp Val Pro Asp Pro Ser Lys Asn Glu Asn Thr Arg Tyr Phe
        195                 200                 205
```

```
Gly Thr Tyr Thr Gly Gly Glu Asn Val Pro Pro Val Leu His Ile Thr
        210                 215                 220

Asn Thr Ala Thr Thr Val Leu Leu Asp Glu Gln Gly Val Gly Pro Leu
225                 230                 235                 240

Cys Lys Ala Asp Ser Leu Tyr Val Ser Ala Asp Val Asp Ile Cys Gly
                245                 250                 255

Leu Phe Thr Asn Thr Ser Gly Thr Gln Gln Trp Lys Gly Leu Pro Arg
                260                 265                 270

Tyr Phe Lys Ile Thr Leu Arg Lys Arg Ser Val Lys Asn Pro Tyr Pro
            275                 280                 285

Ile Ser Phe Leu Leu Ser Asp Leu Ile Asn Arg Arg Thr Gln Arg Val
        290                 295                 300

Asp Gly Gln Pro Met Ile Gly Met Ser Ser Gln Val Glu Glu Val Arg
305                 310                 315                 320

Val Tyr Glu Asp Thr Glu Glu Leu Pro Gly Asp Pro Asp Met Ile Arg
                325                 330                 335

Tyr Ile Asp Glu Phe Gly Gln Thr Thr Thr Arg Met Gln
                340                 345

<210> SEQ ID NO 3
<211> LENGTH: 133
<212> TYPE: PRT
<213> ORGANISM: JC virus

<400> SEQUENCE: 3

Asn Val Pro Pro Val Leu His Ile Thr Asn Thr Ala Thr Thr Val Leu
1               5                   10                  15

Leu Asp Glu Phe Gly Val Gly Pro Leu Cys Lys Gly Asp Asn Leu Tyr
                20                  25                  30

Leu Ser Ala Val Asp Val Cys Gly Met Phe Thr Asn Arg Ser Gly Ser
            35                  40                  45

Gln Gln Trp Arg Gly Leu Ser Arg Tyr Phe Lys Val Gln Leu Arg Lys
        50                  55                  60

Arg Arg Val Lys Asn Pro Tyr Pro Ile Ser Phe Leu Leu Thr Asp Leu
65                  70                  75                  80

Ile Asn Arg Arg Thr Pro Arg Val Asp Gly Gln Pro Met Tyr Gly Met
                85                  90                  95

Asp Ala Gln Val Glu Glu Val Arg Val Phe Glu Gly Thr Glu Glu Leu
                100                 105                 110

Pro Gly Asp Pro Asp Met Met Arg Tyr Val Asp Arg Tyr Gly Gln Leu
            115                 120                 125

Gln Thr Lys Met Leu
    130

<210> SEQ ID NO 4
<211> LENGTH: 133
<212> TYPE: PRT
<213> ORGANISM: JC virus

<400> SEQUENCE: 4

Asn Val Pro Pro Val Leu His Ile Thr Asn Thr Ala Thr Thr Val Leu
1               5                   10                  15

Leu Asp Glu Phe Gly Val Gly Pro Leu Cys Lys Gly Asp Asn Leu Tyr
                20                  25                  30

Leu Ser Ala Val Asp Val Cys Gly Met Phe Thr Asn Arg Ser Gly Ser
            35                  40                  45
```

```
Gln Gln Trp Arg Gly Leu Ser Arg Tyr Phe Lys Val Gln Leu Arg Lys
         50                  55                  60

Arg Arg Val Lys Asn Pro Tyr Pro Ile Ser Phe Leu Leu Thr Asp Leu
 65              70                  75                      80

Ile Asn Arg Arg Thr Pro Arg Val Asp Gly Gln Pro Met Tyr Gly Met
                 85                  90                  95

Asp Ala Gln Val Glu Glu Val Arg Val Phe Glu Gly Thr Glu Glu Leu
                100                 105                 110

Pro Gly Asp Pro Asp Met Met Arg Tyr Val Asp Arg Tyr Gly Gln Leu
            115                 120                 125

Gln Thr Lys Met Leu
        130

<210> SEQ ID NO 5
<211> LENGTH: 354
<212> TYPE: PRT
<213> ORGANISM: JC virus

<400> SEQUENCE: 5

Met Ala Pro Thr Lys Arg Lys Gly Glu Arg Lys Asp Pro Val Gln Val
 1               5                  10                  15

Pro Lys Leu Leu Ile Arg Gly Gly Val Glu Val Leu Glu Val Lys Thr
             20                  25                  30

Gly Val Asp Ser Ile Thr Glu Val Glu Cys Phe Leu Thr Pro Glu Met
             35                  40                  45

Gly Asp Pro Asp Glu His Phe Arg Gly Phe Ser Lys Ser Ile Ser Ile
 50                  55                  60

Ser Asp Thr Phe Glu Ser Asp Ser Pro Asn Lys Asp Met Leu Pro Cys
 65                  70                  75                  80

Tyr Ser Val Ala Arg Ile Pro Leu Pro Asn Leu Asn Glu Asp Leu Thr
                 85                  90                  95

Cys Gly Asn Ile Leu Met Trp Glu Ala Val Thr Leu Lys Thr Glu Val
                100                 105                 110

Ile Gly Val Thr Thr Leu Met Asn Val His Ser Asn Gly Gln Ala Ala
             115                 120                 125

His Asp Asn Gly Ala Gly Lys Pro Val Gln Gly Thr Ser Phe His Phe
130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
```

```
            275                 280                 285
Lys Asn Pro Tyr Pro Ile Ser Phe Leu Leu Thr Asp Leu Ile Asn Arg
        290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Leu Pro Gly Asp
                    325                 330                 335

Pro Asp Met Met Arg Tyr Val Asp Arg Tyr Gly Gln Leu Gln Thr Lys
            340                 345                 350

Met Leu

<210> SEQ ID NO 6
<211> LENGTH: 354
<212> TYPE: PRT
<213> ORGANISM: JC virus

<400> SEQUENCE: 6

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Phe Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Thr
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Thr Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
```

```
            290                 295                 300
Arg Thr Pro Arg Val Asp Gly Gln Pro Met Tyr Gly Met Asp Ala Gln
305                 310                 315                 320

Val Glu Glu Val Arg Val Phe Glu Gly Thr Glu Leu Pro Gly Asp
                325                 330                 335

Pro Asp Met Met Arg Tyr Val Asp Arg Tyr Gly Gln Leu Gln Thr Lys
            340                 345                 350

Met Leu

<210> SEQ ID NO 7
<211> LENGTH: 354
<212> TYPE: PRT
<213> ORGANISM: JC virus

<400> SEQUENCE: 7

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
                20                  25                  30

Gly Val Asp Ser Ile Thr Glu Val Glu Cys Phe Leu Thr Pro Glu Met
            35                  40                  45

Gly Asp Pro Asp Glu His Leu Arg Gly Phe Ser Lys Ser Ile Ser Ile
50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Ala
            115                 120                 125

His Asp Asn Gly Ala Gly Lys Pro Val Gln Gly Thr Ser Phe His Phe
130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Phe Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
290                 295                 300

Arg Thr Pro Arg Val Asp Gly Gln Pro Met Tyr Gly Met Asp Ala Gln
```

```
305                 310                 315                 320
Val Glu Glu Val Arg Val Phe Glu Gly Thr Glu Glu Leu Pro Gly Asp
                325                 330                 335

Pro Asp Met Met Arg Tyr Val Asp Arg Tyr Gly Gln Leu Gln Thr Lys
                340                 345                 350

Met Leu

<210> SEQ ID NO 8
<211> LENGTH: 354
<212> TYPE: PRT
<213> ORGANISM: JC virus

<400> SEQUENCE: 8

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
                20                  25                  30

Gly Val Asp Ser Ile Thr Glu Val Glu Cys Phe Leu Thr Pro Glu Met
            35                  40                  45

Gly Asp Pro Asp Glu His Leu Arg Gly Phe Ser Lys Ser Ile Ser Ile
        50                  55                  60

Ser His Thr Phe Glu Ser Asp Ser Pro Asn Arg Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
                100                 105                 110

Ile Gly Val Thr Ser Leu Met Asn Val His Ser Asn Gly Gln Ala Thr
            115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Leu Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
                180                 185                 190

Asn Lys Ala Tyr Pro Val Glu Cys Trp Val Pro Asp Pro Thr Arg Asn
            195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
                260                 265                 270

Arg Gly Leu Ser Arg Tyr Phe Lys Val Gln Leu Arg Lys Arg Arg Val
            275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
```

```
                    325                 330                 335
Pro Asp Met Met Arg Tyr Val Asp Lys Tyr Gly Gln Leu Gln Thr Lys
                340                 345                 350
Met Leu

<210> SEQ ID NO 9
<211> LENGTH: 354
<212> TYPE: PRT
<213> ORGANISM: JC virus

<400> SEQUENCE: 9

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Ser Leu Met Asn Val His Ser Asn Gly Gln Ala Thr
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Leu Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Leu Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Lys Tyr Gly Gln Leu Gln Thr Lys
```

Met Leu

<210> SEQ ID NO 10
<211> LENGTH: 354
<212> TYPE: PRT
<213> ORGANISM: JC virus

<400> SEQUENCE: 10

```
Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Ser Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Ser Leu Met Asn Val His Ser Asn Gly Gln Ala Ala
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Leu Pro Gly Asp
                325                 330                 335

Pro Asp Met Met Arg Tyr Val Asp Lys Tyr Gly Gln Leu Gln Thr Lys
            340                 345                 350

Met Leu
```

```
<210> SEQ ID NO 11
<211> LENGTH: 354
<212> TYPE: PRT
<213> ORGANISM: JC virus

<400> SEQUENCE: 11
```

| | | | | | | | | | | | | | | |
|---|---|---|---|---|---|---|---|---|---|---|---|---|---|---|
|Met|Ala|Pro|Thr|Lys|Arg|Lys|Gly|Glu|Arg|Lys|Asp|Pro|Val|Gln|Val|
|1| | | |5| | | | |10| | | | |15|

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
            35                  40                  45

Gly Asp Pro Asp Glu His Leu Arg Gly Phe Ser Lys Ser Ile Ser Ile
50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Leu Gly Val Thr Thr Leu Met Asn Val His Ser Asn Gly Gln Ala Thr
            115                 120                 125

His Asp Asn Gly Ala Gly Lys Pro Val Gln Gly Thr Ser Phe His Phe
130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
            195                 200                 205

Glu Asn Thr Arg Tyr Phe Gly Thr Leu Thr Gly Gly Glu Asn Val Pro
210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Phe Gln Gln Trp
            260                 265                 270

Arg Gly Leu Ser Arg Tyr Phe Lys Val Gln Leu Arg Lys Arg Arg Val
            275                 280                 285

Lys Asn Pro Tyr Pro Ile Ser Phe Leu Leu Thr Asp Leu Ile Asn Arg
290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Arg Tyr Gly Gln Leu Gln Thr Lys
            340                 345                 350

Met Leu

```
<210> SEQ ID NO 12
```

<211> LENGTH: 354
<212> TYPE: PRT
<213> ORGANISM: JC virus

<400> SEQUENCE: 12

```
Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Leu Gly Val Thr Thr Leu Met Asn Val His Ser Asn Gly Gln Ala Thr
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Arg Tyr Gly Gln Leu Gln Thr Lys
            340                 345                 350

Met Leu
```

<210> SEQ ID NO 13
<211> LENGTH: 354
<212> TYPE: PRT
<213> ORGANISM: JC virus

<400> SEQUENCE: 13

```
Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Leu Gly Val Thr Thr Leu Met Asn Val His Ser Asn Gly Gln Ala Thr
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Arg Tyr Gly Gln Leu Gln Thr Lys
            340                 345                 350

Met Leu
```

<210> SEQ ID NO 14
<211> LENGTH: 354
<212> TYPE: PRT
<213> ORGANISM: JC virus

<400> SEQUENCE: 14

```
Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
                35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
                100                 105                 110

Leu Gly Val Thr Thr Leu Met Asn Val His Ser Asn Gly Gln Ala Thr
            115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
    195                 200                 205

Glu Asn Thr Arg Tyr Phe Gly Thr Leu Thr Gly Gly Glu Asn Val Pro
210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Phe Gln Gln Trp
            260                 265                 270

Arg Gly Leu Ser Arg Tyr Phe Lys Val Gln Leu Arg Lys Arg Arg Val
    275                 280                 285

Lys Asn Pro Tyr Pro Ile Ser Phe Leu Leu Thr Asp Leu Ile Asn Arg
290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Arg Tyr Gly Gln Leu Gln Thr Lys
            340                 345                 350

Met Leu

<210> SEQ ID NO 15
<211> LENGTH: 354
<212> TYPE: PRT
<213> ORGANISM: JC virus

<400> SEQUENCE: 15

Met Ala Pro Thr Lys Arg Lys Gly Glu Arg Lys Asp Pro Val Gln Val
1               5                   10                  15
```

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
            35                  40                  45

Gly Asp Pro Asp Glu His Leu Arg Gly Phe Ser Lys Ser Ile Ser Ile
50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Thr
            115                 120                 125

His Asp Asn Gly Ala Gly Lys Pro Val Gln Gly Thr Ser Phe His Phe
130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
            195                 200                 205

Glu Asn Thr Arg Tyr Phe Gly Thr Leu Thr Gly Gly Glu Asn Val Pro
210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Tyr Gln Gln Trp
            260                 265                 270

Arg Gly Leu Ser Arg Tyr Phe Lys Val Gln Leu Arg Lys Arg Arg Val
            275                 280                 285

Lys Asn Pro Tyr Pro Ile Ser Phe Leu Leu Thr Asp Leu Ile Asn Arg
290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Arg Tyr Gly Gln Leu Gln Thr Lys
            340                 345                 350

Met Leu

<210> SEQ ID NO 16
<211> LENGTH: 354
<212> TYPE: PRT
<213> ORGANISM: JC virus

<400> SEQUENCE: 16

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

```
Gly Val Asp Ser Ile Thr Glu Val Glu Cys Phe Leu Thr Pro Glu Met
             35                  40                  45

Gly Asp Pro Asp Glu His Leu Arg Gly Phe Ser Lys Ser Ile Ser Ile
 50                  55                  60

Ser Asp Thr Phe Glu Ser Asp Ser Pro Asn Lys Asp Met Leu Pro Cys
 65                  70                  75                  80

Tyr Ser Val Ala Arg Ile Pro Leu Pro Asn Leu Asn Glu Asp Leu Thr
                 85                  90                  95

Cys Gly Asn Ile Leu Met Trp Glu Ala Val Thr Leu Lys Thr Glu Val
                100                 105                 110

Leu Gly Val Thr Thr Leu Met Asn Val His Ser Asn Gly Gln Ala Thr
             115                 120                 125

His Asp Asn Gly Ala Gly Lys Pro Val Gln Gly Thr Ser Phe His Phe
130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Phe Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Leu Pro Gly Asp
                325                 330                 335

Pro Asp Met Met Arg Tyr Val Asp Arg Tyr Gly Gln Leu Gln Thr Lys
            340                 345                 350

Met Leu

<210> SEQ ID NO 17
<211> LENGTH: 354
<212> TYPE: PRT
<213> ORGANISM: JC virus

<400> SEQUENCE: 17

Met Ala Pro Thr Lys Arg Lys Gly Glu Arg Lys Asp Pro Val Gln Val
 1               5                  10                  15

Pro Lys Leu Leu Ile Arg Gly Gly Val Glu Val Leu Glu Val Lys Thr
             20                  25                  30

Gly Val Asp Ser Ile Thr Glu Val Glu Cys Phe Leu Thr Pro Glu Met
             35                  40                  45
```

```
Gly Asp Pro Asp Glu His Leu Arg Gly Phe Ser Lys Ser Ile Ser Ile
        50                  55                  60

Ser Asp Thr Phe Glu Ser Asp Ser Pro Asn Lys Asp Met Leu Pro Cys
 65                  70                  75                  80

Tyr Ser Val Ala Arg Ile Pro Leu Pro Asn Leu Asn Glu Asp Leu Thr
                 85                  90                  95

Cys Gly Asn Ile Leu Met Trp Glu Ala Val Thr Leu Lys Thr Glu Val
                100                 105                 110

Ile Gly Val Thr Thr Leu Met Asn Val His Ser Asn Gly Gln Ala Thr
                115                 120                 125

His Asp Asn Gly Ala Gly Lys Pro Val Gln Gly Thr Ser Phe His Phe
        130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
                180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Tyr Gln Gln Trp
                260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
        290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Arg Tyr Gly Gln Leu Gln Thr Lys
                340                 345                 350

Met Leu

<210> SEQ ID NO 18
<211> LENGTH: 354
<212> TYPE: PRT
<213> ORGANISM: JC virus

<400> SEQUENCE: 18

Met Ala Pro Thr Lys Arg Lys Gly Glu Arg Lys Asp Pro Val Gln Val
 1               5                  10                  15

Pro Lys Leu Leu Ile Arg Gly Gly Val Glu Val Leu Glu Val Lys Thr
                 20                  25                  30

Gly Val Asp Ser Ile Thr Glu Val Glu Cys Phe Leu Thr Pro Glu Met
             35                  40                  45

Gly Asp Pro Asp Glu His Leu Arg Gly Phe Ser Lys Ser Ile Ser Ile
        50                  55                  60
```

```
Ser Asp Thr Phe Glu Ser Asp Ser Pro Ser Lys Asp Met Leu Pro Cys
 65                  70                  75                  80

Tyr Ser Val Ala Arg Ile Pro Leu Pro Asn Leu Asn Glu Asp Leu Thr
                 85                  90                  95

Cys Gly Asn Ile Leu Met Trp Glu Ala Val Thr Leu Lys Thr Glu Val
            100                 105                 110

Ile Gly Val Thr Ser Leu Met Asn Val His Ser Asn Gly Gln Ala Ala
            115                 120                 125

His Asp Asn Gly Ala Gly Lys Pro Val Gln Gly Thr Ser Phe His Phe
        130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
                180                 185                 190

Asn Lys Ala Tyr Pro Val Glu Cys Trp Val Pro Asp Pro Thr Arg Asn
            195                 200                 205

Glu Asn Thr Arg Tyr Phe Gly Thr Leu Thr Gly Gly Glu Asn Val Pro
        210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
                260                 265                 270

Arg Gly Leu Ser Arg Tyr Phe Lys Val Gln Leu Arg Lys Arg Arg Val
            275                 280                 285

Lys Asn Pro Tyr Pro Ile Ser Phe Leu Leu Thr Asp Leu Ile Asn Arg
        290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Lys Tyr Gly Gln Leu Gln Thr Lys
                340                 345                 350

Met Leu

<210> SEQ ID NO 19
<211> LENGTH: 354
<212> TYPE: PRT
<213> ORGANISM: JC virus

<400> SEQUENCE: 19

Met Ala Pro Thr Lys Arg Lys Gly Glu Arg Lys Asp Pro Val Gln Val
 1               5                  10                  15

Pro Lys Leu Leu Ile Arg Gly Gly Val Glu Val Leu Glu Val Lys Thr
                20                  25                  30

Gly Val Asp Ser Ile Thr Glu Val Glu Cys Phe Leu Thr Pro Glu Met
            35                  40                  45

Gly Asp Pro Asp Glu His Leu Arg Gly Phe Ser Lys Ser Ile Ser Ile
        50                  55                  60

Ser Asp Thr Phe Glu Ser Asp Ser Pro Ser Lys Asp Met Leu Pro Cys
 65                  70                  75                  80
```

```
Tyr Ser Val Ala Arg Ile Pro Leu Pro Asn Leu Asn Glu Asp Leu Thr
             85                  90                  95

Cys Gly Asn Ile Leu Met Trp Glu Ala Val Thr Leu Lys Thr Glu Val
            100                 105                 110

Ile Gly Val Thr Ser Leu Met Asn Val His Ser Asn Gly Gln Ala Ala
            115                 120                 125

His Asp Asn Gly Ala Gly Lys Pro Val Gln Gly Thr Ser Phe His Phe
            130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
            195                 200                 205

Glu Asn Thr Arg Tyr Phe Gly Thr Leu Thr Gly Gly Glu Asn Val Pro
            210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Phe Gln Gln Trp
            260                 265                 270

Arg Gly Leu Ser Arg Tyr Phe Lys Val Gln Leu Arg Lys Arg Arg Val
            275                 280                 285

Lys Asn Pro Tyr Pro Ile Ser Phe Leu Leu Thr Asp Leu Ile Asn Arg
            290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Lys Tyr Gly Gln Leu Gln Thr Lys
            340                 345                 350

Met Leu

<210> SEQ ID NO 20
<211> LENGTH: 354
<212> TYPE: PRT
<213> ORGANISM: JC virus

<400> SEQUENCE: 20

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
            35                  40                  45

Gly Asp Pro Asp Glu His Leu Arg Gly Phe Ser Lys Ser Ile Ser Ile
            50                  55                  60

Ser Asp Thr Phe Glu Ser Asp Ser Pro Ser Lys Asp Met Leu Pro Cys
65                  70                  75                  80

Tyr Ser Val Ala Arg Ile Pro Leu Pro Asn Leu Asn Glu Asp Leu Thr
                85                  90                  95
```

-continued

Cys Gly Asn Ile Leu Met Trp Glu Ala Val Thr Leu Lys Thr Glu Val
                100                 105                 110

Ile Gly Val Thr Ser Leu Met Asn Val His Ser Asn Gly Gln Ala Ala
            115                 120                 125

His Asp Asn Gly Ala Gly Lys Pro Val Gln Gly Thr Ser Phe His Phe
        130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Phe Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Leu Pro Gly Asp
                325                 330                 335

Pro Asp Met Met Arg Tyr Val Asp Lys Tyr Gly Gln Leu Gln Thr Lys
            340                 345                 350

Met Leu

<210> SEQ ID NO 21
<211> LENGTH: 344
<212> TYPE: PRT
<213> ORGANISM: JC virus

<400> SEQUENCE: 21

Met Gly Ala Ala Leu Ala Leu Leu Gly Asp Leu Val Ala Thr Val Ser
1               5                   10                  15

Glu Ala Ala Ala Ala Thr Gly Phe Ser Val Ala Glu Ile Ala Ala Gly
                20                  25                  30

Glu Ala Ala Ala Thr Ile Glu Val Glu Ile Ala Ser Leu Ala Thr Val
            35                  40                  45

Glu Gly Ile Thr Ser Thr Ser Glu Ala Ile Ala Ile Gly Leu Thr
        50                  55                  60

Pro Glu Thr Tyr Ala Val Ile Thr Gly Ala Pro Gly Ala Val Ala Gly
65                  70                  75                  80

Phe Ala Ala Leu Val Gln Thr Val Thr Gly Gly Ser Ala Ile Ala Gln
                85                  90                  95

Leu Gly Tyr Arg Phe Phe Ala Asp Trp Asp His Lys Val Ser Thr Val
            100                 105                 110

```
Gly Leu Phe Gln Gln Pro Ala Met Ala Leu Gln Leu Phe Asn Pro Glu
            115                 120                 125
Asp Tyr Tyr Asp Ile Leu Phe Pro Gly Val Asn Ala Phe Val Asn Asn
        130                 135                 140
Ile His Tyr Leu Asp Pro Arg His Trp Gly Pro Ser Leu Phe Ser Thr
145                 150                 155                 160
Ile Ser Gln Ala Phe Trp Asn Leu Val Arg Asp Asp Leu Pro Ser Leu
                165                 170                 175
Thr Ser Gln Glu Ile Gln Arg Arg Thr Gln Lys Leu Phe Val Glu Ser
            180                 185                 190
Leu Ala Arg Phe Leu Glu Glu Thr Thr Trp Ala Ile Val Asn Ser Pro
        195                 200                 205
Val Asn Leu Tyr Asn Tyr Ile Ser Asp Tyr Tyr Ser Arg Leu Ser Pro
210                 215                 220
Val Arg Pro Ser Met Val Arg Gln Val Ala Gln Arg Glu Gly Thr Tyr
225                 230                 235                 240
Ile Ser Phe Gly His Ser Tyr Thr Gln Ser Ile Asp Asp Ala Asp Ser
                245                 250                 255
Ile Gln Glu Val Thr Gln Arg Leu Asp Leu Lys Thr Pro Asn Val Gln
            260                 265                 270
Ser Gly Glu Phe Ile Glu Lys Ser Ile Ala Pro Gly Gly Ala Asn Gln
        275                 280                 285
Arg Ser Ala Pro Gln Trp Met Leu Pro Leu Leu Leu Gly Leu Tyr Gly
    290                 295                 300
Thr Val Thr Pro Ala Leu Glu Ala Tyr Glu Asp Gly Pro Asn Lys Lys
305                 310                 315                 320
Lys Arg Arg Lys Glu Gly Pro Arg Ala Ser Ser Lys Thr Ser Tyr Lys
                325                 330                 335
Arg Arg Ser Arg Ser Ser Arg Ser
            340

<210> SEQ ID NO 22
<211> LENGTH: 354
<212> TYPE: PRT
<213> ORGANISM: JC virus

<400> SEQUENCE: 22

Met Ala Pro Thr Lys Arg Lys Gly Glu Arg Lys Asp Pro Val Gln Val
1               5                   10                  15
Pro Lys Leu Leu Ile Arg Gly Gly Val Glu Val Leu Glu Val Lys Thr
            20                  25                  30
Gly Val Asp Ser Ile Thr Glu Val Glu Cys Phe Leu Thr Pro Glu Met
        35                  40                  45
Gly Asp Pro Asp Glu His Leu Arg Gly Phe Ser Lys Ser Ile Ser Ile
    50                  55                  60
Ser Asp Thr Phe Glu Ser Asp Ser Pro Asn Lys Asp Met Leu Pro Cys
65                  70                  75                  80
Tyr Ser Val Ala Arg Ile Pro Leu Pro Asn Leu Asn Glu Asp Leu Thr
                85                  90                  95
Cys Gly Asn Ile Leu Met Trp Glu Ala Val Thr Leu Lys Thr Glu Val
            100                 105                 110
Ile Gly Val Thr Thr Leu Met Asn Val His Ser Asn Gly Gln Ala Thr
        115                 120                 125
His Asp Asn Gly Ala Gly Lys Pro Val Gln Gly Thr Ser Phe His Phe
    130                 135                 140
```

-continued

```
Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Arg Tyr Gly Gln Leu Gln Thr Lys
            340                 345                 350

Met Leu

<210> SEQ ID NO 23
<211> LENGTH: 354
<212> TYPE: PRT
<213> ORGANISM: JC virus

<400> SEQUENCE: 23

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
                20                  25                  30

Gly Val Asp Ser Ile Thr Glu Val Glu Cys Phe Leu Thr Pro Glu Met
            35                  40                  45

Gly Asp Pro Asp Glu His Leu Arg Gly Phe Ser Lys Leu Ile Ser Ile
        50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Thr
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160
```

```
Tyr Arg Thr Lys Tyr Pro Asp Gly Thr Ile Phe Pro Lys Asn Ala Thr
            165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
            195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Arg Tyr Gly Gln Leu Gln Thr Lys
            340                 345                 350

Met Leu

<210> SEQ ID NO 24
<211> LENGTH: 354
<212> TYPE: PRT
<213> ORGANISM: JC virus

<400> SEQUENCE: 24

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
            35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Thr
            115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175
```

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
            195                 200                 205

Glu Asn Thr Arg Tyr Phe Gly Thr Leu Thr Gly Gly Glu Asn Val Pro
210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
            245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
            275                 280                 285

Lys Asn Pro Tyr Pro Ile Ser Phe Leu Leu Thr Asp Leu Ile Asn Arg
            290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
            325                 330                 335

Pro Asp Met Met Arg Tyr Val Asp Arg Tyr Gly Gln Leu Gln Thr Lys
            340                 345                 350

Met Leu

<210> SEQ ID NO 25
<211> LENGTH: 354
<212> TYPE: PRT
<213> ORGANISM: JC virus

<400> SEQUENCE: 25

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
            35                  40                  45

Gly Asp Pro Asp Glu His Leu Arg Gly Phe Ser Lys Ser Ile Ser Ile
50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
            85                  90                  95

Cys Gly Asn Ile Leu Met Trp Glu Ala Val Thr Leu Lys Thr Glu Val
            100                 105                 110

Leu Gly Val Thr Thr Leu Met Asn Val His Ser Asn Gly Gln Ala Thr
            115                 120                 125

His Asp Asn Gly Ala Gly Lys Pro Val Gln Gly Thr Ser Phe His Phe
130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
            165                 170                 175

Val Gln Ser Gln Val Met Asn Thr Glu His Lys Ala Tyr Leu Asp Lys
            180                 185                 190

```
Asn Lys Ala Tyr Pro Val Glu Cys Trp Val Pro Asp Pro Thr Arg Asn
            195                 200                 205

Glu Asn Thr Arg Tyr Phe Gly Thr Leu Thr Gly Gly Glu Asn Val Pro
            210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
                260                 265                 270

Arg Gly Leu Ser Arg Tyr Phe Lys Val Gln Leu Arg Lys Arg Arg Val
            275                 280                 285

Lys Asn Pro Tyr Pro Ile Ser Phe Leu Leu Thr Asp Leu Ile Asn Arg
            290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Leu Pro Gly Asp
                325                 330                 335

Pro Asp Met Met Arg Tyr Val Asp Arg Tyr Gly Gln Leu Gln Thr Lys
                340                 345                 350

Met Leu

<210> SEQ ID NO 26
<211> LENGTH: 354
<212> TYPE: PRT
<213> ORGANISM: JC virus

<400> SEQUENCE: 26

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
                20                  25                  30

Gly Val Asp Ser Ile Thr Glu Val Glu Cys Phe Leu Thr Pro Glu Met
            35                  40                  45

Gly Asp Pro Asp Glu His Leu Arg Gly Phe Ser Lys Ser Ile Ser Ile
50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Leu Gly Val Thr Thr Leu Met Asn Val His Ser Asn Gly Gln Ala Thr
            115                 120                 125

His Asp Asn Gly Ala Gly Lys Pro Val Gln Gly Thr Ser Phe His Phe
        130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
            195                 200                 205
```

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                    245                 250                 255

Val Asp Val Cys Gly Met Phe Thr Asn Arg Ser Gly Tyr Gln Gln Trp
                260                 265                 270

Arg Gly Leu Ser Arg Tyr Phe Lys Val Gln Leu Arg Lys Arg Arg Val
            275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                    325                 330                 335

Pro Asp Met Met Arg Tyr Val Asp Arg Tyr Gly Gln Leu Gln Thr Lys
                340                 345                 350

Met Leu

<210> SEQ ID NO 27
<211> LENGTH: 354
<212> TYPE: PRT
<213> ORGANISM: JC virus

<400> SEQUENCE: 27

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
                20                  25                  30

Gly Val Asp Ser Ile Thr Glu Val Glu Cys Phe Leu Thr Pro Glu Met
            35                  40                  45

Gly Asp Pro Asp Glu His Leu Arg Gly Phe Ser Met Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Leu Gly Val Thr Thr Leu Met Asn Val His Ser Asn Gly Gln Ala Thr
    115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

```
Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
                325                 330                 335

Pro Asp Met Met Arg Tyr Val Asp Arg Tyr Gly Gln Leu Gln Thr Lys
            340                 345                 350

Met Leu

<210> SEQ ID NO 28
<211> LENGTH: 354
<212> TYPE: PRT
<213> ORGANISM: JC virus

<400> SEQUENCE: 28

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
                20                  25                  30

Gly Val Asp Ser Ile Thr Glu Val Glu Cys Phe Leu Thr Pro Glu Met
            35                  40                  45

Gly Asp Pro Asp Glu His Leu Arg Gly Phe Ser Lys Ser Ile Ser Ile
        50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
                100                 105                 110

Leu Gly Val Thr Thr Leu Met Asn Val His Cys Asn Gly Gln Ala Thr
            115                 120                 125

His Asp Asn Gly Ala Gly Lys Pro Val Gln Gly Thr Ser Phe His Phe
        130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240
```

```
Phe Gly Val Gly Pro Leu Cys Lys Gly Asp Asn Leu Tyr Leu Ser Ala
            245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Val
            275                 280                 285

Lys Asn Pro Tyr Pro Ile Ser Phe Leu Leu Thr Asp Leu Ile Asn Arg
            290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Glu Leu Pro Gly Asp
            325                 330                 335

Pro Asp Met Met Arg Tyr Val Asp Arg Tyr Gly Gln Leu Gln Thr Lys
            340                 345                 350

Met Leu

<210> SEQ ID NO 29
<211> LENGTH: 354
<212> TYPE: PRT
<213> ORGANISM: JC virus

<400> SEQUENCE: 29

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
            35                  40                  45

Gly Asp Pro Asp Glu His Leu Arg Gly Phe Ser Lys Ser Ile Ser Ile
        50                  55                  60

Ser Asp Thr Phe Glu Ser Asp Ser Pro Asn Lys Asp Met Leu Pro Cys
65              70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Leu Gly Val Thr Thr Leu Met Asn Val His Cys Asn Gly Gln Ala Thr
            115                 120                 125

His Asp Asn Gly Ala Gly Lys Pro Val Gln Gly Thr Ser Phe His Phe
        130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
            210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255
```

-continued

```
Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Leu Pro Gly Asp
                325                 330                 335

Pro Asp Met Met Arg Tyr Val Asp Arg Tyr Gly Gln Leu Gln Thr Lys
            340                 345                 350

Met Leu

<210> SEQ ID NO 30
<211> LENGTH: 245
<212> TYPE: PRT
<213> ORGANISM: JC virus

<400> SEQUENCE: 30

Phe Leu Thr Pro Glu Met Gly Asp Pro Asp Glu His Leu Arg Gly Phe
1               5                   10                  15

Ser Lys Ser Ile Ser Ile Ser Asp Thr Phe Glu Ser Asp Ser Pro Asn
            20                  25                  30

Lys Asp Met Leu Pro Cys Tyr Ser Val Ala Arg Ile Pro Leu Pro Asn
        35                  40                  45

Leu Asn Glu Asp Leu Thr Cys Gly Asn Ile Leu Met Trp Glu Ala Val
50                  55                  60

Thr Leu Lys Thr Glu Val Ile Gly Val Thr Thr Leu Met Asn Val His
65                  70                  75                  80

Ser Asn Gly Gln Ala Thr His Asp Asn Gly Ala Gly Lys Pro Val Gln
            85                  90                  95

Gly Thr Ser Phe His Phe Phe Ser Val Gly Gly Glu Ala Leu Glu Leu
        100                 105                 110

Gln Gly Val Val Phe Asn Tyr Arg Thr Lys Tyr Pro Asp Gly Thr Ile
    115                 120                 125

Phe Pro Lys Asn Ala Thr Val Gln Ser Gln Val Met Asn Thr Glu His
130                 135                 140

Lys Ala Tyr Leu Asp Lys Asn Lys Ala Tyr Pro Val Glu Cys Trp Val
145                 150                 155                 160

Pro Asp Pro Thr Arg Asn Glu Asn Thr Arg Tyr Phe Gly Thr Leu Thr
            165                 170                 175

Gly Gly Glu Asn Val Pro Pro Val Leu His Ile Thr Asn Thr Ala Thr
        180                 185                 190

Thr Val Leu Leu Asp Glu Phe Gly Val Gly Pro Leu Cys Lys Gly Asp
    195                 200                 205

Asn Leu Tyr Leu Ser Ala Val Asp Val Cys Gly Met Phe Thr Asn Arg
210                 215                 220

Ser Gly Ser Gln Gln Trp Arg Gly Leu Ser Arg Tyr Phe Lys Val Gln
225                 230                 235                 240

Leu Arg Lys Arg Arg
            245

<210> SEQ ID NO 31
```

```
<211> LENGTH: 245
<212> TYPE: PRT
<213> ORGANISM: JC virus

<400> SEQUENCE: 31

Phe Leu Thr Pro Glu Met Gly Asp Pro Asp Glu His Leu Arg Gly Phe
1               5                   10                  15

Ser Lys Ser Ile Ser Ile Ser His Thr Phe Glu Ser Asp Ser Pro Asn
            20                  25                  30

Lys Asp Met Leu Pro Cys Tyr Ser Val Ala Arg Ile Pro Leu Pro Asn
        35                  40                  45

Leu Asn Glu Asp Leu Thr Cys Gly Asn Ile Leu Met Trp Glu Ala Val
    50                  55                  60

Thr Leu Lys Thr Glu Val Ile Gly Val Thr Thr Leu Met Asn Val His
65                  70                  75                  80

Ser Asn Gly Gln Ala Thr His Asp Asn Gly Ala Gly Lys Pro Val Gln
                85                  90                  95

Gly Thr Ser Phe His Phe Phe Ser Val Gly Gly Glu Ala Leu Glu Leu
            100                 105                 110

Gln Gly Val Val Phe Asn Tyr Arg Thr Lys Tyr Pro Asp Gly Thr Ile
        115                 120                 125

Phe Pro Lys Asn Ala Thr Val Gln Ser Gln Val Met Asn Thr Glu His
    130                 135                 140

Lys Ala Tyr Leu Asp Lys Asn Lys Ala Tyr Pro Val Glu Cys Trp Val
145                 150                 155                 160

Pro Asp Pro Thr Arg Asn Glu Asn Thr Arg Tyr Phe Gly Thr Leu Thr
                165                 170                 175

Gly Gly Glu Asn Val Pro Pro Val Leu His Ile Thr Asn Thr Ala Thr
            180                 185                 190

Thr Val Leu Leu Asp Glu Phe Gly Val Gly Pro Leu Cys Lys Gly Asp
        195                 200                 205

Asn Leu Tyr Leu Ser Ala Val Asp Val Cys Gly Met Phe Thr Asn Arg
    210                 215                 220

Ser Gly Ser Gln Gln Trp Arg Gly Leu Ser Arg Tyr Phe Lys Val Gln
225                 230                 235                 240

Leu Arg Lys Arg Arg
                245

<210> SEQ ID NO 32
<211> LENGTH: 245
<212> TYPE: PRT
<213> ORGANISM: JC virus

<400> SEQUENCE: 32

Phe Leu Thr Pro Glu Met Gly Asp Pro Asp Glu His Leu Arg Gly Phe
1               5                   10                  15

Ser Lys Ser Ile Ser Ile Ser Asn Thr Phe Glu Ser Asp Ser Pro Asn
            20                  25                  30

Lys Asp Met Leu Pro Cys Tyr Ser Val Ala Arg Ile Pro Leu Pro Asn
        35                  40                  45

Leu Asn Glu Asp Leu Thr Cys Gly Asn Ile Leu Met Trp Glu Ala Val
    50                  55                  60

Thr Leu Lys Thr Glu Val Ile Gly Val Thr Thr Leu Met Asn Val His
65                  70                  75                  80

Ser Asn Gly Gln Ala Thr His Asp Asn Gly Ala Gly Lys Pro Val Gln
                85                  90                  95
```

```
Gly Thr Ser Phe His Phe Phe Ser Val Gly Gly Glu Ala Leu Glu Leu
                100                 105                 110

Gln Gly Val Val Phe Asn Tyr Arg Thr Lys Tyr Pro Asp Gly Thr Ile
            115                 120                 125

Phe Pro Lys Asn Ala Thr Val Gln Ser Gln Val Met Asn Thr Glu His
130                 135                 140

Lys Ala Tyr Leu Asp Lys Asn Lys Ala Tyr Pro Val Glu Cys Trp Val
145                 150                 155                 160

Pro Asp Pro Thr Arg Asn Glu Asn Thr Arg Tyr Phe Gly Thr Leu Thr
                165                 170                 175

Gly Gly Glu Asn Val Pro Pro Val Leu His Ile Thr Asn Thr Ala Thr
            180                 185                 190

Thr Val Leu Leu Asp Glu Phe Gly Val Gly Pro Leu Cys Lys Gly Asp
        195                 200                 205

Asn Leu Tyr Leu Ser Ala Val Asp Val Cys Gly Met Phe Thr Asn Arg
    210                 215                 220

Ser Gly Ser Gln Gln Trp Arg Gly Leu Ser Arg Tyr Phe Lys Val Gln
225                 230                 235                 240

Leu Arg Lys Arg Arg
                245

<210> SEQ ID NO 33
<211> LENGTH: 245
<212> TYPE: PRT
<213> ORGANISM: JC virus

<400> SEQUENCE: 33

Phe Leu Thr Pro Glu Met Gly Asp Pro Asp Glu His Leu Arg Gly Phe
1               5                   10                  15

Ser Glu Ser Ile Ser Ile Ser His Thr Phe Glu Ser Asp Ser Pro Asn
            20                  25                  30

Lys Asp Met Leu Pro Cys Tyr Ser Val Ala Arg Ile Pro Leu Pro Asn
        35                  40                  45

Leu Asn Glu Asp Leu Thr Cys Gly Asn Ile Leu Met Trp Glu Ala Val
50                  55                  60

Thr Leu Lys Thr Glu Val Ile Gly Val Thr Thr Leu Met Asn Val His
65                  70                  75                  80

Ser Asn Gly Gln Ala Thr His Asp Asn Gly Ala Gly Lys Pro Val Gln
                85                  90                  95

Gly Thr Ser Phe His Phe Phe Ser Val Gly Gly Glu Ala Leu Glu Leu
                100                 105                 110

Gln Gly Val Val Phe Asn Tyr Arg Thr Lys Tyr Pro Asp Gly Thr Ile
            115                 120                 125

Phe Pro Lys Asn Ala Thr Val Gln Ser Gln Val Met Asn Thr Glu His
130                 135                 140

Lys Ala Tyr Leu Asp Lys Asn Lys Ala Tyr Pro Val Glu Cys Trp Val
145                 150                 155                 160

Pro Asp Pro Thr Arg Asn Glu Asn Thr Arg Tyr Phe Gly Thr Leu Thr
                165                 170                 175

Gly Gly Glu Asn Val Pro Pro Val Leu His Ile Thr Asn Thr Ala Thr
            180                 185                 190

Thr Val Leu Leu Asp Glu Phe Gly Val Gly Pro Leu Cys Lys Gly Asp
        195                 200                 205

Asn Leu Tyr Leu Ser Ala Val Asp Val Cys Gly Met Phe Thr Asn Arg
```

```
              210                 215                 220
Ser Gly Ser Gln Gln Trp Arg Gly Leu Ser Arg Tyr Phe Lys Val Gln
225                 230                 235                 240

Leu Arg Lys Arg Arg
            245

<210> SEQ ID NO 34
<211> LENGTH: 245
<212> TYPE: PRT
<213> ORGANISM: JC virus

<400> SEQUENCE: 34

Phe Leu Thr Pro Glu Met Gly Asp Pro Asp Glu His Leu Arg Gly Phe
1               5                   10                  15

Ser Lys Ser Ile Ser Ile Ser Asp Thr Phe Glu Ser Asp Ser Pro Asn
            20                  25                  30

Lys Asp Met Leu Pro Cys Tyr Ser Val Ala Arg Ile Pro Leu Pro Asn
        35                  40                  45

Leu Asn Glu Asp Leu Thr Cys Gly Asn Ile Leu Met Trp Glu Ala Val
    50                  55                  60

Thr Leu Lys Thr Glu Val Leu Gly Val Thr Thr Leu Met Asn Val His
65                  70                  75                  80

Ser Asn Gly Gln Ala Thr His Asp Asn Gly Ala Gly Lys Pro Val Gln
                85                  90                  95

Gly Thr Ser Phe His Phe Phe Ser Val Gly Gly Glu Ala Leu Glu Leu
            100                 105                 110

Gln Gly Val Val Phe Asn Tyr Arg Thr Lys Tyr Pro Asp Gly Thr Ile
        115                 120                 125

Phe Pro Lys Asn Ala Thr Val Gln Ser Gln Val Met Asn Thr Glu His
    130                 135                 140

Lys Ala Tyr Leu Asp Lys Asn Lys Ala Tyr Pro Val Glu Cys Trp Val
145                 150                 155                 160

Pro Asp Pro Thr Arg Asn Glu Asn Thr Arg Tyr Phe Gly Thr Leu Thr
                165                 170                 175

Gly Gly Glu Asn Val Pro Pro Val Leu His Ile Thr Asn Thr Ala Thr
            180                 185                 190

Thr Val Leu Leu Asp Glu Phe Gly Val Gly Pro Leu Cys Lys Gly Asp
        195                 200                 205

Asn Leu Tyr Leu Ser Ala Val Asp Val Cys Gly Met Phe Thr Asn Arg
    210                 215                 220

Phe Gly Ser Gln Gln Trp Arg Gly Leu Ser Arg Tyr Phe Lys Val Gln
225                 230                 235                 240

Leu Arg Lys Arg Arg
            245

<210> SEQ ID NO 35
<211> LENGTH: 245
<212> TYPE: PRT
<213> ORGANISM: JC virus

<400> SEQUENCE: 35

Phe Leu Thr Pro Glu Met Gly Asp Pro Asp Glu His Leu Arg Gly Phe
1               5                   10                  15

Ser Met Ser Ile Ser Ile Ser Asp Thr Phe Glu Ser Asp Ser Pro Asn
            20                  25                  30

Lys Asp Met Leu Pro Cys Tyr Ser Val Ala Arg Ile Pro Leu Pro Asn
```

```
                35                  40                  45
Leu Asn Glu Asp Leu Thr Cys Gly Asn Ile Leu Met Trp Glu Ala Val
 50                  55                  60
Thr Leu Lys Thr Glu Val Ile Gly Val Thr Thr Leu Met Asn Val His
 65                  70                  75                  80
Ser Asn Gly Gln Ala Thr His Asp Asn Gly Ala Gly Lys Pro Val Gln
                 85                  90                  95
Gly Thr Ser Phe His Phe Phe Ser Val Gly Gly Glu Ala Leu Glu Leu
                100                 105                 110
Gln Gly Val Val Phe Asn Tyr Arg Thr Lys Tyr Pro Asp Gly Thr Ile
                115                 120                 125
Phe Pro Lys Asn Ala Thr Val Gln Ser Gln Val Met Asn Thr Glu His
            130                 135                 140
Lys Ala Tyr Leu Asp Lys Asn Lys Ala Tyr Pro Val Glu Cys Trp Val
145                 150                 155                 160
Pro Asp Pro Thr Arg Asn Glu Asn Thr Arg Tyr Phe Gly Thr Leu Thr
                165                 170                 175
Gly Gly Glu Asn Val Pro Pro Val Leu His Ile Thr Asn Thr Ala Thr
                180                 185                 190
Thr Val Leu Leu Asp Glu Phe Gly Val Gly Pro Leu Cys Lys Gly Asp
            195                 200                 205
Asn Leu Tyr Leu Ser Ala Val Asp Val Cys Gly Met Phe Thr Asn Arg
210                 215                 220
Ser Gly Ser Gln His Trp Arg Gly Leu Ser Arg Tyr Phe Lys Val Gln
225                 230                 235                 240
Leu Arg Lys Arg Arg
                245

<210> SEQ ID NO 36
<211> LENGTH: 245
<212> TYPE: PRT
<213> ORGANISM: JC virus

<400> SEQUENCE: 36

Phe Leu Thr Pro Glu Met Gly Asp Pro Asp Glu His Leu Arg Gly Phe
 1               5                  10                  15
Ser Lys Ser Ile Ser Ile Ser His Thr Phe Glu Ser Asp Ser Pro Asn
                20                  25                  30
Lys Asp Met Leu Pro Cys Tyr Ser Val Ala Arg Ile Pro Leu Pro Asn
             35                  40                  45
Leu Asn Glu Asp Leu Thr Cys Gly Asn Ile Leu Met Trp Glu Ala Val
 50                  55                  60
Thr Leu Lys Thr Glu Val Ile Gly Val Thr Thr Leu Met Asn Val His
 65                  70                  75                  80
Ser Asn Gly Gln Ala Thr His Asp Asn Gly Ala Gly Lys Pro Val Gln
                 85                  90                  95
Gly Thr Ser Phe His Phe Phe Ser Val Gly Gly Glu Ala Leu Glu Leu
                100                 105                 110
Gln Gly Val Val Phe Asn Tyr Arg Thr Lys Tyr Pro Asp Gly Thr Ile
                115                 120                 125
Phe Pro Lys Asn Ala Thr Val Gln Ser Gln Val Met Asn Thr Glu His
            130                 135                 140
Lys Ala Tyr Leu Asp Lys Asn Lys Ala Tyr Pro Val Glu Cys Trp Val
145                 150                 155                 160
```

```
Pro Asp Pro Thr Arg Asn Glu Asn Thr Arg Tyr Phe Gly Thr Leu Thr
                165                 170                 175

Gly Gly Glu Asn Val Pro Pro Val Leu His Ile Thr Asn Thr Ala Thr
            180                 185                 190

Thr Val Leu Leu Asp Glu Phe Gly Val Gly Pro Leu Cys Lys Gly Asp
        195                 200                 205

Asn Leu Tyr Leu Ser Ala Val Asp Val Cys Gly Met Phe Thr Asn Arg
    210                 215                 220

Ser Gly Ser Gln Gln Trp Arg Gly Leu Ser Arg Tyr Phe Lys Val Gln
225                 230                 235                 240

Leu Arg Lys Arg Arg
                245

<210> SEQ ID NO 37
<211> LENGTH: 245
<212> TYPE: PRT
<213> ORGANISM: JC virus

<400> SEQUENCE: 37

Phe Leu Thr Pro Glu Met Gly Asp Pro Asp Glu His Leu Arg Gly Phe
1               5                   10                  15

Ser Lys Ser Ile Ser Ile Ser Asp Thr Phe Glu Ser Asp Ser Pro Asn
            20                  25                  30

Lys Asp Met Leu Pro Cys Tyr Ser Val Ala Arg Ile Pro Leu Pro Asn
        35                  40                  45

Leu Asn Glu Asp Leu Thr Cys Gly Asn Ile Leu Met Trp Glu Ala Val
    50                  55                  60

Thr Leu Lys Thr Glu Val Leu Gly Val Thr Thr Leu Met Asn Val His
65                  70                  75                  80

Ser Asn Gly Gln Ala Thr His Asp Asn Gly Ala Gly Lys Pro Val Gln
                85                  90                  95

Gly Thr Ser Phe His Phe Phe Ser Val Gly Gly Glu Ala Leu Glu Leu
            100                 105                 110

Gln Gly Val Val Phe Asn Tyr Arg Thr Lys Tyr Pro Asp Gly Thr Ile
        115                 120                 125

Phe Pro Lys Asn Ala Thr Val Gln Ser Gln Val Met Asn Thr Glu His
    130                 135                 140

Lys Ala Tyr Leu Asp Lys Asn Lys Ala Tyr Pro Val Glu Cys Trp Val
145                 150                 155                 160

Pro Asp Pro Thr Arg Asn Glu Asn Thr Arg Tyr Phe Gly Thr Leu Thr
                165                 170                 175

Gly Gly Glu Asn Val Pro Pro Val Leu His Ile Thr Asn Thr Ala Thr
            180                 185                 190

Thr Val Leu Leu Asp Glu Phe Gly Val Gly Pro Leu Cys Lys Gly Asp
        195                 200                 205

Asn Leu Tyr Leu Ser Ala Val Asp Val Cys Gly Met Phe Thr Asn Arg
    210                 215                 220

Ser Gly Phe Gln Gln Trp Arg Gly Leu Ser Arg Tyr Phe Lys Val Gln
225                 230                 235                 240

Leu Arg Lys Arg Arg
                245

<210> SEQ ID NO 38
<211> LENGTH: 245
<212> TYPE: PRT
<213> ORGANISM: JC virus
```

```
<400> SEQUENCE: 38

Phe Leu Thr Pro Glu Met Gly Asp Pro Asp Glu His Leu Arg Gly Phe
1               5                   10                  15

Ser Lys Ser Ile Ser Ile Ser Asp Thr Phe Glu Ser Asp Ser Pro Asn
            20                  25                  30

Lys Asp Met Leu Pro Cys Tyr Ser Val Ala Arg Ile Pro Leu Pro Asn
            35                  40                  45

Leu Asn Glu Asp Leu Thr Cys Gly Asn Ile Leu Met Trp Glu Ala Val
50                  55                  60

Thr Leu Lys Thr Glu Val Leu Gly Val Thr Thr Leu Met Asn Val His
65                  70                  75                  80

Ser Asn Gly Gln Ala Thr His Asp Asn Gly Ala Gly Lys Pro Val Gln
            85                  90                  95

Gly Thr Ser Phe His Phe Ser Val Gly Gly Glu Ala Leu Glu Leu
            100                 105                 110

Gln Gly Val Val Phe Asn Tyr Arg Thr Lys Tyr Pro Asp Gly Thr Ile
            115                 120                 125

Phe Pro Lys Asn Ala Thr Val Gln Ser Gln Val Met Asn Thr Glu His
130                 135                 140

Lys Ala Tyr Leu Asp Lys Asn Lys Ala Tyr Pro Val Glu Cys Trp Val
145                 150                 155                 160

Pro Asp Pro Thr Arg Asn Glu Asn Thr Arg Tyr Phe Gly Thr Leu Thr
            165                 170                 175

Gly Gly Glu Asn Val Pro Pro Val Leu His Ile Thr Asn Thr Ala Thr
            180                 185                 190

Thr Val Leu Leu Asp Glu Phe Gly Val Gly Pro Leu Cys Lys Gly Asp
            195                 200                 205

Asn Leu Tyr Leu Ser Ala Val Asp Val Cys Gly Met Phe Thr Asn Arg
210                 215                 220

Phe Gly Ser Gln Gln Trp Arg Gly Leu Ser Arg Tyr Phe Lys Val Gln
225                 230                 235                 240

Leu Arg Lys Arg Arg
            245

<210> SEQ ID NO 39
<211> LENGTH: 245
<212> TYPE: PRT
<213> ORGANISM: JC virus

<400> SEQUENCE: 39

Phe Leu Thr Pro Glu Met Gly Asp Pro Asp Glu His Leu Arg Gly Phe
1               5                   10                  15

Ser Lys Ser Ile Ser Ile Ser Asp Thr Phe Glu Ser Asp Ser Pro Asn
            20                  25                  30

Lys Asp Met Leu Pro Cys Tyr Ser Val Ala Arg Ile Pro Leu Pro Asn
            35                  40                  45

Leu Asn Glu Asp Leu Thr Cys Gly Asn Ile Leu Met Trp Glu Ala Val
50                  55                  60

Thr Leu Lys Thr Glu Val Ile Gly Val Thr Thr Leu Met Asn Val His
65                  70                  75                  80

Ser Asn Gly Gln Ala Thr His Asp Asn Gly Ala Gly Lys Pro Val Gln
            85                  90                  95

Gly Thr Ser Phe His Phe Ser Val Gly Gly Glu Ala Leu Glu Leu
            100                 105                 110
```

```
Gln Gly Val Val Phe Asn Tyr Arg Thr Lys Tyr Pro Asp Gly Thr Ile
            115                 120                 125
Phe Pro Lys Asn Ala Thr Val Gln Ser Gln Val Met Asn Thr Glu His
130                 135                 140
Lys Ala Tyr Leu Asp Lys Asn Lys Ala Tyr Pro Val Glu Cys Trp Val
145                 150                 155                 160
Pro Asp Pro Thr Arg Asn Glu Asn Thr Arg Tyr Phe Gly Thr Leu Thr
                165                 170                 175
Gly Gly Glu Asn Ala Pro Pro Val Leu His Ile Thr Asn Thr Ala Thr
            180                 185                 190
Thr Val Leu Leu Asp Glu Phe Gly Val Gly Pro Leu Cys Lys Gly Asp
        195                 200                 205
Asn Leu Tyr Leu Ser Ala Val Asp Val Cys Gly Met Phe Thr Asn Arg
    210                 215                 220
Ser Gly Ser Gln Gln Trp Arg Gly Leu Ser Arg Tyr Phe Lys Val Gln
225                 230                 235                 240
Leu Arg Lys Arg Arg
                245

<210> SEQ ID NO 40
<211> LENGTH: 245
<212> TYPE: PRT
<213> ORGANISM: JC virus

<400> SEQUENCE: 40

Phe Leu Thr Pro Glu Met Gly Asp Pro Asp Glu His Leu Arg Gly Phe
1               5                   10                  15
Ser Lys Ser Ile Ser Ile Ser Asp Thr Phe Asp Ser Asp Ser Pro Asn
            20                  25                  30
Lys Asp Met Leu Pro Cys Tyr Ser Val Ala Arg Ile Pro Leu Pro Asn
        35                  40                  45
Leu Asn Glu Asp Leu Thr Cys Gly Asn Ile Leu Met Trp Glu Ala Val
    50                  55                  60
Thr Leu Lys Thr Glu Val Ile Gly Val Thr Thr Leu Met Asn Val His
65                  70                  75                  80
Ser Asn Gly Gln Ala Thr His Asp Asn Gly Ala Gly Lys Pro Val Gln
                85                  90                  95
Gly Thr Ser Phe His Phe Phe Ser Val Gly Gly Glu Ala Leu Glu Leu
            100                 105                 110
Gln Gly Val Val Phe Asn Tyr Arg Thr Lys Tyr Pro Asp Gly Thr Ile
            115                 120                 125
Phe Pro Lys Asn Ala Thr Val Gln Ser Gln Val Met Asn Thr Glu His
130                 135                 140
Lys Ala Tyr Leu Asp Lys Asn Lys Ala Tyr Pro Val Glu Cys Trp Val
145                 150                 155                 160
Pro Asp Pro Thr Arg Asn Glu Asn Thr Arg Tyr Phe Gly Thr Leu Thr
                165                 170                 175
Gly Gly Glu Asn Val Pro Pro Val Leu His Ile Thr Asn Thr Ala Thr
            180                 185                 190
Thr Val Leu Leu Asp Glu Phe Gly Val Gly Pro Leu Cys Lys Gly Asp
        195                 200                 205
Asn Leu Tyr Leu Ser Ala Val Asp Val Cys Gly Met Phe Thr Asn Arg
    210                 215                 220
Ser Gly Phe Gln Gln Trp Arg Gly Leu Ser Arg Tyr Phe Lys Val Gln
```

Leu Arg Lys Arg Arg
            245

<210> SEQ ID NO 41
<211> LENGTH: 354
<212> TYPE: PRT
<213> ORGANISM: JC virus

<400> SEQUENCE: 41

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Ala
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Val Glu Glu Val Arg Val Phe Glu Gly Thr Glu Leu Pro Gly Asp
                325                 330                 335

Pro Asp Met Met Arg Tyr Val Asp Arg Tyr Gly Gln Leu Gln Thr Lys
            340                 345                 350

Met Leu

<210> SEQ ID NO 42
<211> LENGTH: 354
<212> TYPE: PRT
<213> ORGANISM: JC virus

<400> SEQUENCE: 42

```
Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Leu Gly Val Thr Thr Leu Met Asn Val His Ser Asn Gly Gln Ala Thr
        115                 120                 125

His Asp Asn Gly Ala Gly Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Lys Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Thr Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Ile Glu Glu Val Arg Val Phe Glu Gly Thr Glu Glu Leu Pro Gly Asp
                325                 330                 335

Pro Asp Met Met Arg Tyr Val Asp Arg Tyr Gly Gln Leu Gln Thr Lys
            340                 345                 350

Met Leu
```

-continued

```
<210> SEQ ID NO 43
<211> LENGTH: 354
<212> TYPE: PRT
<213> ORGANISM: JC virus

<400> SEQUENCE: 43
```

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Leu Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Thr
        115                 120                 125

His Asp Asn Gly Ala Ala Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Thr Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Phe Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Ile Glu Glu Val Arg Val Phe Glu Gly Thr Glu Gln Leu Pro Gly Asp
                325                 330                 335

Pro Asp Met Met Arg Tyr Val Asp Arg Tyr Gly Gln Leu Gln Thr Lys
            340                 345                 350

Met Leu

```
<210> SEQ ID NO 44
<211> LENGTH: 354
<212> TYPE: PRT
```

-continued

<213> ORGANISM: JC virus

<400> SEQUENCE: 44

Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Gly Val Lys Thr
            20                  25                  30

Gly Val Asp Ser Ile Thr Glu Val Glu Cys Phe Leu Thr Pro Glu Met
        35                  40                  45

Gly Asp Pro Asp Glu His Phe Arg Gly Phe Ser Lys Ser Ile Ser Ile
    50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
            100                 105                 110

Ile Gly Val Thr Thr Leu Met Asn Val His Ser Asn Gly Gln Ala Thr
        115                 120                 125

His Asp Asn Gly Ala Ala Lys Pro Val Gln Gly Thr Ser Phe His Phe
    130                 135                 140

Phe Ser Val Gly Gly Glu Ala Leu Glu Leu Gln Gly Val Val Phe Asn
145                 150                 155                 160

Tyr Arg Thr Thr Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
        195                 200                 205

Glu Asn Thr Arg Tyr Phe Gly Thr Leu Thr Gly Gly Glu Asn Val Pro
    210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
            260                 265                 270

Arg Gly Leu Ser Arg Tyr Phe Lys Val Gln Leu Arg Lys Arg Arg Val
        275                 280                 285

Lys Asn Pro Tyr Pro Ile Ser Phe Leu Leu Thr Asp Leu Ile Asn Arg
    290                 295                 300

Arg Thr Pro Arg Val Asp Gly Gln Pro Met Tyr Gly Met Asp Ala Gln
305                 310                 315                 320

Ile Glu Glu Val Arg Val Phe Glu Gly Thr Glu Gln Leu Pro Gly Asp
                325                 330                 335

Pro Asp Met Met Arg Tyr Val Asp Arg Tyr Gly Gln Leu Gln Thr Lys
            340                 345                 350

Met Leu

<210> SEQ ID NO 45
<211> LENGTH: 354
<212> TYPE: PRT
<213> ORGANISM: JC virus

<400> SEQUENCE: 45

```
Met Ala Pro Thr Lys Arg Lys Gly Glu Arg Lys Asp Pro Val Gln Val
1               5                   10                  15

Pro Lys Leu Leu Ile Arg Gly Gly Val Glu Val Leu Glu Val Lys Thr
            20                  25                  30

Gly Val Asp Ser Ile Thr Glu Val Glu Cys Phe Leu Thr Pro Glu Met
            35                  40                  45

Gly Asp Pro Asp Glu His Leu Arg Gly Phe Ser Asn Ser Ile Ser Ile
50                  55                  60

Ser Asp Thr Phe Glu Ser Asp Ser Pro Asn Lys Asp Met Leu Pro Cys
65                  70                  75                  80

Tyr Ser Val Ala Arg Ile Pro Leu Pro Asn Leu Asn Glu Asp Leu Thr
                85                  90                  95

Cys Gly Asn Ile Leu Met Trp Glu Ala Val Thr Leu Lys Thr Glu Val
                100                 105                 110

Ile Gly Val Thr Thr Leu Met Asn Val His Ser Asn Gly Gln Ala Thr
            115                 120                 125

His Asp Asn Gly Ala Ala Lys Pro Val Gln Gly Thr Ser Phe His Phe
130                 135                 140

Phe Ser Val Gly Gly Glu Ala Leu Glu Leu Gln Gly Val Val Phe Asn
145                 150                 155                 160

Tyr Arg Thr Thr Tyr Pro Asp Gly Thr Ile Phe Pro Lys Asn Ala Thr
                165                 170                 175

Val Gln Ser Gln Val Met Asn Thr Glu His Lys Ala Tyr Leu Asp Lys
            180                 185                 190

Asn Lys Ala Tyr Pro Val Glu Cys Trp Val Pro Asp Pro Thr Arg Asn
            195                 200                 205

Glu Asn Thr Arg Tyr Phe Gly Thr Leu Thr Gly Gly Glu Asn Val Pro
210                 215                 220

Pro Val Leu His Ile Thr Asn Thr Ala Thr Thr Val Leu Leu Asp Glu
225                 230                 235                 240

Phe Gly Val Gly Pro Leu Cys Lys Gly Asp Asn Leu Tyr Leu Ser Ala
                245                 250                 255

Val Asp Val Cys Gly Met Phe Thr Asn Arg Ser Gly Ser Gln Gln Trp
                260                 265                 270

Arg Gly Leu Ser Arg Tyr Phe Lys Val Gln Leu Arg Lys Arg Arg Val
            275                 280                 285

Lys Asn Pro Tyr Pro Ile Ser Phe Leu Leu Thr Asp Leu Ile Asn Arg
            290                 295                 300

Arg Thr Pro Arg Val Asp Gly Gln Pro Met Tyr Gly Met Asp Ala Gln
305                 310                 315                 320

Ile Glu Glu Val Arg Val Phe Glu Gly Thr Glu Gln Leu Pro Gly Asp
                325                 330                 335

Pro Asp Met Met Arg Tyr Val Asp Arg Tyr Gly Gln Leu Gln Thr Lys
                340                 345                 350

Met Leu

<210> SEQ ID NO 46
<211> LENGTH: 245
<212> TYPE: PRT
<213> ORGANISM: JC virus

<400> SEQUENCE: 46

Phe Leu Thr Pro Glu Met Gly Asp Pro Asp Glu His Leu Arg Gly Phe
1               5                   10                  15
```

-continued

Ser Lys Ser Ile Ser Ile Ser Asp Thr Phe Glu Ser Asp Ser Pro Asn
            20                  25                  30

Lys Asp Met Leu Pro Cys Tyr Ser Val Ala Arg Ile Pro Leu Pro Asn
            35                  40                  45

Leu Asn Glu Asp Leu Thr Cys Gly Asn Ile Leu Met Trp Glu Ala Val
 50                  55                  60

Thr Leu Lys Thr Glu Val Leu Gly Val Thr Thr Leu Met Asn Val His
 65                  70                  75                  80

Ser Asn Gly Gln Ala Thr His Asp Asn Gly Ala Gly Lys Pro Val Gln
            85                  90                  95

Gly Thr Ser Phe His Phe Phe Ser Val Gly Gly Glu Ala Leu Glu Leu
            100                 105                 110

Gln Gly Val Val Phe Asn Tyr Arg Thr Lys Tyr Pro Asp Gly Thr Ile
            115                 120                 125

Phe Pro Lys Asn Ala Thr Val Gln Ser Gln Val Met Asn Thr Glu His
 130                 135                 140

Lys Ala Tyr Leu Asp Lys Asn Lys Ala Tyr Pro Val Glu Cys Trp Val
145                 150                 155                 160

Pro Asp Pro Thr Arg Asn Glu Asn Thr Arg Tyr Phe Gly Thr Leu Thr
            165                 170                 175

Gly Gly Glu Asn Val Pro Pro Val Leu His Ile Thr Asn Thr Ala Thr
            180                 185                 190

Thr Val Leu Leu Asp Glu Phe Gly Val Gly Pro Leu Cys Lys Gly Asp
            195                 200                 205

Asn Leu Tyr Leu Ser Ala Val Asp Val Cys Gly Met Phe Thr Asp Arg
            210                 215                 220

Ser Gly Ser Gln Gln Trp Arg Gly Leu Ser Arg Tyr Phe Lys Val Gln
225                 230                 235                 240

Leu Arg Lys Arg Arg
            245

<210> SEQ ID NO 47
<211> LENGTH: 245
<212> TYPE: PRT
<213> ORGANISM: JC virus

<400> SEQUENCE: 47

Phe Leu Thr Pro Glu Met Gly Asp Pro Asp Glu His Phe Arg Gly Phe
 1                   5                  10                  15

Ser Lys Ser Ile Ser Ile Ser Asp Thr Phe Glu Ser Asp Ser Pro Asn
            20                  25                  30

Lys Asp Met Leu Pro Cys Tyr Ser Val Ala Arg Ile Pro Leu Pro Asn
            35                  40                  45

Leu Asn Glu Asp Leu Thr Cys Gly Asn Ile Leu Met Trp Glu Ala Val
 50                  55                  60

Thr Leu Lys Thr Glu Val Ile Gly Val Thr Thr Leu Met Asn Val His
 65                  70                  75                  80

Ser Asn Gly Gln Ala Thr His Asp Asn Gly Ala Gly Lys Pro Val Gln
            85                  90                  95

Gly Thr Ser Phe His Phe Phe Ser Val Gly Gly Glu Ala Leu Glu Leu
            100                 105                 110

Gln Gly Val Val Phe Asn Tyr Arg Thr Lys Tyr Pro Asp Gly Thr Ile
            115                 120                 125

Phe Pro Lys Asn Ala Thr Val Gln Ser Gln Val Met Asn Thr Glu His

```
            130                 135                 140
Lys Ala Tyr Leu Asp Lys Asn Lys Ala Tyr Pro Val Glu Cys Trp Val
145                 150                 155                 160

Pro Asp Pro Thr Arg Asn Glu Asn Thr Arg Tyr Phe Gly Thr Leu Thr
                165                 170                 175

Gly Gly Glu Asn Val Pro Pro Val Leu His Ile Thr Asn Thr Ala Thr
                180                 185                 190

Thr Val Leu Leu Asp Glu Phe Gly Val Gly Pro Leu Cys Lys Gly Asp
            195                 200                 205

Asn Leu Tyr Leu Ser Ala Val Asp Val Cys Gly Met Phe Thr Asn Arg
210                 215                 220

Ser Gly Ser Gln Gln Trp Arg Gly Leu Ser Arg Tyr Phe Lys Val Gln
225                 230                 235                 240

Leu Arg Lys Arg Arg
            245

<210> SEQ ID NO 48
<211> LENGTH: 245
<212> TYPE: PRT
<213> ORGANISM: JC virus

<400> SEQUENCE: 48

Phe Leu Thr Pro Glu Met Gly Asp Pro Asp Glu His Leu Arg Gly Phe
1               5                   10                  15

Ser Lys Ser Ile Ser Ile Ser Asp Thr Phe Glu Ser Asp Ser Pro Asn
                20                  25                  30

Lys Asp Met Leu Pro Cys Tyr Ser Val Ala Arg Ile Pro Leu Pro Asn
            35                  40                  45

Leu Asn Glu Asp Leu Thr Cys Gly Asn Ile Leu Met Trp Glu Ala Val
        50                  55                  60

Thr Leu Lys Thr Glu Val Leu Gly Val Thr Thr Leu Met Asn Val His
65                  70                  75                  80

Ser Asn Gly Gln Ala Thr His Asp Asn Gly Ala Gly Lys Pro Val Gln
                85                  90                  95

Gly Thr Ser Phe His Phe Phe Ser Val Gly Gly Glu Ala Leu Glu Leu
            100                 105                 110

Gln Gly Val Val Phe Asn Tyr Arg Thr Lys Tyr Pro Asp Gly Thr Ile
        115                 120                 125

Phe Pro Lys Asn Ala Thr Val Gln Ser Gln Val Met Asn Thr Glu His
    130                 135                 140

Lys Ala Tyr Leu Asp Lys Asn Lys Ala Tyr Pro Val Glu Cys Trp Val
145                 150                 155                 160

Pro Asp Pro Thr Arg Asn Glu Asn Thr Arg Tyr Phe Gly Thr Leu Thr
                165                 170                 175

Gly Gly Glu Asn Val Pro Pro Val Leu His Ile Thr Asn Thr Ala Thr
            180                 185                 190

Thr Val Leu Leu Asp Glu Phe Gly Val Gly Pro Leu Cys Lys Gly Asp
        195                 200                 205

Asn Leu Tyr Leu Ser Ala Val Asp Val Cys Gly Met Phe Thr Asp Arg
210                 215                 220

Ser Gly Ser Gln Gln Trp Arg Gly Leu Ser Arg Tyr Phe Lys Val Gln
225                 230                 235                 240

Leu Arg Lys Arg Arg
            245
```

<210> SEQ ID NO 49
<211> LENGTH: 245
<212> TYPE: PRT
<213> ORGANISM: JC virus

<400> SEQUENCE: 49

Phe Leu Thr Pro Glu Met Gly Asp Pro Asp Glu His Leu Arg Gly Phe
1               5                   10                  15

Ser Lys Ser Ile Ser Ile Ser Asp Thr Phe Glu Ser Asp Ser Pro Asn
            20                  25                  30

Lys Asp Met Leu Pro Cys Tyr Ser Val Ala Arg Ile Pro Leu Pro Asn
        35                  40                  45

Leu Asn Glu Asp Leu Thr Cys Gly Asn Ile Leu Met Trp Glu Ala Val
    50                  55                  60

Thr Leu Lys Thr Glu Val Leu Gly Val Thr Thr Leu Met Asn Val His
65                  70                  75                  80

Cys Asn Gly Gln Ala Thr His Asp Asn Gly Ala Gly Lys Pro Val Gln
                85                  90                  95

Gly Thr Ser Phe His Phe Phe Ser Val Gly Gly Glu Ala Leu Glu Leu
            100                 105                 110

Gln Gly Val Val Phe Asn Tyr Arg Thr Lys Tyr Pro Asp Gly Thr Ile
        115                 120                 125

Phe Pro Lys Asn Ala Thr Val Gln Ser Gln Val Met Asn Thr Glu His
    130                 135                 140

Lys Ala Tyr Leu Asp Lys Asn Lys Ala Tyr Pro Val Glu Cys Trp Val
145                 150                 155                 160

Pro Asp Pro Thr Arg Asn Glu Asn Thr Arg Tyr Phe Gly Thr Leu Thr
                165                 170                 175

Gly Gly Glu Asn Val Pro Pro Val Leu His Ile Thr Asn Thr Ala Thr
            180                 185                 190

Thr Val Leu Leu Asp Glu Phe Gly Val Gly Pro Leu Cys Lys Gly Asp
        195                 200                 205

Asn Leu Tyr Leu Ser Ala Val Asp Val Cys Gly Met Phe Thr Asn Arg
    210                 215                 220

Ser Gly Ser Gln Gln Trp Arg Gly Leu Ser Arg Tyr Phe Lys Val Gln
225                 230                 235                 240

Leu Arg Lys Arg Arg
                245

<210> SEQ ID NO 50
<211> LENGTH: 245
<212> TYPE: PRT
<213> ORGANISM: JC virus

<400> SEQUENCE: 50

Phe Leu Thr Pro Glu Met Gly Asp Pro Asp Glu His Leu Arg Gly Phe
1               5                   10                  15

Ser Lys Ser Ile Ser Ile Ser Asp Thr Phe Glu Ser Asp Ser Pro Asn
            20                  25                  30

Lys Asp Met Leu Pro Cys Tyr Ser Val Ala Arg Ile Pro Leu Pro Asn
        35                  40                  45

Leu Asn Glu Asp Leu Thr Cys Gly Asn Ile Leu Met Trp Glu Ala Val
    50                  55                  60

Thr Leu Lys Thr Glu Val Ile Gly Val Thr Thr Leu Met Asn Val His
65                  70                  75                  80

```
Ser Asn Gly Gln Ala Thr His Asp Asn Gly Ala Gly Lys Pro Val Gln
            85                  90                  95

Gly Thr Ser Phe His Phe Phe Ser Val Gly Gly Glu Ala Leu Glu Leu
        100                 105                 110

Gln Gly Val Val Phe Asn Tyr Arg Thr Lys Tyr Pro Asp Gly Thr Ile
            115                 120                 125

Phe Pro Lys Asn Ala Thr Val Gln Ser Gln Val Met Asn Thr Glu His
130                 135                 140

Lys Ala Tyr Leu Asp Lys Asn Lys Ala Tyr Pro Val Glu Cys Trp Val
145                 150                 155                 160

Pro Asp Pro Thr Arg Asn Glu Asn Thr Arg Tyr Phe Gly Thr Leu Thr
                165                 170                 175

Gly Gly Glu Asn Val Pro Pro Val Leu His Ile Thr Asn Thr Ala Thr
            180                 185                 190

Thr Val Leu Leu Asp Glu Phe Gly Val Gly Pro Leu Cys Lys Gly Asp
        195                 200                 205

Asn Leu Tyr Leu Ser Ala Val Asp Val Cys Gly Met Phe Thr Asn Arg
    210                 215                 220

Ser Gly Phe Gln Gln Trp Arg Gly Leu Ser Arg Tyr Phe Lys Val Gln
225                 230                 235                 240

Leu Arg Lys Arg Arg
            245

<210> SEQ ID NO 51
<211> LENGTH: 245
<212> TYPE: PRT
<213> ORGANISM: JC virus

<400> SEQUENCE: 51

Phe Leu Thr Pro Glu Met Gly Asp Pro Asp Glu His Leu Arg Gly Phe
1               5                   10                  15

Ser Lys Ser Ile Ser Ile Ser Asp Thr Phe Glu Ser Asp Ser Pro Asn
            20                  25                  30

Lys Asp Met Leu Pro Cys Tyr Ser Val Ala Arg Ile Pro Leu Pro Asn
        35                  40                  45

Leu Asn Glu Asp Leu Thr Cys Gly Asn Ile Leu Met Trp Glu Ala Val
    50                  55                  60

Thr Leu Lys Thr Glu Val Leu Gly Val Thr Thr Leu Met Asn Val His
65                  70                  75                  80

Cys Asn Gly Gln Ala Thr His Asp Asn Gly Ala Gly Lys Pro Val Gln
            85                  90                  95

Gly Thr Ser Phe His Phe Phe Ser Val Gly Gly Glu Ala Leu Glu Leu
        100                 105                 110

Gln Gly Val Val Phe Asn Tyr Arg Thr Lys Tyr Pro Asp Gly Thr Ile
            115                 120                 125

Phe Pro Lys Asn Ala Thr Val Gln Ser Gln Val Met Asn Thr Glu His
130                 135                 140

Lys Ala Tyr Leu Asp Lys Asn Lys Ala Tyr Pro Val Glu Cys Trp Val
145                 150                 155                 160

Pro Asp Pro Thr Arg Asn Glu Asn Thr Arg Tyr Phe Gly Thr Leu Thr
                165                 170                 175

Gly Gly Glu Asn Val Pro Pro Val Leu His Ile Thr Asn Thr Ala Thr
            180                 185                 190

Thr Val Leu Leu Asp Glu Phe Gly Val Gly Pro Leu Cys Lys Gly Asp
        195                 200                 205
```

```
Asn Leu Tyr Leu Ser Ala Val Asp Val Cys Gly Met Phe Thr Asn Arg
    210                 215                 220

Ser Gly Ser Gln Gln Trp Arg Gly Leu Ser Arg Tyr Phe Lys Val Gln
225                 230                 235                 240

Leu Arg Lys Arg Arg
            245

<210> SEQ ID NO 52
<211> LENGTH: 245
<212> TYPE: PRT
<213> ORGANISM: JC virus

<400> SEQUENCE: 52

Phe Leu Thr Pro Glu Met Gly Asp Pro Asp Glu His Phe Arg Gly Phe
1               5                   10                  15

Ser Lys Ser Ile Ser Ile Ser Asp Thr Phe Glu Ser Asp Ser Pro Asn
            20                  25                  30

Lys Asp Met Leu Pro Cys Tyr Ser Val Ala Arg Ile Pro Leu Pro Asn
        35                  40                  45

Leu Asn Glu Asp Leu Thr Cys Gly Asn Ile Leu Met Trp Glu Ala Val
50                  55                  60

Thr Leu Lys Thr Glu Val Ile Gly Val Thr Thr Leu Met Asn Val His
65                  70                  75                  80

Ser Asn Gly Gln Ala Thr His Asp Asn Gly Ala Gly Lys Pro Val Gln
                85                  90                  95

Gly Thr Ser Phe His Phe Phe Ser Val Gly Gly Glu Ala Leu Glu Leu
            100                 105                 110

Gln Gly Val Val Phe Asn Tyr Arg Thr Lys Tyr Pro Asp Gly Thr Ile
        115                 120                 125

Phe Pro Lys Asn Ala Thr Val Gln Ser Gln Val Met Asn Thr Glu His
130                 135                 140

Lys Ala Tyr Leu Asp Lys Asn Lys Ala Tyr Pro Val Glu Cys Trp Val
145                 150                 155                 160

Pro Asp Pro Thr Arg Asn Glu Asn Thr Arg Tyr Phe Gly Thr Leu Thr
                165                 170                 175

Gly Gly Glu Asn Val Pro Pro Val Leu His Ile Thr Asn Thr Ala Thr
            180                 185                 190

Thr Val Leu Leu Asp Glu Phe Gly Val Gly Pro Leu Cys Lys Gly Asp
        195                 200                 205

Asn Leu Tyr Leu Ser Ala Val Asp Val Cys Gly Met Phe Thr Asn Arg
    210                 215                 220

Ser Gly Ser Gln Gln Trp Arg Gly Leu Ser Arg Tyr Phe Lys Val Gln
225                 230                 235                 240

Leu Arg Lys Arg Arg
            245

<210> SEQ ID NO 53
<211> LENGTH: 245
<212> TYPE: PRT
<213> ORGANISM: JC virus

<400> SEQUENCE: 53

Phe Leu Thr Pro Glu Met Gly Asp Pro Asp Glu His Leu Arg Gly Phe
1               5                   10                  15

Ser Lys Ser Ile Ser Ile Ser Asp Thr Phe Glu Ser Asp Ser Pro Asn
            20                  25                  30
```

Lys Asp Met Leu Pro Cys Tyr Ser Val Ala Arg Ile Pro Leu Pro Asn
            35                  40                  45

Leu Asn Glu Asp Leu Thr Cys Gly Asn Ile Leu Met Trp Glu Ala Val
 50                  55                  60

Thr Leu Lys Thr Glu Val Ile Gly Val Thr Thr Leu Met Asn Val His
 65                  70                  75                  80

Ser Asn Gly Gln Ala Thr His Asp Asn Gly Ala Gly Lys Pro Val Gln
                85                  90                  95

Gly Thr Ser Phe His Phe Phe Ser Val Gly Gly Glu Ala Leu Glu Leu
               100                 105                 110

Gln Gly Val Val Phe Asn Tyr Arg Thr Lys Tyr Pro Asp Gly Thr Ile
               115                 120                 125

Phe Pro Lys Asn Ala Thr Val Gln Ser Gln Val Met Asn Thr Glu His
           130                 135                 140

Lys Ala Tyr Leu Asp Lys Asn Lys Ala Tyr Pro Val Glu Cys Trp Val
145                 150                 155                 160

Pro Asp Pro Thr Arg Asn Glu Asn Thr Arg Tyr Phe Gly Thr Leu Thr
                165                 170                 175

Gly Gly Glu Asn Val Pro Pro Val Leu His Ile Thr Asn Thr Ala Thr
            180                 185                 190

Thr Val Leu Leu Asp Glu Phe Gly Val Gly Pro Leu Cys Lys Gly Asp
        195                 200                 205

Asn Leu Tyr Leu Ser Ala Val Asp Val Cys Gly Met Phe Thr Asn Arg
    210                 215                 220

Ser Gly Ser Gln Gln Trp Arg Gly Leu Ser Arg Tyr Phe Lys Val Gln
225                 230                 235                 240

Leu Arg Lys Arg Arg
                245

<210> SEQ ID NO 54
<211> LENGTH: 245
<212> TYPE: PRT
<213> ORGANISM: JC virus

<400> SEQUENCE: 54

Phe Leu Thr Pro Glu Met Gly Asp Pro Asp Glu His Leu Arg Gly Phe
1               5                   10                  15

Ser Lys Ser Ile Ser Ile Ser Asp Thr Phe Glu Ser Asp Ser Pro Asn
            20                  25                  30

Lys Asp Met Leu Pro Cys Tyr Ser Val Ala Arg Ile Pro Leu Pro Asn
            35                  40                  45

Leu Asn Glu Asp Leu Thr Cys Gly Asn Ile Leu Met Trp Glu Ala Val
 50                  55                  60

Thr Leu Lys Thr Glu Val Ile Gly Val Thr Thr Leu Met Asn Val His
 65                  70                  75                  80

Ser Asn Gly Gln Ala Thr His Asp Asn Gly Ala Gly Lys Pro Val Gln
                85                  90                  95

Gly Thr Ser Phe His Phe Phe Ser Val Gly Gly Glu Ala Leu Glu Leu
               100                 105                 110

Gln Gly Val Val Phe Asn Tyr Arg Thr Lys Tyr Pro Asp Gly Thr Ile
               115                 120                 125

Phe Pro Lys Asn Ala Thr Val Gln Ser Gln Val Met Asn Thr Glu His
           130                 135                 140

Lys Ala Tyr Leu Asp Lys Asn Lys Ala Tyr Pro Val Glu Cys Trp Val

```
                145                 150                 155                 160
Pro Asp Pro Thr Arg Asn Glu Asn Thr Arg Tyr Phe Gly Thr Leu Thr
                    165                 170                 175
Gly Gly Glu Asn Val Pro Pro Val Leu His Ile Thr Asn Thr Ala Thr
                180                 185                 190
Thr Val Leu Leu Asp Glu Phe Gly Val Gly Pro Leu Cys Lys Gly Asp
            195                 200                 205
Asn Leu Tyr Leu Ser Ala Val Asp Val Cys Gly Met Phe Thr Asp Arg
        210                 215                 220
Ser Gly Ser Gln Gln Trp Arg Gly Leu Ser Arg Tyr Phe Lys Val Gln
225                 230                 235                 240
Leu Arg Lys Arg Arg
            245

<210> SEQ ID NO 55
<211> LENGTH: 20
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 55
gcagccagct atggctttac                                                    20

<210> SEQ ID NO 56
<211> LENGTH: 20
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 56
gctgccattc atgagaggat                                                    20

<210> SEQ ID NO 57
<211> LENGTH: 20
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 57
cctcaatgga tgttgccttt                                                    20

<210> SEQ ID NO 58
<211> LENGTH: 16
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 58
aaaaccaaag acccct                                                        16

<210> SEQ ID NO 59
<211> LENGTH: 24
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 59
ttgactcaat tacagaggta gaat                                               24
```

```
<210> SEQ ID NO 60
<211> LENGTH: 24
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 60
agaaattggg tagggtttt taac                                              24

<210> SEQ ID NO 61
<211> LENGTH: 24
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 61
aggtacgcct tgtgctctgt gttc                                             24

<210> SEQ ID NO 62
<211> LENGTH: 22
<212> TYPE: DNA
<213> ORGANISM: Artificial Sequence
<220> FEATURE:
<223> OTHER INFORMATION: SYNTHETIC OLIGONUCLEOTIDE

<400> SEQUENCE: 62
gtgcagggca ccagctttca tt                                               22
```

METHODS FOR THE DETECTION OF JC POLYOMA VIRUS

RELATED APPLICATIONS

This application is a continuation of U.S. application Ser. No. 13/147,484, filed Jun. 25, 2012, which is a national stage filing under 35 U.S.C. §371 of international application number PCT/US2010/00342, filed Feb. 5, 2010, which claims the benefit under 35 U.S.C. §119(e) from U.S. provisional application Ser. No. 61/150,310, filed Feb. 5, 2009, each of which is incorporated herein by reference.

FIELD OF THE INVENTION

The invention relates to methods for the detection of the human JC polyomavirus virus, diagnosis of progressive multifocal leukoencephalopathy (PML), and the development of therapeutics for PML.

BACKGROUND OF THE INVENTION

JC polyomavirus (JCV) infection in humans can cause a demyelinating disease of the central nervous system, progressive multifocal leukoencephalopathy (PML). However, JCV infection usually does not result in PML in healthy subjects. JCV infection is prevalent in many human populations without causing widespread PML. PML typically only develops in JCV-infected subjects that also have a weakened immune system. Subjects that are immuno-compromised due to a disease or an immunosuppressive treatment may be vulnerable to PML associated with a JCV infection.

SUMMARY OF THE INVENTION

Aspects of the invention relate to methods and compositions for determining whether a subject is susceptible to PML. In particular, the invention provides methods and compositions for determining whether a subject is at risk of developing PML if the subject's immune system is compromised or suppressed. For example, aspects of the invention relate to determining whether a subject is suitable for an initial or continued treatment with an immunosuppressive agent by determining the subject's risk profile for developing PML caused by a JCV infection.

The human genome is exposed to and may acquire many viruses during the lifetime of an individual. One example of such a virus is JC polyomavirus (JCV). JC virus infection is highly prevalent in humans. Primary infection with JCV occurs asymptomatically during childhood (Padgett & Walker, 1973). JCV is then disseminated throughout the body, probably through viraemia (Ikegaya et al., 2004). It is thought that JCV persist mostly in brain and renal tissue. While infection by JCV is asymptomatic in most subjects, infection may result in serious conditions (like PML) and even death in some subjects. Subjects most susceptible to PML are subjects that are immuno-compromised (e.g., AIDS patients) or subjects undergoing treatment with immunosuppressants (for instance after organ transplant or to treat an inflammation related condition such as multiple sclerosis). The present invention provides JCV variants, identifies a panel of variants including novel variants that are associated with increased PML risk, and methods related to discoveries of structural and functional connections between JCV variants and PML.

A "wild type" JCV sequence is used herein to refer to the sequence of any of the archetypes of JCV found in healthy subjects not having PML, and/or not being at risk for PML. In some embodiments, a consensus "wild type" reference sequence may be an average of sequences found in a group of healthy individuals. The discrepancy between high viral prevalence and low incidence of PML suggests that, in addition to immune dysfunction, there could be some unique viral characteristics that regulate the progression from the asymptomatic infection to the PML. In some embodiments, aspects of the invention relate to the discovery that the part of the viral surface protein that is responsible for viral interaction with cellular receptors and host cell infection acquires specific amino acid mutations in the patient somewhere en route from the kidney, the site of asymptomatic infection, to the CNS, the site of PML. Furthermore, in some embodiments PML-specific mutations change the ability of the viral capsid to bind various sialic acids and a variety of peripheral cell types but retain the ability to bind to CNS glial cells.

Based on the mathematical analysis of the published VP1 sequences from PML and non-PML patients, a positive selection of specific amino acid variants during PML is provided. However, since publicly available PML sequences were obtained from CSF or brain tissues of PML patients whereas non-PML sequences were obtained from the urine of healthy subjects, just based on the analysis of Genebank samples it could not unequivocally be demonstrated whether these amino acid variants were produced via a viral mutation in the patients or represented one or more rare viral variants that occur in all JCV clades and are enriched (e.g., positively selected) in PML cases as being more likely to be causing PML. According to aspects of the invention, VP1 substitutions occur within the patient and can lead to PML. This is supported by the analysis of matched urine-CSF and urine-plasma samples from the same patient taken at the same time point. CSF and plasma VP1 sequences from PML patients contained single amino acid substitutions or deletions of several amino acids relative to VP1 sequences isolated from the urine of the same patient. As shown herein, JC viral types found in the CSF, plasma, and urine of the same individual were of the same viral strain, whereas different patients carried different strains. Therefore, but without wishing to be bound by theory, the presence of VP1 amino acid substitutions in the CSF, but not in urine, results from the appearance of a mutation within a patient rather than by a dual infection with two different viral variants.

Some of the amino acid substitutions detected in the CSF and plasma of PML patients were previously described. However, these substitutions had not been directly correlated with increased PML risk and their structural and functional properties had not been associated with aspects of PML development and progression. Additional JCV VP1 mutations and/or deletions associated with PML also are provided herein.

According to aspects of the invention, substitutions in the VP1 protein may be more important for determining early disease progression (e.g., by enabling the virus to migrate from the periphery to the CNS and infecting CNS cells) rather than determining different outcomes in different clinical contexts. However, in some embodiments there may be an association between the type of mutation present in VP1 and certain clinical measurements. For example, lower JCV CSF replication levels were observed in patients with non-mutated virus or virus carrying mutations/deletions at positions 122-134. It also is possible that since mutations affect the strength of viral interaction with cellular receptors, viral release from dead cells also may be hindered for a virus that binds to those receptors tightly. Accordingly, a virus that has a weaker cell binding avidity may be found to be released into the extracellular space more abundantly. This is consistent with the observation that mutants at positions 55-61 and 265-271 lose their ability to bind to sialic acid receptors relative to non-mutated virus, and thus might have a better ability to detach from cell debris (after the virus kills the host cell) and find their way to the CSF.

Accordingly, even though a subject may be concurrently infected with several different versions of JCV (e.g., with different variants in different tissues or organs), PML associated mutations is more likely to arise from an existing JCV virus population in an individual that is infected with a wild-type JCV.

Aspects of the invention are based, at least in part, on the discovery that certain types of mutations in the JCV capsid protein are associated with the conversion of an asymptomatic form of JCV infection into a PML-associated form of JCV. According to aspects of the invention, without committing to any particular mechanism, mutations that disrupt the ability of a JCV particle to bind to or interact with sialic acid can result in the virus no longer being contained in the peripheral compartment of a subject and result in the virus obtaining freer passage to the CNS, a site of PML disease. In some embodiments, these mutations allow virus to achieve that by avoiding "trapping" on certain glycoproteins and glycolipid pseudoreceptors expressed in peripheral organs and cells, including but not limited to immune cells and red blood cells. Additionally, as some of these sites are targets on normal host immune response (antibody and T-cell) these mutations may allow virus evading recognition by the immune system, particularly in subjects with weakened immune systems.

Aspects of the invention provide methods and compositions for evaluating a subject's risk profile for PML.

In some embodiments, aspects of the invention relate to determining whether a subject has been exposed to an infection by any JCV variant. In some aspects, infection by a wild-type JCV variant may increase the risk profile for PML since PML associated mutations may arise from the wild-type JCV, even though these may be rare events. Accordingly, in some embodiments, a subject may be tested for the presence of one or more indicia of JCV infection (e.g., detection of viral proteins or nucleic acid, or indirectly via the detection of an immune response to a JCV infection, e.g., in the form of serum antibodies to JCV viral proteins). It should be appreciated that indicia of any JCV infection (e.g., wild-type or variant) may be evaluated. If a subject has already been exposed to a JCV infection, then the subject may be identified as having a higher risk profile than a non-infected subject. Accordingly, a JCV-infected subject that is being treated with an immunosuppressive agent, may be evaluated for specific JCV mutations or may be monitored more frequently than a non-infected subject.

In some embodiments, a subject that is being treated with (or is going to start a treatment with) an immunosuppressive agent is tested for one or more indicia of JCV infection. If one or more indicia of JCV infection are detected, the subject may be evaluated for the presence of one or more JCV variants associated with PML as described herein. If no indicia for JCV are detected, the subject may be monitored over time, e.g., every 4 weeks, monthly, every three months, every 4 months, every 6 months, or every 12 months, for the presence of any indicia of JCV infection. If a JCV infection is detected, the subject may be further evaluated for the presence of one or more JCV variants. If a JCV variant associated with increased PML risk is detected, the subject may be further monitored to detect any early signs of PML and/or the treatment regimen may be altered as described in more detail herein.

In one aspect the invention provides a method comprising interrogating a biological sample from a subject for at least one indicium of a variant JCV VP1 capsid protein that comprises a substitution of amino acid residue 122, and wherein the subject is determined to have an increased susceptibility for PML if the sample comprises the at least one indicium.

In one aspect the invention provides a method comprising interrogating a biological sample from a subject for at least one indicium of a variant JCV VP1 capsid protein that comprises a substitution of amino acid residue 2, and wherein the subject is determined to have an increased susceptibility for PML if the sample comprises the at least one indicium.

In one aspect the invention provides a method comprising interrogating a biological sample from a subject for at least one indicium of a variant JCV VP1 capsid protein that comprises a substitution of amino acid residue 66, and wherein the subject is determined to have an increased susceptibility for PML if the sample comprises the at least one indicium.

In one aspect the invention provides a method comprising interrogating a biological sample from a subject for at least one indicium of a variant JCV VP1 capsid protein that comprises a substitution of amino acid residue 283, and wherein the subject is determined to have an increased susceptibility for PML if the sample comprises the at least one indicium.

In some embodiments the method further comprises interrogating the biological sample for at least one indicium of a variant JCV VP1 capsid protein that comprises a substitution of at least one of amino acid residues 2 and 66. In some embodiments the method further comprises interrogating the biological sample for at least one indicium of a variant JCV VP1 capsid protein that comprises a substitution of at least one of amino acid residues 122 and 66. In some embodiments the method further comprises interrogating the biological sample for at least one indicium of a variant JCV VP1 capsid protein that comprises a substitution of at least one of amino acid residues 2 and 122. In some embodiments the sample is interrogated using an assay capable of detecting at least one indicium of each of variant JCV VP1 capsid proteins having a substitution of at least one of amino acid residues 2, 66, and 122, and wherein the subject is determined to have an increased susceptibility for PML if the sample comprises at least one indicium of at least one of the variant JCV VP1 capsid proteins. In some embodiments the sample is interrogated using an assay capable of detecting at least one indicium of each of variant JCV VP1 capsid proteins having a substitution of at least one of amino acid residues 2, 66, 122 and 283 and wherein the subject is determined to have an increased susceptibility for PML if the sample comprises at least one indicium of at least one of the variant JCV VP1 capsid proteins.

In some embodiments the method further comprises interrogating the biological sample for at least one indicium of a variant JCV VP1 capsid protein that comprises a deletion of amino acid fragment 50-51. In some embodiments the method further comprises interrogating the biological sample for at least one indicium of a variant JCV VP1 capsid protein that comprises a deletion of amino acid fragment 54-55. In some embodiments the method further comprises interrogating the biological sample for at least one indicium of a variant JCV VP1 capsid protein that comprises a deletion of amino acid fragment 123-125. In some embodiments the method further comprises interrogating the biological sample for at least one indicium of a variant JCV VP1 capsid protein that comprises a deletion of amino acid fragment 125-134. In some embodiments the method further comprises interrogating the biological sample for at least one indicium of a variant JCV VP1 capsid protein that comprises a deletion of amino acid fragment 125-136.

In some embodiments the method further comprises interrogating the biological sample for at least one indicium of a variant JCV VP1 capsid protein that comprises a deletion of one or more of amino acid fragments 50-51, 54-55 and 123-125. In some embodiments the sample is interrogated using an assay capable of detecting at least one indicium of each of variant JCV VP1 capsid proteins having a deletion of at least one of amino acid fragments 50-51, 54-55 and 123-125, and wherein the subject is determined to have an increased susceptibility for PML if the sample comprises at least one indicium of at least one of the variant JCV VP1 capsid proteins.

In some embodiments the method further comprises interrogating the biological sample for at least one indicium of a variant JCV VP1 capsid protein suspected of having low sialic acid binding.

In some embodiments the method further comprises interrogating the biological sample for at least one indicium of a variant JCV VP1 capsid protein that comprises a substitution of at least one of amino acid residues 55, 60, 265, 267, and 269. In some embodiments the sample is interrogated using an assay capable of detecting at least one indicium of each of variant JCV VP1 capsid proteins having a substitution of at least one of amino acid residues 55, 60, 265, 267, and 269, and wherein the subject is determined to have an increased susceptibility for PML if the sample comprises at least one indicium of at least one of the variant JCV VP1 capsid proteins.

In some embodiments the biological sample is a blood sample. In some embodiments the biological sample is a CSF sample. In some embodiments the biological sample is a urine sample.

In some embodiments the subject is known to have been previously infected with a wild-type JCV. In some embodiments a new biological sample from the subject is interrogated for at least one indicium of at least one variant JCV VP1 capsid protein at least twice each year. In some embodiments a new biological sample from the subject is interrogated for at least one indicium of at least one variant JCV VP1 capsid protein at least daily, weekly, monthly, bimonthly, quarterly, twice each year, yearly, every two years or every five years or any frequency in between.

In some embodiments the detection of at least one (e.g., 2, 3, 4, 5, or more) indicium of a variant JCV VP1 capsid protein is used to identify the subject as inappropriate for an immunosuppressive treatment. In some embodiments the detection of at least one, at least two, at least three, at least four, at least five, at least six, at least seven, at least 8, at least 9, at least 10 or more indicia of a variant JCV VP1 capsid protein is used to identify the subject as inappropriate for an immunosuppressive treatment.

In some embodiments the detection of at least one indicium of a variant JCV VP1 capsid protein is used to recommend a modification of an immunosuppressive treatment for the subject. In some embodiments the detection of at least one at least two, at least three, at least four, at least five, at least six, at least seven, at least 8, at least 9, at least 10 or more indicia of a variant JCV VP1 capsid protein is used to recommend a modification of an immunosuppressive treatment for the subject.

In some embodiments the absence of indicia of a variant JCV VP1 capsid protein is used to identify the subject as appropriate for an immunosuppressive treatment.

In some embodiments the absence of indicia of a variant JCV VP1 capsid protein is used to identify the subject as appropriate for continued immunosuppressive treatment.

In some embodiments the biological sample is interrogated for the presence of an antibody that is specific for a variant JCV VP1 capsid protein.

In some embodiments the biological sample is interrogated for the presence of a variant JCV VP1 capsid protein.

In some embodiments the biological sample is interrogated for the presence of a variant JCV VP1 capsid protein.

In some embodiments the biological sample is interrogated for the presence of a nucleic acid sequence that encodes a variant JCV VP1 capsid protein.

In some embodiments the biological sample is interrogated using an ELISA based analysis.

Accordingly, in some embodiments, subjects can be screened to determine whether they are at risk of developing PML. In certain embodiments, subjects can be screened to detect early stage PML before the disease progresses to a serious clinical condition. A subject may be assayed for PML risk or early stage PML by interrogating a biological sample obtained from the subject for indicia of exposure to a PML-associated variant of JCV, for example a JCV variant that is predicted to have reduced binding to sialic acid. The invention provides specific positions in the major JC virus capsid protein (JCV-VP1) that are associated with PML risk and/or PML disease progression. In some embodiments, the risk profile of a subject for PML is determined based on the mutational status at one or more selected positions of the VP1 protein of a JC virus to which the subject has been exposed.

Aspects of the invention are useful for detecting PML risk or early stage disease progression in susceptible subjects, for example, in patients that are immuno-compromised and/or being treated with immuno-suppressive agents.

Accordingly, in one aspect the invention provides methods for determining that a subject is susceptible to PML. In some embodiments, the method comprises determining that a subject is susceptible to PML if the subject harbors a JCV variant suspected of having low sialic acid binding properties (e.g., avidity or affinity).

In some embodiments, the method comprises determining whether a subject harbors a JCV variant suspected of having low sialic acid binding, and identifying the subject as being susceptible to PML if the subject harbors the JCV variant. In some embodiments, the method comprises testing a subject for the presence of a JCV variant suspected of having low sialic acid binding and identifying the subject as susceptible to PML if the presence of a JCV variant suspected of having low sialic acid binding is detected.

In one aspect the invention provides methods for determining that a subject is appropriate for an immunosuppressive treatment. In some embodiments, a method comprises determining that a subject is appropriate for an immunosuppressive treatment if the subject does not harbor a JCV variant suspected of having low sialic acid binding. In some embodiments, a method comprises determining whether a subject harbors a JCV variant suspected of having low sialic acid binding; and identifying the subject as appropriate for an immunosuppressive treatment if the subject does not harbor the JCV variant, or identifying the subject as being inappropriate for an immunosuppressive treatment if the subject harbors the JCV variant.

In one aspect the invention provides methods for determining that a subject is inappropriate for an immunosuppressive treatment. In some embodiments, a method comprises determining that a subject is inappropriate for an immunosuppressive treatment if the subject harbors a JCV variant suspected of having low sialic acid binding.

In some of the embodiments of the methods provided herein determining comprises assaying a biological sample from the subject for an indicium of the JCV variant suspected of having low sialic acid binding. In some of the embodiments of the methods provided herein a biological sample is a urine sample, a blood sample, plasma, serum, mucosal swab, or a CSF sample. In some of the embodiments of the methods provided herein the indicium is the presence of an antibody that can specifically bind to a JCV variant suspected of having low sialic acid binding. In some of the embodiments of the methods provided herein the indicium is the presence of a nucleic acid sequence associated with a JCV polypeptide variant suspected of having low sialic acid binding, wherein the nucleic acid sequence is not present in a wild type JCV.

In some of the embodiments of the methods provided herein the assaying comprises contacting the biological sample with a JCV antibody and evaluating the sample for the presence of a JCV variant or JCV peptide variant. In some of the embodiments of the methods provided herein the assaying comprises contacting the biological sample with a JCV peptide and evaluating the sample for the presence of a JCV antibody. In some of the embodiments of the methods provided herein the assaying comprises performing a PCR reaction on the biological sample and evaluating the sample for the presence of a JCV nucleic acid variant.

In some of the embodiments of the methods provided herein the immunosuppressive treatment comprises administering an immunosuppressant drug. In some of the embodiments of the methods provided herein the immunosuppressive treatment comprises administration of an anti-VLA4 antibody. In some of the embodiments of the methods provided herein, the immunosuppressant drug is natalizumab.

In some of the embodiments of the methods provided herein the JCV variant suspected of having low sialic acid binding is a JCV variant comprising one or more mutations in the JCV sialic acid binding site. In some of the embodiments of the methods provided herein the mutation in the JCV sialic acid binding site is L55F, K60M, K60E, K60N, N265D, N265T, S267F, S267L, S269F, S269Y or S269C.

In some of the embodiments of the methods provided herein the low sialic acid binding of the JCV variant is lower than the sialic binding of WT JCV.

In some of the embodiments of the methods provided herein the subject is in need of treatment with an immunosuppressant drug or the subject is being treated with an immunosuppressant drug.

In one aspect the invention provides a method comprising obtaining a biological sample from a subject, assaying the biological sample for an indicium of a JCV variant suspected of having low sialic acid binding, wherein the subject is identified as being susceptible to PML if the biological sample contains an indicium of the JCV variant.

In one aspect the invention provides a method comprising obtaining a biological sample from a subject, assaying the biological sample for an indicium of a JCV variant suspected of having low sialic acid binding, wherein the subject is identified as either i) appropriate for an immunosuppressive treatment if the biological sample does not contain the indicium of the JCV variant ii) inappropriate for an immunosuppressive treatment if the biological sample contains the indicium of the JCV variant.

In one aspect the invention provides a method comprising monitoring a subject receiving an immunosuppressive treatment for harboring a JCV variant suspected of having low sialic acid binding.

In one aspect the invention provides a method comprising monitoring a subject receiving an immunosuppressive treatment for a sign of exposure to JCV, and, if the sign of exposure to JCV is detected, then monitoring the subject for harboring a JCV variant suspected of having low sialic acid binding.

In some of the embodiments of the methods provided herein the monitoring comprises periodically obtaining and assaying a biological sample from the subject for an indicium of the JCV variant.

In one aspect the invention provides a method comprising obtaining a biological sample from a subject, assaying the biological sample for an indicium of JCV, wherein if the biological sample contains an indicium of JCV, the subject is periodically monitored for the presence of a JCV variant suspected of having low sialic acid binding, and wherein if the clinical sample does not contain JCV, the subject is periodically monitored for an exposure JCV.

In one aspect the invention provides a method of determining whether a treatment regimen for administering an immunosuppressive agent to a subject should be modified, the method comprising obtaining a biological sample from a subject, assaying the biological sample for an indicium of a JCV variant suspected of having low sialic acid binding, wherein the treatment regimen should be modified for the subject if the biological sample has the indicium of the JCV variant.

In some of the embodiments of the methods provided herein the treatment regimen should be modified by administering a lower dose of the immunosuppressive agent, replacing the immunosuppressive agent with a different immunosuppressive agent, or halting administration of the immunosuppressive agent.

In one aspect the invention provides a method comprising administering a first immunosuppressant drug to a subject, and monitoring if the subject harbors a JCV variant suspected of having low sialic acid binding. In some of the embodiments of the methods provided herein the dosage and/or frequency of administration of the first immunosuppressant drug is reduced if the subject harbors the JCV variant. In some of the embodiments of the methods provided herein the first immunosuppressant drug is replaced with a second immunosuppressant drug if the subject harbors the JCV variant. In some of the embodiments of the methods provided herein the subject is screened for a symptom of PML if the subject harbors the JCV variant. In some of the embodiments of the methods provided herein the subject is treated for PML if the subject harbors the JCV variant.

In one aspect the invention provides a method of detecting a JCV variant suspected of having low sialic acid binding, the method comprising interrogating a biological sample from a subject using a high sensitivity assay specific for the indicium of a JCV variant suspected of having low sialic acid binding. In some of the embodiments of the methods provided herein the interrogating comprises contacting the biological sample with an antibody that can specifically bind the JCV variant. In some of the embodiments of the methods provided herein the interrogating comprises contacting the biological sample with a JCV variant polypeptide.

In some of the embodiments of the methods provided herein the interrogating comprises contacting the biological sample with a JCV variant nucleic acid.

Aspects of the invention include panels of JCV-VP1 amino acid positions at which sequence variations are associated with PML risk and/or disease progression. Methods and compositions are provided for screening subjects to identify individuals that have been exposed to a variant JC virus having PML-associated sequence variations at one or more of the VP-1 amino acid positions in a panel.

Aspects of the invention can be used to diagnose PML, or to evaluate and/or monitor PML disease progression, regression, and/or status in a subject.

Certain aspects of the invention relate to evaluating therapeutic treatments for PML.

Other aspects of the invention relate to vaccines against PML-associated JC virus variants.

In one aspect, the invention provides a method for determining if a subject is at risk for, or has, progressive multifocal leukoencephalopathy (PML), the method comprising assaying a biological sample from a subject for an indicium of exposure to a variant JC polyomavirus. In some embodiments the assay interrogates at least one JCV-VP1 position selected from positions 69, 74, 75, 113, 117, 128, 134, 158, 164, 223, 271, 321, 332, and 345 in Table 1A for the presence of a sequence variation, and wherein the subject is identified as being at risk for, or having, PML if a sequence variation is present at one or more of the interrogated positions.

In one aspect, the invention provides a method for determining if a subject is at risk for, or has, progressive multifocal leukoencephalopathy (PML), the method comprising assaying a biological sample from a subject for an indicium of exposure to a variant JC polyomavirus. In some embodiments the assay interrogates one position for the presence of a sequence variation. In some embodiments the position is position 164. In some embodiments the subject is identified as being at risk for, or having, PML if a sequence variation is present at position 164.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates at least eight JCV-VP1 positions selected from the positions in Table 1A for the presence of a sequence variation, and wherein the subject is identified as being at risk for, or having, PML if a sequence variation is present at one or more of the interrogated positions.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates at least eight JCV-VP1 positions selected from the positions in Table 1A for the presence of a sequence variation, wherein a sequence variation is one of the following 55F, 60M, 60E, 61L, 66H, 66N, 69D, 74S, 75R, 113L, 117S, 123C, 128A, 134G, 158L, 164K, 223A, 265D, 265T, 267F, 267L, 269F, 269Y, 271H, 321V, 332E or 345K, and wherein the subject is identified as being at risk for, or having, PML if a sequence variation is present at one or more of the interrogated positions.

In some embodiments, more than eight positions in Table 1A may be interrogated. In some embodiments 9, 10, 11, 12, 13, 14, 15, 16, 17, 18, 19, 20, 21 or 22 positions are interrogated.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates at least five JCV-VP1 positions selected from the positions in Table 1B for the presence of a sequence variation, and wherein the subject is identified as being at risk for, or having, PML if a sequence variation is present at one or more of the interrogated positions.

In some embodiments, more than five positions in Table 1B may be interrogated. In some embodiments six or seven positions are interrogated.

In one aspect, the invention provides a method for determining if a subject is at risk, or has, for progressive multifocal leukoencephalopathy (PML), the method comprising assaying a biological sample from a subject for an indicium of exposure to a variant JC polyomavirus, wherein the assay interrogates at least four JCV-VP1 positions selected from the positions in Table 1C for the presence of a sequence variation, and wherein the subject is identified as being at risk for, or having, PML if a sequence variation is present at one or more of the interrogated positions.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates at least two JCV-VP1 positions selected from the positions in Table 1D for the presence of a sequence variation, and wherein the subject is identified as being at risk for, or having, PML if a sequence variation is present at one or more of the interrogated positions.

In some embodiments, more than two positions in Table 1D may be interrogated. In some embodiments 3, 4 or 5 positions are interrogated.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates at least two JCV-VP1 positions selected from the positions in Table 1F for the presence of a sequence variation, and wherein the subject is identified as being at risk for, or having, PML if a sequence variation is present at one or more of the interrogated positions.

In some embodiments, more than two positions in Table 1F may be interrogated. In some embodiments 3 or 4 positions are interrogated.

In one aspect, the invention provides a method for determining if a subject is at risk for, or has, progressive multifocal leukoencephalopathy (PML), the method comprising: assaying a biological sample from a subject for an indicium of exposure to a variant JC polyomavirus, wherein the assay interrogates at least eight JCV-VP1 positions selected from the positions in Table 1G for the presence of a sequence variation, and wherein the subject is identified as being at risk for, or having, PML if a sequence variation is present at one or more of the interrogated positions.

In some embodiments, more than eight positions in Table 1G may be interrogated. In some embodiments 9, 10, 11, 12, 13, 14 or 15 positions are interrogated.

In one aspect, the invention provides a method for determining if a subject is at risk for, or has, progressive multifocal leukoencephalopathy (PML), the method comprising: assaying a biological sample from a subject for an indicium of exposure to a variant JC polyomavirus, wherein the assay interrogates at least one JCV-VP1 position selected from the positions in Table 1H for the presence of a sequence variation, and wherein the subject is identified as being at low risk for, or not having, PML if a sequence variation is present at one or more of the interrogated positions. In some embodiments two positions in Table 1H are interrogated.

In one aspect, the invention provides a method for determining if a subject is at risk for, or has, progressive multifocal leukoencephalopathy (PML), the method comprising: assaying a biological sample from a subject for an indicium of exposure to a variant JC polyomavirus, wherein the assay interrogates at least one JCV-VP1 position selected from the positions in Table 1H for the presence of a sequence variation, wherein a sequence variation is one of the following 115E or 277K, and wherein the subject is identified as being at low risk for, or not having, PML if a sequence variation is present at one or more of the interrogated positions.

In some embodiments, two positions in Table 1H are interrogated.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates positions in selected regions of JCV-VP1 for the presence of a sequence variation, and wherein the subject is identified as being at low risk for, or not having, PML if less than a selected number of sequence variations are present at the interrogated positions.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates at least positions 55-75 and 265-271 of JCV-VP1 for the presence of a sequence variation, and wherein the subject is identified as being at low risk for, or not having, PML if less than two sequence variations are present at the interrogated positions.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates at least positions 55-75, 113-164, 223, 265-277 and 321-345 of JCV-VP1 for the presence of a sequence variation, and wherein the subject is identified as being at low risk for, or not having, PML if less than three sequence variations are present at the interrogated positions.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates at least positions 55-75, 113-164, 223, 265-277 and 321-345 of JCV-VP1 for the presence of a sequence variation, and wherein the subject is identified as being at low risk for, or not having, PML if less than two sequence variations are present at the interrogated positions.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates position 164 and at least one other JCV-VP1 position selected from the positions in Table 1A for the presence of a sequence variation, and wherein the subject is identified as being at risk for, or having, PML if a sequence variation is present at one or more of the interrogated positions.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates position 164 and at least one other JCV-VP1 position selected from the positions in Table 1A for the presence of a sequence variation, and wherein the subject is identified as being at risk for, or having, PML if a sequence variation is present at two or more of the interrogated positions.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates positions in selected regions of JCV-VP1 for the presence of a sequence variation, and wherein the subject is identified as being at risk for, or having, PML if the number of amino acids with a specific characteristic present at the interrogated positions has increased. In some embodiments, the specific characteristic is non-polarity.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates at least positions 55-75 and 265-271 of JCV-VP1 for the presence of a sequence variation, and wherein the subject is identified as being at risk for, or having, PML if the total number of non-polar amino acid variants (Gly, Ala, Val, Leu, Ile, or Pro) or aromatic variants (Phe, Tyr, or Trp) at the interrogated positions has increased.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates at least positions 55-75, 113-164, 223, 265-277 and 321-345 of JCV-VP1 for the presence of a variant, and wherein the subject is identified as being at risk for, or having, PML if the total number of non-polar amino acid variants or aromatic variants at the interrogated positions has increased.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates at least positions 55-75 and 265-271 of JCV-VP1 for the presence of a sequence variation, and wherein the subject is identified as being at risk for, or having, PML if the one or more of the sequence variations at the interrogated positions result in an increase in non-polar surface area of 10 square angstrom or more per sequence variation.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates positions in selected regions of JCV-VP1 for the presence of a sequence variation, and wherein the subject is identified as being at low risk for, or not having, PML if the number of amino acids with a specific characteristic present at the interrogated positions has decreased. In some embodiments the specific characteristic is polarity.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates at least positions 55-75 and 265-271 of JCV-VP1 for the presence of a sequence variation, and wherein the subject is identified as being at risk for, or having, PML if the total number of polar amino acid variants (Ser, Thr, Cys, Met, Asn, or Gln), positively charged variants (Lys, Arg, or His), or negatively charged variants (Asp or Glu) at the interrogated positions has decreased.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates at least positions 55-75, 113-164, 223, 265-277 and 321-345 of JCV-VP1 for the presence of a sequence variation, and wherein the subject is identified as being at risk for, or having, PML if the total number of polar amino acid variants, positively charged variants, or negatively charged variants at the interrogated positions has decreased.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates at least positions 55-75 and 265-271 of JCV-VP1 for the presence of a sequence variation, and wherein the subject is identified as being at risk for, or having, PML if the one or more of the sequence variations at the interrogated positions result in a decrease in polar surface area of 10 square angstrom or more per sequence variation.

In one aspect, the invention provides methods for interrogating selected JCV-VP1 positions for sequence variations in a biological sample.

In some embodiments, interrogating selected JCV-VP1 positions for sequence variations comprises determining the presence in a biological sample of one or more antibodies that specifically bind polypeptides comprising one or more amino acid sequence variations selected from the panel of Table 1A or 1H. In some embodiments the presence of the one or more antibodies is determined by specific binding to recombinantly produced polypeptides comprising the one or more amino acid sequence variations. In some embodiments the presence of the one or more antibodies is determined by specific binding to synthetically produced polypeptides comprising the one or more amino acid sequence variations.

In some embodiments, interrogating selected JCV-VP1 positions for sequence variations comprises determining the presence in the biological sample of one or more polypeptides comprising the one or more amino acid sequence variations selected from the panel of Table 1A or 1H. In some embodiments the presence of the one or more polypeptides is detected by specific binding of the polypeptides to one or more peptide binding agents. In some embodiments the peptide binding agent is an antibody.

In some embodiments, interrogating selected JCV-VP1 positions for sequence variations comprises determining the presence in a biological sample of nucleic acids that code for the one or more amino acid sequence variations selected from the panel of Table 1A or 1H.

In some embodiments, interrogating selected JCV-VP1 positions for sequence variations is performed in a sample of blood, cerebrospinal fluid, serum, urine, sputum, bone marrow, brain, spleen or kidney, or other tissue.

In some embodiments, the method for determining if a subject is at risk for, or has, progressive multifocal leukoencephalopathy (PML), comprises assaying a biological sample from a subject for an indicium of exposure to a variant JC polyomavirus, wherein the exposure to variant JCV comprises a current infection with a variant JCV.

In some embodiments, the method for determining if a subject is at risk for, or has, progressive multifocal leukoencephalopathy (PML), comprises assaying a biological sample from a subject for an indicium of exposure to a variant JC polyomavirus, the exposure to variant JCV comprises a prior infection, or the variant JCV is not detectable in the blood or urine of the subject.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates at least two JCV-VP1 positions selected from the positions in Table 1F for the presence of a sequence variation, and wherein the subject is identified as being at low risk for, or not having, PML if no sequence variation is present at one of the interrogated positions.

In one aspect, the invention provides a method for determining if a subject is at risk for, or has, progressive multifocal leukoencephalopathy (PML), the method comprising assaying a biological sample from a subject for an indicium of exposure to a variant JC polyomavirus, wherein the assay interrogates at least two JCV-VP1 positions selected from the positions in Table 1G for the presence of a sequence variation, and wherein the subject is identified as being at low risk for, or not having, PML if no sequence variation is present at one of the interrogated positions.

In one aspect, the invention provides kits for diagnosing if a subject is at risk for PML.

In some embodiments the kit for diagnosing if a subject is at risk for PML comprises one or more containers, each container containing a polypeptide comprising one or more amino acid sequence variations selected from the panel of Table 1A, Table 17 and/or Table 18, and/or one or more other variants described herein, and the kit further comprising instructions for using the polypeptide to determine the presence of antibodies that specifically bind these polypeptides.

In some embodiments, the kit for diagnosing if a subject is at risk for PML comprises one or more containers, each container containing a polypeptide comprising one or more amino acid sequence variations selected from the panel of Table 1B, and the kit further comprising instructions for using the polypeptide to determine the presence of antibodies that specifically bind these polypeptides.

In some embodiments, the kit for diagnosing if a subject is at risk for PML comprises one or more containers, each container containing a polypeptide comprising one or more amino acid sequence variations selected from the panel of Table 1C, and the kit further comprising instructions for using the polypeptide to determine the presence of antibodies that specifically bind these polypeptides.

In some embodiments, the kit for diagnosing if a subject is at risk for PML comprises one or more containers, each container containing a polypeptide comprising one or more amino acid sequence variations selected from the panel of Table 1D, and the kit further comprising instructions for using the polypeptide to determine the presence of antibodies that specifically bind these polypeptides.

In some embodiments, the kit for diagnosing if a subject is at risk for PML comprises one or more containers, each container containing a polypeptide comprising one or more amino acid sequence variations selected from the panel of Table 1F, and the kit further comprising instructions for using the polypeptide to determine the presence of antibodies that specifically bind these polypeptides.

In some embodiments, the kit for diagnosing if a subject is at risk for PML comprises one or more containers, each container containing a polypeptide comprising one or more amino acid sequence variations selected from the panel of Table 1G, and the kit further comprising instructions for using the polypeptide to determine the presence of antibodies that specifically bind these polypeptides.

In some embodiments, the kit for diagnosing if a subject is at risk for PML comprises one or more containers, each container containing a polypeptide comprising one or more amino acid sequence variations selected from the panel of Table 1H, and the kit further comprising instructions for using the polypeptide to determine the presence of antibodies that specifically bind these polypeptides.

In some embodiments, the kit for diagnosing if a subject is at risk for PML comprises one or more containers, each container containing a polypeptide comprising an amino acid sequence variations at position 164, and the kit further comprising instructions for using the polypeptide to determine the presence of antibodies that specifically bind these polypeptides.

In one aspect, the invention provides methods for determining onset, progression, or regression, of PML in a subject.

In one embodiment of the method for determining onset, progression, or regression, of PML in a subject, the method comprising determining the number of amino acid sequence variations in variant JCV-VP1 in a first biological sample obtained from the subject, determining the number of amino acid sequence variations in variant JCV-VP1 in a second biological sample obtained from the subject at a later time than the first sample was obtained, comparing the number of sequence variations in the first sample with number of sequence variations in the second sample, wherein a lower number of sequence variations in the first sample compared with the number of sequence variations in the second sample indicates onset or progression of PML in the subject, and wherein a higher number of sequence variations in the first sample compared with the number of sequence variations in the second sample indicates regression of PML in the subject.

In one embodiment of the method for determining onset, progression, or regression, of PML in a subject, the sequence variations are selected from the positions in Table 1A.

In one embodiment of the method for determining onset, progression, or regression, of PML in a subject, the sequence variations are selected from the positions in Table 1B.

In one embodiment of the method for determining onset, progression, or regression, of PML in a subject, the sequence variations are selected from the positions in Table 1C.

In one embodiment of the method for determining onset, progression, or regression, of PML in a subject, the sequence variations are selected from the positions in Table 1D.

In one embodiment of the method for determining onset, progression, or regression, of PML in a subject, the sequence variations are selected from the positions in Table 1F.

In one embodiment of the method for determining onset, progression, or regression, of PML in a subject, the sequence variations are selected from the positions in Table 1G.

In some embodiments of the method for determining onset, progression, or regression, of PML in a subject, the sequence variations are determined by comparing the variant JCV-VP1 to a wild type JCV-VP1.

In one embodiment of the method for determining onset, progression, or regression, of PML in a subject, the method comprises determining if a sequence variation is present at position 164 in variant JCV-VP1 in a first biological sample obtained from the subject, determining if a sequence variation is present at position 164 in variant JCV-VP1 in a second biological sample obtained from the subject at a later time than the first sample was obtained, wherein absence of the sequence variation in the first sample and the presence of the sequence variation in the second sample indicates onset or progression of PML in the subject, and wherein presence of the sequence variation in the first sample and absence of the sequence variation in the second sample indicates regression of PML in the subject.

In some embodiments of the method for determining onset, progression, or regression, of PML in a subject, the method further comprises additional monitoring of the onset, progression, or regression, of PML in a subject by obtaining additional samples from the subject at later time points, determining the number of amino acid sequence variations in JCV-VP1 in these samples, and comparing the number of sequence variations in these samples to the number of sequence variations in one or more previous samples.

In some embodiments of the method for determining onset, progression, or regression, of PML in a subject, the subject is monitored while undergoing treatment with an immunosuppressant. In some embodiments the immunosuppressant is natalizumab.

In one embodiment of the method for determining onset, progression, or regression, of PML in a subject, the method comprises determining the viral load of a variant JCV-VP1 in a first biological sample obtained from the subject, determining the viral load of a variant JCV-VP1 in a second biological sample obtained from the subject at a later time than the first sample was obtained, comparing the viral load in the first sample with viral load in the second sample, wherein a lower viral load in the first sample compared with the viral load in the second sample indicates onset or progression of PML in the subject, and wherein a higher viral load in the first sample compared with the viral load in the second sample indicates regression of PML in the subject.

In some embodiments of the method for determining onset, progression, or regression, of PML in a subject, the method comprising determining the viral load of a variant JCV-VP1, the variant JCV-VP1 comprises one or more sequence variations selected from the positions in Table 1A.

In some embodiments of the method for determining onset, progression, or regression, of PML in a subject, the method comprising determining the viral load of a variant JCV-VP1, the variant JCV-VP1 comprises one or more sequence variations selected from the positions in Table 1B.

In some embodiments of the method for determining onset, progression, or regression, of PML in a subject, the method comprising determining the viral load of a variant JCV-VP1, the variant JCV-VP1 comprises one or more sequence variations selected from the positions in Table 1C.

In some embodiments of the method for determining onset, progression, or regression, of PML in a subject, the method comprising determining the viral load of a variant JCV-VP1, the variant JCV-VP1 comprises one or more sequence variations selected from the positions in Table 1D.

In some embodiments of the method for determining onset, progression, or regression, of PML in a subject, the method comprising determining the viral load of a variant JCV-VP1, the variant JCV-VP1 comprises one or more sequence variations selected from the positions in Table 1F.

In some embodiments of the method for determining onset, progression, or regression, of PML in a subject, the method comprising determining the viral load of a variant JCV-VP1, the variant JCV-VP1 comprises one or more sequence variations selected from the positions in Table 1G.

In some embodiments of the method for determining onset, progression, or regression, of PML in a subject, the method comprising determining the viral load of a variant JCV-VP1, the variant JCV-VP1 comprises a sequence variation at position 164.

In some embodiments of the method for determining onset, progression, or regression, of PML in a subject, the viral load of variant JCV-VP1 is compared to the viral load of a wild type JCV-VP1.

In some embodiments of the method for determining onset, progression, or regression, of PML in a subject, the method comprising determining the viral load of a variant JCV-VP1, the method further comprises additional monitoring of the onset, progression, or regression, of PML in a subject by obtaining additional samples from the subject at later time points, determining the viral load of variant JCV-VP1 in these samples, and comparing the viral load in these samples to the viral load in one or more previous samples.

In some embodiments of the method for determining onset, progression, or regression, of PML in a subject, the method comprising determining the viral load of a variant JCV-VP1, the subject is monitored while undergoing treatment with an immunosuppressant. In some embodiments the immunosuppressant is natalizumab.

In one aspect, the invention provides methods for monitoring response to treatment for PML in a subject.

In some embodiments of the method for monitoring response to treatment for PML in a subject, the method comprises determining the number of amino acid sequence variations in JCV-VP1 in a first biological sample obtained from the subject, administering the PML treatment to the subject, determining the number of amino acid sequence variations in JCV-VP1 in a second sample, wherein the second sample is obtained from the subject after treatment and at a time later than the first sample, and comparing the number of amino acid sequence variations in the first sample with the number of amino acid sequence variations in the second sample, wherein a lower number of amino acid sequence variations in the second sample than in the first sample indicates that the subject is responsive to the PML treatment.

In some embodiments of the method for monitoring response to treatment for PML in a subject, the method comprises determining the viral load of a JCV variant in a first biological sample obtained from the subject, administering the PML treatment to the subject, determining the viral load of a JCV variant in a second sample, wherein the second sample is obtained from the subject after treatment and at a time later than the first sample, and comparing the viral load in the first sample with the viral load in the second sample, wherein a lower viral load in the second sample than in the first sample indicates that the subject is responsive to the PML treatment.

In one aspect, the invention provides methods for selecting a course of treatment of a subject having or suspected of having PML.

In some embodiments of the method for selecting a course of treatment of a subject having or suspected of having PML, the method comprises determining the number of amino acid sequence variations in JCV-VP1 in a biological sample obtained from the subject, comparing the number of sequence variations to a control number of sequence variations, determining the stage of PML based at least in part on the difference in the number of sequence variations in the sample compared to the control number of sequence variations, and selecting a course of treatment for the subject appropriate to the stage of PML of the subject.

In some embodiments of the method for selecting a course of treatment of a subject having or suspected of having PML, the method comprises determining the viral load of a JCV variant in a biological sample obtained from the subject, comparing the viral load to the viral load in a control sample, determining the stage of PML based at least in part on the difference in viral load in the sample compared to the control sample, and selecting a course of treatment for the subject appropriate to the stage of PML of the subject.

In one aspect, the invention provides methods for deciding or aiding in the decision to discontinue treatment of a subject with one or more immunosuppressants.

In some embodiments of the method for deciding or aiding in the decision to discontinue treatment of a subject with one or more immunosuppressants comprises determining the number of amino acid sequence variations in JCV-VP1 in a biological sample obtained from the subject, comparing the number of sequence variations to a control number of sequence variations, determining a decision to discontinue treatment of a subject with one or more immunosuppressants based at least in part on the difference in the number of sequence variations in the sample compared to the control number of sequence variations.

In some embodiments of the method for deciding or aiding in the decision to discontinue treatment of a subject with one or more immunosuppressants comprises determining the vial load of a JCV variant in a biological sample obtained from the subject, comparing the viral load to a viral load in a control sample, determining a decision to discontinue treatment of a subject with one or more immunosuppressants based at least in part on the difference in viral load in the sample compared to the control sample.

In some embodiments of the method for deciding or aiding in the decision to discontinue treatment of a subject with one or more immunosuppressants, the immunosuppressant is natalizumab.

In one aspect, the invention provides methods for identifying candidate therapeutic compounds.

In some embodiments of the method for identifying a candidate therapeutic compound, the method comprises contacting an isolated polypeptide comprising one or more amino acid sequence variations selected from the panel of Table 1A, Table 17 and/or Table 18, and/or one or more other variants described herein, with a compound to determine if the compound binds to the isolated polypeptide, wherein if the compound binds to the isolated polypeptide the compound is a candidate therapeutic compound.

In one aspect, the invention also provides candidate therapeutic compounds identified by contacting an isolated polypeptide comprising one or more amino acid sequence variations selected from the panel of Table 1A, Table 17 and/or Table 18, and/or one or more other variants described herein.

In some embodiments of the method for identifying a candidate therapeutic compound, the method comprises determining a number of amino acid sequence variations in JCV-VP1 in a first biological sample obtained from the subject, administering a compound, determining the number of amino acid sequence variations in JCV-VP1 in a second biological sample obtained from the subject at a time after administration of the compound, wherein if the number of amino acid sequence variations in JCV-VP1 in the second sample is lower than in the first sample the compound is a candidate therapeutic compound.

In one aspect, the invention also provides candidate therapeutic compounds identified by determining a number of amino acid sequence variations in JCV-VP1 in a first biological sample obtained from the subject, administering a compound, and determining the number of amino acid sequence variations in JCV-VP1 in a second biological sample obtained from the subject at a time after administration of the compound.

In some embodiments of the method for identifying a candidate therapeutic compound, the method comprises determining a viral load of a JCV variant in a first biological sample obtained from the subject, administering a compound, determining the viral load of a JCV variant in a second biological sample obtained from the subject at a time after administration of the compound, wherein if the viral load in the second sample is lower than in the first sample the compound is a candidate therapeutic compound.

In one aspect, the invention also provides candidate therapeutic compounds identified by determining a viral load of a JCV variant in a first biological sample obtained from the subject, administering a compound and determining the viral load of a JCV variant in a second biological sample obtained from the subject at a time after administration of the compound In one aspect, the invention also provides vaccines comprising a polypeptide having a sequence variation at one or more JCV-VP1 positions selected from the positions in Table 1A, Table 17 and/or Table 18, and/or one or more other variants described herein. In some embodiments the vaccine comprises two or more polypeptides having a sequence variation at one or more JCV-VP1 positions selected from the positions in Table 1A. In some embodiments, the vaccine further comprises an adjuvant.

In one aspect, the invention also provides methods of immunizing a subject against PML, the method comprising administering a vaccine comprising one or more polypeptides having a sequence variation at one or more JCV-VP1 positions selected from the positions in Table 1A, Table 17 and/or Table 18, and/or one or more other variants described herein.

In one aspect, the invention also provides an isolated antibody that specifically binds to a polypeptide having a sequence variation at one or more JCV-VP1 positions selected from the positions in Table 1A. In some embodiments the polypeptide has 2, 3, 4, 5, or more sequence variations at JCV-VP1 positions selected from the positions in Table 1A, Table 17 and/or Table 18, and/or one or more other variants described herein. In some embodiments, the antibody is a monoclonal antibody. In some embodiments the antibody is a polyclonal antibody.

In certain embodiments, the antibody specifically binds to a VP1 particle comprising at least one VP1 polypeptide containing a sequence variation described herein. A VP1 particle useful in the invention can be produced using methods known in the art, in general by expressing a recombinant VP1 polypeptide comprising a variant described herein. A VP1 particle contains at least 2, 4, 10, 20, 30, 40, or 50 VP1 polypeptides. In some embodiments, the VP1 particle comprises only VP1 polypeptides containing a variant. In other embodiments, the VP1 particle is a heterogeneous particle containing more than one VP1 polypeptide sequence; e.g., more than one variant polypeptide or at least one variant polypeptide and at least one wild type polypeptide.

The invention also encompasses an isolated nucleic acid sequence encoding a VP1 polypeptide variant (e.g., containing one or more variants described in Tables 1A-1H, Table 17 and/or Table 18, and/or one or more other variants described herein) or a peptide of such a polypeptide, the polypeptide or peptide includes the sialic acid binding region of a VP1 polypeptide. In some cases, the invention includes such an isolated nucleic acid sequence operatively linked to a heterologous expression control sequence. The invention also includes vectors and host cells, transiently or stably transfected containing such nucleic acid sequences. Methods for producing such sequences, vectors, and host cells are known in the art.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing", "involving", and variations thereof herein, is meant to encompass the items listed thereafter and equivalents thereof as well as additional items.

BRIEF DESCRIPTION OF THE DRAWINGS

FIG. 1 shows the comparison of a reference JCV-VP1 sequence (SEQ ID NO: 1) to the SV40 COA sequence (SEQ ID NO: 2);

FIGS. 3-1 to 3-8 show VP1 peptide sequences;

FIG. 6 shows the quality of the viral like particles;

FIG. 7 shows that WT JCV binds to some glycans;

FIG. 8 shows the structure of selected gangliosides and their ability to bind to WT JCV;

FIG. 15 compares mutant JCV and WT JCV antibodies for their ability to bind to a mutant JCV-VLP;

FIG. 16 compares mutant JCV and WT JCV antibodies for their ability to bind to a mutant JCV-VLP;

DETAILED DESCRIPTION OF THE INVENTION

Figure 2:
FIG. 2 shows a model of JCV-VP1.

Aspects of the invention relate to identifying and managing the healthcare of subjects who are at increased risk of progressive multifocal leukoencephalopathy (PML). PML can be caused by a JC polyomavirus (JCV) infection in humans, particularly in subjects that have a weakened immune system. However, PML does not develop in all JCV-infected subjects having weakened immune systems. According to the invention, only certain JCV variants cause PML. In some embodiments, JCV variants that have reduced sialic acid binding are particularly likely to cause PML. Accordingly, aspects of the invention relate to methods and compositions for detecting the presence of JCV variants predicted to have reduced binding to sialic acid.

According to aspects of the invention, and without wishing to be bound by theory, a JCV variant that has low sialic acid binding, relative to the sialic binding of a wild-type JCV, has reduced binding to peripheral sites (e.g., sialic acid on peripheral cells, proteins, sugars, or other molecules). Therefore, in some embodiments these variants are more likely to spread to other parts of the body, for example, the CNS. In addition, according to aspects of the invention, subjects with healthy immune systems control the spread of certain JCV variants with reduced sialic acid binding. However, in subjects with compromised immune systems, these variants are more likely to evade the immune system and progress to PML.

Accordingly, aspects of the invention relate to compositions and methods for detecting the presence of JCV variants that are predicted to have low sialic acid binding (e.g., low binding or avidity) relative to the binding of normal or wild-type JCV. In some embodiments, JCV variants with one or more mutations in the sialic acid binding domain of a JCV capsid protein are predicted to have low sialic acid binding properties. In some embodiments, specific variants described herein are predicted to have low sialic acid binding properties.

According to aspects of the invention, subjects that harbor JCV variants with one or more mutations that are predicted to reduce sialic acid binding are identified as having increased susceptibility to PML (e.g., compared to a subject that does not harbor JCV or such a JCV variant), particularly if their immune system is compromised. Accordingly, subjects that harbor a reduced sialic acid binding JCV variant are at risk of developing PML if they are treated with an immunosuppressive drug (e.g., natalizumab or other immunosuppressive drug).

In some embodiments, JCV mutations that are associated with PML susceptibility in a subject are mutations at positions 122, 2, and 66 and deletions of amino acids 50-51, 123-125 and 126-134 in the VP1 capsid protein of JCV. In some embodiments, JCV mutations that are associated with PML susceptibility in a subject are H122R, A2V, and D66G. In some embodiments, JCV mutations that are associated with PML susceptibility in a subject are H122R, A2V, and D66G and 2831. In some embodiments a subject is susceptible to PML if the JCV VP1 capsid protein comprises a substitution of at least one of amino acid residues 122, 2, 66, 55, 60, 265, 267, and 269, or one or more deletions of amino acids 50-51, 123-125 and 126-134.

Aspects of the invention are useful to assist in the selection and/or monitoring of a therapy for a subject that is in need of an immunosuppressive treatment (e.g., a subject with multiple sclerosis, or any other condition that can be treated with one or more immunosuppressive drugs). In some embodiments, aspects of the invention can be used to identify subjects that are susceptible to PML prior to initiating an immunosuppressive treatment. In some embodiments, subjects that are receiving an immunosuppressive treatment may be monitored for the appearance of JCV variants that are associated with increased risk for PML. In some embodiments, if a subject is identified as having a JCV variant with reduced binding to sialic acid, then the subject is i) not treated with an immunosuppressive drug, ii) treated with a low dosage or frequency of drug administration, and/or iii) monitored regularly for early symptoms of PML. If symptoms of PML appear during treatment, the treatment may be halted or the amount or frequency of drug administration may be reduced. In some embodiments, an alternative immunosuppressive drug may be substituted for a first drug if one or more symptoms of PML are present.

Aspects of the invention may be used to implement patient monitoring procedures. In some embodiments, patients are first assayed to determine whether they have been exposed to JCV (e.g., by assaying patient serum for the presence of a JCV antibody). Patients that have not been exposed to JCV are identified as having a low risk for PML. However, in some embodiments, such patients are monitored periodically to determine whether or when they are exposed to JCV. If signs of JCV exposure are identified in a subject prior to treatment or during treatment, then the subject can be evaluated for the presence of one or more JCV variants associated with increased risk for PML (e.g., one or more variants predicted to have reduced sialic acid binding relative to a normal or wild type form of JCV). Patients may be monitored periodically for the presence of PML-associated JCV variants. If a patient is found to harbor one or more PML-associated JCV variants, then the patient may be monitored carefully for signs of PML, the patient's treatment may be stopped or altered, and/or the patient may be treated with one or more prophylactic or therapeutic drugs to help protect the patient from PML.

In some embodiments a patient or subject is monitored daily, weekly, biweekly, monthly, bimonthly, quarterly, twice a year, yearly or each two years. In some embodiments a patient or subject is monitored when the patient or subject is undergoing treatment with immunosuppressants.

According to aspects of the invention, a JCV variant may be predicted to have low sialic acid binding (e.g., affinity or avidity) if the variant has one or more mutations in the sialic binding pocket of the JVC VP1 protein. In some embodiments, mutations in any one or more of the amino acids that are within 12 Angstroms of a molecule bound in the sialic acid binding pocket can be predicted to affect sialic acid binding. A list of VP1 amino acids within 12 Angstoms of a molecule bound in the sialic acid binding pocket is provided in Table 16 in Example 12. Accordingly, a JCV variant with a mutation in one or more of these amino acids may be identified as being a candidate for reduced binding to sialic acid and therefore increased risk for causing PML.

According to aspects of the invention, several different naturally-occurring JCV VP1 sequences may be used as normal or wild-type reference sequences if they are from JCV variants that are not associated with increased risk for PML as described herein. Examples of such reference sequences are described in more detail herein and, for example, in Cubitt et al., Predicted amino acid sequences for 100 JCV strains, Journal of NeuroVirology, 7: 339-344, 2001, the sequence disclosures of which are incorporated herein by reference in their entirety.

According to aspects of the invention, the sialic acid binding properties (e.g., affinity or avidity) of a variant JCV may be measured using any suitable assay. For example, JCV and or JCV VP1 binding to sialic acid may measured using hemmaglutination assays, direct binding to immobilized molecules (e.g., gangliosides, sugars, glycoproteins, etc.), cell-based binding assays (e.g., where binding is detected with labeled antibodies using flow cytometry), etc., or any combination thereof. In some embodiments, low binding is more than a 5 fold reduction in binding (e.g., avidity or affinity) relative to the binding of a normal or wild-type JCV reference as described herein. However, in some embodiments, low binding is more than about 10 fold, 50 fold, 100 fold, 200 fold, 500 fold, 1,000 fold, 5,000, 10,000 fold or greater reduction in binding relative to a normal or wild-type JCV reference.

Accordingly, aspects of the invention relate to determining whether a subject is susceptible to PML due to the presence of a PML-associated JCV variant. In some embodiments, this information can be used to determine whether the subject is suitable for treatment with an immunosuppressive agent. In some embodiments, this information can be used to determine whether a subject being treated with an immunosuppressive agent should continue the treatment or should be switched to a different dosage, regimen, and/or type of immunosuppressive drug. In certain embodiments, the detection of a PML-associated JCV variant in a subject being treated with an immunosuppressive agent provides a basis for discontinuing the treatment, at least for a predetermined period of time.

Patients being treated with an immunosuppressive agent can be monitored periodically for the presence of a JCV infection. In some embodiments, if a subject is known or identified to have a JCV infection, the subject may be periodically monitored for the presence of a JCV variant that is predicted to have a reduced binding for sialic acid.

Accordingly, the invention provides methods and compositions for determining if a subject is at risk for progressive multifocal leukoencephalopathy (PML) or has PML (e.g., early stage PML). In one embodiment, a biological sample of a subject is interrogated for exposure to a variant JC virus having one or more sequence variations associated with PML, for example, one or more sequence variants predicted to result in reduced sialic acid binding. In some embodiments a plurality of specific predetermined VP-1 positions are interrogated for their mutational status. The pattern of sequence variations found at the specific positions provides a risk profile of the subject for PML.

In some embodiments, the invention provides panels of JCV-VP1 amino acid positions at which sequence variations are associated with PML risk and/or PML disease progression. Methods and compositions are provided for assaying biological samples for indicia of PML risk. In some embodiments, JC virus polypeptides and/or nucleic acids may be isolated and analyzed to determine whether they have sequence variations at one or more predetermined VP-1 positions. However, in certain circumstances, JC virus can be difficult to isolate from certain biological samples obtained from subjects that have low JC viral loads even through they have been exposed to JC virus and may have a current JC viral infection. Nonetheless, a subject's exposure to a PML-associated variant JC virus can be inferred from the presence, in a biological sample obtained from the subject, of antibodies (e.g., serum antibodies) against one or more PML-associated variant JCV-VP1 polypeptides.

JCV sequences in the brain of PML patients are so variable that identical JCV sequences have never been detected in different PML patients (Yogo & Sugimoto, 2001). However, aspects of the invention are based on an analysis of JCV sequences from healthy and PML subjects and the identification of a subset of positions in the VP1 sequence at which amino acid substitutions are strongly correlated with PML. In one aspect, the invention provides guidance as to which positions in JCV-VP1 need to be interrogated to arrive at a risk profile for PML. In one aspect, the invention provides novel panels of VP1 amino acid positions at which sequence variations are predictive of a risk of PML in a subject infected with the corresponding variant JCV. Aspects of the invention relate to screening subjects for the presence of signs or indicia of JCV variants with reduced binding to sialic acid. In some embodiments, panels of JCV sequence variations associated with different PML risk profiles are provided in Table 1A-1H and described in more detail herein.

JCV and VP1

In some embodiments, JCV sequence variations associated with PML are found at selected positions in the major capsid protein (VP1) of JCV. Sequences of many VP1 proteins described in the literature have been analyzed to identify a subset of VP1 positions where sequence variations are strongly associated with PML. According to the invention, an amino acid is identified as mutant or variant at a specific position on VP-1 if it differs from the amino acid at that position in a consensus sequence or other reference sequence (e.g., the sequence of a wild type archetype virus). In some embodiments the consensus sequence for the VP1 protein of JCV from healthy subjects is provided by GenBank ID No#37050849 (AAQ88264; shown as the VP1 sequence in FIG. 1). JCV-VP1 is conserved when compared to SV40 as shown in FIG. 1. A number of different archetypes of JCV have been identified. As used herein, an archetype is a JCV found in the urine of healthy individuals. In some embodiments, the VP1 sequence of FIG. 1 is a reference sequence. In some embodiments, a reference sequence is one or more of the archetypes of Zheng et al. (2005). The three main archetypes are determined by region (EU archetype is found in people of European ancestry and the CY and MY archetypes are found in people of Asian ancestry). While PML-associated sequence variations were identified based on comparisons to a "consensus" sequence, several archetypes have the same amino acids at the positions identified as PML-associated, and the invention can therefore be practiced based on sequence comparisons to any of the archetypal sequences. In other embodiments, assays can be based on determining whether a JCV has one or more predetermined amino acids at certain positions without performing a comparison to a reference sequence. It should be appreciated that methods for determining the presence of certain JCV-VP1 variant sequences can be based on a direct characterization of JCV nucleic acids or polypeptides isolated from a subject. Alternatively, the presence of variant JCV in a subject (or prior exposure of the subject to variant JCV) can be inferred by detecting subject antibodies (e.g., serum antibodies) that are specific for one or more of the variant JCV-VP1 sequences. It should be appreciated that aspects of the invention also provide for comparing a JCV-VP1 sequence to other reference sequences. However, even if other reference sequences are used, an analysis may involve determining the identity of an amino acid at one or more of the PML associated VP1 positions described herein.

According to the invention, the sequence analysis of VP1 variants identified "hot spot" regions of sequence variations associated with risk for PML. In some embodiments, sequence variations that are indicative of risk for PML are located in the surface loops of the VP1 protein. These positions can be found in Tables 1B-1D. In some embodiments, the total number of sequence variations in a specific area of the VP1 protein may be indicative of risk for PML (See Table 2). In some embodiments, the presence of variant amino acids at 2 or more (e.g., 3, 4, 5, 6, 7, 8, 9, 10, or more) of the positions described herein may be indicative of risk for PML. The polarity of these regions may be indicative of risk for PML and the risk for PML may increase if polar amino acids are replaced with non-polar amino acids. In some embodiments, a loss of a polar amino acid at any one or more of the positions identified in Table 1A or Tables 1B-1D results in a JCV virus having an increased association with PML. In some embodiments, a loss of a polar amino acid at any one or more positions within one of the structural regions shown in FIG. 2 (e.g., within a region defined by positions 55-75 or 265-271 of the JCV-VP1 polypeptide sequence) results in a JC virus having an increased association with PML. Similarly, in certain embodiments a gain of a non-polar amino acid at any one or more of the positions identified in Table 1A or Tables 1B-1D results in a JCV virus having an increased association with PML. Also, in certain embodiments, a gain of a non-polar amino acid at any one or more positions within one of the structural regions shown in FIG. 2 (e.g., within a region defined by positions 55-75 or 265-271 of the JCV-VP1 polypeptide sequence) results in a JC virus having an increased association with PML. FIG. 2 shows a predicted JCV-VP1 structure highlighting regions where certain amino acids positions identified as being associated with PML were mapped to the structure. The predicted structure of the JCV-VP1 protein is based on the crystal structure of the SV40 coat protein 1 and the sequence similarity between the JCV and SV40 proteins. Parsing of the sequence variations showed that a decrease in the number of polar amino acids and/or an increase in the number of non-polar amino acids on the surface area of the VP1 protein resulted in an increased risk for PML (See Example 3). In one embodiment, a subject is at risk for PML if a sequence variation in one or more of the surface loops results in an increase in non-polar surface area of 10-square angstrom or more per sequence variation, or a decrease in polar surface area of 10-square angstrom or more per sequence variation. While the current invention is not limited to a specific mechanism it is believed that the changes in the surface loop may impede antibodies from binding to the JCV-VP1 and/or facilitate the JCV VP1 interaction with its receptors such as carbohydrate and/or a protein receptor, such as 5HT2A. Changes in a surface loop of VP1 (e.g., an increase in non-polar amino acids or surface area and/or a decrease in polar amino acids or surface area) may increase the affinity of VP1 for the cell receptor and facilitate viral entry and/or infection of a host cell, or certain specific host cells important for PML progression.

Panels of Sequence Variations

It should be appreciated that interrogating a position may comprises both determining the amino acid at that position and comparing that amino acid to a reference amino acid (e.g., the amino acid found in the wild type/control variant, for example in the consensus sequence or an archetype sequence).

It should be appreciated that any single variant or combination of variants can be indicative of risk for PML. It should be appreciated that the total number of variants present in a certain region or in a selected group of interrogated variants may indicate a risk for PML.

Aspects of the invention relate to providing one or more positions on a JCV-VP1 amino acid sequence that correspond to JCV variants that are associated with risk for PML. For example, each of the positions shown in Table 1A are associated with risk for PML and any suitable assay can be used to detect the presence of, or indicators (indicia) of past exposure to, a JCV variant having an amino acid variant at one or more of the selected positions. In some embodiments, an assay can be used to detect the presence of, or exposure to, a JCV variant having a variant amino acid variant at two or more positions selected from the positions listed in Table 1A, wherein the presence of the variant/variants is indicative of PML.

In some embodiments, JCV mutations that are associated with PML susceptibility in a subject are mutations at positions 122, 2, and 66 and deletions of amino acids 50-51, 123-125 and 126-134 in the VP1 capsid protein of JCV. In some embodiments, JCV mutations that are associated with PML susceptibility in a subject are H122R, A2V, and D66G. In some embodiments a subject is susceptible to PML if the JCV VP1 capsid protein comprises a substitution of at least one of amino acid residues 122, 2, 66, 55, 60, 265, 267, and 269, or one or more deletions of amino acids 50-51, 123-125 and 126-134.

In some embodiments, the selected positions are interrogated by comparing the amino acid present at that position to the amino acid present in a reference. If the amino acid present at a selected position differs from the amino acid found in the reference, the position is said to be mutated. Accordingly, in some aspects the invention provides tables (e.g., databases) of containing lists of variants that are related to a risk for PML. The databases also provide variants and variants that are protective of PML. In some embodiments any variant found at a selected position is indicative of risk for PML. In further embodiments the tables provide groups of variants associated with PML that can be interrogated as a group to arrive at a risk profile for PML for a subject. It should be appreciated that many of the variants identified in the reference database are not very common. For instance a variant indicative of risk for PML may be found in only 10% of the samples of a person known to be at risk for PML. To arrive at a risk profile for a subject more than one position may need to be interrogated. Accordingly, in one aspect the invention provides tables of groups of positions and number of positions within that group that need to be identified to arrive at a risk profile for PML. In some embodiments, at least 8 (e.g., 8, 9, 10 or more, or all) positions in Table 1A need to be interrogated to be arrive at a subject's risk profile for PML. Similarly, 2, 3, 4, 5, 6, 7, 8, 9, 10 or more or all positions in any of the tables may be interrogated.

Amino acids found at the positions indicated in the Tables may be indicative of risk for PML by comparing the amino acid to an amino acid found in a reference. For instance, in Table 1A, the wild type (e.g., reference/consensus) amino acid at position 55 is leucine (L). In some embodiments, any amino acid found at position 55 that is not leucine is indicative of risk for PML. In some embodiments, a particular variant is associated with risk for PML. For instance, the presence of a phenylalanine (F) at position 55 may be indicative of risk for PML. Accordingly, the emergence of a variant amino acid (e.g., Phe) at position 55 may be indicative of onset or progression of PML. Similarly, the emergence of one or more other variant amino acids described herein for PML-associated positions on VP1 may be indicative of onset or progression of PML. In some embodiments, the presence of an amino acid with a particular characteristic may be indicative of the risk for PML. For instance, the presence in the JCV variant of an amino acid that is less polar than the amino acid found in the reference sequence is indicative of risk for PML. In addition to being indicative for risk for PML, the variants found at specific positions may also be used to determine onset, progression or regression in a subject. In some embodiments, the variants found at specific positions allow for the monitoring of treatment of a subject for PML. In some embodiments, the variants found at specific positions allow for the selection of a treatment of a subject having or suspected of having PML.

In some embodiments, amino acids found at specific amino positions can be indicative as being protective for PML, e.g., identifying the person for being at lower risk for developing PML.

It should be appreciated that in some embodiments, the risk for PML can be determined without comparing the amino acid determined at a particular position to a reference sequence. For instance, if in a sample position 55 is interrogated and the amino acid found at that position is a phenylalanine, then the subject is determined to be at risk for PML. This determination can be made without comparing the amino acid found at position 55 to a wild type reference.

It should be appreciated that the invention provides methods for determining both the current and past existence of JCV variants. A subject that has been exposed to a JCV variant, but that currently can not be identified as being infected with that JCV variant, can be determined to be exposed to that JCV variant by determining the presence of indicators for that JCV variant. A subject can develop antibodies against any foreign agent, including viruses and bacteria, to which the subject is exposed. The presence of a virus, or variant of the virus in a subject can therefore be diagnosed by the detection of an antibody specific to that virus or virus variant. If the virus replicates and mutates (and thus creates a new variant) the body will develop new antibodies specific for the mutated version of the virus. Even if a specific virus variant is no longer present in the body, past exposure to the variant can still be determined by the presence of the antibody. Accordingly, in one embodiment the mutational status of the JCV variants (both current and past exposure) is determined by the detection of the presence of antibodies against one or more specific variants. In one embodiment, the presence of a VP1-antibody is determined by specific binding of the antibody to one or more polypeptides comprising one or more of the variants. It should be appreciated that antibodies can be determine qualitatively and quantitatively. An antibody detection assay of the invention therefore facilitates the determination of all viral variants the subject has ever been exposed to and an estimate of the viral load of variants currently present in the body through the quantization of the specific antibodies.

In one embodiment, the amino acid variants are detected directly, e.g., the presence of virus variants in a subject is determined by determining the presence of polypeptides comprising one or more variants of the variants. Agents are developed that can specifically bind a particular polypeptide. In some embodiments these agents are antibodies. In some embodiments, the variants are determined by determining the sequence of the nucleic acids encoding the variants. A sample is obtained from a subject and analyzed for the presence of a particular virus variant. It should be appreciated that specific JCV variants may only be present in the brain and spinal fluid, while "wild type" variants may be present in other tissues in the same subject. The presence of polypeptides may be determined by antibodies specific for these polypeptides. The assay will allow for the determination of both the presence of specific variants and the quantitation of these variants (the viral load), in addition the ratio of variant to wild type can be determined.

It should be appreciated that an immunosupressive agent may increase the susceptibility of a subject to the progression or flare up of a latent microbial infection or to the contraction of a new microbial infection. In some embodiments the microbial infection is infection by JCV, which caused PML. Accordingly, the risk for PML may be assessed prior to initiating treatment with an immunosuppressive agent, during administration of an immunosupressive agent, or assessed after an immunosupressive agent has been administered or after treatment with immunosupressive treatment has been terminated.

In some embodiments, the risk for PML as determined by the methods of the invention will aid in deciding on treatment with immunosuppressants or immunosuppresive agents. In some embodiments an increased risk for PML diagnosed during treatment with immunossuppressents may suggest a modification or termination of the treatment regimen with immunosuppressants.

TABLE 1A

Panel of JCV-VP1 variants

| JCV VP1 | | Healthy individuals | | | | PML patients (brain + peripheral tissue) | | | | PML patients (peripheral tissue) | | | | PML patients (brain tissue) | | | |
|---|---|---|---|---|---|---|---|---|---|---|---|---|---|---|---|---|---|
| pos | WT | #seq | #mut | % mut | mut | #seq | #mut | % mut | mut | #seq | #mut | % mut | mut | #seq | #mut | % mut | mut |
| 55 | L | 29 | 0 | 0 | | 50 | 5 | 10 | 5F | 13 | 3 | 23 | 3F | 37 | 2 | 5 | 2F |
| 60 | K | 29 | 0 | 0 | | 50 | 4 | 8 | 2M 1E 1N | 13 | 1 | 8 | 1N | 37 | 3 | 8 | 2M 1E |

TABLE 1A-continued

Panel of JCV-VP1 variants

| JCV VP1 | | Healthy individuals | | | | PML patients (brain + peripheral tissue) | | | | PML patients (peripheral tissue) | | | | PML patients (brain tissue) | | | |
|---|---|---|---|---|---|---|---|---|---|---|---|---|---|---|---|---|---|
| pos | WT | #seq | #mut | % mut | mut | #seq | #mut | % mut | mut | #seq | #mut | % mut | mut | #seq | #mut | % mut | mut |
| 61 | S | 29 | 0 | 0 | | 50 | 1 | 2 | 1L | 13 | 0 | 0 | | 37 | 1 | 3 | 1L |
| 66 | D | 29 | 0 | 0 | | 50 | 5 | 10 | 4H 1N | 13 | 0 | 0 | | 37 | 5 | 14 | 4H 1N |
| 69 | E | 29 | 0 | 0 | | 50 | 1 | 2 | 1D | 13 | 0 | 0 | | 37 | 1 | 3 | 1D |
| 74 | N | 29 | 0 | 0 | | 50 | 4 | 8 | 4S | 13 | 0 | 0 | | 37 | 4 | 11 | 4S |
| 75 | K | 29 | 0 | 0 | | 50 | 3 | 6 | 3R | 13 | 0 | 0 | | 37 | 3 | 8 | 3R |
| 113 | I | 41 | 3 | 7 | 3L | 50 | 18 | 36 | 18L | 13 | 5 | 38 | 5L | 37 | 13 | 35 | 13L |
| 117 | T | 41 | 1 | 2 | 1S | 50 | 8 | 16 | 8S | 13 | 0 | 0 | | 37 | 8 | 22 | 8S |
| 123 | S | 41 | 0 | 0 | | 50 | 4 | 8 | 4C | 13 | 2 | 15 | 2C | 37 | 2 | 5 | 2C |
| 128 | T | 41 | 2 | 5 | 2A | 50 | 6 | 12 | 6A | 13 | 0 | 0 | | 37 | 6 | 16 | 6A |
| 134 | A | 41 | 20 | 49 | 20G | 50 | 47 | 94 | 47G | 13 | 10 | 77 | 10G | 37 | 37 | 100 | 37G |
| 158 | V | 29 | 0 | 0 | | 50 | 4 | 8 | 4L | 13 | 0 | 0 | | 37 | 4 | 11 | 4L |
| 164 | T | 29 | 5 | 17 | 5K | 50 | 46 | 92 | 46K | 13 | 10 | 77 | 10K | 37 | 36 | 97 | 36K |
| 223 | V | 42 | 0 | 0 | | 52 | 1 | 2 | 1A | 14 | 0 | 0 | | 38 | 1 | 3 | 1A |
| 265 | N | 42 | 0 | 0 | | 52 | 4 | 8 | 3D 1T | 14 | 4 | 29 | 3D 1T | 38 | 0 | 0 | |
| 267 | S | 42 | 0 | 0 | | 52 | 4 | 8 | 3F 1L | 14 | 1 | 7 | 1F | 38 | 3 | 8 | 2F 1L |
| 269 | S | 42 | 0 | 0 | | 52 | 12 | 23 | 9F 3Y | 14 | 1 | 7 | 1F | 38 | 11 | 29 | 8F 3Y |
| 271 | Q | 42 | 0 | 0 | | 52 | 1 | 2 | 1H | 14 | 0 | 0 | | 38 | 1 | 3 | 1H |
| 321 | I | 42 | 20 | 48 | 20V | 32 | 28 | 88 | 28V | 5 | 1 | 20 | 1V | 27 | 27 | 100 | 27V |
| 332 | Q | 42 | 20 | 48 | 20E | 32 | 29 | 91 | 29E | 5 | 2 | 40 | 2E | 27 | 27 | 100 | 27E |
| 345 | R | 42 | 0 | 0 | | 32 | 8 | 25 | 8K | 5 | 0 | 0 | | 27 | 8 | 30 | 8K |

TABLE 1B

Panel of Group I JCV-VP1 variants

| JCV VP1 | | Healthy individuals | | | | PML patients (brain + peripheral tissue) | | | | PML patients (peripheral tissue) | | | | PML patients (brain tissue) | | | |
|---|---|---|---|---|---|---|---|---|---|---|---|---|---|---|---|---|---|
| pos | WT | #seq | #mut | % mut | mut | #seq | #mut | % mut | mut | #seq | #mut | % mut | mut | #seq | #mut | % mut | mut |
| 55 | L | 29 | 0 | 0 | | 50 | 5 | 10 | 5F | 13 | 3 | 23 | 3F | 37 | 2 | 5 | 2F |
| 60 | K | 29 | 0 | 0 | | 50 | 4 | 8 | 2M 1E 1N | 13 | 1 | 8 | 1N | 37 | 3 | 8 | 2M 1E |
| 61 | S | 29 | 0 | 0 | | 50 | 1 | 2 | 1L | 13 | 0 | 0 | | 37 | 1 | 3 | 1L |
| 66 | D | 29 | 0 | 0 | | 50 | 5 | 10 | 4H 1N | 13 | 0 | 0 | | 37 | 5 | 14 | 4H 1N |
| 69 | E | 29 | 0 | 0 | | 50 | 1 | 2 | 1D | 13 | 0 | 0 | | 37 | 1 | 3 | 1D |
| 74 | N | 29 | 0 | 0 | | 50 | 4 | 8 | 4S | 13 | 0 | 0 | | 37 | 4 | 11 | 4S |
| 75 | K | 29 | 0 | 0 | | 50 | 3 | 6 | 3R | 13 | 0 | 0 | | 37 | 3 | 8 | 3R |

TABLE 1C

Panel of Group II JCV-VP1 variants

| JCV VP1 | | Healthy individuals | | | | PML patients (brain + peripheral tissue) | | | | PML patients (peripheral tissue) | | | | PML patients (brain tissue) | | | |
|---|---|---|---|---|---|---|---|---|---|---|---|---|---|---|---|---|---|
| pos | WT | #seq | #mut | % mut | mut | #seq | #mut | % mut | mut | #seq | #mut | % mut | mut | #seq | #mut | % mut | mut |
| 265 | N | 42 | 0 | 0 | | 52 | 4 | 8 | 3D 1T | 14 | 4 | 29 | 3D 1T | 38 | 0 | 0 | |
| 267 | S | 42 | 0 | 0 | | 52 | 4 | 8 | 3F 1L | 14 | 1 | 7 | 1F | 38 | 3 | 8 | 2F 1L |
| 269 | S | 42 | 0 | 0 | | 52 | 12 | 23 | 9F 3Y | 14 | 1 | 7 | 1F | 38 | 11 | 29 | 8F 3Y |
| 271 | Q | 42 | 0 | 0 | | 52 | 1 | 2 | 1H | 14 | 0 | 0 | | 38 | 1 | 3 | 1H |

TABLE 1D

Panel of Group III JCV-VP1 variants

| JCV VP1 | | Healthy individuals | | | | PML patients (brain + peripheral tissue) | | | | PML patients (peripheral tissue) | | | | PML patients (brain tissue) | | | |
|---|---|---|---|---|---|---|---|---|---|---|---|---|---|---|---|---|---|
| pos | WT | #seq | #mut | % mut | mut | #seq | #mut | % mut | mut | #seq | #mut | % mut | mut | #seq | #mut | % mut | mut |
| 113 | I | 41 | 3 | 7 | 3L | 50 | 18 | 36 | 18L | 13 | 5 | 38 | 5L | 37 | 13 | 35 | 13L |
| 123 | S | 41 | 0 | 0 | | 50 | 4 | 8 | 4C | 13 | 2 | 15 | 2C | 37 | 2 | 5 | 2C |
| 158 | V | 29 | 0 | 0 | | 50 | 4 | 8 | 4L | 13 | 0 | 0 | | 37 | 4 | 11 | 4L |
| 164 | T | 29 | 5 | 17 | 5K | 50 | 46 | 92 | 46K | 13 | 10 | 77 | 10K | 37 | 36 | 97 | 36K |
| 345 | R | 42 | 0 | 0 | | 32 | 8 | 25 | 8K | 5 | 0 | 0 | | 27 | 8 | 30 | 8K |

TABLE 1E

Panel of Groups I-III JCV-VP1 variants

| JCV VP1 | | Healthy individuals | | | | PML patients (brain + peripheral tissue) | | | | PML patients (peripheral tissue) | | | | PML patients (brain tissue) | | | |
|---|---|---|---|---|---|---|---|---|---|---|---|---|---|---|---|---|---|
| pos | WT | #seq | #mut | % mut | mut | #seq | #mut | % mut | mut | #seq | #mut | % mut | mut | #seq | #mut | % mut | mut |
| 55 | L | 29 | 0 | 0 | | 50 | 5 | 10 | 5F | 13 | 3 | 23 | 3F | 37 | 2 | 5 | 2F |
| 60 | K | 29 | 0 | 0 | | 50 | 4 | 8 | 2M 1E 1N | 13 | 1 | 8 | 1N | 37 | 3 | 8 | 2M 1E |
| 61 | S | 29 | 0 | 0 | | 50 | 1 | 2 | 1L | 13 | 0 | 0 | | 37 | 1 | 3 | 1L |
| 66 | D | 29 | 0 | 0 | | 50 | 5 | 10 | 4H 1N | 13 | 0 | 0 | | 37 | 5 | 14 | 4H 1N |
| 69 | E | 29 | 0 | 0 | | 50 | 1 | 2 | 1D | 13 | 0 | 0 | | 37 | 1 | 3 | 1D |
| 74 | N | 29 | 0 | 0 | | 50 | 4 | 8 | 4S | 13 | 0 | 0 | | 37 | 4 | 11 | 4S |
| 75 | K | 29 | 0 | 0 | | 50 | 3 | 6 | 3R | 13 | 0 | 0 | | 37 | 3 | 8 | 3R |
| 113 | I | 41 | 3 | 7 | 3L | 50 | 18 | 36 | 18L | 13 | 5 | 38 | 5L | 37 | 13 | 35 | 13L |
| 123 | S | 41 | 0 | 0 | | 50 | 4 | 8 | 4C | 13 | 2 | 15 | 2C | 37 | 2 | 5 | 2C |
| 158 | V | 29 | 0 | 0 | | 50 | 4 | 8 | 4L | 13 | 0 | 0 | | 37 | 4 | 11 | 4L |
| 164 | T | 29 | 5 | 17 | 5K | 50 | 46 | 92 | 46K | 13 | 10 | 77 | 10K | 37 | 36 | 97 | 36K |
| 265 | N | 42 | 0 | 0 | | 52 | 4 | 8 | 3D 1T | 14 | 4 | 29 | 3D 1T | 38 | 0 | 0 | |
| 267 | S | 42 | 0 | 0 | | 52 | 4 | 8 | 3F 1L | 14 | 1 | 7 | 1F | 38 | 3 | 8 | 2F 1L |
| 269 | S | 42 | 0 | 0 | | 52 | 12 | 23 | 9F 3Y | 14 | 1 | 7 | 1F | 38 | 11 | 29 | 8F 3Y |
| 271 | Q | 42 | 0 | 0 | | 52 | 1 | 2 | 1H | 14 | 0 | 0 | | 38 | 1 | 3 | 1H |
| 345 | R | 42 | 0 | 0 | | 32 | 8 | 25 | 8K | 5 | 0 | 0 | | 27 | 8 | 30 | 8K |

TABLE 1F

Panel of JCV-VP1 variants found in most PML brain samples

| JCV VP1 | | Healthy individuals | | | | PML patients (brain + peripheral tissue) | | | | PML patients (peripheral tissue) | | | | PML patients (brain tissue) | | | |
|---|---|---|---|---|---|---|---|---|---|---|---|---|---|---|---|---|---|
| pos | WT | #seq | #mut | % mut | mut | #seq | #mut | % mut | mut | #seq | #mut | % mut | mut | #seq | #mut | % mut | mut |
| 134 | A | 41 | 20 | 49 | 20G | 50 | 47 | 94 | 47G | 13 | 10 | 77 | 10G | 37 | 37 | 100 | 37G |
| 164 | T | 29 | 5 | 17 | 5K | 50 | 46 | 92 | 46K | 13 | 10 | 77 | 10K | 37 | 36 | 97 | 36K |
| 321 | I | 42 | 20 | 48 | 20V | 32 | 28 | 88 | 28V | 5 | 1 | 20 | 1V | 27 | 27 | 100 | 27V |
| 332 | Q | 42 | 20 | 48 | 20E | 32 | 29 | 91 | 29E | 5 | 2 | 40 | 2E | 27 | 27 | 100 | 27E |

TABLE 1G

Panel of JCV-VP1 risk variants no found in samples from healthy individuals

| JCV VP1 | | Healthy individuals | | | | PML patients (brain + peripheral tissue) | | | | PML patients (peripheral tissue) | | | | PML patients (brain tissue) | | | |
|---|---|---|---|---|---|---|---|---|---|---|---|---|---|---|---|---|---|
| pos | WT | #seq | #mut | % mut | mut | #seq | #mut | % mut | mut | #seq | #mut | % mut | mut | #seq | #mut | % mut | mut |
| 55 | L | 29 | 0 | 0 | | 50 | 5 | 10 | 5F | 13 | 3 | 23 | 3F | 37 | 2 | 5 | 2F |
| 60 | K | 29 | 0 | 0 | | 50 | 4 | 8 | 2M 1E 1N | 13 | 1 | 8 | 1N | 37 | 3 | 8 | 2M 1E |
| 61 | S | 29 | 0 | 0 | | 50 | 1 | 2 | 1L | 13 | 0 | 0 | | 37 | 1 | 3 | 1L |

TABLE 1G-continued

Panel of JCV-VP1 risk variants no found in samples from healthy individuals

| JCV VP1 | | Healthy individuals | | | | PML patients (brain + peripheral tissue) | | | | PML patients (peripheral tissue) | | | | PML patients (brain tissue) | | | |
|---|---|---|---|---|---|---|---|---|---|---|---|---|---|---|---|---|---|
| pos | WT | #seq | #mut | % mut | mut | #seq | #mut | % mut | mut | #seq | #mut | % mut | mut | #seq | #mut | % mut | mut |
| 66 | D | 29 | 0 | 0 | | 50 | 5 | 10 | 4H 1N | 13 | 0 | 0 | | 37 | 5 | 14 | 4N 1N |
| 69 | E | 29 | 0 | 0 | | 50 | 1 | 2 | 1D | 13 | 0 | 0 | | 37 | 1 | 3 | 1D |
| 74 | N | 29 | 0 | 0 | | 50 | 4 | 8 | 4S | 13 | 0 | 0 | | 37 | 4 | 11 | 4S |
| 75 | K | 29 | 0 | 0 | | 50 | 3 | 6 | 3R | 13 | 0 | 0 | | 37 | 3 | 8 | 3R |
| 123 | S | 41 | 0 | 0 | | 50 | 4 | 8 | 4C | 13 | 2 | 15 | 2C | 37 | 2 | 5 | 2C |
| 158 | V | 29 | 0 | 0 | | 50 | 4 | 8 | 4L | 13 | 0 | 0 | | 37 | 4 | 11 | 4L |
| 223 | V | 42 | 0 | 0 | | 52 | 1 | 2 | 1A | 14 | 0 | 0 | | 38 | 1 | 3 | 1A |
| 265 | N | 42 | 0 | 0 | | 52 | 4 | 8 | 3D 1T | 14 | 4 | 29 | 3D 1T | 38 | 0 | 0 | |
| 267 | S | 42 | 0 | 0 | | 52 | 4 | 8 | 3F 1L | 14 | 1 | 7 | 1F | 38 | 3 | 8 | 2F 1L |
| 269 | S | 42 | 0 | 0 | | 52 | 12 | 23 | 9F 3Y | 14 | 1 | 7 | 1F | 38 | 11 | 29 | 8F 3Y |
| 271 | Q | 42 | 0 | 0 | | 52 | 1 | 2 | 1H | 14 | 0 | 0 | | 38 | 1 | 3 | 1H |
| 345 | R | 42 | 0 | 0 | | 32 | 8 | 25 | 8K | 5 | 0 | 0 | | 27 | 8 | 30 | 8K |

TABLE 1H

Panel of JCV-VP1 variants found in healthy individuals

| JCV VP1 | | Healthy individuals | | | | PML patients (brain + peripheral tissue) | | | | PML patients (peripheral tissue) | | | | PML patients (brain tissue) | | | |
|---|---|---|---|---|---|---|---|---|---|---|---|---|---|---|---|---|---|
| pos | WT | #seq | #mut | % mut | mut | #seq | #mut | % mut | mut | #seq | #mut | % mut | mut | #seq | #mut | % mut | mut |
| 115 | V | 41 | 1 | 2 | 1E | 50 | 0 | 0 | | 13 | 0 | 0 | | 37 | 0 | 0 | |
| 277 | R | 42 | 1 | 2 | 1K | 52 | 0 | 0 | | 14 | 0 | 0 | | 38 | 0 | 0 | |

TABLE 2A

Healthy Subjects

| SEQUENCE | #MUT | #REGION | LENGTH | VARIANTS | |
|---|---|---|---|---|---|
| AAQ88264_gi\|37050849\|gb\|AAQ | 0 | 0 | 347 | CONSENSUS | |
| AAB60589_gi\|1161330\|gb\|AAB6 | 2 | 0 | 27 | 128 A | 134 G |
| AAC54623_gi\|1161332\|gb\|AAC5 | 0 | 0 | 27 | | |
| AAG48112_gi\|12056896\|gb\|AAG | 2 | 0 | 142 | 321 V | 332 E |
| AAG48114_gi\|12056899\|gb\|AAG | 2 | 0 | 142 | 321 V | 332 E |
| AAG48119_gi\|12056907\|gb\|AAG | 2 | 0 | 142 | 321 V | 332 E |
| AAG48121_gi\|12056910\|gb\|AAG | 2 | 0 | 142 | 321 V | 332 E |
| AAG48123_gi\|12056913\|gb\|AAG | 2 | 0 | 142 | 321 V | 332 E |
| AAG48125_gi\|12056916\|gb\|AAG | 2 | 0 | 142 | 321 V | 332 E |
| AAG48127_gi\|12056919\|gb\|AAG | 2 | 0 | 142 | 321 V | 332 E |
| AAG48544_gi\|12082440\|gb\|AAG | 1 | 0 | 56 | 134 G | |
| AAG48545_gi\|12082442\|gb\|AAG | 1 | 0 | 56 | 134 G | |
| AAG48546_gi\|12082444\|gb\|AAG | 1 | 0 | 56 | 134 G | |
| AAG48547_gi\|12082446\|gb\|AAG | 1 | 0 | 56 | 134 G | |
| AAG48548_gi\|12082448\|gb\|AAG | 1 | 0 | 56 | 134 G | |
| AAG48549_gi\|12082450\|gb\|AAG | 2 | 1 | 56 | 113 L | 134 G |
| AAG48550_gi\|12082452\|gb\|AAG | 2 | 1 | 56 | 113 L | 134 G |
| AAG48551_gi\|12082454\|gb\|AAG | 2 | 1 | 56 | 113 L | 134 G |
| AAL12481_gi\|16118426\|gb\|AAL | 2 | 0 | 142 | 321 V | 332 E |
| AAL12483_gi\|16118429\|gb\|AAL | 2 | 0 | 142 | 321 V | 332 E |
| AAR06661_gi\|37993002\|gb\|AAR | 0 | 0 | 347 | | |
| AAR12957_gi\|38156673\|gb\|AAR | 1 | 0 | 347 | 134 G | |
| AAR13077_gi\|38176429\|gb\|AAR | 1 | 0 | 347 | 134 G | |
| AAR13659_gi\|38195910\|gb\|AAR | 0 | 0 | 347 | | |
| AAR32743_gi\|39939397\|gb\|AAR | 0 | 0 | 347 | | |
| AAR89187_gi\|40737215\|gb\|AAR | 0 | 0 | 347 | | |
| AAR89193_gi\|40737222\|gb\|AAR | 0 | 0 | 347 | | |
| AAR89199_gi\|40737229\|gb\|AAR | 0 | 0 | 347 | | |
| AAR89205_gi\|40737236\|gb\|AAR | 0 | 0 | 347 | | |
| AAR89211_gi\|40737243\|gb\|AAR | 1 | 0 | 347 | 277 K | |
| AAR89217_gi\|40737250\|gb\|AAR | 0 | 0 | 347 | | |
| AAR89223_gi\|40737257\|gb\|AAR | 0 | 0 | 347 | | |
| AAR89229_gi\|40737264\|gb\|AAR | 0 | 0 | 347 | | |

TABLE 2A-continued

Healthy Subjects

| SEQUENCE | #MUT | #REGION | LENGTH | VARIANTS | | | |
|---|---|---|---|---|---|---|---|
| AAR89235_gi\|40737271\|gb\|AAR | 0 | 0 | 347 | | | | |
| AAR89241_gi\|40737278\|gb\|AAR | 0 | 0 | 347 | | | | |
| AAR89247_gi\|40737285\|gb\|AAR | 0 | 0 | 347 | | | | |
| AAR89253_gi\|40737292\|gb\|AAR | 0 | 0 | 347 | | | | |
| AAR89259_gi\|40737299\|gb\|AAR | 1 | 0 | 347 | 134 G | | | |
| AAR89265_gi\|40737543\|gb\|AAR | 0 | 0 | 347 | | | | |
| AAR89271_gi\|40737550\|gb\|AAR | 1 | 0 | 347 | 115 E | | | |
| AAR89277_gi\|40737557\|gb\|AAR | 0 | 0 | 347 | | | | |
| AAR89283_gi\|40737564\|gb\|AAR | 0 | 0 | 347 | | | | |
| ABA60111_gi\|76885940\|gb\|ABA | 0 | 0 | 58 | | | | |
| BAA01963_gi\|425204\|dbj\|BAA0 | 4 | 1 | 347 | 134 G | 164 K | 321 V | 332 E |
| BAA01964_gi\|425205\|dbj\|BAA0 | 4 | 1 | 347 | 134 G | 164 K | 321 V | 332 E |
| BAA07834_gi\|1772312\|dbj\|BAA | 2 | 0 | 134 | 321 V | 332 E | | |
| BAA07836_gi\|1785835\|dbj\|BAA | 2 | 0 | 134 | 321 V | 332 E | | |
| BAA07838_gi\|1785837\|dbj\|BAA | 2 | 0 | 134 | 321 V | 332 E | | |
| BAA07840_gi\|1772321\|dbj\|BAA | 2 | 0 | 134 | 321 V | 332 E | | |
| BAB11698_gi\|9796401\|dbj\|BAB | 4 | 1 | 347 | 134 G | 164 K | 321 V | 332 E |
| BAB11704_gi\|9796408\|dbj\|BAB | 4 | 1 | 347 | 134 G | 164 K | 321 V | 332 E |
| BAB11716_gi\|9796422\|dbj\|BAB | 3 | 0 | 347 | 134 G | 321 V | 332 E | |
| BAB11722_gi\|9796429\|dbj\|BAB | 3 | 0 | 347 | 134 G | 321 V | 332 E | |
| Average Values | 1.2 | 0.1 | 234.7 | | | | |

TABLE 2B

PML Samples

| Sequence | #mut | #region | Length | Variants | | | | | | | |
|---|---|---|---|---|---|---|---|---|---|---|---|
| AAB62680_gi\|2246607\|gb\|AA | 5 | 1 | 347 | 128 A | 134 G | 164 K | 321 V | 332 E | | | |
| AAT09819_gi\|47078338\|gb\|A | 5 | 3 | 347 | 113 L | 134 G | 164 K | 265 T | 332 E | | | |
| AAT09825_gi\|47078345\|gb\|A | 1 | 1 | 347 | 267 F | | | | | | | |
| AAT09831_gi\|47078352\|gb\|A | 1 | 1 | 347 | 55 F | | | | | | | |
| AAT09837_gi\|47078359\|gb\|A | 1 | 1 | 347 | 60 N | | | | | | | |
| BAE02848_gi\|68445641\|dbj\| | 4 | 3 | 246 | 113 L | 134 G | 164 K | 265 D | | | | |
| BAE02849_gi\|68445643\|dbj\| | 3 | 2 | 246 | 55 F | 134 G | 164 K | | | | | |
| BAE02850_gi\|68445645\|dbj\| | 4 | 3 | 246 | 113 L | 134 G | 164 K | 265 D | | | | |
| BAE02851_gi\|68445647\|dbj\| | 4 | 3 | 246 | 113 L | 123 C | 134 G | 164 K | | | | |
| BAE02852_gi\|68445649\|dbj\| | 3 | 2 | 246 | 134 G | 164 K | 269 F | | | | | |
| BAE02853_gi\|68445651\|dbj\| | 4 | 3 | 246 | 113 L | 123 C | 134 G | 164 K | | | | |
| BAE02854_gi\|68445653\|dbj\| | 3 | 2 | 246 | 55 F | 134 G | 164 K | | | | | |
| BAE02855_gi\|68445655\|dbj\| | 2 | 1 | 246 | 134 G | 164 K | | | | | | |
| BAE02856_gi\|68445657\|dbj\| | 3 | 2 | 246 | 134 G | 164 K | 265 D | | | | | |
| AAB60586_gi\|1161322\|gb\|AAB | 2 | 0 | 134 | 321 V | 332 E | | | | Partial | | |
| AAB60584_gi\|1161319\|gb\|AAB | 2 | 0 | 134 | 321 V | 332 E | | | | Partial | | |
| AAB62687_gi\|2246615\|gb\|AAB | 6 | 2 | 347 | 55 F | 128 A | 134 G | 164 K | 321 V | 332 E | | |
| AAB94036_gi\|2735983\|gb\|AAB | 4 | 1 | 347 | 55 F | 134 G | 321 V | 332 E | | | | |
| BAA01965_gi\|425206\|dbj\|BAA | 6 | 2 | 347 | 128 A | 134 G | 164 K | 269 F | 321 V | 332 E | | |
| BAA01966_gi\|425207\|dbj\|BAA | 9 | 5 | 347 | 66 H | 75 R | 117 S | 134 G | 158 L | 164 K | 321 V | 332 E | 345 K |
| BAA01967_gi\|425208\|dbj\|BAA | 8 | 4 | 347 | 117 S | 134 G | 158 L | 164 K | 267 L | 321 V | 332 E | 345 K |
| BAA01968_gi\|425209\|dbj\|BAA | 8 | 3 | 347 | 74 S | 117 S | 128 A | 134 G | 164 K | 321 V | 332 E | 345 K |
| BAA01969_gi\|425210\|dbj\|BAA | 6 | 3 | 347 | 113 L | 134 G | 164 K | 269 F | 321 V | 332 E | | |
| BAA01970_gi\|425211\|dbj\|BAA | 5 | 2 | 347 | 113 L | 134 G | 164 K | 321 V | 332 E | | | |
| BAA05636_gi\|538231\|dbj\|BAA | 5 | 2 | 347 | 113 L | 134 G | 164 K | 321 V | 332 E | | | |
| BAA05637_gi\|538234\|dbj\|BAA | 6 | 3 | 347 | 113 L | 134 G | 164 K | 269 F | 321 V | 332 E | | |
| BAA05638_gi\|538238\|dbj\|BAA | 5 | 2 | 347 | 134 G | 164 K | 269 Y | 321 V | 332 E | | | |
| BAB11728_gi\|9796436\|dbj\|BA | 6 | 3 | 347 | 113 L | 134 G | 164 K | 269 F | 321 V | 332 E | | |
| BAB11734_gi\|9796443\|dbj\|BA | 5 | 2 | 347 | 134 G | 164 K | 269 Y | 321 V | 332 E | | | |
| BAE00011_gi\|67968154\|dbj\|B | 8 | 3 | 347 | 74 S | 117 S | 128 A | 134 G | 164 K | 321 V | 332 E | 345 K |
| BAE00117_gi\|67968161\|dbj\|B | 9 | 4 | 347 | 74 S | 117 S | 128 A | 134 G | 164 K | 269 F | 321 V | 332 E | 337 K |
| BAE00123_gi\|67968168\|dbj\|B | 9 | 4 | 347 | 74 S | 117 S | 128 A | 134 G | 164 K | 269 F | 321 V | 332 E | 337 K |
| BAE00129_gi\|67968175\|dbj\|B | 4 | 1 | 347 | 134 G | 164 K | 321 V | 332 E | | | | |
| BAE00135_gi\|67968182\|dbj\|B | 5 | 2 | 347 | 61 L | 134 G | 164 K | 321 V | 332 E | | | |
| BAE00141_gi\|67968189\|dbj\|B | 4 | 1 | 347 | 134 G | 164 K | 321 V | 332 E | | | | |
| BAE00147_gi\|67968204\|dbj\|B | 5 | 2 | 347 | 113 L | 134 G | 164 K | 321 V | 332 E | | | |
| BAE00153_gi\|67968211\|dbj\|B | 6 | 3 | 347 | 113 L | 134 G | 164 K | 269 Y | 321 V | 332 E | | |
| BAE00159_gi\|67968218\|dbj\|B | 6 | 3 | 347 | 60 M | 113 L | 134 G | 164 K | 321 V | 332 E | | |
| BAE00165_gi\|67968225\|dbj\|B | 6 | 3 | 347 | 113 L | 123 C | 134 G | 164 K | 321 V | 332 E | | |
| BAE00171_gi\|67968232\|dbj\|B | 6 | 3 | 347 | 105 L | 123 C | 134 G | 164 K | 321 V | 332 E | | |
| BAE02837_gi\|68445619\|dbj\|B | 2 | 1 | 246 | 134 G | 164 K | | | | | | |
| BAE02838_gi\|68445621\|dbj\|B | 3 | 2 | 246 | 66 H | 134 G | 164 K | | | | | |
| BAE02839_gi\|68445623\|dbj\|B | 3 | 2 | 246 | 66 H | 134 G | 164 K | | | | | |
| BAE02840_gi\|68445625\|dbj\|B | 4 | 3 | 246 | 60 E | 66 H | 134 G | 164 K | | | | |
| BAE02841_gi\|68445627\|dbj\|B | 4 | 3 | 246 | 113 L | 134 G | 164 K | 267 F | | | | |

TABLE 2B-continued

PML Samples

| Sequence | #mut | #region | Length | Variants | | | | | | |
|---|---|---|---|---|---|---|---|---|---|---|
| BAE02842_gi|68445629|dbj|B | 4 | 3 | 246 | 60 M | 134 G | 164 K | 270 H | | | |
| BAE02843_gi|68445631|dbj|B | 3 | 2 | 246 | 66 H | 134 G | 164 K | | | | |
| BAE02844_gi|68445633|dbj|B | 4 | 3 | 246 | 113 L | 134 G | 164 K | 269 F | | | |
| BAE02845_gi|68445635|dbj|B | 4 | 3 | 246 | 113 L | 134 G | 164 K | 267 F | | | |
| BAE02846_gi|68445637|dbj|B | 3 | 1 | 246 | 134 G | 164 K | 223 A | | | | |
| BAE02847_gi|68445639|dbj|B | 4 | 3 | 246 | 69 D | 134 G | 164 K | 269 F | | | |
| P03089_gi|116626|sp|P03089 | 8 | 4 | 347 | 75 R | 117 S | 134 G | 158 L | 164 K | 321 V | 332 E | 345 K |
| BAB11710_gi|9796415|dbj|BAB | 8 | 4 | 347 | 75 R | 117 S | 134 G | 158 L | 164 K | 321 V | 332 E | 345 K MAD-1 |
| Average values | 4.7 | 2.4 | 300.8 | | | | | | | | |

Diagnostics

Accordingly, methods of the invention are useful in one aspect for determining if a subject is at risk for, or has, PML based on the panels and groups of variant/variants of the invention. Assaying a biological sample from a subject for an indicium of exposure to a variant JCV will allow for the determination if a person is at risk for, or has, PML, or is infected by a JCV variant associated with PML. The determination of whether a subject has been exposed to, or is infected with, a JCV variant having a sequence variation at one or more of the VP1 positions described herein allows for the assessment of whether a subject is at risk for PML (variants at VP1 positions of a JCV variant associated with PML are also referred to as variants of the invention). In one aspect, the invention provides correlations between the mutational status at predetermined positions of a JCV variant and risk for PML. In some embodiments the variants are located on the JCV-VP1 protein.

As used herein, "diagnosing" and "identifying" PML means the recognition of whether a person is at risk for PML, or has PML. The diagnosis of being at risk for PML is not limited to the determination of variants at positions indicative of exposure to a JCV variant and may be combined with diagnosis methods routine in the art. These diagnostic assays include but are not limited to histopathology, immunohistochemistry, flow cytometry, cytology, patho-physiological assays, including MRI and tomography, neurological assays biochemical assays. Detection of JCV DNA by PCR in CSF is the most widely accepted diagnostic test of PML. It has 99% specificity and 70% selectivity. In the absence of a positive JCV PCR result for CSF, a brain biopsy could be performed. JCV DNA detection in brain tissue can be used as a positive diagnosis of PML. Biochemical assays include but are not limited to variant analysis other than at the predetermined positions, viral genome analysis, ELISA analysis of specific proteins, platelet count etc. Those of ordinary skill in the art will be aware of numerous diagnostic protocols and parameters that are routinely utilized in the art.

Diagnosis also covers a determination of the amount of JCV variant (viral load) and the ratio of JCV variant versus JCV wild type in a sample and/or subject.

Methods and/or kits of the invention can be used to screen subjects for having PML and being at risk for PML as indicated by the presence of variants at predetermined positions indicative of exposure to a JCV variant (the variants of the invention), in which the presence of one or more variants of the invention is associated with being at risk for PML. Methods of the invention may be used to diagnose the risk for PML by assessing the variants of the invention in a sample from a subject that has been exposed or is suspected of having been exposed to a JCV variant associated with PML.

The invention, in some aspects, includes various assays to determine whether a subject has been exposed to a JCV variant having one or more variants at specific positions in the VP1 protein. Methods and assays of the invention may be used to monitor changes in the status of variants of the invention in a sample and or a subject over time. In addition, methods of the invention may be used to monitor the amount of JCV variant present in subject over time, by obtaining multiple sample from the subject at different time points. Thus, methods of the invention may be used to examine changes in variants of the invention and/or amount of JCV variant in a subject or sample over time. This allows monitoring of mutational status in a subject who is suspected to be at risk of developing PML and also enables quantitative monitoring in a subject who is known to have been exposed to a JCV variant.

Detection of JCV-VP1 Variant Nucleic Acids, Polypeptides and Antibodies

In one aspect the invention provides methods for the detection of JCV-VP1 variant polypeptides and/or antibodies that can specifically bind the JCV variant polypeptides in a biological sample (also referred to as polypeptides and antibodies of the invention, respectively). Methods of detecting polypeptides and antibodies are well known in the art and the invention is not limited to any specific detection method. In addition, the polypeptides and antibodies may be detected indirectly, through the detection of nucleic acids encoding the polypeptides or antibodies of the invention. Methods for the detection of nucleic acids are well known in the art and non-limiting examples are PCR, sequencing, hybridization analysis, probe analysis and microarray analysis, which are all embraced by the current invention. Non-limiting examples of methods for the detection of polypeptides and/or antibodies include peptide sequencing, mass spectrometry and immunosorbent assays (e.g., binding of the polypeptide to an antibody) and protein arrays.

Enzyme-linked immunosorbent assays (ELISAs) are a well-known assays used for the detection of various antigens including polypeptides. The invention embraces any ELISA that can detect the presence of a polypeptides of the invention and any ELISA that can detect the presence of antibodies of the invention in a sample.

In one embodiment a first step of an ELISA comprises providing a primary antibody specific for a JCV-VP1 polypeptide bound to a multiwell plate. The invention is not limited to multiwell plates and the antibodies may be immobilized onto any surface including beads and glass slides. The invention is also not limited to antibodies and any peptide binding moiety, including aptamers, antibody fragments and small molecules are embraced by the invention. The invention embraces both the qualitative and quantitative determination of the presence of polypeptides of the invention. In one embodiment, the wells can be blocked using a buffer containing a high concentration of irrelevant protein, such as bovine serum albumin or casein. The blocking step ensures that any uncoated areas of the surface will be occupied with non-reactive protein, if needed. Excess blocking agent is then removed by one or more washes. In some embodiments the ELISA is a multiplex assay and each well of a multiwell plate comprises an antibody specific for one specific JCV-VP1 polypeptide variant. Once the surface is blocked, a sample containing a JCV-VP1 polypeptide, or a sample to be tested for presence of a JCV-VP1 polypeptide, can be contacted with the primary antibody and is allowed to incubate under conditions and for an amount of time suitable to permit specific binding of the JCV-VP1 polypeptide to the primary antibody. Such conditions and amount of time can be, for example, room temperature for 3-4 hours, or 4° C. for 10-16 hours. Excess sample is then removed by one or more washes. As a next step, a secondary antibody, also specific for the JCV-VP1 polypeptide, is contacted to the primary antibody-polypeptide complex and is allowed to incubate under conditions and for an amount of time suitable to permit specific binding of the JCV-VP1 polypeptide by the secondary antibody. Such conditions and amount of time can be, for example, antibody at 1-10 microgram/ml, room temperature for 1-4 hours, and 4° C. for 10-16 hours. In some embodiments, the secondary antibody is connected to a fluorescent tag or to a metabolizing enzyme, allowing for the detection of bound JCV-VP1 polypeptide. Alternatively, bound JCV-VP1 polypeptide can be determined by contacting the secondary antibody with a labeled tertiary antibody. The above-described ELISA is referred to as a sandwich ELISA as the JCV-VP1 polypeptide is sandwiched between two antibodies (the primary antibody and the secondary antibody).

In some embodiments, the presence of antibodies specific for JCV-VP1 polypeptides is determined. The invention embraces both the qualitative and quantitative determination of presence of antibodies of the invention. Determination of the presence of antibodies can allow for the determination of both current and past infection. In most instances, the human body will develop an antibody against a foreign polypeptide, such as a JCV proteins. Even if the virus (e.g., viral nucleic acid) itself is no longer detected in the body, antibodies against the virus may still be present, thereby being an indicator of exposure to the virus. In one embodiment of a method for detecting antibodies specific for variant JCV-VP1 polypeptides, one or more solid surfaces (e.g., a multi-well plate, bead or slide) are provided wherein each surface has an immobilized unique JCV-VP1 polypeptide variant.

In some embodiments the JCV-VP1 polypeptide variants are immobilized as JCV particles (e.g., recombinant VP1 proteins that contain one or more variants and that are self-assembled to form particles that are immobilized, for example, on an assay surface). These particles may contain one or more of the variants described herein (see, e.g., Tables 1A-1H, Table 17 and/or Table 18, and/or one or more other variants described herein).

Each polypeptide variant comprises one or more of the variants of Tables 1A-1H, Table 17 and/or Table 18 and/or one or more other variants described herein. Multiple peptides may cover the same one or more variants. In one embodiment combinations of polypeptides variants are attached to the solid surface. In some embodiments the solid surface a multi-well plate is provided wherein each well comprises one or more variants. In some embodiments a multi-well plate comprises wells with peptides covering all variants described herein that are indicative of risk for PML. A sample comprising or suspected of comprising one or more antibodies that can bind to a JCV-VP1 Polypeptide variant described herein is contacted with the immobilized peptides under conditions suitable for the antibodies to bind to the immobilized JCV-VP1 polypeptide. The presence of the bound antibodies is subsequently detected through binding of a secondary antibody.

The ELISAs of the invention are not limited to the above described embodiments, but also embraces competitive ELISAs and any form of ELISA that allows for the detection of the polypeptides and antibodies of the invention.

Onset, Progression, Regression

Methods and/or kits of the invention can be used to obtain useful prognostic information by providing an early indicator of PML onset, progression, and/or regression. The invention includes methods to monitor the onset, progression, or regression of PML and/or JCV variant infection in a subject by, for example, obtaining samples at sequential times from a subject and assaying such samples for exposure to JCV variants of the invention. A subject may be suspected of having PML or may be believed not to have PML and in the latter case, the sample may serve as a normal baseline level for comparison with subsequent samples.

Onset of a condition is the initiation of the changes associated with the condition in a subject. Such changes may be evidenced by physiological symptoms. However, a patient may be clinically asymptomatic. For example, the onset of PML and/or JCV infection may be followed by a period during which there may be PML-associated pathogenic changes in the subject, even though clinical symptoms may not be evident at that time. The progression of PML follows onset and is the advancement of the pathogenic (e.g., physiological) elements of the condition, which may or may not be marked by an increase in clinical symptoms. In contrast, the regression of PML and/or JCV infection may include a decrease in physiological characteristics of the condition, perhaps with a parallel reduction in symptoms, and may result from a treatment or may be a natural reversal in the condition. Onset of PML and/or JCV infection may be indicated by a change in the variants at the interrogated positions in samples obtained from the subject. For example, if the number of variants at the interrogated positions is lower in a first sample from a subject, than in a second or subsequent sample from the subject, it may indicate the onset or progression of PML and/or JCV infection. In some embodiments the presence of only one variant may be indicative of the onset or progression of PML. In some embodiments the variant is at position 164. In a particular embodiment, the emergence of a variant amino acid (e.g., Lys) at position 164 is indicative of onset or progression of PML. In some embodiments onset of PML and/or JCV infection is indicated by a change in viral load of JCV variant and/or ratio of JCV variant to JCV wild type. In some embodiments an increase in viral load is accompanied by an increase in the number of variants.

Progression and regression of PML and/or JCV infection may be generally indicated by the increase or decrease in the number of variants at interrogated positions in a subject's samples over time. For example, if the number of variants is low in a first sample from a subject and increased levels of variants are determined to be present in a second or subsequent sample from the subject, it may indicate the progression of PML and/or JCV infection, respectively. It should be appreciated that both an increase and a decrease in the number of variants, may be indicative of progression or regression of PML and/or JCV infection, respectively. For instance, the number of variants at certain positions may increase, while the number of variants at other positions may decrease, with both changes being indicative of PML and/or JCV infection.

Progression of PML and/or JCV infection may also be indicated by the increase in viral load of a JCV variant or an increase in the ratio of JCV variant to JCV wild type, while regression may be indicated by a decrease in viral load of a JCV variant or a decrease in the ratio of JCV variant to JCV wild type.

Onset, progression and regression can be determined by assaying multiple samples that are obtained from a subject at different time points. For instance, even if a first group of samples taken at different time points does not show onset, progression or regression of PML an additional sample may be obtained and assayed for the variants of the invention and compared to earlier samples to determine whether onset, progression or regression are occurring. In some embodiments additional samples are assayed when the administration regimes of one or more immunosuppressants is modified.

Assays for PML Treatment

Methods of the invention may also be used to assess the efficacy of a therapeutic treatment of PML by interrogation for exposure to a variant of JC virus in a subject at various time points. For example, the number of variants indicative of exposure to a variant JC virus can be obtained prior to the start of a therapeutic regimen (either prophylactic or as a treatment of cancer or a precancerous condition), during the treatment regimen, and/or after a treatment regimen, thus providing information on the effectiveness of the regimen in the subject. In addition, the abundance of JCV variants indicative of PML risk can also be monitored over time. In some embodiments, the amount of JCV variant (viral load) or ratio of JCV variant to wild type JCV may provides information on the effectiveness of the regimen in the subject. Methods of the invention may be used to compare the mutated positions in two or more samples obtained from a subject at different times. In some embodiments, a sample is obtained from a subject, the subject is administered a treatment for PML and a subsequent sample is obtained from the subject. A comparison of a subject's variants of the invention or viral load of the JC variant or ratio of JC variant to JCV wild type is determined in samples obtained at different times and/or on different days, thereby providing a measure of the status of the subject's PML, which can be used to determine the effectiveness of any treatment for PML and/or JCV infection in a subject.

As used herein, PML treatment encompasses both prophylactic and therapeutic treatment, and it embraces both the prevention and treatment of PML. A subject can receive PML treatment because the subject has been determined to be at risk for PML or alternatively, the subject may have PML. Thus, a treatment may reduce or eliminate PML and/or JCV infection altogether or prevent it from becoming worse. "Evaluation of treatment" as used herein, means the comparison of a subject's levels of variants indicative for exposure to a JCV variant or the viral load of the JCV variant in samples obtained from the subject at different sample times, for example, at least one day apart. In some embodiments, the time to obtain the second sample from the subject is at least 5, 10, 20, 30, 40, 50, minutes after obtaining the first sample from the subject. In certain embodiments, the time to obtain the second sample from the subject is at least 1, 2, 3, 4, 5, 6, 7, 8, 9, 10, 11, 12, 13, 14, 15, 16, 17, 18, 19, 20, 21, 22, 23, 24, 36, 48, 72, 96, 120 or more hours after obtaining the first sample from the subject. In some embodiments, the time to obtain the second sample from the subject is at least 1, 2, 3, 4, 5, 6, 7, 8, 9, 10, 11, 12, 13, 14, 15, 16, 17, 18, 19, 20, 21, 28, 35, 42, 49, 56, 60, 90, 120, 150, 180, 360 or more days after obtaining the first sample from the subject.

Treatment of PML

In one embodiment, a therapeutic agent for the treatment of PML is an anti-infective agent. A therapeutic agent may be an anti-infective agent that treats a microbial infection, e.g., a therapeutic agent that is effective to treat an infection of the CNS. In some embodiments, an anti-infective agent may be an siRNA. However, other suitable anti-infective agents may be used. Anti-infective agents may be antimicrobial agents such as antiviral agents. Antiviral agents may be combined with additional anti-infective agents such as antifungal agents or antibacterial agents. Therapeutic agents of the invention may be naturally occurring or synthetic molecules or compounds. A therapeutic agent useful in methods and compositions of the invention may be a polypeptide, chemical, small molecule, lipid, nucleic acid, or other compound.

Examples of nucleic acids that can be used as therapeutic agents (e.g., anti-infective agents) in methods and compositions of the invention are small interfering RNA molecules (siRNA), antisense DNA, antisense RNA, or aptamers that can be used to prevent and/or treat a CNS disease or disorder, including PML. A "small interfering RNA" or "siRNA," as used herein, refers to a RNA molecule that can be derived from the successive cleavage of a double-stranded RNA (dsRNA) within a cell to produce an RNA molecule. An effective siRNA generally has a length of between 15 and 30 nucleotides, and more often between 20 and 25 nucleotides. siRNAs function to direct the destruction of corresponding mRNA targets during RNA interference in animals. Methods of the invention, in part, include the administration of siRNA molecules to treat a CNS disease or disorder (e.g., a CNS infection) associated with a variant JC virus. In some aspects, methods of the invention may include administering to a subject a therapeutic composition that includes an siRNA and/or a precursor siRNA as a treatment of a CNS disease or condition. A precursor siRNA molecule is a double-stranded RNA molecule that after administration can be reduced in size, for example by the enzyme Dicer, to form the intended siRNA, this becoming functional for RNAi treatment of a CNS disease or condition. Thus, methods of the invention may include administration of an siRNA or a precursor siRNA molecule to treat a CNS disease or condition.

Selecting Treatment

In some embodiments, methods of the invention may be used to help select a treatment for a subject with PML or at risk for PML. Selection of a treatment for PML may be based upon the determination of the variants indicative of exposure to a JCV variant. Selection of treatment may also be based on the amount of JCV variant in a sample (viral load) or on the ratio of variant JCV to wildtype JCV. Methods of selecting a treatment may be useful to assess and/or adjust treatment of subjects already receiving a drug or therapy for PML. Based on the variants found that are indicative of exposure to a JCV variant, it may be appropriate to alter a therapeutic regimen for a subject. For example, detection of a change in one or more of the positions indicative of exposure to a JCV variant in a subject who has received or is receiving PML or JCV treatment may indicate that the treatment regimen should be adjusted (e.g., the dose or frequency of dosing, increased, new treatment initiated, etc.). In some embodiments, the change in viral load of a JCV variant or ratio of variant JCV to wildtype JCV may indicate that the treatment regimen should be adjusted. In some embodiments, a subject may be free of any present treatment for PML and/or JCV infection and monitoring of variants at positions indicative of exposure to JCV variant and/or viral load of the JCV variant and/or the ratio of JCV variant to JCV wildtype may identify the subject as a candidate for a treatment for PML and or JCV infection. Thus, subjects may be selected and treated with elevated levels of the same drugs or with different therapies as a result of assays for indicia of exposure to a JCV variant and/or a viral load of the JCV variant and/or a ratio of JCV variant to JCV wild type.

According to the present invention, some subjects may be free of symptoms otherwise calling for treatment with a particular therapy, and the detection of indicia of exposure to a JCV variant and/or a viral load of a JCV variant and/or a ratio of JCV variant to JCV wild type may identify the subject as needing treatment. This means that absent the use of the methods of the invention to identify indicia of exposure to a JCV variant and/or a viral load of a JCV variant and/or a ratio of JCV variant to JCV wild type, the subject would not according to convention as of the date of the filing of the present application have symptoms calling for treatment with a particular PML and/or JCV infection therapy.

In one aspect, the invention provides methods for the decision on treatment regimens for PML. A clinician can make decisions on treatment options at least in part based on the diagnostic assays of the invention.

Treatment Relating to Immunosuppressants

Methods of selecting treatment may be useful for persons undergoing treatment not directed to PML or JCV infection, but directed to a different condition. In one embodiment, the treatment is a treatment comprising immunosuppressants. In some embodiments, a person suspected of being at risk for developing PML is a person undergoing treatment with immunosuppressants.

In some embodiments, detection of a change in one or more indicia of exposure to a JCV variant in a subject who has received or is receiving treatment not directed to PML, may indicate that the treatment regimen should be adjusted. In some embodiments, detection of a change in one or more indicia of exposure to a JCV variant in a subject who has received or is receiving treatment with immunosuppressants may indicate that the treatment regimen should be adjusted. In some embodiments, detection of a change in viral load of a JCV variant or ratio of JCV variant to wild type in a subject who has received or is receiving treatment with immunosuppressants may indicate that the treatment regimen should be adjusted. In some embodiments, detection of a sequence change in one or more predetermined VP1 positions of a JCV in a subject who has received or is receiving treatment with immunosuppressants may indicate that the treatment regimen should be terminated or interrupted. In some embodiments, the immunosuppressant is natalizumab. In some embodiments, detection of an increase in the viral load of a JCV variant and/or the ratio of JCV variant to JCV wild type in a subject who has received or is receiving treatment with immunosuppressants may indicate that the treatment regimen should be terminated or interrupted.

In one aspect, the invention provides methods for the decision on treatment regimens. A clinician can make decisions on treatment options at least in part based on the diagnostic assays of the invention. In some embodiments the methods of the invention provide a diagnostic assay to decide on a suitable treatment with immunosuppressive agents. In some embodiments, a clinician may decide to terminate or interrupt treatment with immunosuppressive agents based on the outcome of one or more JCV-VP1 diagnostic assays of the invention. In some embodiments, the methods of the invention provide a diagnostic assay for the treatment of a subject, wherein the subject is immunocompromised. In some embodiments, a clinician may decide to terminate or interrupt treatment of the immuno-compromised subject based on the outcome of a JCV-VP1 diagnostic assays of the invention Immuno-Compromised Subjects or Subjects Undergoing Treatment with Immuno-Suppressants Assays of the invention may be particularly useful for immuno-compromised subjects and/or subjects being treated with one or more immuno-suppressants.

Subjects may receive treatment with one or more immunosuppressive agents (also called immuno-suppressants) directed to different diseases or conditions, including one or more of the following non-limiting examples: cancer, organ or tissue transplant, inflammatory conditions or diseases, multiple sclerosis (MS), arthritis, etc., or any combination thereof.

Subjects may also be immuno-compromised. Non-limiting examples of immuno-compromised subjects are subject that are HIV positive or have AIDS or lymphoma or any other condition resulting in a suppression of the immune response.

The term "immuno-suppressive agent" as used herein refers to substances that act to suppress or mask the immune system of a subject being treated herein. Immunosupressive agents may be substances that suppress cytokine production, down-regulate or suppress self-antigen expression, or mask the MHC antigens. Examples of such agents include 2-amino-6-aryl-5-substituted pyrimidines (see U.S. Pat. No. 4,665,077); nonsteroidal anti-inflammatory drugs (NSAIDs); ganciclovir, tacrolimus, glucocorticoids such as cortisol or aldosterone, anti-inflammatory agents such as a cyclooxygenase inhibitor, a 5-lipoxygenase inhibitor, or a leukotriene receptor antagonist; purine antagonists such as azathioprine or mycophenolate mofetil (MMF); alkylating agents such as cyclophosphamide; bromocryptine; danazol; dapsone; glutaraldehyde (which masks the MHC antigens, as described in U.S. Pat. No. 4,120,649); anti-idiotypic antibodies for MHC antigens and MHC fragments; cyclosporin A; steroids such as corticosteroids or glucocorticosteroids or glucocorticoid analogs, e.g., prednisone, methylprednisolone, and dexamethasone; dihydrofolate reductase inhibitors such as methotrexate (oral or subcutaneous); hydroxycloroquine; sulfasalazine; leflunomide; cytokine or cytokine receptor antagonists including anti-interferon-alpha, -beta, or -gamma antibodies, anti-tumor necrosis factor-alpha antibodies (infliximab or adalimumab), anti-TNF-alpha immunoahesin (etanercept), anti-tumor necrosis factor-beta antibodies, anti-interleukin-2 antibodies and anti-IL-2 receptor antibodies; anti-LFA-1 antibodies, including anti-CD11a and anti-CD18 antibodies; anti-CD20 antibodies (e.g., rituximab, for example available under the trademark RITUXAN); anti-L3T4 antibodies; anti-VLA-4 antibodies (e.g., natalizumab, for example available under the trademark TYSABRI); heterologous anti-lymphocyte globulin; pan-T antibodies, for example anti-CD3 or anti-CD4/CD4a antibodies; soluble peptide containing a LFA-3 binding domain (WO 90/08187 published Jul. 26, 1990); streptokinase; TGF-beta; streptodornase; RNA or DNA from the host; FK506; RS-61443; deoxyspergualin; rapamycin;

T-cell receptor (Cohen et al., U.S. Pat. No. 5,114,721); T-cell receptor fragments (Offner et al., Science, 251: 430432 (1991); WO 90/11294; Ianeway, Nature, 341: 482 (1989); and WO 91/01133); and T cell receptor antibodies (EP 340,109) such as T10B9. However, subjects receiving other immunosupressive agents may selected for diagnostic assays and/or treated as the invention is not limited in this respect.

Screening for Candidate Therapeutic Agents

The invention also embraces methods for screening for candidate therapeutic agents or strategies to prevent and/or treat PML and/or JCV infection. Assessment of the efficacy of candidate therapeutic agents and strategies may be done using assays of the invention in subjects (e.g., non-human animals) and in cells from culture. In some embodiments, a candidate therapeutic agent may be a compound or molecule that can interact with a polypeptide comprising one or more JCV-VP1 variants associated with PML. In some embodiments, a candidate therapeutic agent may be a compound or molecule that can change the pattern and number of JCV-VP1 variants in a subject having a JCV infection. In some embodiments, a candidate therapeutic is an agent that can reduce the amount of JCV variant (viral load) in a sample or subject. In some embodiments, a candidate therapeutic is an agent that can reduce the ratio of variant JCV to wild type JCV. In some embodiments, a candidate therapeutic is an agent (e.g., a small molecule) that mimics the JCV receptor and can compete for JCV binding. In some embodiments, administration to the subject of an agent, or exposing a sample to the candidate agent or candidate treatment, will result in a change in the pattern of JCV-VP1 variants associated with a JCV infection in a subject. In some embodiments, administering to the subject of an agent, or exposing a sample to the candidate agent or candidate treatment, will result in a change in the number of PML associated JCV-VP1 variants in a JCV infection. In some embodiments, administering to the subject of an agent, or exposing a sample to the candidate agent or candidate treatment, will result in a decrease of JCV variant viral load and/or ratio of JCV variant to JCV wild type.

In one embodiment, a sample comprising cells expressing a JCV variant is exposed to a candidate therapeutic agent or treatment. A sample comprising cells exposed to the candidate, that do not express the JCV variant will function as a control. The level of expression of the JCV variant (viral load) is monitored upon administration of the candidate therapeutic or treatment, and the change in expression of the JCV variant is compared to samples that did not get treated with the candidate therapeutic agent. If the level of viral load of the JCV variant of the invention in the sample that has been exposed to the agent has changed compared with the control sample, the agent is a candidate therapeutic or candidate treatment. In some embodiments JCV variants are expressed and secreted from cells and subjected to contacting with a candidate agent. Any candidate agent that can bind the JCV variant is a candidate therapeutic agent. In some embodiments, the candidate therapeutic agent binds to a VP1 polypeptide of the JCV variant.

In some embodiments, the invention provides methods for identifying candidate therapeutic agents that suppress the number or level of PML-associated VP1 variants in a JCV infection, and that suppress the risk for PML. In some embodiments, the candidate therapeutic agents are directed to a disease or condition that is not PML or JCV infection. In some embodiments, the candidate therapeutic agents are immunosuppressants. In some embodiments, the candidate therapeutic agents are agents that are being prescribed in immunosuppressant therapy.

Methods of screening for agents or treatments that modulate levels of expression of JCV variants are encompassed by the invention. Screening methods may include mixing the candidate agent with cells or tissues or in a subject or exposing cells or tissues or a subject to the candidate treatment and using methods of assaying viral load of the JCV variants to determine the level of expression before and after contact with the candidate agent or treatment. A decrease in the amount of expression of the JCV variant compared to a control is indicative that the candidate agent or treatment is capable of treating PML and/or JCV infection in a cell, tissue, and/or subject.

In some embodiments, an assay mixture for testing a candidate agent comprises a candidate agent. A candidate agent may be an antibody, a small organic compound, or a polypeptide, and accordingly can be selected from combinatorial antibody libraries, combinatorial protein libraries, or small organic molecule libraries. Typically, pluralities of reaction mixtures are run in parallel with different agent concentrations to obtain a different response to the various concentrations. Typically, one of these concentrations serves as a negative control, e.g., at zero concentration of agent or at a concentration of agent below the limits of assay detection.

Any molecule or compound can be a candidate therapeutic. Non-limiting examples of candidate therapeutics are small molecules, RNA including siRNAs, DNA including aptamers, and proteins including antibodies and antibody fragments. The invention also embraces candidate therapeutic with different modes of action.

Candidate agents encompass numerous chemical classes, although typically they are organic compounds, proteins or antibodies (and fragments thereof that bind antigen). In some embodiments, the candidate agents are small organic compounds, e.g., those having a molecular weight of more than 50 yet less than about 2500, for example less than about 1000 and, in certain embodiments, less than about 500. Candidate agents comprise functional chemical groups necessary for structural interactions with polypeptides and/or nucleic acids, and may include at least an amine, carbonyl, hydroxyl, or carboxyl group, optionally at least two of the functional chemical groups or at least three of the functional chemical groups. The candidate agents can comprise cyclic carbon or heterocyclic structure and/or aromatic or polyaromatic structures substituted with one or more of the above-identified functional groups. Candidate agents also can be biomolecules such as nucleic acids, polypeptides, saccharides, fatty acids, sterols, isoprenoids, purines, pyrimidines, derivatives or structural analogs of the above, or combinations thereof and the like.

Candidate agents are obtained from a wide variety of sources including libraries of synthetic or natural compounds. For example, numerous means are available for random and directed synthesis of a wide variety of organic compounds and biomolecules, including expression of randomized oligonucleotides, synthetic organic combinatorial libraries, phage display libraries of random or non-random polypeptides, combinatorial libraries of proteins or antibodies, and the like. Alternatively, libraries of natural compounds in the form of bacterial, fungal, plant, and animal extracts are available or readily produced. Additionally, natural and synthetically produced libraries and compounds can be readily be modified through conventional chemical, physical, and biochemical means. Further, known agents may be subjected to directed or random chemical modifications such as acylation, alkylation, esterification, amidification, etc., to produce structural analogs of the agents.

A variety of other reagents also can be included in the mixture. These include reagents such as salts, buffers, neutral proteins (e.g., albumin), detergents, etc., which may be used to facilitate optimal protein-protein and/or protein-agent binding. Such a reagent may also reduce non-specific or background interactions of the reaction components. Other reagents that improve the efficiency of the assay such as protease inhibitors, nuclease inhibitors, antimicrobial agents, and the like may also be used.

Kits

In some aspects of the invention, kits are provided. Kits of the invention may contain nucleic acid, polypeptides, antibodies or other molecules of the invention for use in vitro diagnosis, prognosis, monitoring of PML and/or JCV infection, exposure to JCV variants and/or testing of candidate therapeutic agents. Components of the kits can be packaged either in aqueous medium or in lyophilized form. Reagents for use in PCR and ELISA assays may also be included in kits of the invention as can detectable labeling agents in the form of intermediates or as separate moieties to be conjugated as part of procedures to assay risk for PML, JCV infection or exposure to a JCV variant. In some embodiments of a kit of the invention, the kit may include instructions for determining the presence of the variants of the invention and/or for determining the viral load of a JCV variant. The kit may also include control values (e.g., reference numbers) that can be used for interpreting results of methods used in the invention.

A kit of the invention may include nucleic acid, antibodies or polypeptides that can be used to identify one or more indicia of exposure to JCV variants having one or more PML-associated VP1 variants. In some embodiments, kits include materials for use in standard techniques of ELISA to identify antibodies that can bind one or more polypeptides comprising one or more variants indicative of exposure to a JCV variant. In some embodiments, a kit of the invention may include nucleic acid components for binding to and detecting nucleic acids encoding one or more variants or variant combinations described herein as associated with PML. In some embodiments, a kit may include one or more different antibodies that specifically bind to one or more polypeptides comprising one or more variants or combinations of variants of the invention. A kit also may include components for use with the antibodies to determine expression of JCV variants or exposure to JCV variants in a cell, tissue or subject.

A kit may comprise a carrier being compartmentalized to receive in close confinement therein one or more container means or series of container means such as test tubes, vials, flasks, bottles, syringes, or the like. The kit may also contain a control sample. In some embodiments, the kit comprises instructions for interpreting test results such as instructions for determining whether a test indicates whether the level of a detected agent in the assay correlates with exposure to a JCV infection (e.g., by a wild-type or variant JCV).

Biological Samples

Methods for assaying for exposure to a JCV variant may be carried out on any suitable biological sample. In some embodiments, a sample may obtained from a subject and directly processed and assayed for indicia of JCV as described herein. In some embodiments, cells may be isolated from a biological sample and grown in culture prior to analysis. As used herein, a subject may be a human or a non-human animal, including, but not limited to a non-human primate, cow, horse, pig, sheep, goat, dog, cat, or rodent. Methods of the invention may be used to assay for exposure to a variant of JCV in subjects not yet diagnosed with PML. Methods of the invention may be used to assay for exposure to a JCV variant in subjects not yet diagnosed as being infected with JCV. In addition, methods of the invention may be applied to subjects who have been diagnosed with PML and/or infection by a JCV variant. A sample may comprise one or more cells. A sample may originate directly from a subject or from a cell culture. A sample may be processed (e.g., to prepare a cell lysate) or partially processed prior to use in methods of the invention. In some embodiments, a sample from a subject or culture may be processed to obtain nucleic acids or polypeptides for use in assays to detect exposure to a variant of JC virus as described herein. Thus, an initial step in an assay may include isolation of a genomic nucleic acid sample and/or other nucleic acids and/or polypeptides from a cell, tissue, and/or other sample. Extraction of nucleic acids and/or polypeptides may be by any suitable means, including routine methods used by those of ordinary skill in the art such as methods that include the use of detergent lysates, sonication, and/or vortexing with glass beads, etc.

As used herein, the term "sample" means any animal material containing DNA or RNA or protein, such as, for example, tissue or fluid isolated from an individual (including without limitation plasma, serum, cerebrospinal fluid, urine, lymph, tears, saliva and tissue sections) or from in vitro cell culture constituents. A sample containing nucleic acids may contain of deoxyribonucleic acids (DNA), ribonucleic acids (RNA), or copolymers of deoxyribonucleic acids and ribonucleic acids or combinations thereof. A sample containing polypeptides may contain peptides and/or proteins. In some embodiments the sample contains antibodies. A sample may have been subject to purification (e.g., extraction) and/or other treatment. The term "sample" may also refer to a "biological sample."

As used herein, the term "biological sample" may refer to tissue, cells or component parts (e.g., body fluids, including but not limited to blood, mucus, lymphatic fluid, synovial fluid, cerebrospinal fluid, saliva, amniotic fluid, amniotic cord blood, urine, stool, vaginal fluid, and semen, etc.) of a subject. A "biological sample" may also refer to a homogenate, lysate, or extract prepared from tissues, cells or component parts, or a fraction or portion thereof, including but not limited to, for example, plasma, serum, spinal fluid, lymph fluid, urine, the external sections of the skin, respiratory, intestinal, and genitourinary tracts, tears, saliva, stool, milk, blood cells, tumors, or organs, CNS biopsies, etc.

Sample sources may include tissues, including, but not limited to lymph tissues; body fluids (e.g., blood, lymph fluid, etc.), cultured cells; cell lines; histological slides; tissue embedded in paraffin; etc. The term "tissue" as used herein refers to both localized and disseminated cell populations including, but not limited to: brain, heart, serum, breast, colon, bladder, epidermis, skin, uterus, prostate, stomach, testis, ovary, pancreas, pituitary gland, adrenal gland, thyroid gland, salivary gland, mammary gland, kidney, liver, intestine, spleen, thymus, bone marrow, trachea, and lung. Biological fluids include, but are not limited to, blood, lymph fluid, cerebrospinal fluid, tears, saliva, urine, and feces, etc. Invasive and non-invasive techniques can be used to obtain such samples and are well documented in the art. A control sample may include a bodily fluid, a cell, a tissue, or a lysate thereof. In some embodiments, a control sample may be a sample from a cell or subject that is free of PML and/or infection by, or exposure to, a JCV variant. In some embodiments, a control sample may be a sample that is from a cell or subject that has PML and/or has been exposed to a JCV variant. In some embodiments a control sample is a sample comprising wild-type JC virus.

Vaccines

The present invention further relates to a vaccine for immunizing a mammal against PML or infection by a PML-associated JCV variant. A vaccine may comprise at least one polypeptide comprising one or more JCV variant sequences of the invention. In some embodiments, a vaccine may include one or more variant JCV or JCV peptides described herein as predicted to reduce sialic acid binding. In some embodiments, a vaccine may include a plurality of different peptides (e.g., 2, 3, 4, 5, 6, 7, 8, 9, 10, 10-15, 15-20, 20-50, or more) to provide a broad range of different epitopes. In some embodiments, the polypeptide is a full length JCV-VP1 variant polypeptide. In still another embodiment, the polypeptide is a full length JCV-VP1 polypeptide selected from the group consisting of the polypeptides described herein (e.g., in FIG. 3 or Table 1 or 2B, Table 17 and/or Table 18, and/or one or more other variants described herein), or any fragment thereof (e.g., a 10, 20, 30, 40, 50, 60, 70, 80, 90, 100, 100-150, 150-200 amino acid long polypeptide, or a longer, shorter, or intermediate length polypeptide) having at least one variant amino acids (e.g., 1, 2, 3, 4, 5, 6, 7, 8, 9, 10, or more variant amino acids) at one or more of the predetermined positions described herein. In some embodiments, the polypeptide is a fragment of a JCV-VP1 protein comprising one or more variant amino acids of the invention. In a further aspect, the invention relates to a pharmaceutical composition comprising at least one JCV variant polypeptide and a suitable excipient, diluent or carrier. In some embodiments a polypeptide in the vaccine is about 5, about 10, about 20, about 30, about 40, or about 50 amino acids in length, or comprises the total length of the JCV-VP1 protein. These compositions are suitable for preventing or treating PML and/or an infection by a JCV variant associated with PML. A pharmaceutical composition may be administered to a subject in an effective amount to stimulate the production of protective antibody or protective T-cell response. In some embodiments, the vaccine is a nucleic acid vaccine comprising nucleic acids that encode one or more variant JCV polypeptides of the invention.

The term "immunizing" refers to the ability of a substance to cause a humoral and/or cellular response in a subject, whether alone or when linked to a carrier, in the presence or absence of an adjuvant, and also refers to an immune response that blocks the infectivity, either partially or fully, of an infectious agent. A PML "vaccine" is an immunogenic composition capable of eliciting protection against PML, whether partial or complete. A vaccine may also be useful for treating a subject having PML. Administration regimes for vaccines are known to a person of ordinary skill in the art. In some embodiments, ranges of amounts of polypeptide vaccines for prophylaxis of PML are from 0.01 to 100 microgram/dose, for example 0.1 to 50 microgram/dose. Several doses may be needed per subject in order to achieve a sufficient immune response and subsequent protection against PML or infection by a JCV variant associated with PML.

Pharmaceutically acceptable carriers include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers; and inactive virus particles. Such carriers are well known to those of ordinary skill in the art.

Adjuvants to enhance effectiveness of the polypeptide vaccines of the invention include, but are not limited to: aluminum hydroxide (alum), N-acetyl-muramyl-L-threonyl-D-isoglutamine (thr-MDP) as found in U.S. Pat. No. 4,606,918, N-acetyl-normuramyl-L-alanyl-D-isoglutamine (nor-MDP), N-acetylmuramyl-L-alanyl-D-isoglutaminyl-L-alanine-2-(1'-2'-dipalmitoyl-s-n-glycero-3-hydroxyphosphoryloxy)-ethylamine (MTP-PE) and RIBI, which contains three components extracted from bacteria, monophosphoryl lipid A, trehalose dimycolate, and cell wall skeleton (MPL+TDM+CWS) in a 2% squalene/Tween 80 emulsion. Any of the three components MPL, TDM or CWS may also be used alone or in combinations of two. In some embodiments, one or more peptides of the invention may be used for immunization using one or more techniques described in Goldmann et al., 1999, Journal of Virology, Vol. 73, No. 5, pp 4465-4469, the disclosure of which is incorporated herein by reference.

In some embodiments, a vaccine can be administered to a subject prior to or along with the initiation of an immunosuppressive therapy, or any other treatment that may affect (e.g., weaken) the immune system.

Antibodies

In certain embodiments, antibodies or antigen-binding fragments thereof to JCV variants are also encompassed by the invention. Antibodies may be used in detection assays described herein (e.g., ELISA assays). Antibodies may be used in therapy to treat subjects with PML and/or to prevent or reduce infection by JCV variants. Suitable antibodies or fragments thereof may be selected for the ability to bind one or more JCV variant polypeptides described herein. The antibody or antigen-binding fragment thereof may be an IgG1, IgG2, IgG3, IgG4, IgM, IgA1, IgA2, IgAsec, IgD, IgE or may have an immunoglobulin constant and/or variable domain of an IgG1, IgG2, IgG3, IgG4, IgM, IgA1, IgA2, IgAsec, IgD or IgE. In some embodiments, the antibody is a bispecific or multispecific antibody. In further embodiments, the antibody is a recombinant antibody, a polyclonal antibody, a monoclonal antibody, a humanized antibody or a chimeric antibody, or a mixture of these. In some embodiments, the antibody is a human antibody, e.g., a human monoclonal antibody, polyclonal antibody or a mixture of monoclonal and polyclonal antibodies. Antigen-binding fragments may include a Fab fragment, a F(ab')$_2$ fragment, and/or a F$_v$ fragment CDR3.

Antibodies can be raised against a full length JCV-VP1 protein variant or against polypeptides variants comprising a partial sequence of JCV-VP1 protein variant. Antibodies can be generated by injecting an animal, for example a rabbit or goat or mouse, with the antigen (e.g., a polypeptide of a JCV-VP1 variant).

In order to prepare polyclonal antibodies, fusion proteins containing a JCV-VP1 variant can be synthesized in bacteria by expression of corresponding DNA sequences in a suitable cloning vehicle. The protein can then be purified, coupled to a carrier protein and mixed with Freund's adjuvant (to help stimulate the antigenic response by the rabbits) and injected into rabbits or other laboratory animals. Alternatively, the polypeptides can be isolated from cultured cells expressing the protein. Following booster injections at bi-weekly intervals, the rabbits or other laboratory animals are then bled and the sera isolated. The sera can be used directly or purified prior to use, e.g., by methods such as affinity chromatography, Protein A-Sepharose, Antigen Sepharose, Anti-mouse-Ig-Sepharose. The sera can then be used to probe protein extracts run on a polyacrylamide gel to identify the JCV variant polypeptides. Alternatively, synthetic JCV variant polypeptides can be made and used to inoculate animals.

To produce monoclonal JCV variant antibodies, mice are injected multiple times (see above), the mice spleens are removed and resuspended in a phosphate buffered saline (PBS). The spleen cells serve as a source of lymphocytes, some of which produce antibodies of the appropriate specificity. These are then fused with a permanently growing myeloma partner cell, and the products of the fusion are plated into a number of tissue culture wells in the presence of a selective agent such as HAT. The wells are then screened by ELISA to identify those containing cells expressing useful antibody. These are then freshly plated. After a period of growth, these wells are again screened to identify antibody-producing cells. Several cloning procedures are carried out until over 90% of the wells contain single clones which are positive for antibody production. From this procedure a stable line of clones is established to produce the antibody. A monoclonal antibody can then be purified by affinity chromatography using Protein A Sepharose, ion-exchange chromatography, as well as variations and combinations of these techniques (See e.g., U.S. Pat. No. 6,998,467).

In some embodiments, 'humanized' antibodies are used in therapy in humans. Humanization of antibodies involves replacing native mouse sequences with human sequences to lower the chance of an immune response once the therapeutic antibody is introduced into humans.

CNS Infections

JC polyomavirus is a virus that infects the brain and CNS (Central Nervous System). Subjects suffering from microbial infections of the CNS may be susceptible to variant JC virus infection and/or proliferation in the CNS. Microbial infections of the CNS may include, but are not limited to, bacterial, fungal, protozoan, virus-like, and viral infections. Infections include both acute and chronic conditions. Exemplary microbial CNS infections can result in a brain abscess, meningitis, encephalitis, vasculitis, or progressive multifocal leukoencephalopathy (PML). Most abscess-forming infections of the CNS are spread by the blood and are related to septicemia and endocarditis, although there may be direct infection that arises from sinus or middle ear/mastoid infection. Bacterial infections of the CNS may include, but are not limited to infection by *Streptococcus pneumonia, Streptococcus pyogenes, Staphylococcus aureu, Staphylococcus epidermidis, Enterobacteriacea, Propionibacterium, Pseudomonoas aeruginosa, Neisseria meningitis, Haemophilus influenzae* or *Listeria moncytogenes*. Fungal infections of the CNS are less common than bacterial infections, but may arise in individuals with Acquired Immune Deficiency Syndrome (AIDS) and in other immunocompromised individuals, such as those undergoing chemotherapy or immunosuppressive therapy. An example of a protozoan infection of the CNS is late-stage neurological trypanosomiasis, or sleeping sickness, which is caused by infection of the CNS by *trypanosoma* protozoa.

Viral infections of the CNS may include, but are not limited to aseptic meningitis, encephalitis, and progressive multifocal leukoencephalopathy (PML). Acute neurological syndromes associated with viral infection include, for example, acute viral encephalitis, flaccid paralysis, aspectic meningitis, and post infectious encephalomyelitis. Acute viral encephalitis may be caused by for example, herpes simplex virus, cytomegalovirus, varicella, rabies or an arbovirus. Common viral agents of asceptic meningitis include, for example, enteroviruses, mumps virus and lymphocytic choriomeningitis virus. Post infectious encephalomyelitis is a complication of infection with measles, mumps, rubella and primary varicella-zoster virus infection, for example. Guillain-barre syndrome is also an acute neurological syndrome associated with viral infection.

Additional chronic neurological diseases attributable to viral infection include, subacute sclerosing pan encephalitis (caused by persistent measles infection), spongiform encephalopathies (prion diseases) (e.g., Creutzfeldt-Jakob disease (CJD), Gerstmann-Streussler Syndrome), and retroviral diseases (e.g., HIV-1 and HIV-2) characterized by paralysis, wasting, and ataxia.

Accordingly, aspects of the invention may be used to evaluate the risk of PML in subjects having one or more symptoms of a microbial CNS infection.

Studies of JCV Variants

Both host and viral genetics may contribute to PML. Earlier studies focusing on viral genetic factors identified duplications and rearrangements in the regulatory region of the viral genome [Pfister L A, Letvin N L, Koralnik I J (2001) J C virus regulatory region tandem repeats in plasma and central nervous system isolates correlate with poor clinical outcome in patients with progressive multifocal leukoencephalopathy. *J Virol* 75: 5672-5676; Major E O, Amemiya K, Tornatore C S, Houff S A, Berger J R (1992) Pathogenesis and molecular biology of progressive multifocal leukoencephalopathy, the J C virus-induced demyelinating disease of the human brain. Clin Microbiol Rev 5: 49-73; Loeber G, Dorries K (1988) DNA rearrangements in organ-specific variants of polyomavirus J C strain G S. *J Virol* 62: 1730-1735; Martin J D, King D M, Slauch J M, Frisque R J (1985) Differences in regulatory sequences of naturally occurring J C virus variants. *J Virol* 53: 306-311; and Zheng H Y, Takasaka T, Noda K, Kanazawa A, Mori H, et al. (2005) New sequence polymorphisms in the outer loops of the JC polyomavirus major capsid protein (VP1) possibly associated with progressive multifocal leukoencephalopathy. *J Gen Virol* 86: 2035-2045]. Several studies with very limited sample numbers from PML and healthy individuals also reported conflicting results on possible association of several mutations in VP1 protein with PML [Zheng H Y, Takasaka T, Noda K, Kanazawa A, Mori H, et al. (2005) New sequence polymorphisms in the outer loops of the JC polyomavirus major capsid protein (VP1) possibly associated with progressive multifocal leukoencephalopathy. *J Gen Virol* 86: 2035-2045; Zheng H Y, Ikegaya H, Takasaka T, Matsushima-Ohno T, Sakurai M, et al. (2005) Characterization of the VP1 loop mutations widespread among JC polyomavirus isolates associated with progressive multifocal leukoencephalopathy. *Biochem Biophys Res Commun* 333: 996-1002; Kato A, Sugimoto C, Zheng H Y, Kitamura T, Yogo Y (2000) Lack of disease-specific amino acid changes in the viral proteins of JC virus isolates from the brain with progressive multifocal leukoencephalopathy. *Arch Virol* 145: 2173-2182]. No comprehensive analysis of an association of changes in protein coding genes of JCV with PML has been reported. Pathogenicity of viruses ranging from influenza virus [Srinivasan A, Viswanathan K, Raman R, Chandrasekaran A, Raguram S, et al. (2008) Quantitative biochemical rationale for differences in transmissibility of 1918 pandemic influenza A viruses. *Proc Natl Acad Sci USA* 105: 2800-2805; and Chandrasekaran A, Srinivasan A, Raman R, Viswanathan K, Raguram S, et al. (2008) Glycan topology determines human adaptation of avian H5N1 virus hemagglutinin. *Nat Biotechnol* 26: 107-113] to the mouse polyomavirus [Bauer P H, Bronson R T, Fung S C, Freund R, Stehle T, et al. (1995) Genetic and structural analysis of a virulence determinant in polyomavirus V P1. *J Virol* 69: 7925-7931; and Bauer P H, Cui C, Liu W R, Stehle T, Harrison S C, et al. (1999) Discrimination between sialic acid-containing receptors and pseudoreceptors regulates polyomavirus spread in the mouse. *J Virol* 73: 5826-5832], a close relative of human JCV, was shown to be determined by amino acid sequences involved in the binding of a viral capsid protein to sialylated glycan receptors. Changes in the affinity and specificity of the virus for its cellular receptor(s) affect viral infectivity and transmission, hence playing a crucial role in virulence. For example, a study of the mouse polyomavirus showed that VP1 amino acid changes rather than changes in the non-coding regulatory region are responsible for the increased pathogenicity of the virus.

Aspects of the invention are illustrated by experiments relating to the VP1 protein and its relationship to PML. Methods of molecular evolution were used to determine the presence of putative adaptive changes in the VP1 amino acid sequence associated with PML. The advantage of this approach over simple statistical association of sequence variants with the disease, is that it takes into account the phylogenetic relationship of viral strains and also allows identification of functionally significant amino acid positions by examining the rate of sequence evolution.

According to aspects of the invention, a virus harboring substitutions is adequately infectious if it was sufficiently abundant in the CNS of PML patients to be isolated. In some embodiments, changes in glycan specificity are predicted to allow JCV to lose its specificity to sialated glycans expressed outside of the CNS (e.g., RBCs). Thus, such a virus would avoid getting trapped on "pseudoreceptors" in the periphery and travel unhindered from sites of viral shedding to enter the brain. Mutated virus must still maintain its specificity to glycans expressed on oligodendrocytes. This is consistent with the observation from the mouse polyomavirus model where a mutation in a position orthologous to position 269 of JCV affected viral ability to bind RBCs and also lead to the dramatic increase in viral dissemination through the animal with a lethal outcome [Dubensky T W, Freund R, Dawe C J, Benjamin T L (1991) Polyomavirus replication in mice: influences of VP1 type and route of inoculation. *J Virol* 65: 342-349; and Freund R, Garcea R L, Sahli R, Benjamin T L (1991) A single-amino-acid substitution in polyomavirus VP1 correlates with plaque size and hemagglutination behavior. *J Virol* 65: 350-355]. Furthermore, there are several reports of JCV detection in tonsils of many asymptomatically infected individuals [Kato A, Kitamura T, Takasaka T, Tominaga T, Ishikawa A, et al. (2004) Detection of the archetypal regulatory region of JC virus from the tonsil tissue of patients with tonsillitis and tonsilar hypertrophy. *J Neurovirol* 10: 244-249; and Monaco M C, Jensen P N, Hou J, Durham L C, Major E O (1998) Detection of JC virus DNA in human tonsil tissue: evidence for site of initial viral infection. *J Virol* 72: 9918-99231. Although this observation was taken as a support for the JCV infection of tonsil cells, it also could be explained by the viral trapping in lymphoid tissues. This is consistent with JCV binding to sialic acid in the tonsil tissue [Eash S, Tavares R, Stopa E G, Robbins S H, Brossay L, et al. (2004) Differential distribution of the JC virus receptor-type sialic acid in normal human tissues. *Am J Pathol* 164: 419-428].

According to the invention, given the large number of mutations that are specific for PML, it is likely that more than a single mechanism (e.g., two or more mechanisms) may play a role in PML etiology in different PML cases. According to some aspects of the invention, PML associated VP1 mutations may increase JCV tropism for brain white matter cells leading to the increased viral infectivity and replication in oligodendrocytes. According to other aspects of the invention, mutations in PML may allow for immune-escape by the virus. Out of the polyclonal immune response directed against the VP1 molecule only a limited number of antibodies directed against the cell receptor binding site (sialic acid) may provide protection against the spread of the viral infection. Mutation of an amino acid within an epitope crucial for the protective immunity may allow virus to bind to its target cells and spread uninhibited.

Experiments described herein address how certain mutations occur in PML and why, despite a very high prevalence of JCV, only a small proportion of immune deficient patients develop PML. According to aspects of the invention, the absence of clustering of the mutations on the viral phylogenetic tree suggests that they arise independently in individual patients rather than persist in the general populations as pathogenic viral variants. According to aspects of the invention, and based on the experiments described herein, VP1 mutations play a very significant role in the mechanism of PML emergence. Once a specific mutation affecting sialic acid binding occurs it allows virus to spread to the brain and infect oligodendrocytes. The fact that the mutant virus was not detected in the kidney suggests that that particular change in glycan binding does not offer any selective advantage to the mutated virus in kidney. The mutations might have occurred and hence allowed the virus to establish the residence in the brain under the conditions of immune suppression shortly or long before the PML. Since no viral replication was detected in brains of asymptomatic individuals it is unlikely that compartmentalized evolution (e.g., intra CNS) prior to PML development could account for the presence of mutated VP1 in CNS of PML patients. However, the issue of JCV latency in normal brain still remains controversial so it is still formally possible that non-mutated virus had entered the brain and mutations arose in the brain and not periphery, e.g., kidney.

According to aspects of the invention, the healthy immune system effectively controls viral activation in the brain. However, as soon as the immune system fails in certain individuals harboring such a mutated virus, the virus begins actively proliferating in oligodendrocytes causing PML. It is also possible that a healthy immune system may efficiently suppresses newly developed mutants in their peripheral site (e.g., kidney) and prevent them from spreading and infecting new target cells. Thus the timing of PML development may be mutation limited and the interplay with environmental or host genetic factors may contribute to the non-deterministic development of PML. In addition, PML development may be controlled by interactions of VP1 mutations with additional genetic alterations of the virus including rearrangement of the viral regulatory region as it might give the virus additional selective advantage in increasing viral replication in oligodendrocytes.

According to aspects of the invention, and as illustrated by the Examples described herein, JCV VP1 mutations affecting its receptor specificity may be responsible for PML pathology. These results provide opportunities for the discovery of novel anti-polyomavirus therapeutics and diagnostics of diseases caused by these viruses. The precise role that these mutations play in etiology of PML as well as how and where they arise requires further extensive investigation that would involve VP1 sequence analysis of longitudinal and time matching samples from different organs (e.g., urine, blood, CSF) and from a variety of PML patients.

The study of VP1 sequences from sequential samples, as described herein, showed the persistence of the same viral strains through the course of disease. Since the mutated virus represented the prevalent or sole population and it was maintained over time, it appears to be both necessary and sufficient for propagation of the infection. Notably, additional substitutions were acquired in case of relapse in a patient who survived the first PML episode. This observation suggests, first, that the old mutated virus survives efficiently, either in the CNS or in the periphery, and, second, that the emergence of a new substitution may trigger a new PML episode. In some embodiments, a newly mutated virus may arise in a context of virus activation under suboptimal immune control and once it emerges, it may not be promptly recognized by the immune system.

In some embodiments, aspects of the invention relate to the identity of CSF and plasma VP1 sequences in PML patients. It appears that both plasma-isolated and CSF-isolated virus are equally distinct from urine-isolated virus, even if the mutation was excluded from the analysis. This indicates that the CSF and plasma populations did not arise independently from urine but rather one of these populations originated from the same source as the urine population and the other originated from the first one. Although VP1 sequences carrying PMLgenic mutations were not observed in the urine of PML patients it is possible that that a mutation that was originally acquired during viral replication in the kidney did not receive any competitive advantage over the resident non-mutant virus to become a dominant or even a detectable population in the kidney site. This is consistent with the observation that VLPs prepared from most mutant VP1 molecules have lost the ability to bind to the renal tubular epithelial cells, the site of viral infection in the kidney.

According to aspects of the invention, without wishing to be limited by theory, when a mutation causes a virus to lose it's specificity for one or more widely occurring sialic acid containing receptors, the mutant virus (in the blood circulation) is more likely than a wild-type virus to escape being trapped by a multitude of sialo-containing oligosacharide pseudoreceptors expressed on a great majority of cells in the periphery. Accordingly, the mutant virus may be more likely to reach the brain, or at least blood brain barrier (BBB). Once the virus manages to bypass peripheral obstacles and reaches the BBB it still has to cross the endothelial cell layer to get to the CNS. In some embodiments, the extremely rare occurrence of PML, even in patients with significant immune suppression, may be due to the required temporal constellation of independently rare events such as the appearance of certain mutant virus particle and the presence of a BBB opening.

The hypothesis that mutations in VP1 protein contribute to PML progression by increasing viral chances of escaping peripheral circulation to enter CNS is consistent with the observation that ~10% of all PML cases contained non-mutated virus. Thus even non-mutant virus might also enter CNS given high level of viremia which could overwhelm the peripheral defense of viral pseudoreceptors and also given the temporally coincident opening in BBB. However, once a virus enters the brain there might be no difference between mutant and non-mutant virus in their ability to infect oligodendrocytes and spread in CNS which would be consistent with retained ability of mutant VLPs to bind CNS derived astrocytes, another target of JCV during ongoing brain infection. Alternatively, VP1 mutation might have arisen during viral replication in CNS as became dominant in CSF because it provided some competitive advantage for the virus to spread through the brain. Since most of the samples analyzed had all or >95% of all isolated clones containing mutations in order for the last hypothesis to be true the mutations must have to occur very early during viral replication in the brain. Since virus without mutations in VP1 can infect CNS cells quite successfully mutations would not provided competitive advantage via gain of viral tropism to toward CNS cells although they might have improved it. Still, the possibility that at least in some cases virus enters the brain in non-mutated form and acquires the mutation during its activation within the CNS under the condition of immune suppression in a patient cannot formally be excluded.

Regardless of the site of selection, JCV VP1 substitutions appear to be key for viral PML-genic potential. Viral capsid and envelope proteins are critical to mediate viral attachment to viral target cells and infectivity. Thus, mutations in influenza HA protein allow the virus to change its subtle specificity for the sialic acid binding and ability of the virus to switch from zootropic to human infectivity. Similarly, some of these mutations were shown to be associated with increased influenza virulence in human population as underscored by the example of 1918 influenza by changing specificity from the sialic acid preferentially expressed on cells in the upper portion of lung lobes to those expressed in lower portion of lung. Another mechanism by which a virus could gain an increase in virulence is probably via losing its wide receptor specificity which causes virus to be trapped on cells that it does not infect productively. One of the best studied examples of such a mechanism comes from the studies of another polyomavirus, murine polyomavirus infection in mice. It was demonstrated in this model that a mutation at position 296, which is structurally orthologous to the critical PMLgenic position 269 of JCV, dramatically changed viral specificity for the sialic acids and affected viral ability to bind target cells and RBCs and also lead to the dramatic increase in viral dissemination through the animal resulting in a lethal outcome. Thus, it appears that a change in viral coat protein that affects viral binding to its receptor is an extremely common mechanism that plays a crucial role in altering viral pathogenesis and virulence with human polyomaviruses being no exception.

In some aspects, mutations at positions 55 and 269 to phenylanine are detected in a sample from a subject. In other aspects, at least these mutations are detected and indicate that the subject appeared to be most common, suggesting that these 2 sites are under strong selective pressure and provide JC virus with most advantage to cause PML. This observation strongly correlates with the ability of mutations at these two sites to abrogate viral binding to peripheral cells and sialic acid containing oligosaccharides thus suggesting that that particular loss of function is most advantageous for the virus to be positively selected more frequently than other mutations. As described in more detail elsewhere herein, each of these sites accounted for 25% of all mutations in the current study, with positions 267, 265 and 60 being next highest in frequency, each with 7.5% of all cases. Interestingly, CSF samples from several patients contained two or more different viral populations each carrying its own PML-specific mutation with no virus contained two such mutations simultaneously. Accordingly, some aspects of this invention provide that several different mutations may arise independently during normal viral replication and all might get selected if each provides the virus the competitive advantage over non-mutated virus. In three cases, or ~10% of all cases from this study, no PML-associated substitutions could be found in CSF and/or plasma. Other genetic changes of JCV genome, e.g., involving mutations in the minor viral capsid proteins VP2 or VP3, might also be hypothesized in these cases to explain the presence of these viruses in association with PML.

The present invention is further illustrated by the following Examples, which in no way should be construed as further limiting. The entire contents of all of the references (including literature references, issued patents, published patent applications, and co-pending patent applications) cited throughout this application are hereby expressly incorporated by reference.

EXAMPLES

Example 1

Detection of JCV Variants by PCR

Nucleic acids are isolated from a biological sample using established protocols (e.g., cell lysis). Because the viral DNA may have integrated in the genomic DNA or may still be present as a smaller entity, both genomic DNA and shorter DNA sequences are isolated and subjected to PCR analysis. Upon isolation the nucleic acids are resuspended in a buffer that will facilitate PCR analysis. Buffers that facilitate PCR analysis are known to the skilled artisan (e.g., Maniatis) and are also commercially available from manufacturers of PCR enzymes (e.g., New England Biolabs, Beverly, Mass.). Nucleotide primers are designed to result in the amplification of the JCV-VP1 gene. PCR amplification is an established laboratory technique and comprises the addition of nucleotide primers, a polymerase and single nucleotides, and polymerase buffer and subjection this mixture to cycles of annealing, amplification and dissociation resulting in the amplification of a desired DNA sequence. Upon amplification, the JCV-VP1 gene is separated from the residual DNA and excess single nucleotides. The amplified JCV-VP1 DNA is sequenced and the resulting nucleotide sequence is translated into a peptide sequence. This peptide sequence is subsequently compared to the variant panels to determine which JCV-VP1 polypeptide variants are present in the biological sample.

Example 2

Detection of JCV Variants Using ELISA

Proteins and peptides are isolated from a biological sample using standard laboratory techniques (e.g., Maniatis). Both the cellular proteins and proteins of non-cellular components are subjected to the analysis. In one assay the sample is interrogated for the presence of JCV-VP1 polypeptides comprising one or more variants of the invention. The polypeptides are detected using sandwich ELISA comprising antibodies specific for JCV-VP1 polypeptides of the invention. The antibodies are generated by inoculating animals (e.g., rabbits) with the JCV-VP1 polypeptides of the invention resulting in polyclonal antibodies. If so desired, cells can be harvested from the inoculated animal to generate monoclonal antibodies. Methods for the generation of both polyclonal and monoclonal antibodies are routine in the art. The antibodies against JCV-VP1 polypeptide variants are immobilized on a solid surface (e.g., a 96-well plate), with one antibody type per well or surface area. The biological samples comprising the polypeptides are added to the wells and incubated with the immobilized antibodies. Any polypeptide JCV-VP1 variants present in the sample will bind to an antibody specific for the polypeptide. After incubation, the sample is removed and the solid surfaces are washed to remove any unbound material. As a next step, a solution containing additional antibodies specific for JCV-VP1 peptides is added to the wells. This second aliquot of antibodies will create the "sandwich" (e.g., immobilized antibody: JCV-VP1 polypeptide: second antibody). This second antibody can be detected using, for instance, a labeled tertiary antibody, allowing for the detection of JCV-VP1 variant polypeptides. Alternatively, the secondary antibody itself may be labeled.

In a second ELISA assay, biological samples are assayed for the presence of antibodies against one or more of the JCV-VP1 variant polypeptides. This assay can be use to determine whether a subject is currently infected with, or has previously been exposed to, a JCV-VP1 variant. Even if the JCV-VP1 variant is no longer present, antibodies against the variant may still be present in the biological sample and can be detected. In this ELISA assay JCV-VP1 polypeptides are attached to a solid surface and the biological samples are incubated with these polypeptides. If antibodies specific for these polypeptides are present in the biological samples they will bind to the polypeptides. Any unbound material is again removed. The presence of bound antibody is detected using a labeled secondary antibody.

Example 3

Determining Solvent Accessible Surface Area Composition of VP1 Protein

Accessible surface area calculations require the knowledge of the 3D coordinates of biomolecule. A homology model of JCV VP1 virus-like particle was constructed using structure of CoA1 of SV40 virus-like particle as a template (PDB ID: 1SVA). MODELER (A. Sali & T. L. Blundell. Comparative protein modelling by satisfaction of spatial restraints. *J. Mol. Biol.* 234, 779-815, 1993) algorithm was used for model building and the SCWRL3 (A. A. Canutescu, A. A. Shelenkov, and R. L. Dunbrack, Jr. A graph theory algorithm for protein side-chain prediction. *Protein Science* 12, 2001-2014 (2003)) approach was used for side-chain position refinement. The polar and non-polar solvent accessible surface areas of amino acid sidechains were calculated using Lee and Richards's method (B. Lee B & F. M. Richards. The Interpretation of Protein Structures: Estimation of Static Accessibility. *J. Mol. Biol* 55, 379-400 (1971)). Subsequently, 3D models of virus-like particles of JCV VP1 variants were constructed, and polar and non-polar solvent accessible surface areas of their side-chains were subsequently calculated. Difference in polar surface area upon variant was calculated by subtracting polar solvent accessible surface areas of the consensus sequence from the polar solvent accessible surface areas of the variant on per amino acid side chain basis. Difference in non-polar surface area upon variant was calculated by subtracting non-polar solvent accessible surface areas of the consensus sequence from the non-polar solvent accessible surface areas of the variant on per amino acid side chain basis. The calculation results are presented in Table 3.

TABLE 3

| Variant | Gain in Non-Polar SA | Gain in Polar SA |
|---|---|---|
| L55->F55 | 14.12 | 0 |
| K60->M60 | 27.35 | −13.22 |
| K60->N60 | −10.18 | −3.54 |
| K60->E60 | −5.55 | −2.1 |
| S61->L61 | 49.72 | −9.78 |
| D TABLE 4-continued AAK98030, AAK98024, AAK98018, AAK98010, AAK98006, AAK98000, BAE45438, BAE45390, BAD06108,
BAD06102, BAD06096, BAD06090, BAD06084, BAD06048, BAD06030, BAD06018, BAD06054, BAD06042,
BAD06036, AAG30857, BAE45366, AAN85455, BAD06150, AAN85449, AAK98042, BAD06174, BAD06156,
BAD06072, BAD06060, AAN85473, BAC81840, BAF40841, BAF40835, BAF40829, BAF40823, BAF40811,
BAF40847, BAF40781, BAF40817, BAF40799, BAF40793, BAF40787, BAF40745, AAN85467, AAN85461,
BAC81834, BAF40751, BAF40805, BAA01961, BAD98972, BAD98966, BAD06227, BAC66430, BAC66412,
BAD91887, BAD21235, BAD27118, BAC66424, BAA01958, BAB11710, BAD21265, BAD21259, BAD21253,
BAD21241, BAD21229, BAD21247, BAD21283, BAD21271, BAD21295, BAD21289, BAA01959, BAA01960,
BAD11848, BAD11842, AAM89339, AAM89327, BAD11836, BAC81852, BAC81858, BAD06144, AAG37198,
AAM89315, BAD06138, BAD11890, BAD11884, BAD11878, BAD11872, BAD11866, AAK97994, BAB11698,
BAC81940, BAC81964, AAK97946, BAD06066, BAF40769, BAC81870, BAC81864 BAC81934 BAC66376,
BAC81874 BAC81846 AAK97940, BAC81898 BAC81892, AAK97916 AAK97910, AAK97922, AAK97982,
BAF40763, BAD06078, AAK97958, BAD11860, BAF40757, BAD06162, AAM89321, BAD11854, AAK97928,
BAD11830, BAF40775, BAB11704, BAC81928, AAK97988, BAD11902, BAD11824, BAD06233, BAC81886,
BAC81880, AAM89345, BAD06168, AAM89333, BAD06132, BAC82365, AAK97952, BAA01964, BAA01963,
AAK97934, BAD06114, AAK97976, BAD21277, AAR13077, BAE02908, AAR12957, AAR02463, AAR02457,
BAE03058, AAR89235, BAE02896, AAR89241, BAE02890, BAE03064, BAE03070, BAE03082, AAG34673,
AAG34667, AAR89205, AAR89217, AAR13659, BAE03088, BAE03160, AAQ88264, AAR89187, AAR89283,
AAK28472, AAR06661, AAR89253, AAR89247, AAR89199, AAR89193, AAR89229, AAR89223, AAR89265,
AAR32743, AAR89277, BAE03166, BAE02920, BAE02914, BAE03112, BAE03106, BAE03100, BAE03094,
BAE03076, BAE02944, BAE02998, BAE02992, BAE02986, BAE02980, BAE02974, BAE02968, BAE02962,
BAE03016, BAE02902, BAE03040, AAR89211, AAR89271, BAE02956, BAE02938, BAE02932, BAE03148,
BAE02950, BAE03004, BAE03154, BAE03142, BAE03136, BAE03130, BAE03124, BAE03118, BAE02926.

| N | DNA accession # | Protein accession # | DNA Source | Isolate name | AA length, | Start AA | Patient # |
|---|---|---|---|---|---|---|---|
| 1 | AF015537 | AAB94036 | brain | 601 | 354 | 1 | 1 |
| 2 | AB183539 | BAE00111 | brain | 1-1 | 354 | 1 | 2 |
| 3 | AB183540 | BAE00117 | brain | 1-2 | 354 | 1 | 2 |
| 4 | AB183541 | BAE00123 | brain | 1-3 | 354 | 1 | 2 |
| 5 | AB183542 | BAE00129 | brain | 2-1 | 354 | 1 | 3 |
| 6 | AB183543 | BAE00135 | brain | 2-2 | 354 | 1 | 3 |
| 7 | AB183544 | BAE00141 | brain | 2-3 | 354 | 1 | 3 |
| 8 | AB190449 | BAE00147 | brain | 3-1 | 354 | 1 | 4 |
| 9 | AB190453 | BAE00171 | brain | 3-5 | 354 | 1 | 4 |
| 10 | AB190452 | BAE00165 | brain | 3-4 | 354 | 1 | 4 |
| 11 | AB190451 | BAE00159 | brain | 3-3 | 354 | 1 | 4 |
| 12 | AB190450 | BAE00153 | brain | 3-2 | 354 | 1 | 4 |
| 13 | AY536239 | AAT09819 | CSF | SA21_01 | 354 | 1 | 5 |
| 14 | AB212952 | BAE94726 | brain | ac-1 | 354 | 1 | 6 |
| 15 | AB212953 | BAE94732 | brain | ac-2 | 354 | 1 | 7 |
| 16 | D26589 | BAA05636 | brain | Aic-1a | 354 | 1 | 8 |
| 17 | AF004349 | AAB62680 | kidney | GS/K | 354 | 1 | 9 |
| 18 | AF004350 | AAB62687 | brain | GS/B | 354 | 1 | 9 |
| 19 | D11365 | BAA01967 | brain | Her1-Br | 354 | 1 | 10 |
| 20 | AB214923 | BAE02848 | CSF | JVL-10 | 245 | 39 | 11 |
| 21 | AB214924 | BAE02849 | CSF | JVL-11 | 245 | 39 | 12 |
| 22 | AB214925 | BAE02850 | CSF | JVL-12 | 245 | 39 | 13 |
| 23 | AB214926 | BAE02851 | CSF | JVL-13 | 245 | 39 | 14 |
| 24 | AB214927 | BAE02852 | CSF | JVL-16 | 245 | 39 | 15 |
| 25 | AB214928 | BAE02853 | CSF | JVL-17 | 245 | 39 | 16 |
| 26 | AB214929 | BAE02854 | CSF | JVL-18 | 245 | 39 | 17 |
| 27 | AB214930 | BAE02855 | CSF | JVL-19 | 245 | 39 | 18 |
| 28 | AB214912 | BAE02837 | brain | JVL-1a | 245 | 39 | 19 |
| 29 | AB214913 | BAE02838 | brain | JVL-1b | 245 | 39 | 19 |
| 30 | AB214914 | BAE02839 | brain | JVL-1c | 245 | 39 | 19 |
| 31 | AB214915 | BAE02840 | brain | JVL-1d | 245 | 39 | 19 |
| 32 | AB214916 | BAE02841 | brain | JVL-2 | 245 | 39 | 20 |
| 33 | AB214931 | BAE02856 | CSF | JVL-20 | 245 | 39 | 21 |
| 34 | AB214917 | BAE02842 | brain | JVL-3 | 245 | 39 | 22 |
| 35 | BAE02843 | BAE02843 | brain | JVL-4 | 245 | 39 | 23 |
| 36 | AB214919 | BAE02844 | brain | JVL-5 | 245 | 39 | 24 |
| 37 | AB214920 | BAE02845 | brain | JVL-7 | 245 | 39 | 25 |
| 38 | AB214921 | BAE02846 | brain | JVL-8 | 245 | 39 | 26 |
| 39 | AB214922 | BAE02847 | brain | JVL-9 | 245 | 39 | 27 |
| 40 | J02226 | AAA82101 | brain | Mad-1 | 354 | 1 | 28 |
| 41 | D11364 | BAA01966 | brain | Mad11-Br | 354 | 1 | 29 |
| 42 | D11363 | BAA01965 | brain | Mad8-Br | 354 | 1 | 30 |
| 43 | D11366 | BAA01968 | brain | NY-1B | 354 | 1 | 31 |
| 44 | AB212954 | BAE94738 | brain | oh-1 | 354 | 1 | 32 |
| 45 | AY536243 | AAT09843 | CSF | SA27_03 | 354 | 1 | 33 |
| 46 | AY536242 | AAT09837 | CSF | SA28_03 | 354 | 1 | 34 |
| 47 | AY536241 | AAT09831 | CSF | SA296_0 | 354 | 1 | 35 |
| 48 | AY536240 | AAT09825 | CSF | SA84_00 | 354 | 1 | 36 |
| 49 | D11367 | BAA01969 | brain | Sap-1 | 354 | 1 | 37 |
| 50 | D26590 | BAA05637 | brain | Tky-1 | 354 | 1 | 38 |
| 51 | AB038254 | BAB11728 | brain | Tky-1 | 354 | 1 | 39 |
| 52 | AB038255 | BAB11734 | brain | Tky-2a | 354 | 1 | 40 |
| 53 | D26591 | BAA05638 | brain | Tky-2a | 354 | 1 | 41 |
| 54 | D11368 | BAA01970 | brain | Tokyo-1 | 354 | 1 | 42 |

TABLE 4-continued

| 55 | AF030085 | AAC40846 | brain | Tokyo-1? | 354 | 1 | 43 |
| 56 | U21840 | AAB60586 | brain | | 133 | 219 | 44 |
| 57 | U21839 | AAB60584 | brain | | 133 | 219 | 45 |
| 58 | NA | NA | CSF | P9VP1 | 136 | 11 | 46 |
| 59 | NA | NA | CSF | P8VP1 | 136 | 11 | 47 |
| 60 | NA | NA | CSF | P7VP1 | 136 | 11 | 48 |
| 61 | NA | NA | CSF | P5VP1 | 136 | 11 | 49 |
| 62 | NA | NA | CSF | P4VP1 | 136 | 11 | 50 |
| 63 | NA | NA | CSF | P2VP1 | 136 | 11 | 51 |
| 64 | NA | NA | CSF | P1VP1 | 136 | 11 | 52 |
| 65 | NA | NA | CSF | P12VP1 | 136 | 11 | 53 |
| 66 | NA | NA | CSF | P11VP174 | 136 | 11 | 54 |
| 67 | NA | NA | CSF | P11VP173 | 136 | 11 | 54 |
| 68 | NA | NA | CSF | P11VP172 | 136 | 11 | 54 |
| 69 | NA | NA | CSF | P10VP1 | 136 | 11 | 55 |

Figure 4A:
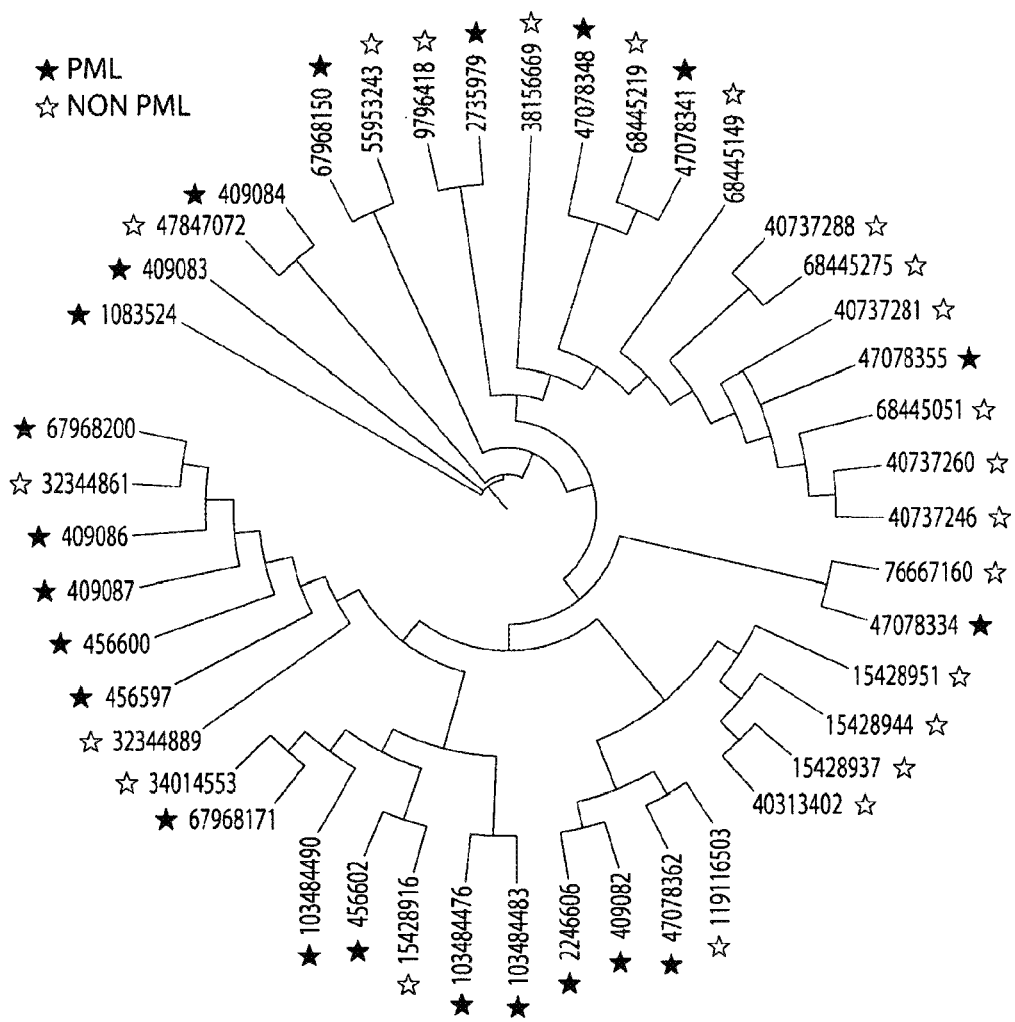
FIGS. 4A-4B show a phylogenetic distribution of PML associated viruses.

Results:

JCV VP1 gene sequences were downloaded from GenBank (Table 4) and used to construct a phylogenetic tree for a random subset of sequences isolated from healthy individual and full-length sequences isolated from distinct PML patients (FIG. 4a). FIG. 4 is a phylogenetic distribution of PML associated viruses. (A) Broad phylogenetic distribution of PML causing JC viruses. Tree branches (labeled by GI numbers) corresponding to PML causing viruses and viruses isolated from healthy subjects are indicated. The tree is constructed based on DNA sequences of VP1 gene using maximum likelihood method. Only one sequence per patient was included. (B) Phylogenetic distribution of mutations in the codon 269. The tree represents VP1 genes (labeled by GI numbers) of viruses isolated from PML patients. Mutations in Ser269 codons are indicated by text inserts. Circles on branches reflect aLRT support. Position 269 was masked prior to constructing the tree to avoid attraction of branches with mutations of this codon. The PhyML maximum likelihood method [Guindon S, Gascuel O (2003) A simple, fast, and accurate algorithm to estimate large phylogenies by maximum likelihood. Syst Biol 52: 696-704.] was used with F84 substitution model [Kishino H, Hasegawa M (1989) Evaluation of the maximum likelihood estimate of the evolutionary tree topologies from DNA sequence data, and the branching order in hominoidea. J Mol Evol 29: 170-179 and Felsenstein J, Churchill G A (1996) A Hidden Markov Model approach to variation among sites in rate of evolution. Mol Biol Evol 13: 93-104]. Application of several methods incorporated in the PHYLIP package maximum likelihood method, distance-based and parsimony-based methods of phylogenetic reconstruction produced similar results. Viral sequences isolated from PML patients do not cluster on the phylogenetic tree and are broadly distributed among viral types and geographic origins of the samples (FIG. 4a). This is further supported by very low population stratification measure $F_{ST}$ [Slatkin M, Maddison W P (1990) Detecting isolation by distance using phylogenies of genes. Genetics 126: 249-260](1.8%). In agreement with earlier studies [Zheng H Y, Takasaka T, Noda K, Kanazawa A, Mori H, et al. (2005) New sequence polymorphisms in the outer loops of the JC polyomavirus major capsid protein (VP1) possibly associated with progressive multifocal leukoencephalopathy. J Gen Virol 86: 2035-2045, Jobes D V, Chima S C, Ryschkewitsch C F, Stoner G L (1998) Phylogenetic analysis of 22 complete genomes of the human polyomavirus JC virus. J Gen Virol 79 (Pt 10): 2491-2498, and Agostini H T, Deckhut A, Jobes D V, Girones R, Schlunck G, et al. (2001) Genotypes of JC virus in East, Central and Southwest Europe. J Gen Virol 82: 1221-1331], PML causing viruses are not limited to a specific viral phylogenetic type.

Sequences from viruses isolated from PML patients were used as well as those from healthy subjects with the goal of determining whether PML associated evolutionary selective pressure is acting on the viral VP1 gene. This analysis utilized the PAML package [Yang Z (1997) PAML: a program package for phylogenetic analysis by maximum likelihood. Comput Appl Biosci 13: 555-556] designed to identify the presence of codons evolving under positive selection. PAML evaluates multiple evolutionary models using the parametric likelihood ratio test. Several models were tested including a model of neutral evolution, a nearly neutral model allowing for purifying (e.g., negative) selection, and a heterogeneous model that allows some codon positions to evolve under positive selection and other codon positions to evolve under negative selection or neutrally (Table 5). A number of more complex models also were tested.

In the case of VP1 sequences from JCV isolated from healthy subjects, the nearly neutral evolutionary model involving a mixture of neutrally evolving codons and codons under purifying selection clearly outperformed the purely neutral model (p-value $7.0 \times 10^{-6}$). However, no statistical support was found for more complex models including models with positive selection. In contrast, for VP1 sequences isolated from PML patients, allowing codons to evolve under positive selection resulted in a highly significant increase in the model likelihood (Table 5). The model with three categories of sites including sites evolving under purifying selection, neutral sites and sites under positive selection explained the data significantly better than the nearly neutral model limited only to neutral sites and the sites under purifying selection (p-value $2.5 \times 10^{-7}$). More complex models did not show significant improvement over the simplest model with three categories of codons.

Four codon positions (corresponding to amino acids 55, 60, 267 and 269) were identified as evolving under positive selection in the PML sampling of full length sequences (Table 5). Bayesian posterior probabilities for positive selection computed by PAML were above 0.5 for these codon positions. The posterior probability for positive selection in codon 269 was close to 1. To increase the power of analysis, partial VP1 sequences were added from JC virus isolated from PML patients. The addition of partial sequences revealed signal of positive selection in codon 265 (Table 5).

TABLE 5

Codons under positive selection in the PML sample.

|  |  |  | Full length sequence set (n = 28) | Partial sequence set codons 43-287 (n = 42) |
|---|---|---|---|---|
|  |  | Mutations | P-value for the positive selection test | |
|  |  |  | $2.5 \times 10^{-7}$ | $3.5 \times 10^{-6}$ |
| Position | WT | Mutant | Bayes Empirical Bayes posterior probability | |
| 55 | L | F | 0.82 | 0.94 |
| 60 | K | M, E, N | <0.5 | 0.94 |
| 265 | N | D, T | <0.5 | 0.85 |
| 267 | S | F, L | 0.80 | 0.92 |
| 269 | S | F, Y, C | 1.00 | 1.00 |

In this example, two VP1 mutations were not observed in the same JCV isolate. Analysis by the Spidermonkey [Poon A F, Lewis F I, Frost S D, Kosakovsky Pond S L (2008) Spidermonkey: rapid detection of co-evolving sites using Bayesian graphical models. Bioinformatics 24: 1949-1950] method revealed epistatic interactions between positions 55 and 269 and between position 60 and 269 (with posterior probabilities 0.88 and 0.70 respectively). This may reflect "diminishing return" epistatic interactions, e.g., subsequent mutations are not beneficial and possibly detrimental on the background of a single mutation.

All substitutions in these five codons are clearly associated with PML. At least 52% of JC viruses (or 36 out of 69 sequences, including partial sequences) isolated from PML patients have at least one of these mutations, whereas none of these substitutions have been observed in 253 full length viral sequences from healthy subjects (Table 6).

TABLE 6

Amino acid variability of JCV VP1 sequences

| | | non-PML | | | PML | | |
|---|---|---|---|---|---|---|---|
| Position | Reference | Sequences with substitutions, (total) | % sequences with substitutions | Mutation (s) | Sequences with substitutions, (total) | % sequences with substitutions | Mutation (s) |
| 8 | G | 4 (253) | 2 | 4A | 0 (32) | 0 | |
| 37 | I | 8 (253) | 3 | 8V | 0 (64) | 0 | |
| 52 | D | 1 (253) | 0 | 1N | 0 (64) | 0 | |
| 55 | L | 0 (253) | 0 | | 10 (64) | 16 | 10F |
| 60 | K | 1 (253) | 0 | 1R | 4 (64) | 6 | 2M 1E 1N |
| 61 | S | 0 (253) | 0 | | 5 (64) | 8 | 1L 4P |
| 64 | D | 0 (253) | 0 | | 6 (64) | 9 | 5H 1N |
| 69 | E | 5 (253) | 2 | 5D | 2 (64) | 3 | 2D |
| 70 | S | 2 (253) | 1 | 2G | 0 (64) | 0 | |
| 74 | N | 6 (253) | 2 | 6S | 12 (64) | 19 | 12S |
| 75 | K | 2 (253) | 1 | 2R | 2 (64) | 3 | 2R |
| 107 | T | 0 (253) | 0 | | 1 (64) | 2 | 1N |
| 113 | I | 59 (253) | 23 | 59L | 18 (64) | 28 | 18L |
| 115 | V | 1 (253) | 0 | 1E | 0 (64) | 0 | |
| 117 | T | 23 (253) | 9 | 23S | 15 (64) | 23 | 15S |
| 123 | S | 0 (253) | 0 | | 3 (64) | 5 | 3C |
| 128 | T | 25 (253) | 10 | 25A | 18 (64) | 28 | 18A |
| 129 | H | 0 (253) | 0 | | 1 (64) | 2 | 1R |
| 131 | N | 1 (253) | 0 | 1K | 0 (64) | 0 | |
| 134 | A | 186 (253) | 74 | 186G | 59 (64) | 92 | 59G |
| 153 | E | 1 (253) | 0 | 1K | 0 (52) | 0 | |
| 158 | V | 5 (253) | 2 | 5L | 3 (52) | 6 | 3L |
| 164 | T | 177 (253) | 70 | 176K 1M | 48 (52) | 92 | 48K |
| 167 | D | 1 (253) | 0 | 1H | 0 (52) | 0 | |
| 171 | F | 1 (253) | 0 | 1Y | 0 (52) | 0 | |
| 185 | E | 1 (253) | 0 | 1D | 0 (52) | 0 | |
| 192 | K | 2 (253) | 1 | 2E | 0 (52) | 0 | |
| 223 | V | 0 (253) | 0 | | 1 (56) | 2 | 1A |
| 258 | D | 1 (253) | 0 | 1Y | 0 (56) | 0 | |
| 265 | N | 0 (253) | 0 | | 4 (56) | 7 | 3D 1T |
| 267 | S | 0 (253) | 0 | | 4 (56) | 7 | 3F 1L |
| 269 | S | 2 (253) | 1 | 1A 1T | 13 (56) | 24 | 9F 3Y 1C |
| 271 | Q | 0 (253) | 0 | | 1 (56) | 2 | 1H |
| 277 | R | 1 (253) | 0 | 1K | 0 (56) | 0 | |
| 287 | R | 1 (253) | 0 | 1K | 0 (56) | 0 | |
| 310 | D | 1 (253) | 0 | 1N | 0 (56) | 0 | |
| 320 | Q | 1 (253) | 0 | 1H | 0 (56) | 0 | |
| 321 | I | 134 (253) | 53 | 134V | 32 (34) | 88 | 30V |
| 332 | Q | 184 (253) | 73 | 184E | 33 (34) | 91 | 31E |
| 345 | R | 20 (253) | 8 | 20K | 8 (34) | 18 | 6K |

Residues highlighted with darker shading are distinct between PML and non-PML groups and have Bayes Empirical Bayes posterior probability for positive selection >0.5 (Table 5). Residues highlighted with lighter shading are distinct between PML and non-PML groups.

Figure 4B:
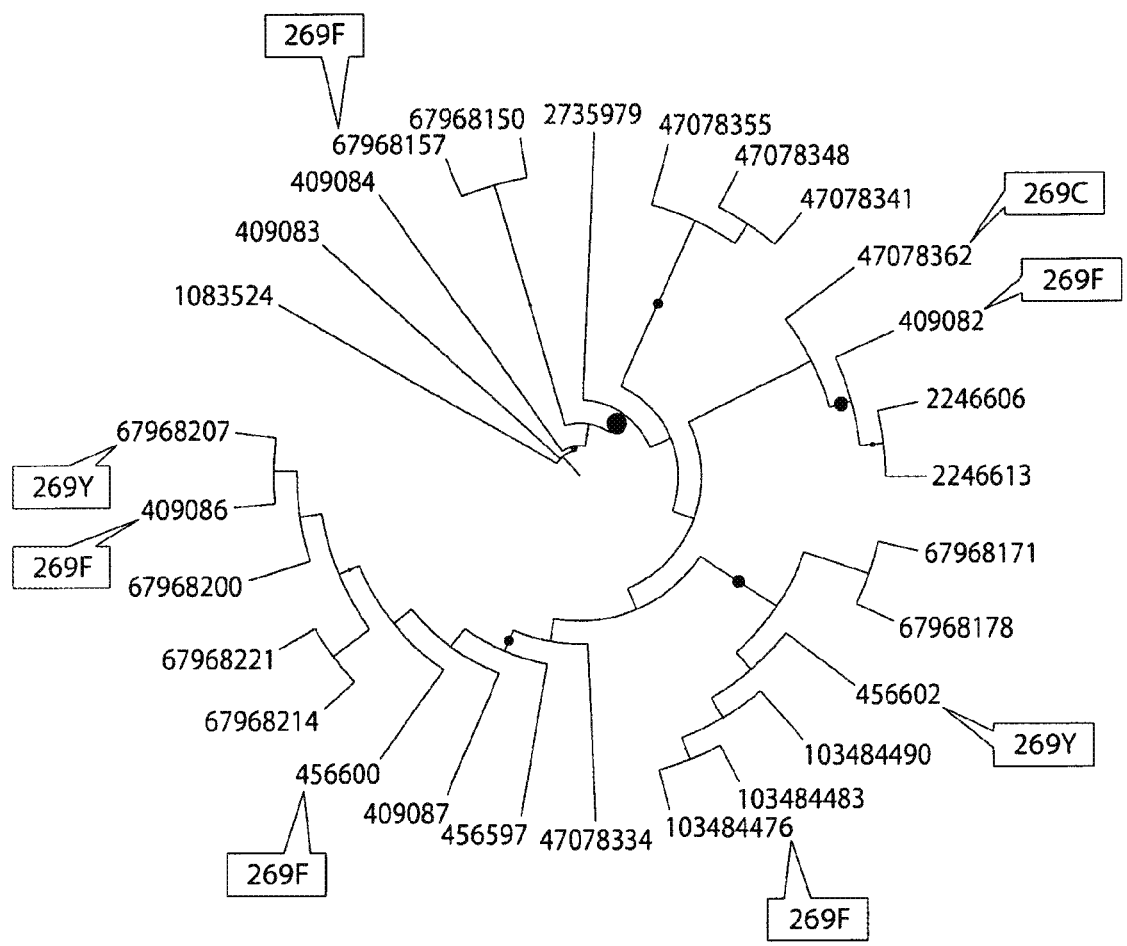

The strongest signal of positive selection in the PML sample was detected for the codon encoding amino acid at position 269. FIG. 4b shows that multiple independent mutations of Ser269 to aromatic residues phenylalanine and tyrosine were observed in VP1 from PML associated viruses. The existence of multiple independent mutations is not an artifact of phylogenetic reconstruction because lineages with mutant variants are separated by multiple branches with over 90% support by bootstrap analysis and support of the likelihood ratio test implemented in PhyML [Guindon S, Gascuel O (2003) A simple, fast, and accurate algorithm to estimate large phylogenies by maximum likelihood. Syst Biol 52: 696-704]. These lineages correspond to different, previously identified, phylogenetic types of JC virus and are from diverse geographic locations [Jobes D V, Chima S C, Ryschkewitsch C F, Stoner G L (1998) Phylogenetic analysis of 22 complete genomes of the human polyomavirus JC virus. J Gen Virol 79 (Pt 10): 2491-2498 and Agostini H T, Deckhut A, Jobes D V, Girones R, Schluncк G, et al. (2001) Genotypes of JC virus in East, Central and Southwest Europe. J Gen Virol 82: 1221-1331].

VP1 sequences isolated from PML patients and random subsets of sequences isolated from healthy subjects were further analyzed using PAML [Yang Z (1997) PAML: a program package for phylogenetic analysis by maximum likelihood. Comput Appl Biosci 13: 555-556].

Multiple models of sequence evolution incorporated in PAML were examined including purely neutral model (M0), nearly neutral model (M1), model with positive selection (M2) and additional more complex models (M3-M8). A likelihood ratio test (LRT) was used to compare the difference between models M1 and M2 to test for positive selection. P-values for positive selection in three datasets are shown together with Bayesian posterior probabilities for each codon position. Residues with Bayes Empirical Bayes posterior probabilities exceeding 0.5 are shown.

Example 5

Identified Mutations Fall in the Sialic Acid Binding Site

Methods:

A homology model of the JCV VP1 protein pentameric unit was built with MODELER [Sali A, Blundell T L (1993) Comparative protein modelling by satisfaction of spatial restraints. J Mol Biol 234: 779-815] using the structure of MPyV VP1 (Protein Data Bank ID: 1VPS [Stehle T, Harrison S C (1997) High-resolution structure of a polyomavirus VP1-oligosaccharide complex: implications for assembly and receptor binding. Embo J 16: 5139-5148] as a template. The model of NeuNAc-($\alpha$2,3)-Gal-($\beta$1,3)-[($\alpha$2,6)-NeuNAc]-Glc-NAc tetrasaccharide was build based on the structure of NeuNAc-($\alpha$2,3)-Gal-($\beta$1,3)-[($\alpha$2,6)-NeuNAc]-Glc-NAc bound to MPyV VP1 [Stehle T, Harrison S C (1997) High-resolution structure of a polyomavirus VP1-oligosaccharide complex: implications for assembly and receptor binding. Embo J 16: 5139-5148]. The model of the JCV VP1/NeuNAc-($\alpha$2,3)-Gal-($\beta$1,3)-[($\alpha$2,6)-NeuNAc]-Glc-NAc tetrasaccharide was extensively refined in CHARMM [Brooks B R, Bruccoleri R E, Olafson B D, States D J, Swaminathan S, et al. (1983) CHARMM: A program for macromolecular energy, minimization, and dynamics calculations. Journal of Computational Chemistry 4: 187-217] and was analyzed using PyMOL visualization software (The PyMOL Molecular Graphics System (2002) DeLano Scientific, Palo Alto, Calif., USA. www.pymol.org).

Figure 5A:
FIGS. 5A-5B show a structural model of JCV VP1/NeuNAc-($\alpha$2,3)-Gal-($\beta$1,3)-[($\alpha$2,6)-NeuNAc]-Glc-NAc tetrasaccharide complex.
Figure 5B:

Results:

According to aspects of the invention, the functional role of the five identified amino acid positions can be evaluated by constructing a three-dimensional molecular model of the JC virus VP1 bound to NeuNAc-($\alpha$2,3)-Gal-($\beta$1,3)-[($\alpha$2,6)-NeuNAc]-Glc-NAc tetrasaccharide based on the crystal structure of MPyV VP1/oligosaccharide complex [Stehle T, Harrison S C (1997) High-resolution structure of a polyomavirus VP1-oligosaccharide complex: implications for assembly and receptor binding. Embo J 16: 5139-5148]. The structural model shown in FIG. 5a suggests that all PAML-identified amino acids are clustered on the surface of the VP1 protein at the sialic acid binding site and are likely to be involved in sialic acid binding. FIG. 5 is a structural model of JCV VP1/NeuNAc-($\alpha$2,3)-Gal-($\beta$1,3)-[($\alpha$2,6)-NeuNAc]-Glc-NAc tetrasaccharide complex. (A) A model of JCV VP1 basic pentamer in complex with NeuNAc-($\alpha$2,3)-Gal-($\beta$1,3)-[($\alpha$2,6)-NeuNAc]-Glc-NAc tetrasaccharide. Surfaces of five chains of JCV VP1 are shown. The RG motif essential for binding of core sialic acid is shown. PML-associated mutated residues confirmed by PAML are indicated (L55, K60, S265, S267, S269). Additional mutations unique to PML-isolated samples also are shown (S61, D66, S123, H129, V223 and Q271). (B) A close-up view of NeuNAc-($\alpha$2,3)-Gal-($\beta$1,3)-[($\alpha$2,6)-NeuNAc]-Glc-NAc tetrasaccharide/JCV VP1 complex. The location of V296 of MPyV VP1 which is predicted to be equivalent to S269 of JCV VP1 is shown in mesh. Additionally, in some embodiments the L55F, K60M, S267F, and S269F substitutions may induce steric clashes with the modeled saccharide leading to a decrease in the affinity of the interaction. Affinity to sialic acid was related to viral pathogenicity in multiple studies of flu virus, mouse polyomavirus, and mouse minute virus [Srinivasan A, Viswanathan K, Raman R, Chandrasekaran A, Raguram S, et al. (2008) Quantitative biochemical rationale for differences in transmissibility of 1918 pandemic influenza A viruses. Proc Natl Acad Sci USA 105: 2800-2805, Bauer P H, Cui C, Liu W R, Stehle T., Harrison S C, et al. (1999) Discrimination between sialic acid-containing receptors and pseudoreceptors regulates polyomavirus spread in the mouse. J Virol 73: 5826-5832 and Nam H J, Gurda-Whitaker B, Gan W Y, Ilaria S, McKenna R, et al. (2006) Identification of the sialic acid structures recognized by minute virus of mice and the role of binding affinity in virulence adaptation. J Biol Chem 281: 25670-25677. Particularly, pathogenicity of mouse polyomavirus, a close relative of the JC virus, was mapped to a VP1 amino acid substitution at position 296 [Bauer P H, Bronson R T, Fung S C, Freund R, Stehle T, et al. (1995) Genetic and structural analysis of a virulence determinant in polyomavirus VP1. J Virol 69: 7925-7931], a position orthologous to position 269 in human JC virus that showed the strongest signal of positive selection in PML-causing viral isolates in this study. As shown in FIG. 5b, serine 269 of the human JC virus and valine 296 of the mouse polyomavirus occupy identical locations in the sialic acid binding pocket.

Positions 61, 66, 123, 129, 223 and 271 are all limited to the PML sample (Table 6) and also line up with the sialic acid binding pocket (FIG. 5b). It is possible that those residues went undetected by the PAML analysis due to the small sample size and that the development of PML is accompanied by positive selection for amino acids involved in sialic acid binding in a majority of cases. The length of the phylogenetic tree in the analysis is short thus limiting the power to detect positive selection [Anisimova M, Bielawski J P, Yang Z (2001) Accuracy and power of the likelihood ratio test in detecting adaptive molecular evolution. Mol Biol Evol 18: 1585-1592 and Anisimova M, Bielawski J P, Yang Z (2002) Accuracy and power of bayes prediction of amino acid sites under positive selection. Mol Biol Evol 19: 950-958]. Likelihood ratio test for detecting positive selection using a short tree is conservative [Anisimova M, Bielawski J P, Yang Z (2001) Accuracy and power of the likelihood ratio test in detecting adaptive molecular evolution. Mol Biol Evol 18: 1585-1592], and Bayes Empirical Bayes analysis is of limited power [Anisimova M, Bielawski J P, Yang Z (2002) Accuracy and power of bayes prediction of amino acid sites under positive selection. Mol Biol Evol 19: 950-958]. Thus, additional PML-specific VP1 mutations can also be positively selected. Mutations at residue 107 are also found exclusively in the PML sample. However, it did not show evidence of positive selection according to PAML and is not located in the sialic acid binding pocket.

Example 6

JCV Mutants and Sialic Acid Binding

Methods: Hemagglutination Assay and Viral Like Particles

Hemagglutination assay was performed as previously described [Chapagain M L, Nguyen T, Bui T, Verma S, Nerurkar V R (2006) Comparison of real-time PCR and hemagglutination assay for quantitation of human polyomavirus JC. Virol J 3: 3 and Padgett B L, Walker D L (1973) Prevalence of antibodies in human sera against JC virus, an isolate from a case of progressive multifocal leukoencephalopathy. J Infect Dis 127: 467-470]. Briefly, human type O blood was washed twice and suspended in Alsever's buffer (20 mM sodium citrate, 72 mM NaCl, 100 mM glucose, pH 6.5 adjusted with acetic acid) at a final concentration of ~0.5%. Serial two-fold dilutions of VLPs were prepared in Alsever's buffer and an equal volume of RBCs was added into each well of a 96-well "U" bottom microtiter plate and incubated at 4° C. for 3-6 hr. Minimum HA concentration is the lowest concentration of VLP protein that still agglutinated RBCs.

Figure 6:
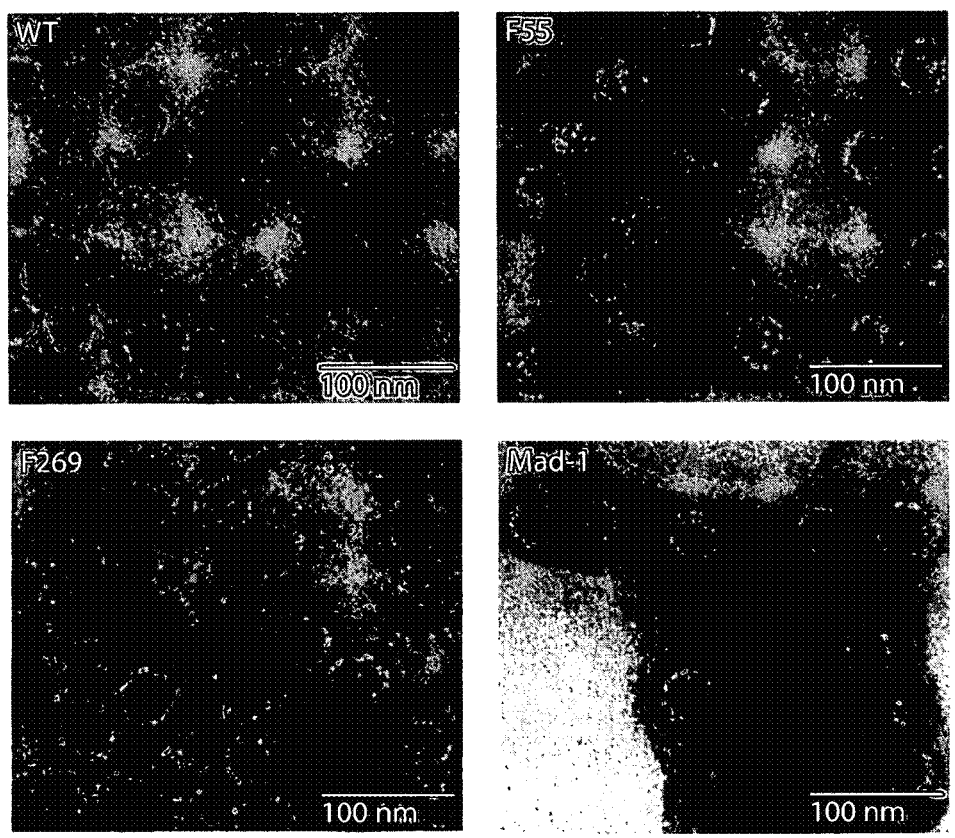

Genes encoding the VP1 protein from JC virus strains BAE00117, AAT09831 and AAQ88264 were created synthetically and cloned into the Gateway pDEST8 (Invitrogen) shuttle vector for transfer into the pFASTBAC baculovirus expression system for baculovirus expression in SF9 cells. Purification of VLPs was performed from roughly 100 grams of frozen cell pellets from 5 liters of culture. Cells were resuspended in 500 ml of PBS containing 0.1 mM CaCl$_2$. The cells are disrupted by passing the cell suspension twice through a Microfuidics Microfluidizer. Cell debris was removed by pelleting at 8000×G for 15 minutes. The supernatant volume was adjusted to 720 ml with PBS/CaCl$_2$ and loaded onto 5 ml 40% sucrose cushions. Virus-like particles were twice pelleted through the sucrose cushions in a SW28 rotor at 100,000×G for 5 hours. The VLP pellets were resuspended in PBS/CaCl$_2$ and then treated with 0.25% deoxycholate for 1 hour at 37° C. followed by the addition of 4M NaCl/0.1 mM CaCl$_2$ for 1 hour at 4° C. Precipitated material was removed by centrifugation at 8000×G for 15 minutes. The resulting supernatant was concentrated and buffer exchanged by ultrafiltration through a Pelicon-2 500,000 MWCO membrane (Millipore). The resulting VLPs were applied to the center of a 25-40% step gradient of Optiprep (Sigma) and banded at 190,000 g for 17 hours in a type 50.2 rotor. VLP bands were collected and then concentrated and buffer exchanged in an Amicon stirred cell with a 300,000 MWCO membrane. VLP quality was determined by gel electrophoresis and electron microscopy (FIG. 6). Protein concentration was determined by the Micro BCA assay (Pierce). Electron microscopy was performed at the Department of Cell Biology at Harvard Medical School. VLP samples were placed on carbon grids, briefly washed in water and negatively stained with uranyl acetate and allowed to dry. The grids were viewed and imaged on a Technai G2 Spirit BioTWIN TEM.

Results:

In order to experimentally verify the role that these substitutions play in sialic acid binding by the VP1 capsid, viral like particles (VLP) were recombinantly produced from VP1 protein encoded by several different naturally occurring viruses. VLPs were generated from viral VP1 sequences encoding substitutions with one of the two strongest signals of positive selection identified by PAML, one with phenylalanine at position 269 (F269) and another one with phenylalanine at position 55 (F55). Two different VP1 genes that were used as controls do not harbor any of the identified PML-associated mutations, one from a healthy individual (WT) and another one from a PML patient (Mad-1) (Table 7).

TABLE 7

Amino acid variability of JCV VP1 sequences between VLPs.

| | 55 | 74 | 75 | 117 | 128 | 134 | 158 | 164 | 269 | 321 | 332 | 345 |
|---|---|---|---|---|---|---|---|---|---|---|---|---|
| WT1 AAQ88264 | L | N | K | T | T | A | V | T | S | I | Q | R |
| 55F AAT09831 | F | N | K | T | T | A | V | T | S | I | Q | R |
| WT2(Mad-1) P03089 | L | N | R | S | T | G | L | K | S | V | E | K |
| 269F BAE00117 | L | S | K | S | A | G | V | K | F | V | E | K |

Viral hemagglutination of red blood cells (RBCs) has been shown to be a reliable measure of sialic acid binding by polyomaviruses [Freund R, Garcea R L, Sahli R, Benjamin T L (1991) A single-amino-acid substitution in polyomavirus VP1 correlates with plaque size and hemagglutination behavior. J Virol 65: 350-355 and Liu C K, Wei G, Atwood W J (1998) Infection of glial cells by the human polyomavirus JC is mediated by an N-linked glycoprotein containing terminal alpha(2-6)-linked sialic acids. J Virol 72: 4643-4649]. All four VLPs were tested in a hemagglutination assay. Strikingly, both F55 and F269 variants displayed more than 8000-fold lower HA activity than either control VLP (Table 7A). Specifically, the F55 variant completely failed to agglutinate human type O RBCs even at 200 µg/ml, the highest concentration tested, and the F269 variant displayed very low HA activity as it caused hemagglutination only at concentrations above 25 µg/ml. At the same time both L55 and S269 carrying variants (WT and Mad-1) caused hemagglutination of RBCs at concentrations down to 0.375 ng/ml and 6.25 ng/ml, correspondingly. In this example, the F55 mutant has the single amino acid difference with its corresponding wild type variant (WT). Therefore the change in hemagglutination can be specifically attributed to this amino acid replacement. In addition to the change in position 269 the F269 mutant variant has two additional amino acid positions that are different from its corresponding control variant (Mad-1). Both of those amino acid changes are not PML specific and are unlikely to explain the difference in hemagglutination. While the Mad-1 isolate had originated from a PML patient [Padgett B L, Walker D L, ZuRhein G M, Eckroade R J, Dessel B H (1971) Cultivation of papova-like virus from human brain with progressive multifocal leucoencephalopathy. Lancet 1: 1257-1260] it does not contain any of the PML-specific mutation which correlates well with its ability to hemagglutinate RBCs. The lack of PML-genic mutations in this PML isolate suggests that VP1 mutations are not an exclusive mechanism leading to PML development.

TABLE 7A

Residues 55 and 269 in VP1 protein play very important role in hemagglutination of RBCs by Viral Like Particles (VLPs).

| Viral variant | Minimum HA VLP concentration, ng/ml |
|---|---|
| WT1 | 0.08 |
| 55F | >200,000 |
| WT2 (Mad-1) | 6.25 |
| 269F | 50,000 |

Hemagglutination was conducted as described in Materials and Methods using serial dilutions of VLPs starting from 200 µg/ml. VLPs were added to type O RBC and incubated at 4° C. for 3 hours. Agglutination is visualized by the lack of a round pellet formed by the settling of RBCs out of suspension. E55 is a VP1 variant with phenylalanine at the position 55 (AAT09831), F269 is a VP1 variant with phenylalanine at the position 269 (BAE0011). WT (AAQ88264) and Mad-1 (P03089) are VP1 variants with leucine and serine at positions 55 and 269 respectively.

Protein sequences were aligned using ClustalW, amino acids different in at least one sequence from the rest of sequences are shown with their positions indicated.

Example 7

Mutant JCVs have Impaired Binding to Gangliosides

Ganglioside ELISA:

The following gangliosides were prepared at 1 mg/ml in methanol: asialo GM1 (human), monosialo GM1 (human), GM2 (human), GM3 (bovine), GM4 (human), disialo GD1a (bovine), GD1b (human), GD2 (human), GD3 (bovine), trisialo GT1b (bovine). All gangliosides purchased from Calbiochem except GM2 which was purchased from American RadioChemicals.

Gangliosides were diluted to 0.1 mg/ml in methanol and added 0.1 ml/well of an ELISA plate (Corning 9018); the methanol was allowed to evaporate overnight. On the following day, the plates were blocked with 0.25 ml/well 1×PBS with $Ca^{2+}$ and $Mg^{2+}$, 1% BSA (Fraction V), 0.1% Tween-20 for one hour. The plates were then transferred onto ice—all consequential incubations were performed at +4° C.

VLPs were prepared at 0.03 mg/ml in block buffer; the buffer was removed from the plate and the VLPs added 0.1 ml/well. The plate was incubated on ice for 60-90 minutes. Anti-JCV VP1 (clone PAB597) was prepared at 0.002 mg/ml in block buffer. The plates were washed with 0.25 ml/well block buffer; anti-VP1 was added 0.1 ml/well. The plate was incubated on ice for 45-60 minutes. HRP-conjugated goat anti-mouse IgG (H+L) (Jackson ImmunoResearch) was prepared at 1:5,000 in block buffer. The plate was washed; 0.1 ml/well of HRP-anti-mouse was added. The plate was incubated on ice for 30 minutes. The plate was washed and developed with 0.1 ml 1-Step Turbo™B (Thermo Scientific Pierce). Color development was monitored and the reaction stopped with addition 0.1 ml 2N $H_3PO_4$. The plates were then read at 450 nm on spectrophotometer (Molecular Devices).

Each ganglioside had control wells (HRP-anti-mouse IgG only, PAB597 and HRP-anti-mouse IgG). The background control was designated as HRP-anti-mouse IgG only. Each experimental well was calculated using the formula (Experimental—Background)/Background.

Figure 7:
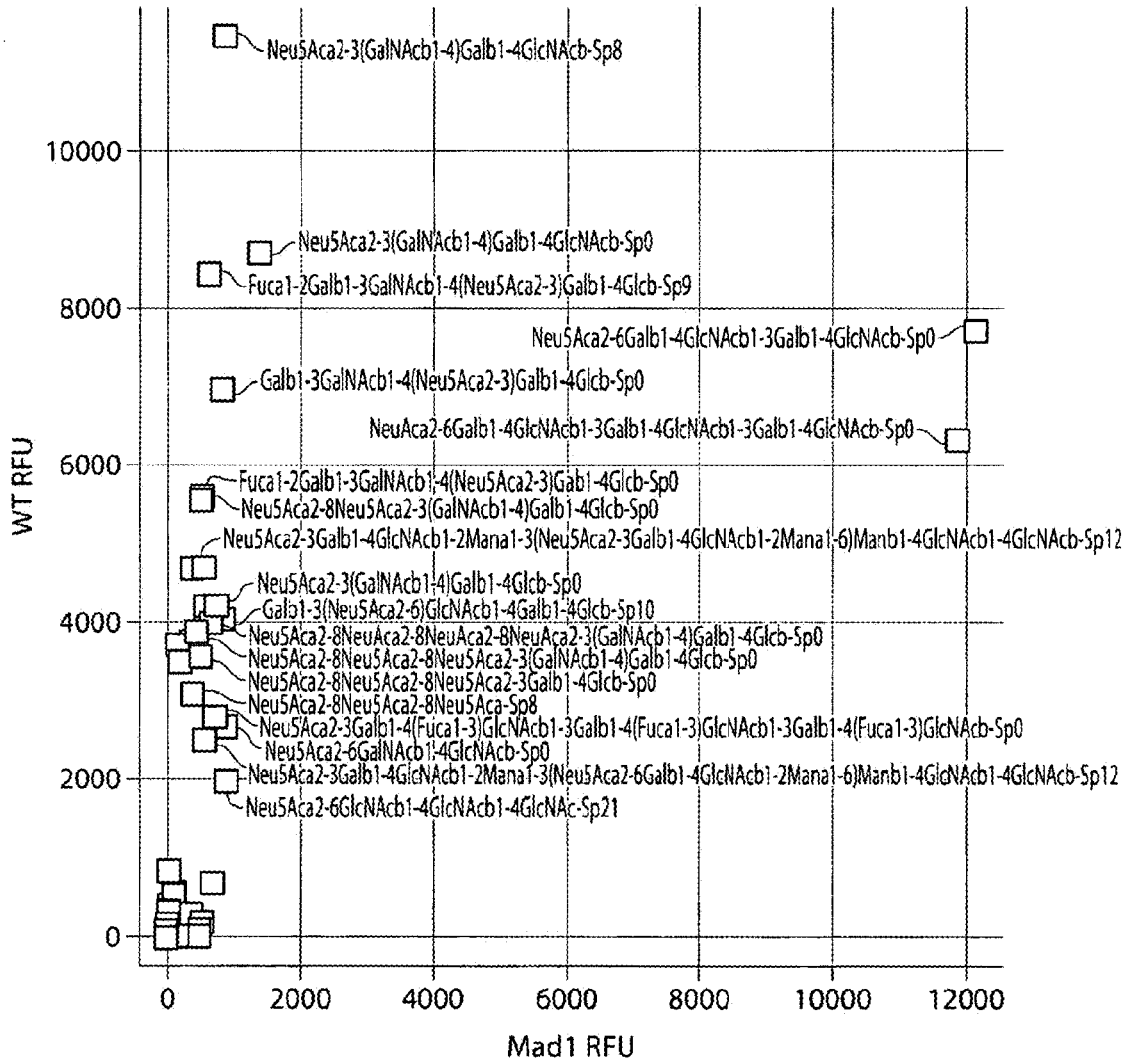
Figure 8:
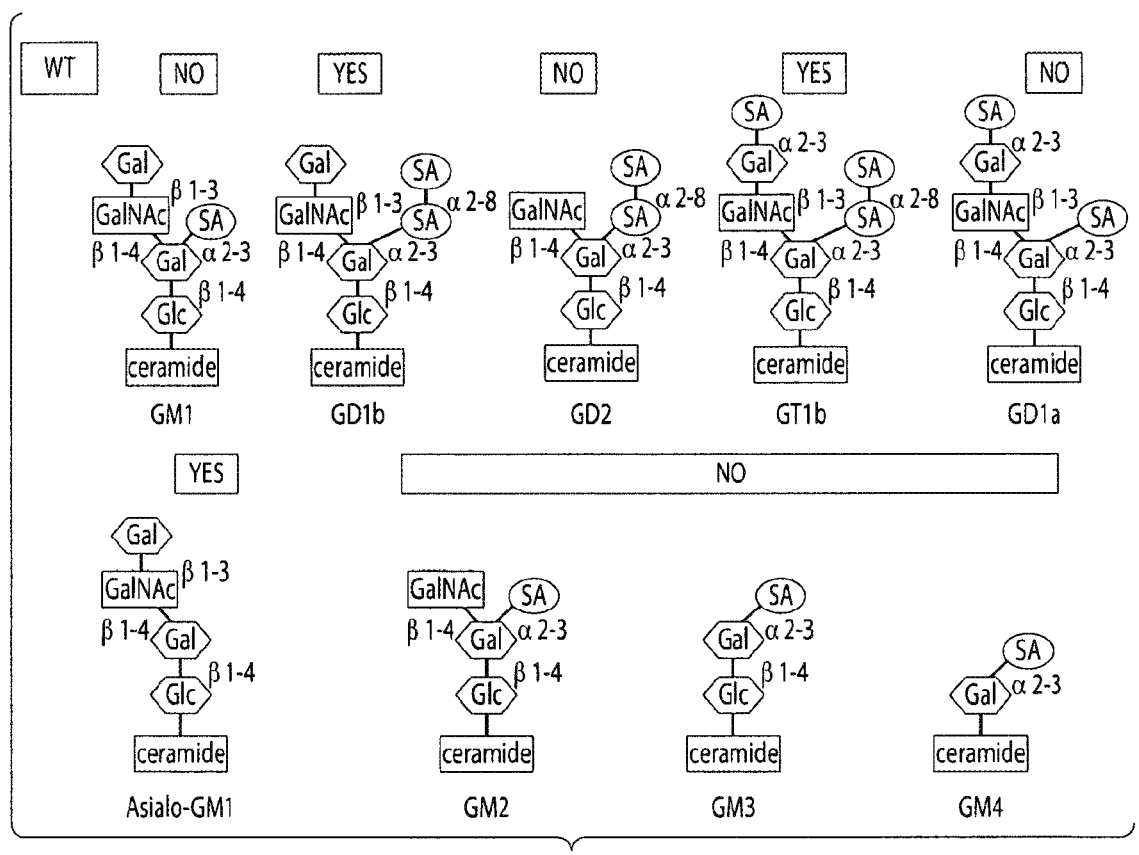

The binding of WT JCV was evaluated against a variety of gangliosides. FIG. 7 shows that WT JCV binds to some glycans, but not to all. The structure of selected gangliosides is shown in FIG. 8 and their ability to bind to WT JCV is indicated.

Figure 9:
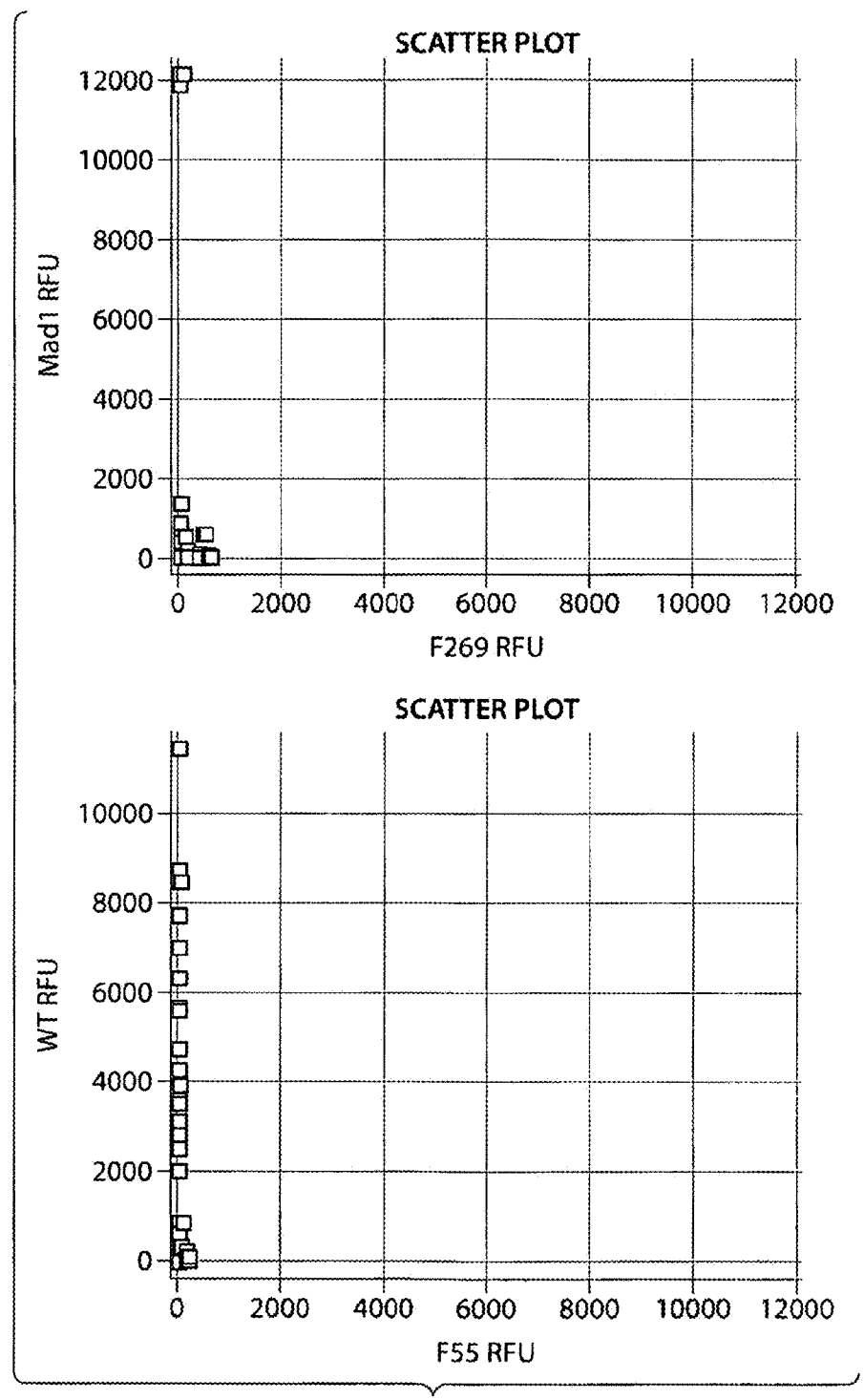
FIG. 9 shows that the F55 and F269 mutations are not capable of binding Neu5Ac$\alpha$(2-3) and $\alpha$(2-6) glycans.
Figure 10:
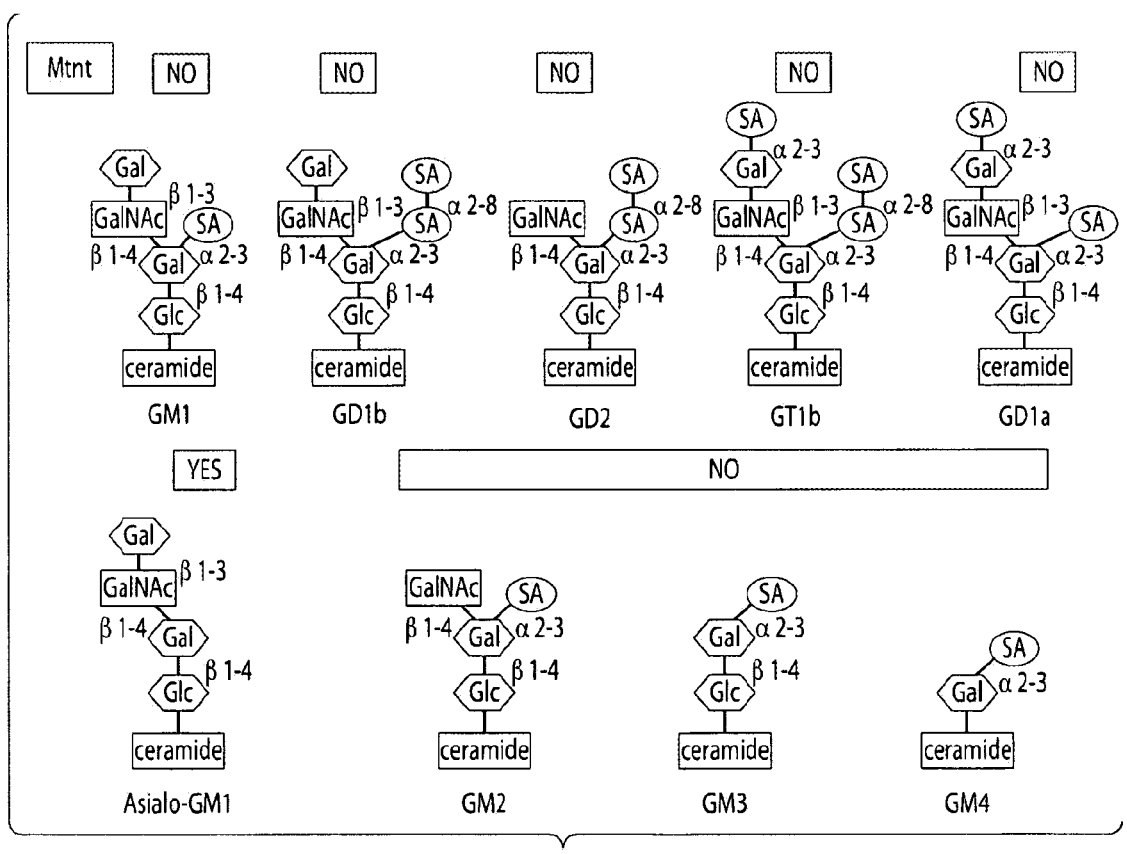
FIG. 10 shows the structure of selected gangliosides and their ability to bind to mutant JCV.

FIG. 9 shows that the F55 and F269 mutations are not capable of binding Neu5Acα(2-3) and α(2-6) glycans. The structure of selected gangliosides is shown in FIG. 10 and their ability to bind to mutant JCV is indicated.

Figure 11:
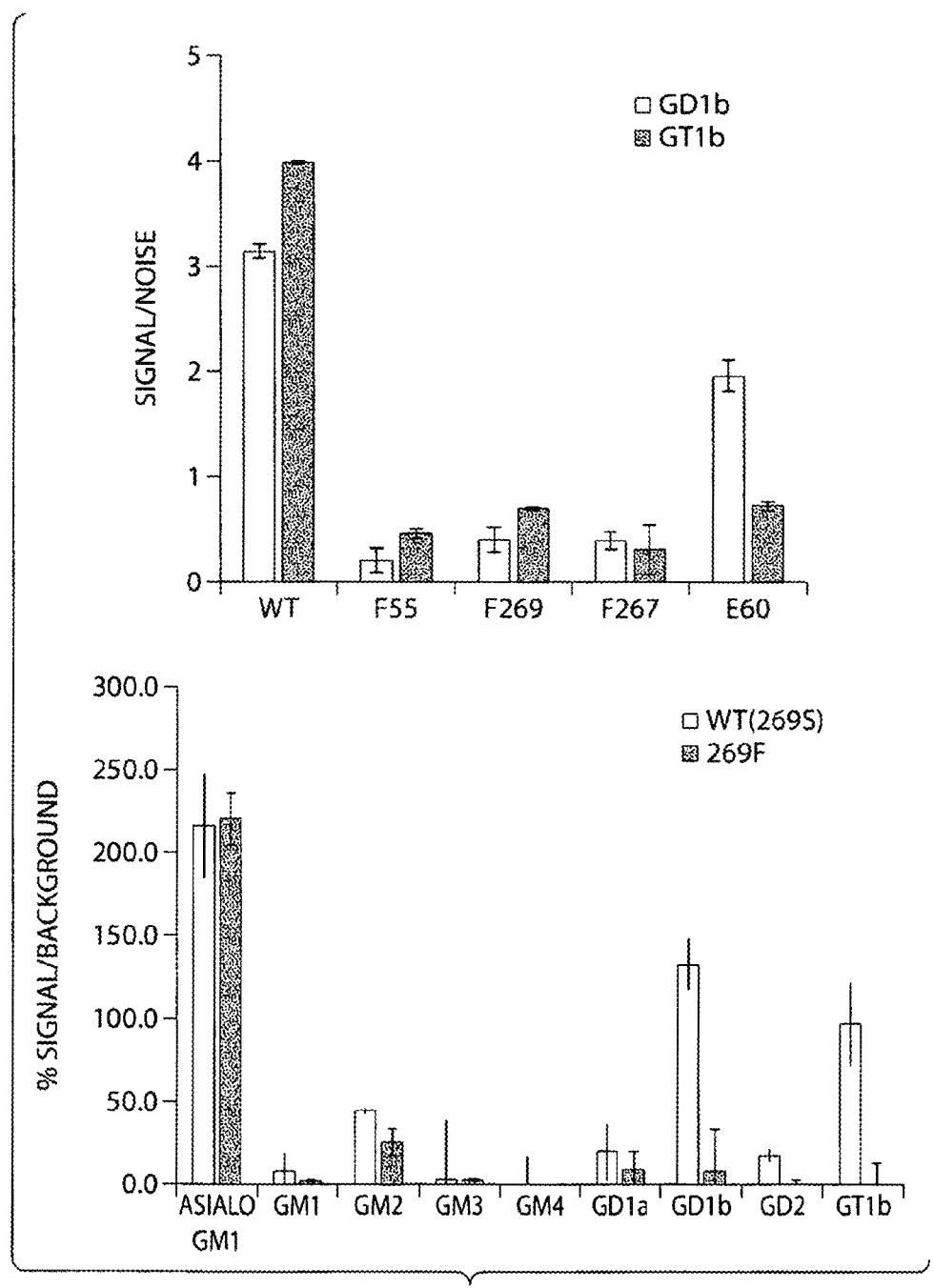
FIG. 11 compares the ability of WT and mutant to JCV to bind selected gangliosides.

FIG. 11 compares the ability of WT and mutant to JCV to bind selected gangliosides.

Example 8

Mutant JCV Binds Glial Cell Lines but not Lymphocytes

Flow Cytometry Analysis of VLP Staining;

The following cells were used: SVG-A (gift from Walter Atwood), isolated peripheral mononuclear cells from donors. Adherent cells were detached using Accutase, collected, and washed. Venous blood was drawn from healthy donors; PMBCs were isolated using a standard protocol involving centrifugation over Ficoll-Hypaque Plus (Amersham Biosciences).

All stainings were performed on ice in PBS buffer containing calcium and magnesium, 1% bovine serum Albumin (fraction V), 2 mM sodium azide.

Cells ($1-5 \times 10^5$ cells/sample) were incubated with 10 µg/ml VLP diluted in FACS buffer, in a total volume of 0.05 ml, on ice for 60-90 minutes in 96 V-bottom well plate. Cells were washed with 0.15 ml FACS buffer and centrifuged at 2000 rpm (~800×g) for 5 minutes. VLP binding was detected by staining cells with anti-JCV VP1 (clone PAB597) at 0.002 mg/ml in 0.05 ml for 45-60 minutes, followed by a wash step and detection with Alexa Fluor 488 anti-mouse IgG (H+L) (Invitrogen) diluted 1:100 in 0.05 ml/sample for an additional 30-45 minutes. Cells were washed and fixed in 0.05 ml Cytofix/Cytoperm (BD) for 15-25 minutes, washed and resuspended in 0.2 ml FACS buffer. The samples were analyzed on a FACS Calibur.

Figure 12:
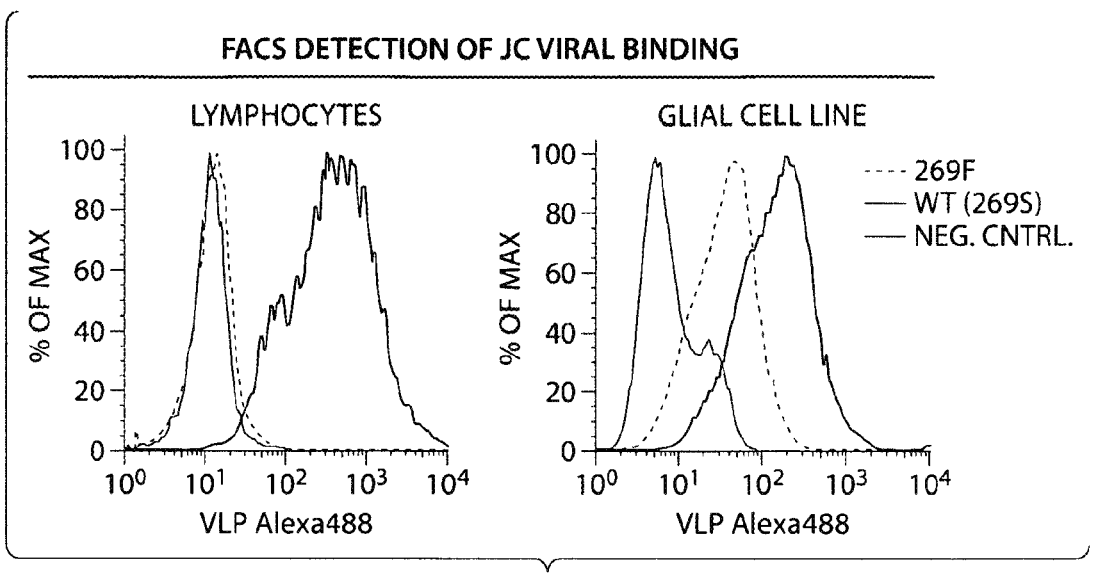
FIG. 12 shows that mutant JVC is still capable of binding glial cell lines.

Mutant JCV (269F) does not bind lymphocytes. However, mutant JVC is still capable of binding glial cell lines (FIG. 12). WT JCV and a negative control are also depicted.

Example 9

Generation of Mutant Specific Anti-JCV Antibodies

For the immunization of rabbits to generate anti-JCV VP1 sera, 0.5 mg of VP1 protein in the form of virus like particles (VLPs) in PBS buffer was injected subcutaneously into 10 spots on the rabbit back (0.05 mg/spot). The primary immunization was followed by 2 boosts at 2-week intervals after which, sera was collected and assayed for anti-VP1 activity.

Detection of Anti-Mutant-JCV Antibody by Competition ELISA:

A: Anti-serum from 269F-VLP immunized rabbit or anti-WT-MAD1-immunized VLP rabbit serum were pre-incubated with or without 100 ug/ml of WT-MAD1-VLP, and were then incubated with a plate coated with 269F-VLP. Bound antibodies were revealed with a peroxidase-conjugated anti-rabbit.

B: Anti-serum from 55F-VLP immunized rabbit or anti-WT-immunized VLP rabbit serum were pre-incubated with or without 100 ug/ml of WT-VLP, and were then incubated with a plate coated with 55F-VLP. Bound antibodies were revealed with a peroxidase-conjugated anti-rabbit.

Figure 13:
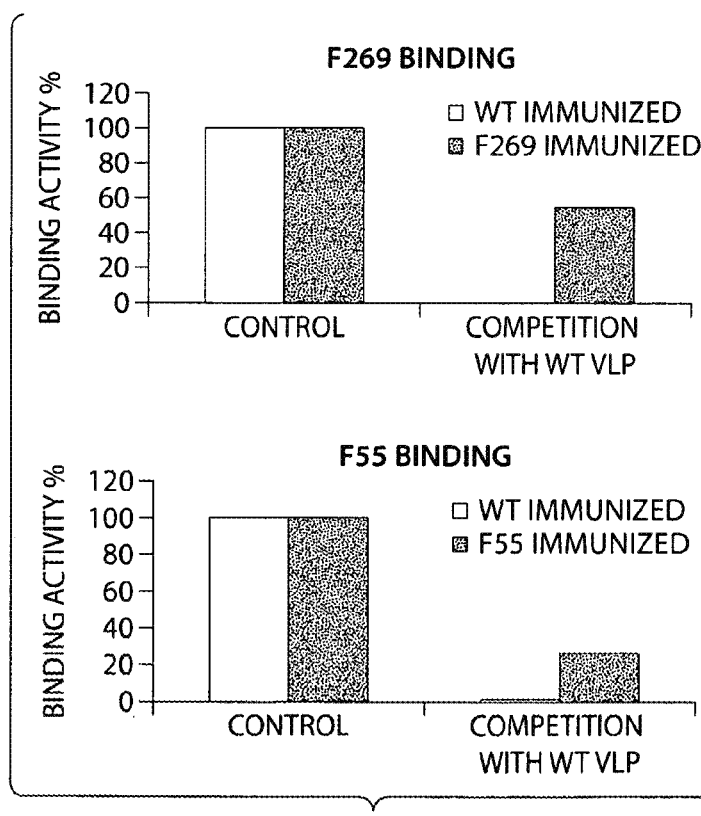
FIG. 13 shows that the mutant specific JCV antibodies can be distinguished from a WT JCV antibody.
Figure 14:
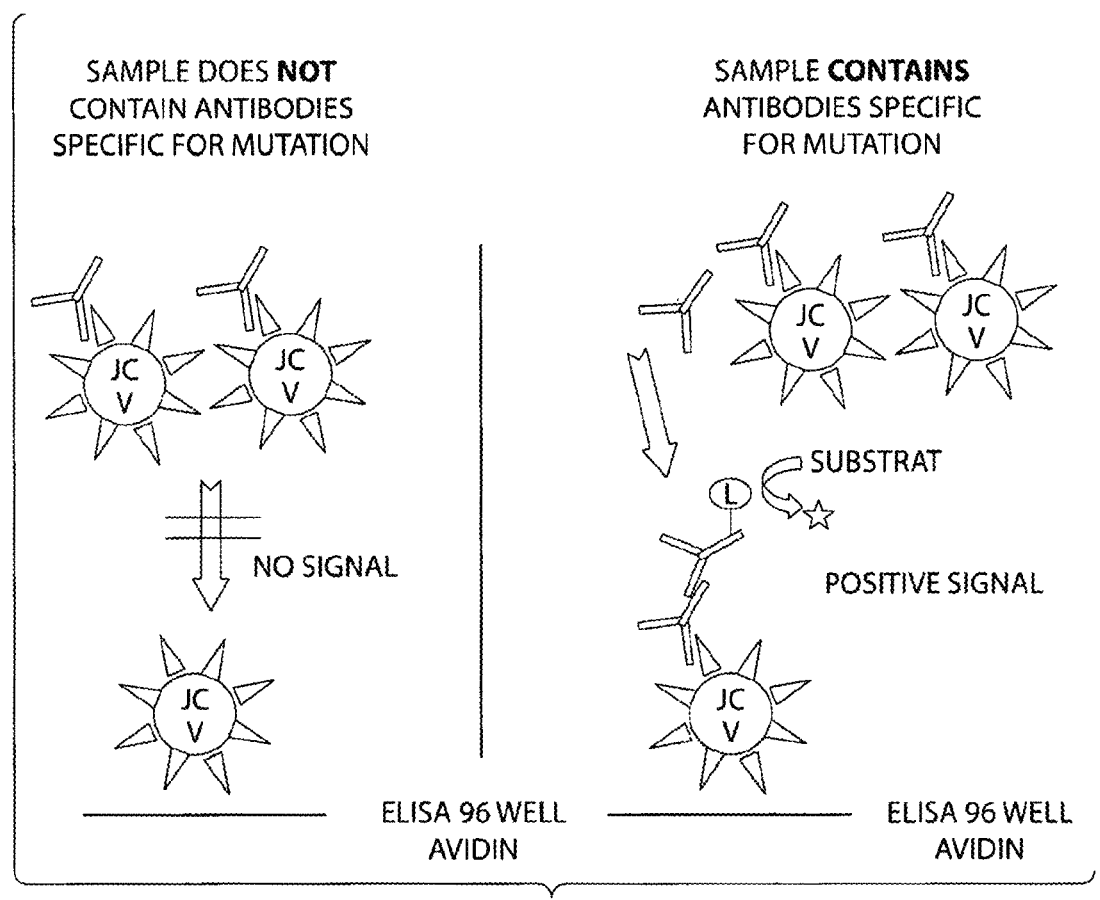
FIG. 14 shows an assay for distinguishing mutant antibodies from WT.

Rabbits were injected with F269 and F55 JCV mutant VP1 VLP resulting in the generation of antibodies specific for mutant JCVs. A competition ELISA showed that the mutant specific JCV antibodies can be distinguished from a WT JCV antibody (FIG. 13). The assay configuration is illustrated in FIG. 14. Antibodies bind mutant VLP (either F55 or F269) captured on the plate. Competition is done with non-mutant VLP to absorb all antibodies directed at "backbone" of the molecule, leaving only antibodies against mutant epitopes (if such are present in the sample) to bind to the plate and be detected.

Figure 15:
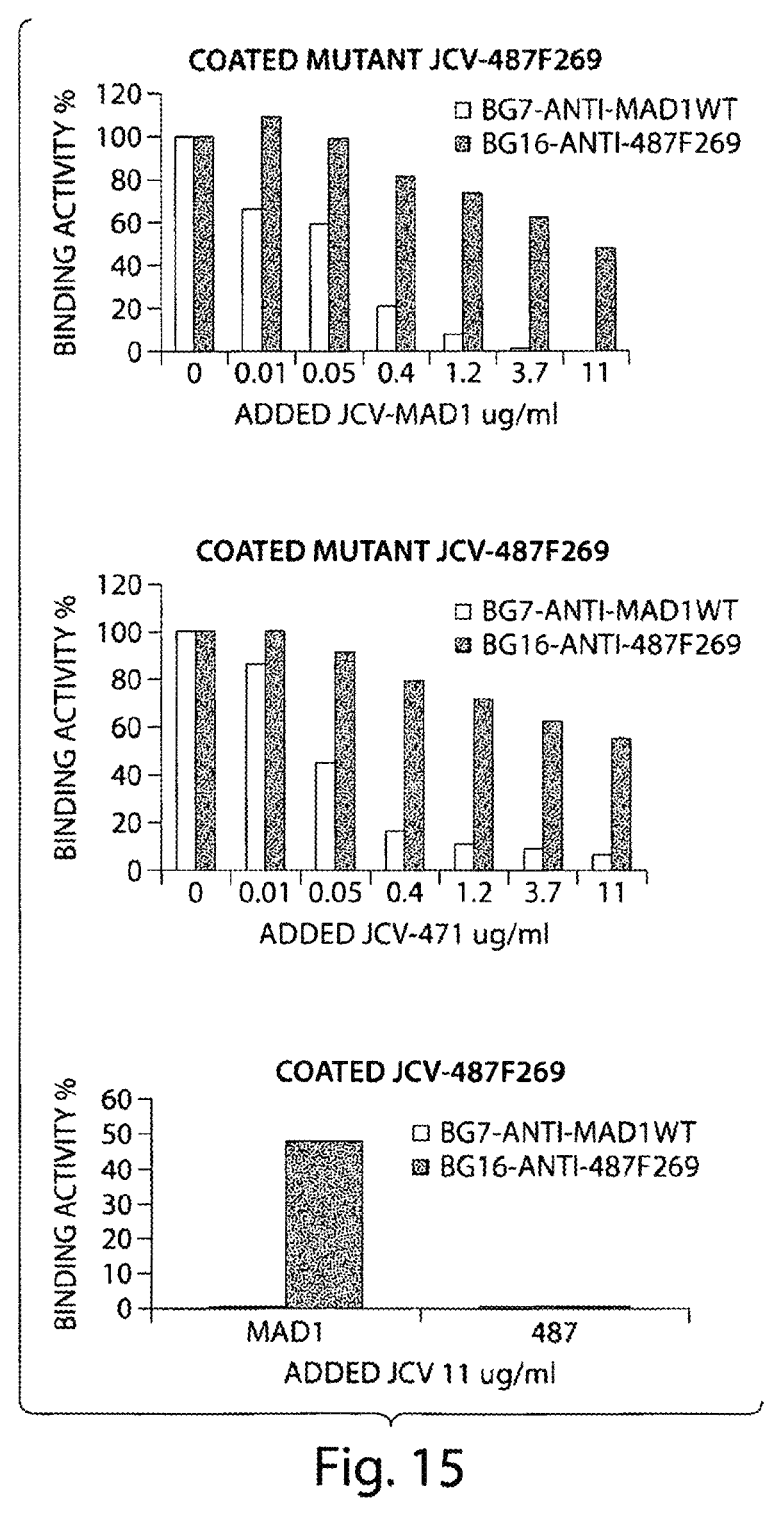
Figure 16:
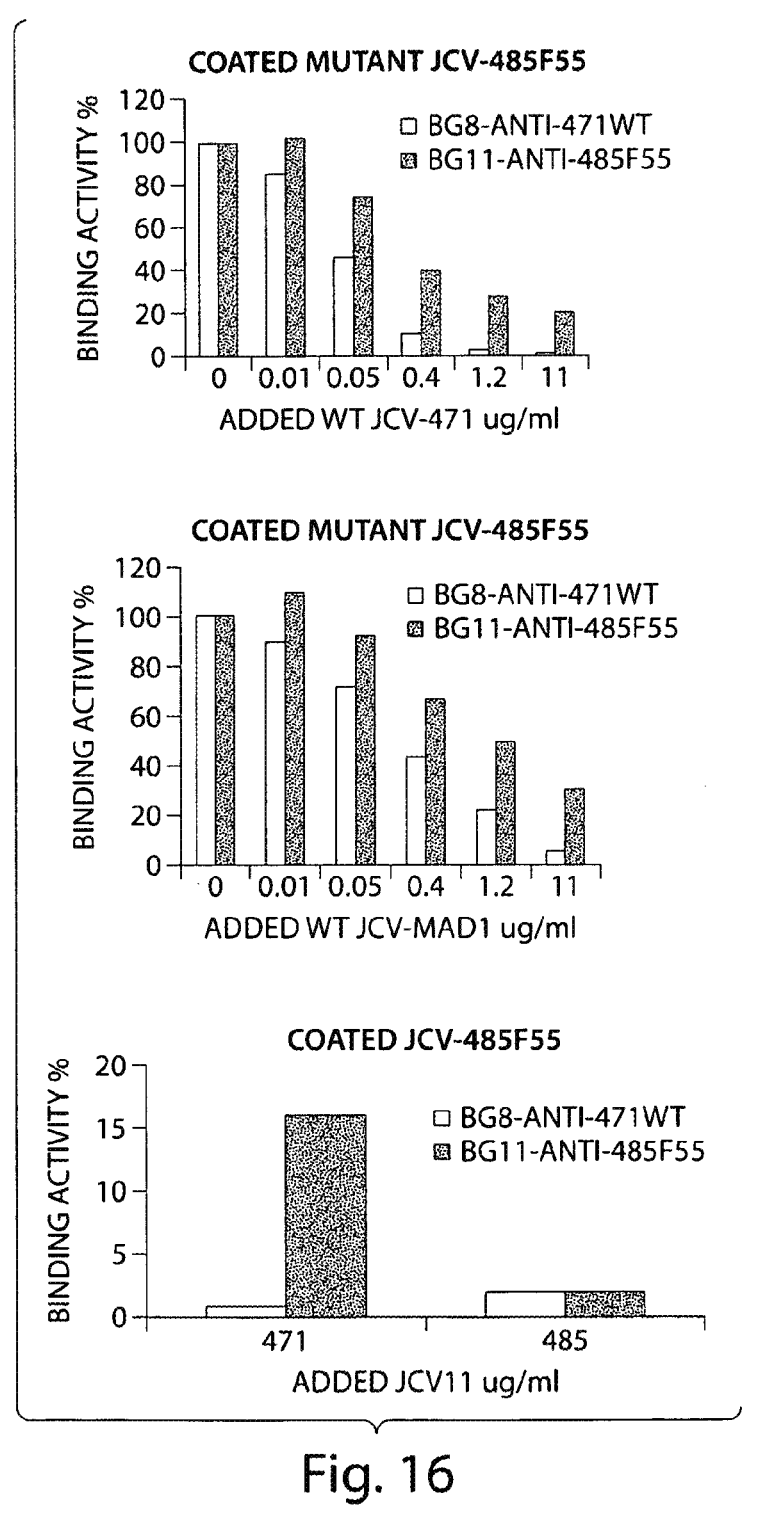

The mutant JCV and WT JCV antibodies were also compared for their ability to bind to a mutant JCV-VLP. ELISA plates were coated with F269 and F55 mutant JCV polypeptides and WT JCV and mutant JCV antibodies were added to the plates (FIGS. 15 and 16). Both the mutants and WT JCV antibodies bind to the coated ELISA plate. Addition of WT JCV (JCV-471 and JCV-MAD1) resulted in the disappearance of the binding of the WT JCV antibody, while the mutant antibodies remain bound to the ELISA plate. Furthermore addition of JCV virus resulted in the disappearance of the bound WT antibody, while the mutant antibody remains bound to the plate.

Example 10

JCV-VP1 Mutations as a Viral Immune Escape Mechanism in Some Patients

Serum from a patient that carries 269F mutation in VP1 protein or anti-WT-MAD1-immunized VLP rabbit serum (as a positive control) were pre-incubated with or without 100 μg/ml of WT-MAD1-VLP, and were then incubated with a plate coated with 269F-VLP. Bound antibodies were revealed with a peroxidase-conjugated anti-human or rabbit antibodies to detect antibody binding to the coated 269F mutant VLP.

Figure 17:
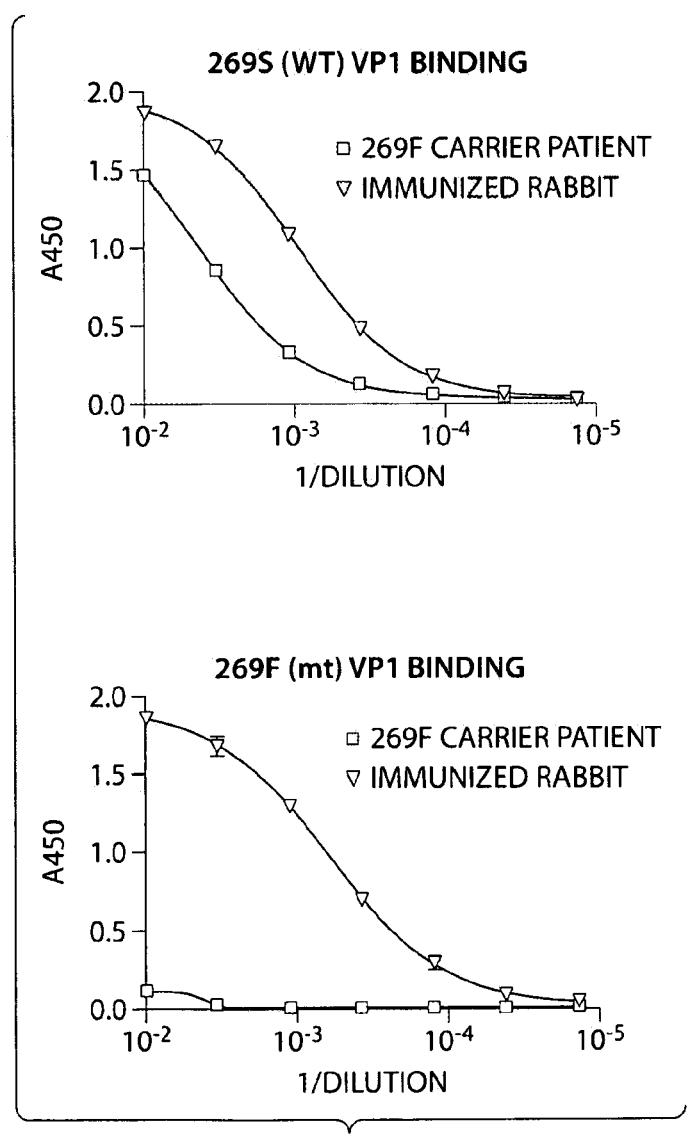
FIG. 17 shows that a patient that has the F269 mutant virus has developed an antibody response against the WT virus but not against the F269 mutant virus.

FIG. 17 shows that a patient that has the F269 mutant virus has developed an antibody response against the WT virus but not against the F269 mutant virus.

Figure 18:
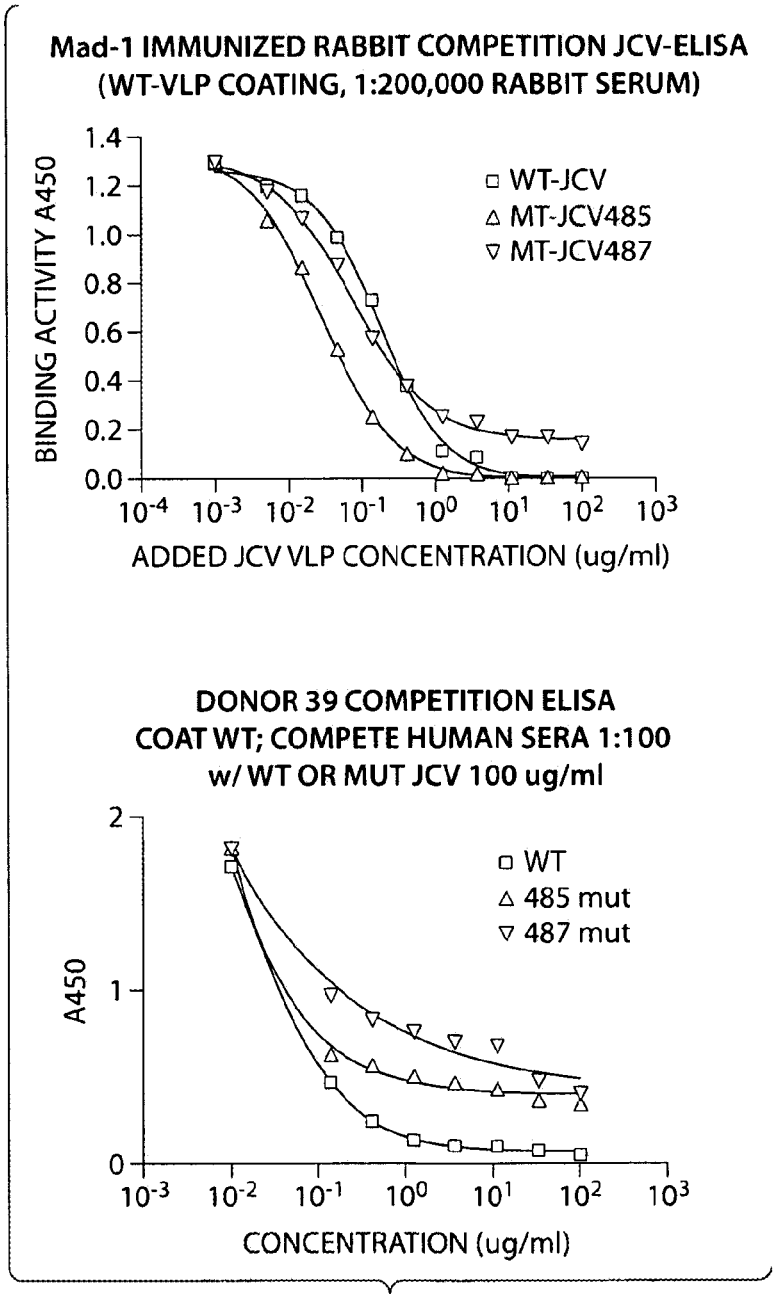
FIG. 18 shows that (top) rabbit immunized with non-mutant VLP raises antibody to the site (S269 in this cases) that could get mutated.

FIG. 18 shows that (top) rabbit immunized with non-mutant VLP raises antibody to the site (S269 in this cases) that could get mutated. In this cases experiment was done similar to schematics on slide 16 (above insert) with several differences, instead of the mutant VLP a non-mutant VLP was coated on the plate and antibody binding in sera was competed with mutant (either F55 or F269) protein), so only antibody to non-mutated AA epitope would be left to bind to the plate. (bottom) shows the same experiment with healthy volunteer sample. The results in Table 8 are based on a similar experiment with several different volunteer samples. Table 8 shows that people that are not suffering from PML can have antibodies against PML mutants. This shows that some people carry antibodies specific for several residues in the sialic acid binding site (e.g., patient 29 has antibodies to L55 and S269), while others have either antibody only to one site, L55 or S269, and still others to no site. According to aspects of the invention, individuals who have no antibodies to the residues in the sialic acid binding site or only to one of those residues might be more vulnerable to JCV escape mutants as they would have less protection from neutralizing antibodies.

TABLE 8

| patient ID | VLP EC50, dilution | L55 | S269 |
|---|---|---|---|
| 9 | 24820 | + | + |
| 19 | 81850 | − | − |
| 22 | 14150 | − | + |
| 29 | 6034 | + | + |
| 31 | 802500 | − | − |
| 33 | 870400 | − | − |
| 39 |  | − | + |
| 42 | 4161 | − | + |
| 49 | 5506 | − | − |
| 51 | 51480 | − | − |
| 59 | 2802 | − | − |
| 60 | 2423 | − | − |

Example 11

JC Virus (JCV) VP1 from Cerebrospinal Fluid (CSF) and Plasma of Patients with Progressive Multifocal Leukoencephalopathy (PML) Carry Specific Mutations of Amino Acid Residues Involved in Sialic Acid Binding As described herein, PML is currently the second most frequent cause of AIDS-related deaths. Unlike other opportunistic infections, it also occurs in HAART-treated patients, either shortly after starting or during chronic successful treatment. Following primary infection, the causative agent, JCV, establishes a persistent benign infection in the urinary tract and is excreted in urine in 30% of healthy persons. The mechanisms leading to JCV reactivation and PML are unclear, but it is known that the major JCV capsid protein, VP1, is involved in cell entry, through binding with cell sialic acid residues and, recently, VP1 amino acid substitutions have been reported in PML.

The entire JCV-VP1 region was amplified, cloned (2 to 48 clones per sample, median 23) and sequenced from the CSF of 26 PML patients (20 with HIV infection), and 11 paired plasma and 6 paired urine samples. From 9 patients, sequential CSF (n=7) or plasma (n=2) samples were also analysed. JCV DNA was measured by real-time PCR. 3D modeling was used to map the mutations on VP1 structure.

DNA Extraction and VP1 Amplification:

DNA was extracted from 200 μL of CSF, plasma or urine using the QIAamp Blood Kit (Qiagen) and eluted in a final volume of 50 μL.

The entire JCV-VP1 region was amplified by nested PCR using the following primers:

```
Outer (2027 bp)
                                (SEQ ID NO: 55)
VP1-LF GCAGCCAGCTATGGCTTTAC (SEQ ID NO: 56)
VP1-LR GCTGCCATTCATGAGAGGAT Inner (1233 bp)
                                (SEQ ID NO: 57)
VP1-SF CCTCAATGGATGTTGCCTTT (SEQ ID NO: 58)
VP1-SR AAAACCAAAGACCCCT
```

PCR reaction mixtures consisted of 5 μL of 10×PCR buffer, 4 mM of each dNTP, 0.7 μM of primers VP1-LF and VP1-LR in the first round and primers VP1-SF and VP1-SR in the second round, 1.25 unit of Platinum Taq HF (Invitrogen) and 1 μL of extracted DNA in a total volume of 50 μL. Cycling parameters were (for both first and second round) 30 cycles at 94° C. for 20 sec, at 58° C. for 30 sec and at 68° C. for 90 sec in an automated thermal cycler (Applied Biosystems).

After the first amplification with the outer primers, 2.5 μl of amplified product was transferred from the first to the second reaction mixture. Following amplification with the inner primers, 10 μl of the amplified product from the second mixture was electrophoresed on a 2% agarose gel containing 0.5 μg/ml ethidium bromide. The results were photographed under U.V. illumination and regarded as positive when a band corresponding to the expected by long DNA fragment was present.

VP1 PCR Cloning:

The amplification product was purified by the Qiagen purification kit. A's were added to the ends of the cleaned up PCR product by Taq polymerase (A-overhang reaction) and cloning was carried out by the TOPO TA cloning kit (Invitrogen). Mini-prep DNA was prepared (Qiagen) from colonies containing the cloned VP1 PCR product.

VP1 Sequencing:

Two to 48 clones were sequenced for each sample (median 23). Following translation of the VP1 sequences, amino acid mutations were marked by comparison to the large selection of VP1 sequences from PML and non-PML cases. Only mutations present in more than one clone for sample were considered.

Real-Time PCR for Quantification of JCV-DNA:

JCV DNA was quantified in CSF, plasma and urine samples by real-time PCR, as described previously (Bossolasco S, Calori G, Moretti F, Boschini A, Bertelli D, Mena M, Gerevini S, Bestetti A, Pedale R, Sala S, Sala S, Lazzarin A, Cinque P. Prognostic significance of JC virus DNA levels in cerebrospinal fluid of patients with HIV-associated progressive multifocal leukoencephalopathy. Clin Infect Dis. 2005 Mar. 1; 40(5):738-44.)

Patients:

PML patients were selected on the basis of the availability of either a) paired CSF and plasma or urine samples or b) sequential CSF samples, all with detectable JCV DNA by real time PCR. Samples had been drawn from patients followed at the Clinic of Infectious Dieaeses, San Raffaele Hospital, Milano, between 1993 and 2008. Sample aliquots were kept stored at −80° C. until the retrospective analyses for the present study. JCV VP1 was successfully amplified from a total of 26 CSF, 11 plasma and 6 urine samples from a total of 30 PML patients.

Analysis of Clinical Samples—Study Design:

1. Analyses of CSF Sequences:

CSF sequences were examined from 26 patients (Table 9) and both type and frequency of mutations, as well as their correlations with patients variables were analysed.

2. Analysis of Sequences from Paired Samples from Same Patients:

Paired CSF/plasma/urine samples ("triplets") were examined in 2 patients. CSF/plasma, CSF/urine and plasma/urine pairs were examined from, respectively, 6, 1 and 3 patients. Sequences obtained from triplets and pairs were compared.

3. Analysis of Sequences from Sequential Samples:

Sequential CSF or plasma samples were available from 5 and 2 patients, respectively. These samples had been drawn close to the diagnosis of PML (baseline) and at different times afterwards. From each patient, 2 to 3 samples drawn over a time frame of 17 to 477 days were analysed. 5 of these patients had a progressive course of PML. One patient experienced virological response after commencement of HAART. One patient underwent clinical and virological remission following treatment with cytarabine, but had a relapse of PML after 6 months and following withdrawal of cytarabine.

TABLE 9

| Characteristics of the 26 PML Patients with JCV VP1 analysis | |
|---|---|
| HIV status (pos:neg) | 20:6 |
| Median age | 37 |
| Sex (M:F) | 18:8 |
| JCV DNA copies/mL (median, IQR) | 22,351 (6416-1,178,877) |
| Ongoing HAART (number of patients) * | 6 |
| Progressors vs. survivors (number of patients) | 18:2 |

* Refers only to patients with HIVrelated PML

Analysis of Clinical Samples—Results:

1. Analyses of CSF Sequences:

VP1 PML-specific mutations were defined as mutations that are not normally present in the urine of patients without PML. These mutations or deletions do not involve mutations at positions determining VP1 genotypes—which distinguish VP1 sequences according to their geographical distribution.

One of 8 different PML-specific mutation or deletion was identified in CSF from 24 of 26 patients (92%). These involved amino acid substitutions in one of the JCV VP1 outer loops (Table 10).

In all of the cases almost all of the clones from the same sample contained the mutation or the deletion. In 5 patients, two different mutations or deletions were identified, either in same clones (n=2) or in different clones (n=3).

TABLE 10

| JCV VP1 mutations in the CSF of patients with PML | | | |
|---|---|---|---|
| Patients | VP1 loop | VP1 mutation or deletion (aa) | Nr of patients |
| HIV-pos (n = 20) | BC | 51-52 del | 1 |
| | | 55F | 5 |
| | | 55F + 271H * | 1 |
| | | 61L | 1 |
| | | 61L + 55 del * | 1 |
| | DE | 122R | 2 |
| | | 122R + 125-127 del | 1 |
| | | 122R + 2V ** | 1 |

TABLE 10-continued

JCV VP1 mutations in the CSF of patients with PML

| Patients | VP1 loop | VP1 mutation or deletion (aa) | Nr of patients |
|---|---|---|---|
| | HI | 265D | 2 |
| | | 267F + 61L * | 1 |
| | | 169F | 2 |
| | | 0 | 2 |
| HIV-neg (n = 6) | BC | 55F | 4 |
| | HI | 265H | 1 |
| | | 269F | 1 |

Figure 19:
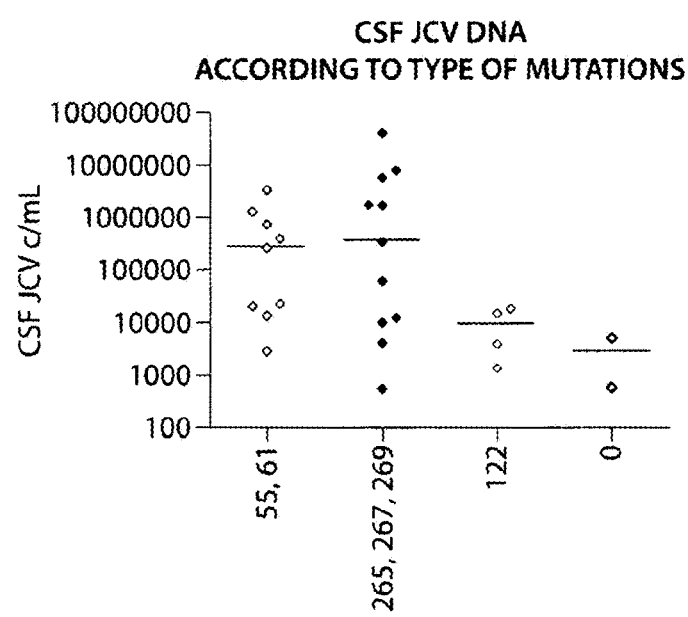
FIG. 19 shows that higher CSF JCV DNA levels were found in patients with mutations of the BC and HI loops than in those with mutations of the DE loop or no mutations.

The BC, DE and HI JCV VP1 loops are defined by similarity of their aa sequences to the VP1 loops of SV40 (Chang D, Liou Z M, Ou W C, Wang K Z, Wang M, Fung C Y, Tsai R T. Production of the antigen and the antibody of the JC virus major capsid protein VP1. J Virol Methods May 1996; 59(1-2):177-87), which were previously determined by X-ray crystallography (Liddington R C, Yan Y, Moulai J, Sahli R, Benjamin T L, Harrison S C. Structure of simian virus 40 at 3.8-A resolution. Nature Nov. 28, 1991; 354(6351):278-84).
* Either mutation/deletion was present in different clones (55F+271H in 15 and 4 clones; 61L+55 del in 18 and 4 clones; 267F+61L in 15 and 4 clones)
** Both mutations/deletions were present in each clone Higher CSF JCV DNA levels were found in patients with mutations of the BC and HI loops than in those with mutations of the DE loop or no mutations (FIG. 19). No correlation was observed in patients with HIV-associated PML between type of mutation and CD4 cell count, plasma HIV-1 RNA level or survival time.

2. Analysis of Sequences from Paired Samples:

The analysis of the 2 CSF/plasma/urine triplets showed the same VP1 PML-specific mutation in CSF and plasma, whereas no PML mutation was present in the corresponding urine sequences (Table 11). Similarly, identical PML-specific mutations were found in CSF and plasma sequences from 6 patients with CSF/plasma pairs (Table 12), but only in either CSF or plasma, but not in urine sequences of 1 patient with CSF/urine pairs or 3 patients with plasma/urine pairs (Table 13).

TABLE 11

JCV VP1 mutations in paired CSF/plasma/urine samples from patients with PML

| Pt Lab ID | Type of sample | PML mutation |
|---|---|---|
| 1 | CSF | 269F |
| | PLASMA* | 269F |
| | URINE | 0 |
| 2 | CSF | 269F |
| | PLASMA | 269F |
| | URINE | 0 |

TABLE 12

JCV VP1 mutations in paired CSF/plasma samples from patients with PML

| Pt Lab ID | Type of sample | JCV DNA c/mL | PML mutation |
|---|---|---|---|
| 3 | CSF | | 269F |
| | PLASMA | | 269F |
| 4 | CSF | | 269F |
| | PLASMA | | 269F |
| 5 | CSF | | 122R |
| | PLASMA | | 122R |
| 6 | CSF | | 0 |
| | PLASMA | | 0 |
| 7 | CSF | | 55F |
| | PLASMA | | 55F |
| 8 | CSF | | 269F |
| | PLASMA | | 269F |

TABLE 13

JCV VP1 mutations in paired CSF/urine or plasma/urine samples from patients with PML

| Pt Lab ID | Type of sample | PML mutation |
|---|---|---|
| 9 | CSF | 55F |
| | URINE | 0 |
| 10 | PLASMA | 122R |
| | URINE | 0 |
| 11 | PLASMA** | 55F |
| | URINE | 0 |
| 12 | PLASMA | 0 |
| | URINE | 0 |

3. Analysis of Sequences from Sequential Samples:

Analysis of sequential CSF or plasma samples revealed the persistence of the PML-specific mutations in 7 patients with progressive disease and stable or increasing JCV DNA in CSF (Tables 14 and 15).

In the patient undergoing virological response, the principal PML mutation present in the first CSF sample was no longer found in a second CSF sample showing a decrease of JCV DNA level; in this latter sample, the emergence of a previously minor represented mutation was observed.

In the patient undergoing PML relapse a few months after clinical and virological remission of a first episode of PML, two different mutations were present in CSF samples drawn during the two episodes.

TABLE 14

PML Mutations in Patients with Sequential CSF Samples

| Pt Lab ID | Days after first sample | PML mutation |
|---|---|---|
| A | 0 | 55F |
| | 17 | 55F |
| | 92 | 55F |
| B | 0 | 269F |
| | 208 | 265D |
| C | 0 | 265D |
| | 56 | 265D |
| D | 0 | 55F |
| | 66 | 55F |
| E | 0 | 122R + 2V ** |
| | 477 | 122R + 2V ** |
| F | 0 | 51-52del |
| | 230 | 51-52del |
| | 0 | 61L + 53-55 del * |
| | 63 | 53-55del |

Tables 14 and 15, notes:
* Either mutation/deletion was present in different clones (55F+271H in 15 and 4 clones; 61L+55 del in 18 and 4 clones; 267F+61L in 15 and 4 clones)
** Both mutations/deletions were present in each clone

TABLE 15

PML Mutations in Patients with Sequential Plasma Samples

| Pt Lab ID | Days after first sample | PML mutation |
|---|---|---|
| H | 0 | 269F |
|   | 21 | 269F |
| I | 0 | 267Y |
|   | 56 | 267Y |

Tables 14 and 15, notes:
* Either mutation/deletion was present in different clones (55F+271H in 15 and 4 clones; 61L+55 del in 18 and 4 clones; 267F+61L in 15 and 4 clones)
** Both mutations/deletions were present in each clone Molecular Modeling of JCV-VP1:

Molecular Modeling of JCV VP1/Tetrasaccharide Complex:

A homology model of the JCV VP1 protein pentameric unit was built with MODELER using the structure of MPyV VP1 (Protein Data Bank ID: 1VPS as a template. The model of NeuNAc($\alpha$2,3)-Gal-($\beta$1,3)-[($\alpha$2,6)-NeuNAc]-Glc-NAc tetrasaccharide was build based on the structure of NeuNAc-($\alpha$2,3)-Gal-($\beta$1,3)-[($\alpha$2,6)-NeuNAc]-Glc-NAc bound to MPyV VP1. The model of the JCV VP1/NeuNAc-($\alpha$2,3)-Gal-($\beta$1,3)-[($\alpha$2,6)-NeuNAc]-Glc-NAc tetrasaccharide was extensively refined in CHARMM and was analyzed using PyMOL visualization software (The PyMOL Molecular Graphics System (2002) DeLano Scientific, Palo Alto, Calif., USA.

Accordingly, compared to wild-type virus (that present in urine of healthy persons) one of 8 specific single mutations or deletions was identified in almost all CSF clones from each of 24/26 patients (92%). These conferred substitutions or deletions in one of the three outer loops of VP1, most frequently involving residues 55 (55F, 7 patients, 27%) and 269 (269F, 6 patients, 23%). Paired plasma always showed the same CSF mutation, but no mutations were identified in urines. Mutations were maintained in sequential samples from 7 patients with progressive disease and stable or increasing JCV DNA in CSF. They were lost in 2 patients: 1 undergoing PML remission and relapse, with onset of a new mutation; and 1 with decreasing CSF JCV DNA, with emergence of a previously minor different mutant variant. By 3D modelling, all mutated residues clustered within or in the immediate proximity to the sialic acid cell receptor binding site on VP1.

Therefore, based on this data, in patients with PML, JCV found from CSF and plasma, but not urine, carries PML-specific VP1 substitutions. These substitutions are maintained during disease progression. They involve the BC, DE or HI external loops of VP1, at critical sites for binding with the sialic acid cell receptor. Accordingly, in PML, JCV from CSF and plasma, but not urine, carries VP1 substitutions at critical sites for cell binding, which are maintained during the disease. These findings support a model whereby JCV acquires adaptive changes during transition from sites of persistence to the brain, eventually leading to PML.

Example 12

Residues in the Sialic Acid Binding Pocket of VP1

Residues within 12 angstroms from the modeled sialic acid containing sugar (as described in the Examples herein) are listed in Table 16.

TABLE 16

| | |
|---|---|
| MET | 48 |
| GLY | 49 |
| ASP | 50 |
| PRO | 51 |
| ASP | 52 |
| GLU | 53 |
| HIS | 54 |
| LEU | 55 |
| ARG | 56 |
| GLY | 57 |
| MET | 57 |
| GLY | 58 |
| PHE | 58 |
| GLN | 59 |
| SER | 59 |
| LYS | 60 |
| PRO | 60 |
| SER | 61 |
| ILE | 62 |
| PRO | 63 |
| SER | 63 |
| ILE | 64 |
| SER | 65 |
| SER | 65 |
| ASP | 66 |
| LEU | 66 |
| THR | 67 |
| THR | 67 |
| GLU | 68 |
| PHE | 68 |
| GLU | 69 |
| GLY | 69 |
| GLY | 70 |
| SER | 70 |
| ASP | 71 |
| GLN | 71 |
| SER | 72 |
| TYR | 72 |
| PRO | 73 |
| TYR | 73 |
| ASN | 74 |
| GLY | 74 |
| LYS | 75 |
| TRP | 75 |
| ASP | 76 |
| SER | 76 |
| ARG | 77 |
| MET | 77 |
| GLY | 78 |
| LEU | 78 |
| ILE | 79 |
| PRO | 79 |
| ASN | 80 |
| LEU | 81 |
| ALA | 82 |
| THR | 83 |
| SER | 84 |
| ASP | 85 |
| THR | 86 |
| GLU | 87 |
| ASP | 88 |
| SER | 89 |
| PRO | 90 |
| GLY | 91 |
| ASN | 92 |
| ASN | 93 |
| THR | 94 |
| LEU | 95 |
| PRO | 96 |
| ASN | 120 |
| VAL | 121 |
| HIS | 122 |
| SER | 123 |
| ASN | 124 |
| GLY | 125 |
| ASP | 130 |
| ASN | 131 |
| GLY | 132 |
| ALA | 133 |
| ALA | 134 |

TABLE 16-continued

| | |
|---|---|
| ASP | 137 |
| VAL | 138 |
| HIS | 139 |
| GLY | 140 |
| PHE | 141 |
| ASN | 142 |
| LYS | 143 |
| THR | 150 |
| LYS | 151 |
| GLY | 152 |
| ILE | 153 |
| SER | 154 |
| PHE | 159 |
| ASN | 160 |
| TYR | 161 |
| ARG | 162 |
| THR | 163 |
| THR | 164 |
| TYR | 165 |
| PRO | 166 |
| ASP | 167 |
| ASP | 180 |
| GLN | 180 |
| ARG | 182 |
| THR | 183 |
| LYS | 184 |
| TYR | 185 |
| LYS | 186 |
| GLU | 187 |
| GLU | 188 |
| VAL | 190 |
| GLN | 206 |
| MET | 262 |
| PHE | 263 |
| THR | 264 |
| ASN | 265 |
| ARG | 266 |
| SER | 267 |
| GLY | 268 |
| SER | 269 |
| GLN | 270 |
| GLN | 271 |
| TRP | 272 |
| ARG | 273 |
| TRP | 288 |
| ARG | 289 |
| VAL | 290 |
| THR | 291 |
| ARG | 292 |
| ASN | 293 |
| TYR | 294 |
| ASP | 295 |
| VAL | 296 |
| VAL | 296 |
| HIS | 297 |
| HIS | 298 |
| TRP | 299 |
| ARG | 300 |

Example 13

CSF and Plasma, but not Urine JCV of PML Patients Carry PML-Associated VP-1 Mutations To investigate whether PML-associated mutations are specifically selected in CSF of PML patients, initially paired CSF and urine sequences from 7 patients were analysed (Table 17). In each patient, CSF JCV-VP1 carried one amino acid substitution that was not present in the urine derived sequence. CSF and urine sequences were otherwise identical within individual patients and characterized by identical polymorphisms as compared to the reference strain (same virus subtype). PML-associated CSF mutations involved codons 55, 60, 267, 269, and also codon 122. Plasma VP1 sequences, available from 13 patients (Table 17), were in all the cases identical to the correspondent CSF-derived sequence, carrying the same PML-associated substitution.

Table 17. JCV VP1 amino acid substitutions in sequences derived from paired urine, CSF and plasma samples from PML patients

TABLE 17

| | Matrix | JCV subtype | PML-associated substitution |
|---|---|---|---|
| 1 | Urine | 1B | none |
| | CSF | 1B | L55F |
| | Plasma | n.a. | n.a. |
| 2 | Urine | Mad-1 | none |
| | CSF | Mad-1 | H122R; A2V |
| | Plasma | n.a. | n.a. |
| 4 | Urine | 1A | none |
| | CSF | 1A | H122R |
| | Plasma | 1A | H122R |
| 5 | Urine | Mad-1 | none |
| | CSF | Mad-1 | S269F |
| | Plasma | Mad-1 | S269F |
| 6 | Urine | Undet. | none |
| | CSF | CONS | S267Y |
| | Plasma | Undet. | S267Y |
| 7 | Urine | 1B | none |
| | CSF | 1B | S269F |
| | Plasma | 1B | S269F |
| 8 | Urine | 1A | none |
| | CSF | 1A | S269F |
| | Plasma | 1A | S269F |
| 9 | Urine | n.a. | n.a. |
| | CSF | Undet. | S269F |
| | Plasma | Undet. | S269F |
| 10 | Urine | n.a. | n.a. |
| | CSF | 2B | S269F |
| | Plasma | 2B | S269F |
| 11 | Urine | n.a. | n.a. |
| | CSF | 4v164K | none |
| | Plasma | 4v164K | none |
| 12 | Urine | n.a. | n.a. |
| | CSF | 1A | L55F |
| | Plasma | 1A | L55F |
| 13 | Urine | n.a. | n.a. |
| | CSF | 4v128A345K | L55F |
| | Plasma | 4v128A345K | L55F |
| 14 | Urine | n.a. | n.a. |
| | CSF | 1Bv117T | S269F |
| | Plasma | 1Bv117T | S269F |
| 16 | Urine | 4v164K | none |
| | CSF | n.a. | n.a. |
| | Plasma | 4v164K | L55F |

U, urine; CSF, cerebrospinal fluid; P, plasma.
* when no substitution is identified, then column value refers to nr of clones without substitution/nr of clones examined.

Example 14

CSF JCV of PML Patients Consistently Carry One of Several Mutations or Deletions Located In Sites Critical for Cell Binding To define type and frequency of VP1 PML-associated substitutions in vivo, CSF-derived VP1 sequences in a larger group of patients were analysed. One main PML-associated mutation or deletion was identified in 37 of 40 patients (90%) (Table 18). The VP1 gene was cloned and sequenced for a number of clones as described in Materials and Methods. Mutations were identified by comparing the sequences to either VP1 sequences from matched urine samples (when available) and to 460 sequences isolated from the urine of non-PML individuals (n=460) as reported in the Genebank. In some patients the mutation H122R was identified. In some patients the mutation 2831 was identified. In some patient the mutations A2V was identified. In some patient the deletion 50-51 was identified. In some patient the deletion 50-51 was identified. In some patient the deletion 54-55 was identified. In some patient the deletion 123-125 was identified. In some patient the deletion 125-134 was identified. In some patient the deletion 126-134 was identified.

Figure 20A:
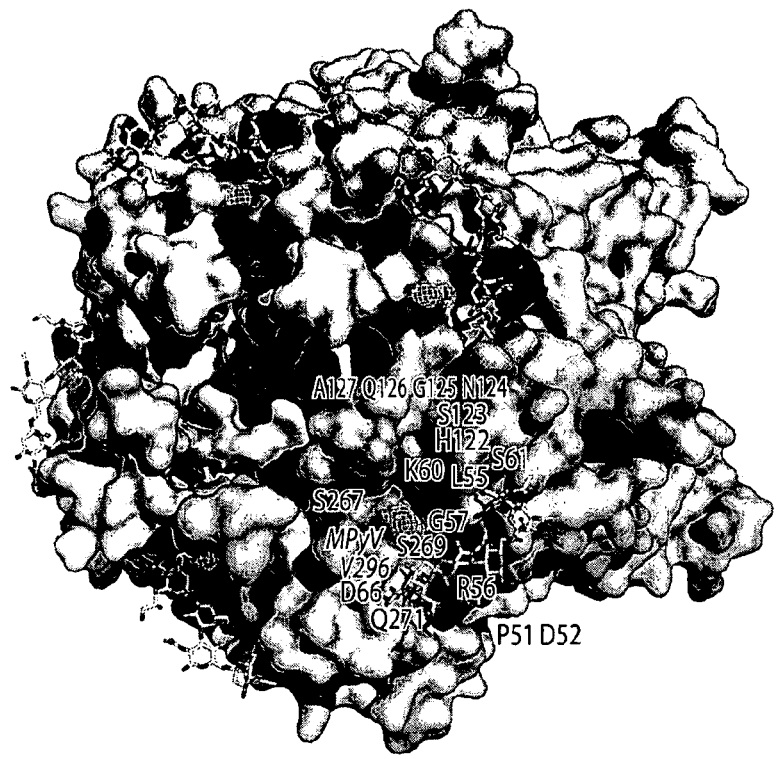
FIGS. 20A-20B show a structural model of JCV VP1/NeuNAc-(a2,3)-Gal-(b1,3)-[(a2,6)-NeuNAc]-Glc-NAc tetrasaccharide complex; and, FIG. 21 shows PML specific mutations of VP1 abolish or drastically change specificity of viral capsid protein VP1 for sialated gangliosides.
Figure 20B:
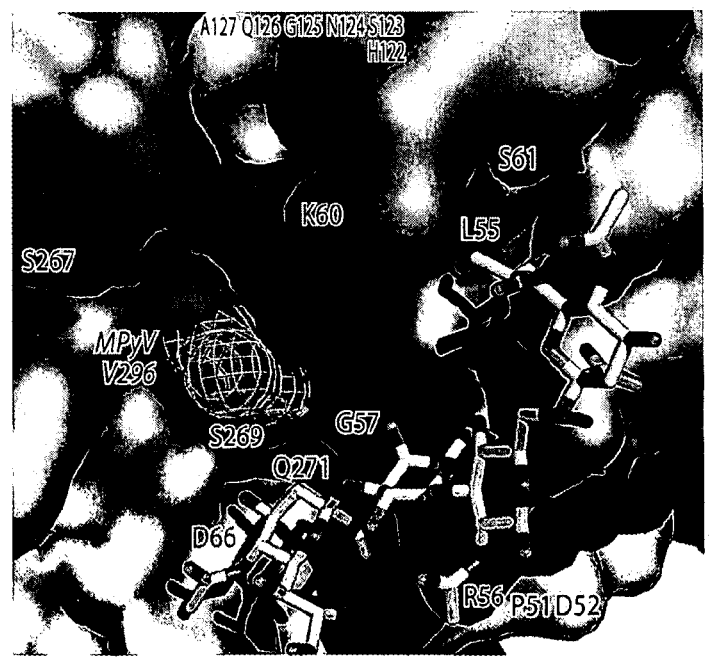

The most frequent changes involved codons 55 and 269, each identified in 25% of the patients. In addition to the substitutions already reported, at codons 55, 60, 61 and 265, 267, 269, several other PML-associated mutations or deletions were newly identified, involving non polymorphic VP1 codons as evidenced by comparison to urine derived sequences from the Genebank. All these newly identified mutations are also located in critical VP1 binding sites (Table 18). FIG. 20 is a structural model of JCV VP1/NeuNAc-(a2,3)-Gal-(b1,3)-[(a2,6)-NeuNAc]-Glc-NAc tetrasaccharide complex. (A). Surfaces of five chains of JCV VP1 are shown. The RG motif essential for binding of core sialic acid is shown. PML-associated mutated residues also are shown (L55, K60, 5265, S269). Additional mutations unique to PML-isolated samples also are indicated (S61, D66, Q271) and (P51, D52, H122, S123, N124, G125, Q126, A127). (B). A close-up view of FIG. 20A. The location of V296 of MPyV VP1 which is predicted to be equivalent to S269 of JCV VP1 is shown in mesh.

TABLE 18

JCV VP1 PML-associated aa substitutions
and deletions in CSF of PML patients

| | JCV VP1 subtype | PML-associated substitution or deletion |
|---|---|---|
| 1 | 4v-164K | none |
| 2 | 1Av-128S | none |
| 4 | 2B | 50-51del |
| | | D66G |
| | | N124S |
| 5 | 1B | L55F |
| 6 | 1A | L55F |
| 7 | 3 | L55F |
| | | Q271H |
| 8 | 1B | L55F |
| 9 | 1A | L55F |
| 10 | 4v-128A345K | L55F |
| 16 | 1B | S61L |
| | | 54-55 del |
| 18 | 1A | H122R |
| 19 | 1A | H122R |
| | | A2V |
| 17 | 1B | 123-125 del |
| 20 | 4v-128A | N265D |
| 21 | 4v-128A | N265D |
| 23 | 1B | S267F |
| | | S61L |
| | | Q271H |
| 24 | 2B | S267F |
| 25 | Undet. | S269F |
| 27 | 1B | S269F |
| 31 | 2B | L55F |
| 34 | 2B | N265H |
| 36 | 2B | S269F |
| 37 | 1Bv117T | S269F |
| 38 | 1B | S269F |
| 39 | 1A | S269F |

Undet., undetermined; Cons., consensus; v, variant a. sequence available up to position 295

Example 15

Relationship Between JC Virus Isolated from Different Compartments

To inquire into the relationship between viral populations in three compartments (kidney, plasma and CSF) population variation of VP1 sequences represented by individually sequenced clones from all three compartments in three patients were analyzed. With the exception of amino acid changes presumably associated with PML development, dominant VP1 genotypes in all three compartments were always identical. All observed sequence variation was due to low frequency single nucleotide variants. This suggests that PML causing virus originated from preexisting resident population in kidney.

The relationship between viral populations in the three compartments can be characterized by the degree of shared low frequency polymorphism. Single nucleotide variants observed in two or more clones were analyzed. In all three patients, the majority of genetic variation was confined to individual compartments as allelic variants present in more than one sequence were observed in a single compartment. Therefore, the viral population is highly structured.

In two of the three patients several allelic variants were shared between CSF and plasma populations and no variant was shared between CSF and kidney populations or plasma and kidney populations. In each of these two patients, the same PML-associated mutation was observed in clones from CSF and plasma. These data are consistent with a single origin of the CSF and plasma populations, presumably due to a one-time escape from kidney event. In this scenario sequence variation shared between the CSF and plasma populations originated after the fixation of the PML-associated mutation outside of kidney (assuming that independent multiple mutations in the same site are not likely). VP1 sequence variation shared between CSF and plasma populations may indicate presence of viral migration between compartments. It is also consistent with a scenario of stepwise infection, where a resident viral population outside of kidney first establishes in one compartment (either CSF or plasma), accumulates genetic variation, and then infects the second compartment.

A third patient presents a different picture of shared polymorphism between compartments. Two variants were shared between CSF and kidney, three variants were shared between plasma and kidney and one variant was shared between all three compartments. All clones isolated from CSF and most of clones isolated from plasma harbored the same PML-associated mutation (S269F). However, three clones isolated from plasma had a different PML-associated mutation (S267F). These clones lacked the dominant PML-associated mutation.

Although the possibility of multiple successive infections of CSF and plasma of Patient 3 cannot be excluded, these observations are not necessarily inconsistent with the scenario of a single origin of CSF and kidney populations after a one-time escape from kidney. The data for Patient 3 might be an example of a soft selective sweep. Soft selective sweep unlike the hard selective sweep does not eliminate preexisting genetic variation completely. The soft sweep scenario is very likely if the product of effective population size and mutation rate (Ne×mu) exceeds one. In this case multiple instances of a beneficial mutation (or several beneficial mutations of equal or comparable selective advantage) likely existed in the original population on different haplotypic backgrounds. After a soft sweep, all sequences would harbor a beneficial mutation but the population remains polymorphic. It is possible that multiple instances of S269F mutation and S267F mutation existed in the kidney population before the escape and the fixation occurred following the soft sweep scenario leading to the co-existence of S269F and S267F VP1 variants in the plasma population and shared variation between all three compartments.

Example 16

Correlation of Various Mutations with the Clinical Outcome

To assess whether individual PML-associated VP1 substitutions could be clinically significant, e.g., being differently selected according to patient and clinical context or associated with different disease outcome, their presence was correlated to a number of variables.

It was observed that JC virus with no VP1 substitutions or substitutions involving positions 122-134 was present at the significantly lower DNA level in CSF as compared to virus with substitutions involving other positions (p=0.013, Mann-Whitney test), e.g., with substitutions either at position 50-61 (p=0.02) or 265-269 (p=0.036) s carrying different VP1 substitutions.

Example 17

PML Associated Mutation Decrease Ability of VP1 to Hemagglutinate RBCs

In order to understand the role PML associated mutations play in disease pathogenesis, the effect of some of these mutations on viral receptor binding was investigated. Since JCV is known to bind to sialic acid structures (Liu), viral ability to cause hemagglutination of RBCs that express those structures has been widely used as a model for viral interaction with its receptor.

Viral like particles (VLPs) prepared from the major JCV capsid protein VP1 has been widely used as a good model investigating the interactions of polyomaviruses with their cell receptors. Similar to viral capsid, VLPs form viral capsid structure as evidenced from electron microscopy (data not shown). Next, binding of VLPs prepared from either a "wild type" or various "mutant" VP1 molecules was investigated. A number of PML-associated mutations that were shown to be positively selected during PML were introduced as point mutations on a backbone of a VP1 molecule from a single viral background (JCV type 3) and compared their ability to hemagglutinate (e.g., bind) red blood cells (RBC). VLPs prepared from VP1 molecule of type 3 virus just like for VLPs prepared from type 1A (e.g., Mad-1) virus can cause RBC hemagglutination, and they do that at the concentration as low as 760 pg/ml. However, VLPs carrying one of most frequently occurring mutations 55F, 267F and mutations at position 269 (F or Y) did not cause hemagglutination even at the highest tested concentration of 100 μg/ml, which corresponds to more than 100,000-fold decrease in activity. Hemoagglutination was still apparent with the 60E, 265D and 271H mutant VLPs, but only at very high concentrations that corresponded to 200 to 25,000-fold losses in activity. Only binding of 66H mutant VLP was not strongly affected and showed only 3-fold decrease in hemoagglutination (3000 pg/ml as the lowest hemagglutinating concentration). Neither 66H nor 271H mutations were observed among the sequences analysed in this example, but these mutations are identified to be PML-associated, based on an analysis of sequences from Genebank. This effect of mutations on the ability of VLPs to cause hemagglutination suggests that the mutations may change viral receptor specificity by abrogating the ability of virus to bind to cell receptor(s).

Example 18

PML-Associated Mutations Lose Ability to Hemagglutinae RBCs from Different Blood Groups VLPs carrying PML-associated mutations lose ability to hemagglutinae RBCs from different blood groups. For hemagglutination assay red blood cells (RBCs) were incubated with serial two-fold dilutions of various VLPs starting from 100 μg/ml. Minimum HA concentration is the lowest concentration of VLP protein that still agglutinated RBCs. Hemaglutination was examined by visual inspection as previously described. All hemagglutination reactions were conducted in duplicates. Mean+/−SD for the minimum HA concentration is calculated based on the hemaglutionation results from four different blood group donors A, B, O and AB). VLPs displaying lowest hemagglutination concentration of 100 μg/ml did not cause any hemagglutination at highest VLP concentration tested (e.g., 100 μg/ml).

Example 19

PML Associated Mutations Change Ganglioside Specificity of VP1

Figure 21:
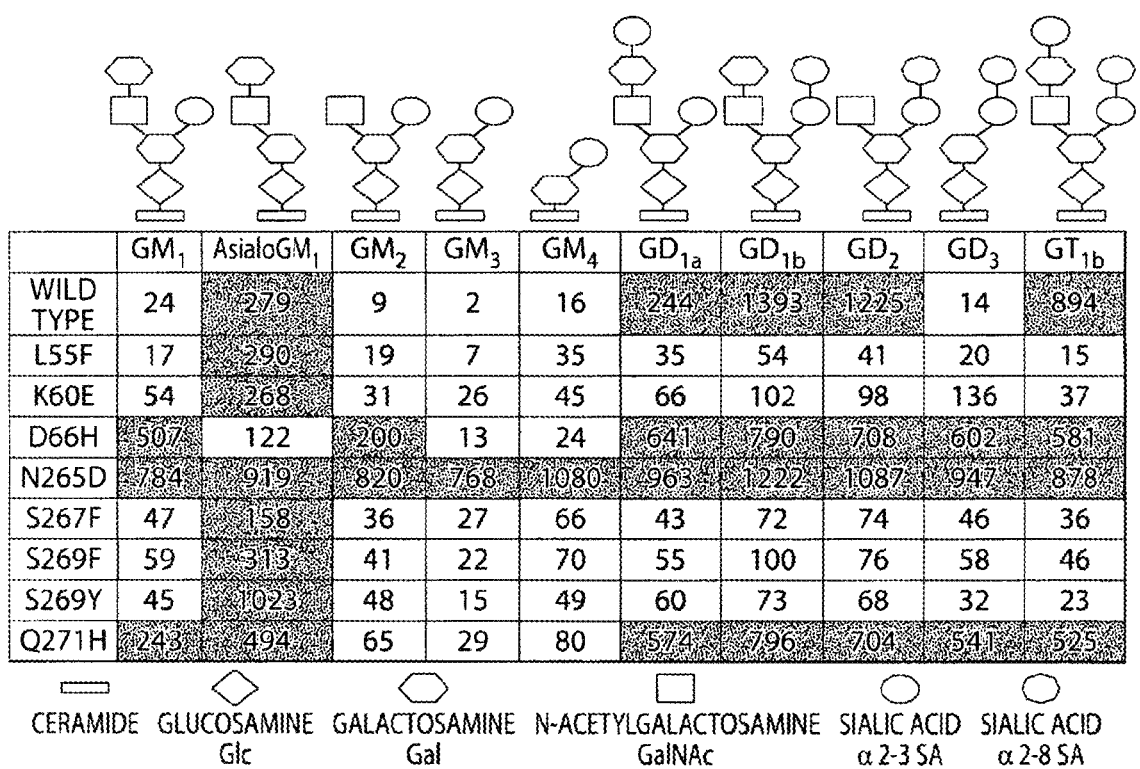

In order to further dissect JCV VP1 receptor specificity binding of various mutant VLPs to different gangliosides was investigated. Gangliosides are a group of complex glycosphingolipids in which oligosaccharide chains containing one or more sialic acids (N-acetylneuraminic acid, NeuNAc) are attached to a ceramide, which anchors the structure to cellular membrane. VLP binding to these ganglioside was measured in ELISA like format, where gangliosides were coated in ELISA plates akin to antigen and followed by addition of VLPs, which binding was detected with VP1 specific monoclonal antibodies. Using a type 3 "wild type" JCV VLP, the strongest binding was observed to GD1b, GD2 and GT1a, with more than 8-12 fold increase of signal as compared to the background produced by binding of VLP to the well without any ganglioside (FIG. 21). PML specific mutations of VP1 abolish or drastically change specificity of viral capsid protein VP1 for sialated gangliosides. Binding of VLPs to an array of gangliosides coated on a 96-well plate was detected with a two step process involving detection of VLPs bound to a ganglioside with VP1-specific murine antibodies and anti-murine IgG HRP labeled antibodies followed by development with TMB solution. VLP binding to a specific ganglioside was calculated as percent increase in the optical density obtained with the specific VLP present relative to that obtained without VLP and antibodies alone in the presence of the same galnlioside, $100*(OD_{450}(\text{plus VLP})-OD_{450}(\text{minus VLP}))/OD_{450}(\text{minus VLP})$. Schematic structure of ganglioside is shown to reveal core binding structure bound by various VLPs. One representative experiment of four conducted is shown. This ganglioside specificity is consistent with what was previously described for the type 1A "wild type" virus Mad-1. Binding of VLPs to asialo-GM1 and GD1a was much weaker but still significant over the background, while binding to other gangliosides was very negligible relative to no-ganglioside background. Based on the binding pattern it appears that the major "core" structure bound by wild type virus consists of a tetrasaccharide GalNAc(β1-4)[Neu5Ac(α2-8)-Neu5Ac(α2-3)] Gal(β1-4)Glc structure, with di-sialic acid motif of Neu5Ac(β2-8)-Neu5Ac(α2-3) being crucial for binding.

However, binding of all mutant VLPs was drastically different from the "wild type" molecule. Specifically, as seen in FIG. 21, the VLP mutants 55F, 60E, 267F, 269F and 269Y completely lost binding to all sialated gangliosides while still showing unchanged binding to asialated GM1 structure (e.g., asialo-GM1). Still, others, such as 66H, 265H and 271H showed a much broader range of ganglioside binding than the original non-mutated VLP molecule.

Example 20

Binding of VLPs to Various Cellular Targets

Results from hemagglutination and direct ganglio side binding assays jointly suggest that PML associated mutations change viral receptor specificity and especially viral ability to bind to sialated oligosaccharide structures. Therefore, it was investigated next how these mutation-conferred changes in specific receptor binding affected JCV ability to bind to its purported target cells. Binding of the above wild-type and mutant VLPs to the three major cell types reported to be important for viral cell cycle: kidney epithelial cells, lymphocytes and CNS cells was measured. Primary human renal proximal tubular epithelial cells (HRPT-ECs) were chosen as cells from the site of viral asymptomatic persistence of non-mutated virus. Primary human B lymphocytes were also chosen, as the cell type suggested to be critical for viral spread from peripheral site to the CNS, as well as other lymphoid cells, e.g., primary T lymphocytes and lymphocytic cell line Jurkat. Although productive infection of lymphoid cells has not been unequivocally demonstrated, lymphocytes have been shown to bind JCV via their sialic acid structures (Atwood et al.) and thus could potentially carry the virus in vivo. Primary human fetal astrocytes and the human glial cell line SVG-A were also employed as a model cell type for CNS infection during PML. Infection of astrocytes has been well documented in PML patients and both of these glial cell types can be infected by JCV in vitro.

PML-ogenic mutants of VP1 lose binding ability to kidney and blood cells but bind to the glial cells. Glial cell line SVG-A(A), primary human astrocytes (B), human brain microvascular endothelial cell (C), kidney tubular epithelial cells (D), or peripheral blood mononuclear cells (E and F) cells were first incubated with different VLP (as indicated on the x-axis) and further incubated with anti-VP1 antibodies followed by staining with fluorescently labeled antibodies. Binding of VLPs to T-(E) and B-lymphocytes(E) was evaluated after co-staining of PBMCs with antibodies specific for human CD3 and CD20 markers and gating on the corresponding population. Ratio of mean fluorescent intensity (MFI) of cells stained with anti-VP1 antibodies in the presence of VLPs relative to the background MFI of cells stained only with the detection antibodies in the absence of VLP is plotted for each VLP. Mean MFI ratio+/SD is calculated based on the results from several independent experiments (N is indicated on the graph). VLPs made from "wild type" VP1 strongly bound to all of the above cell types with MFI of more than 2-fold above background staining. However, binding of mutant VLPs was dependent on both the cell type and the position of the mutated amino acid. Specifically, the most frequent PML associated mutations 55F, 267F, 269F and 269Y abrogated binding of VLPs to kidney tubular epithelial cell and all lymphocytic cells, but not to the primary astrocytes or glial cell line SVG-A. Both CNS cell types still strongly bound VLPs carrying these mutations (with the exception of 55F that bind SVG-A cells but not primary astrocytes). VLPs carrying 60E, 66H and 271H still bound all cell types, including kidney epithelial cells and lymphocytes, although binding of 271H was strongly diminished.

Example 21

VLPs Carrying PML-Associated Mutations Bind Glial Cells in Sialic Acid Independent Fashion Since binding of the virus to cells has been previously demonstrated to be sialic acid dependent (e.g., Atwood et al.), but the data demonstrate that most PML-associated mutations abolish binding of VLPs to sialic acid containing gangliosides, it was tested next whether binding of mutant VLPs to cells is still sialic acid dependent. To do that either SVG-A or Jurkat cells were treated with Neuraminidase to remove sialic acid from cell surface. Staining of the cells with lectins specific for various conformations of neuraminic acids (e.g., *Sambucus Nigra* Lectin (SNA) and *Maackia amurensis* lectin (MAA)) proved neuraminidase treatment effectiveness in sialic acid removal. Binding of PML-ogenic mutants of VP1 to glial cells is sialic acid independent. Glial cell line SVG-A cells or lymphoid cell line Jurkats were first either pretreated with α2-3,6 neuraminidase for 60 min at 37° C. or mock treated followed by incubation at 4 C with the indicated VLP and staining with the detection antibodies as described herein.

Binding of type 3 wild type VLPs to both SVG-A and Jurkat cells is sialic acid dependent, confirming what was previously shown for Mad-1 virus (e.g., type 1A wild type). However, binding of all tested but K60E mutant VLPs to SVG-A cells was not affected by neuraminidase treatment suggesting that binding of these mutants to these cells is sialic acid-independent. Interestingly, those mutants that were still able to bind to Jurkat cells (e.g., K60E, D66H, N265D and Q271H) bound in a sialic acid dependent manner as evidenced by diminished binding to Jurkat cells treated with the neuraminidase.

As can be seen from summary Table 19, binding of VLPs to Jurkat cells appears to be largely sialic acid mediated, so that mutant VLPs that do not show any binding to sialated gangliosides do not bind to Jurkat cells and those that do also bind to Jurkat cells in sialic acid dependent fashion. One notable exception to that observation is N265D mutant, which, based on direct binding to gangliosides, seemed to have gained very broad sialic acid binding, but still lost its binding to Jurkat cell. Based on the above results it appears that VLP binding results are in line with VLP binding to RBCs as judged from hemagglutination results.

In summary, it appears that PML associated mutations largely abolish sialic acid dependent binding of the virus to many different peripheral cells types, including RBCs, kidney tubular epithelial cells and lymphoid cells. Binding of mutant virus to CNS-specific glial cells appears to be largely unaffected and sialic acid independent.

TABLE 19

Correlation of VLP binding between various assays

| | HA | SA | HRPTEC | Jurkat | Astrocytes | SVG-A | SA-dependent SVG-Jurkat | SA-dependent A |
|---|---|---|---|---|---|---|---|---|
| Wild Type 3 | +++ | ++ | +++ | +++ | +++ | +++ | YES | YES |

TABLE 19-continued

Correlation of VLP binding between various assays

| | HA | SA | HRPTEC | Jurkat | Astrocytes | SVG-A | SVG-Jurkat A | SA-dependent |
|---|---|---|---|---|---|---|---|---|
| L55F | − | − | − | − | +/− | +++ | NO | NO |
| K60E | − | − | +++ | ++ | ++++ | +++ | YES | Part. |
| D66H | ++ | +++ | +++ | +++ | +++++ | +++ | Part. | NO |
| N265D | + | ++++ | − | − | +++ | ++++ | NO | NO |
| S267F | − | − | − | − | ++ | ++ | NO | NO |
| S269F | − | − | − | − | ++ | +++ | NO | NO |
| S269Y | − | − | − | − | ++ | +++++ | NO | NO |
| Q271H | +/− | +++ | + | + | +++ | +++++ | YES | NO |

The following methods and materials were used in connection with examples 13-21:

Patients and Samples

The present study was approved by the Ethical Committee of the Institution. To investigate the presence and evolution of PML-associated mutations in vivo, from a large cohort of PML patients, followed at the Department of Infectious Diseases of San Raffaele Hospital between 1992 and 2009, 40 patients were initially selected from whom paired CSF, plasma or urine samples were available and contained JCV DNA as determined by real-time PCR (Bossolasco). VP1 was eventually amplified from at least two different types of samples in 14 of these patients.

43 additional PML patients were subsequently selected with only CSF available and JCV DNA detected in CSF by real-time PCR. JCV VP1 was successfully amplified from 28 of these patients. Thus, paired samples from 14 patients and CSF-derived sequences from a total of 40 patients could be studied.

JCV VP1 PCR

DNA Extraction and VP1 Amplification

DNA was extracted from 200 µL of CSF, plasma or urine using the QIAamp Blood Kit (Qiagen) and eluted in a final volume of 50 µL. VP1 was amplified either using primers flanking the whole VP1 gene (full VP1 PCR), or, when amplification with this method was not successful, by a semi-nested PCR assay that amplified separately shorter VP1 regions (short fragment VP1 PCR).

The full VP1 PCR consisted of a nested assay that used the outer primers VP1-LF and VP1-LR, amplifying a 2027 bp fragment; and the inner primers VP1-SF and VP1-SR, amplifying a 1233 bp long fragment. The PCR reaction mixture consisted of 5 µL of 10×PCR buffer, 4 mM of each dNTP, 0.7 µM of primers VP1-LF and VP1-LR in the first round and primers VP1-SF and VP1-SR in the second round, 1.25 unit of Platinum Taq HF (Invitrogen) and 1 µL of extracted DNA (first round) or 2.5 µl of amplified product (second round) in a total volume of 50 µL. Cycling parameters were (for both first and second round) 30 cycles at 94° C. for 20 sec, at 58° C. for 30 sec and at 68° C. for 90 sec in an automated thermal cycler (Applied Biosystems).

The short fragment PCR consisted of a semi-nested PCR that used primers VP1-1 and VP1-4a in the first round, amplifying a 797 bp fragment, followed by two semi-nested assays with primers VP1-1 and VP1-2a, amplifying a 481 bp-long fragment, or with primers VP1-1.5 and VP1-4a, amplifying a 490 bp-long fragment (Zheng)(Table 20) The PCR reaction mixture consisted of 2.5 µL 10×PCR buffer, 200 µM of each dNTP, 1.5 mM MgCl2, 0.5 µM primers and 1.25 unit of AmpliTaq Gold DNA Polymerase (Applied Biosystems). In the first round 4 µL of extracted DNA were added in a total volume of 25 µL and the cycling parameters were 20 cycles at 94° C. for 20 sec, at 55° C. for 30 sec and at 68° C. for 90 sec in an automated thermal cycler (Applied Biosystems). This first step PCR product was purified with ExoSAP-IT PCR Clean-up Kit, the protocol consists of a single pipetting step (enzyme mixture addition), a 30-min incubation at 37° C. followed by enzyme inactivation at 80° C. for a further 15 min. In the second round of semi-nested PCR 4 µL of cleaned PCR product were added in a total volume of 25 µL and the cycling parameters were 40 cycles at 94° C. for 20 sec, at 62° C. for 30 sec and at 68° C. for 90 sec in an automated thermal cycler (Applied Biosystems).

With both assays, following amplification with the inner primers, 10 µl of the amplified product from the second mixture was electrophoresed on a 2% agarose gel containing 0.5 µg/ml ethidium bromide. The results were photographed under U.V. illumination and regarded as positive when a band corresponding to the expected by long DNA fragment was present.

TABLE 20

Nucleotide sequences of the primers used in the full length nested PCR and short-fragment semi-nested PCR for JCV-VP1

| Name | Sequence | Nt. Number * |
|---|---|---|
| VP1-LF | GCAGCCAGCTATGGCTTTAC | (SEQ ID NO: 55) |
| VP1-LR | GCTGCCATTCATGAGAGGAT | (SEQ ID NO: 56) |
| VP1-SF | CCTCAATGGATGTTGCCTTT | (SEQ ID NO: 57) |
| VP1-SR | AAAACCAAAGACCCCT | (SEQ ID NO: 58) |
| VP1-1 | TTGACTCAATTACAGAGGTAGAAT | (SEQ ID NO: 59) |
| VP1-4a | AGAAATTGGGTAGGGGTTTTTAAC | (SEQ ID NO: 60) |
| VP1-2a | AGGTACGCCTTGTGCTCTGTGTTC | (SEQ ID NO: 61) |
| VP1-1.5 | GTGCAGGGCACCAGCTTTCATT | (SEQ ID NO: 62) |

* according to the Mad-1 strain (ref)

VP1 PCR Cloning and Sequencing

The amplification product was purified by the Qiagen purification kit. A's were added to the ends of the cleaned up PCR product by Taq polymerase (A-overhang reaction) and cloning was carried out by the TOPO TA cloning kit (Invitrogen). Mini-prep DNA was prepared (Qiagen) from colonies containing the cloned VP1 PCR product. Two to 48 clones were sequenced for each sample (median 23). Following translation of the VP1 sequences, amino acid mutations were marked by comparison to the large selection of VP1 sequences from PML and non-PML cases. Only mutations present in more than one clone for sample were considered.

Real-Time PCR for Quantification of JCV-DNA

JCV DNA was quantified in CSF, plasma and urine samples by real-time PCR, as described previously (Bossolasco S. et al. 2005)

Hemagglutination Assay

Red blood cells (RBCs) from type O+ donors were washed twice and suspended in Alsever's buffer (20 mM sodium citrate, 72 mM NaCl, 100 mM glucose, pH 6.5 adjusted with acetic acid) at a final concentration of ~0.5%. Serial two-fold dilutions starting from 100 g/ml of VLPs were prepared in Alsever's buffer and an equal volume of RBCs was added into each well of a 96-well "U" bottom microtiter plate and incubated at 4° C. for 3-6 hr (24 two-fold dilutions were performed). Minimum HA concentration is the lowest concentration of VLP protein that still agglutinated RBCs.

Ganglioside ELISA

Specific gangliosides (resuspended in methanol) were coated onto a microtiter plate (10 µg) overnight. The plates were blocked (1% BSA (Fraction V), 0.1% Tween-20, PBS with Ca++, Mg++). VLPs were prepared at 30 µg/ml in block buffer and added (100 µl/well). All incubations were performed on ice. After 90 minutes, the plates were washed with block buffer. VLP binding was detected with a two step process involving binding of anti-VP1 (PAB597 at 2 µg/ml) and HRP-anti-mIgG (1:100). Plates were washed and developed with TMB Turbo ELISA solution. The reaction was stopped with acid and the plate read on a spectrophotometer at 450 nm.

Flow Cytometry Analysis of VLP Binding to Cells

Cells were detached and collected (SVG-A, Jurkat, Human Astrocytes, Human Renal Proximal Tubular Epithelials). A sample (1-5×105 cells) was first incubated with VLP (10-30 µg/ml) in FACS Buffer (1% BSA [Fraction V], 2 mM sodium azide, PBS with Ca++, Mg++) in a volume of 50 µl for 60-90 minutes on ice. Cells were washed with FACS Buffer and further incubated with anti-VP1 (PAB597 2 µg/ml) for 60 minutes, followed by washing and incubation with AlexaFluor488-anti-mIgG (1:100) for another 30-45 minutes. Cells were washed and fixed in Cytofix/Cytoperm for 20 minutes, followed by a final wash and resuspension in FACS buffer. The cells were analyzed on a BD FACSCalibur. Appropriate controls and staining with other antibodies (isotype control, GM1, asialo GM1, GD1a, GT1b) and lectins (Peanut Agglutinin (PNA), *Sambucus Nigra* Lectin (SNA), *Maackia Amurensis* Lectin II (Mal II)) where necessary. In some cases cells were pretreated with α2-3 neuraminidase, a 2-3,6 neuraminidase, or PNGaseF to alter their cell surface suger structures.

The foregoing written specification is considered to be sufficient to enable one skilled in the art to practice the invention. The present invention is not to be limited in scope by examples provided, since the examples are intended as a single illustration of one aspect of the invention and other functionally equivalent embodiments are within the scope of the invention. Various modifications of the invention in addition to those shown and described herein will become apparent to those skilled in the art from the foregoing description and fall within the scope of the appended claims. The advantages and objects of the invention are not necessarily encompassed by each embodiment of the invention.

The contents of all references, patents and published patent applications cited throughout this application are incorporated herein by reference in their entirety.

What is claimed is:

1. A method comprising:
   contacting a solid surface that comprises an immobilized variant John Cunningham polyomavirus (JCV) VP1 capsid protein that has arginine at a position corresponding to amino acid 122 of SEQ ID NO: 1, with a biological sample obtained from a subject; and
   assaying for the presence or absence of a serum antibody that binds to the immobilized variant JCV VP1 capsid protein.

2. The method of claim 1, wherein the biological sample is a blood sample.

3. The method of claim 1, wherein the biological sample is a serum sample.

4. The method of claim 1, wherein the biological sample is a cerebrospinal fluid (CSF) sample.

5. The method of claim 1, wherein the subject is known to have been previously infected with a wild-type JCV.

6. The method of claim 5, wherein the presence or absence of the serum antibody to said variant of JCV capsid protein for the subject is assayed at least twice each year.

7. The method of claim 1, wherein the assaying step comprises performing an enzyme-linked immunosorbent assay (ELISA) to detect the presence or absence of the antibody.

8. The method of claim 1, further comprising assaying the biological sample obtained from the subject for the presence or absence of the variant JCV VP1 capsid protein.

9. The method of claim 8, where the biological sample is assayed for the presence or absence of a nucleic acid encoding the variant JCV VP1 capsid protein.

10. The method of claim 1, wherein the subject has the variant JCV VP1 capsid protein.

11. A method comprising:
    obtaining from a subject a biological sample, wherein the subject has a variant John Cunningham polyomavirus (JCV) VP1 capsid protein that has arginine at a position corresponding to amino acid 122 of SEQ ID NO: 1;
    contacting a solid surface that comprises an immobilized variant JCV VP1 capsid protein that has arginine at a position corresponding to amino acid 122 of SEQ ID NO: 1, with the biological sample; and
    assaying for the presence or absence of a serum antibody that binds to the immobilized variant JCV VP1 capsid protein.

12. The method of claim 11, wherein the biological sample is a blood sample.

13. The method of claim 11, wherein the biological sample is a serum sample.

14. The method of claim 11, wherein the biological sample is a cerebrospinal fluid (CSF) sample.

15. The method of claim 11, wherein the assaying step comprises performing an enzyme-linked immunosorbent assay (ELISA) to detect the presence or absence of the antibody.

* * * * *

UNITED STATES PATENT AND TRADEMARK OFFICE
CERTIFICATE OF CORRECTION

PATENT NO. : 9,696,307 B2  
APPLICATION NO. : 14/603002  
DATED : July 4, 2017  
INVENTOR(S) : Leonid Gorelik et al.

Page 1 of 1

It is certified that error appears in the above-identified patent and that said Letters Patent is hereby corrected as shown below:

On the Title Page

Item (71) should read:  
(71) Applicant: Biogen MA Inc., Cambridge, MA

Signed and Sealed this  
Nineteenth Day of December, 2017

Joseph Matal  
*Performing the Functions and Duties of the*  
*Under Secretary of Commerce for Intellectual Property and*  
*Director of the United States Patent and Trademark Office*